(12) United States Patent
Pinto et al.

(10) Patent No.: US 6,506,771 B2
(45) Date of Patent: Jan. 14, 2003

(54) HETEROARYL-PHENYL HETEROBICYCLIC FACTOR XA INHIBITORS

(75) Inventors: Donald J. P. Pinto, Kennett Square, PA (US); Mimi L. Quan, Newark, DE (US); Francis J. Woerner, Bear, DE (US); Renhua Li, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/887,850

(22) Filed: Jun. 22, 2001

(65) Prior Publication Data

US 2002/0119986 A1 Aug. 29, 2002

Related U.S. Application Data

(60) Provisional application No. 60/214,032, filed on Jun. 23, 2000.

(51) Int. Cl.[7] .................... C07D 471/04; C07D 487/04; A61K 31/415
(52) U.S. Cl. ........................ 514/303; 546/119; 546/120
(58) Field of Search ................................ 546/119, 120; 514/303

(56) References Cited

FOREIGN PATENT DOCUMENTS

| WO | WO97/23212 A | 7/1997 |
|---|---|---|
| WO | WO98/28269 A | 7/1998 |
| WO | WO98/28282 A | 7/1998 |
| WO | WO98/57934 A | 12/1998 |
| WO | WO98/57937 A | 12/1998 |
| WO | WO98/57951 A | 12/1998 |
| WO | WO99/32454 A | 7/1999 |
| WO | WO9950255 A | 10/1999 |
| WO | WO00/20416 A | 4/2000 |
| WO | WO0039131 A | 7/2000 |
| WO | WO00/40583 A | 7/2000 |
| WO | WO01/05784 A | 1/2001 |

OTHER PUBLICATIONS

Fevig J. M. et al. "Synthesis and SAR of benzamidine factor Xa inhibitors containing a vicinally–substituted heterocyclic core". Bioorganic & Medicinal Chemistry Letters (2001), 11(5), 641–645.

*Primary Examiner*—Bruck Kifle
(74) *Attorney, Agent, or Firm*—David H. Vance

(57) ABSTRACT

The present application describes heteroaryl-phenyl heterobicycles and derivatives thereof, or pharmaceutically acceptable salt forms thereof, which are useful as inhibitors of factor Xa.

36 Claims, No Drawings

HETEROARYL-PHENYL HETEROBICYCLIC FACTOR XA INHIBITORS

This application claims the benefit of U.S. Provisional Application No. 60/214,032, filed 06/23/2000.

FIELD OF THE INVENTION

This invention relates generally to heteroaryl-phenyl heterobicyclic compounds, which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

WO00/20416 and WO00/40583 describe imidazole[4,3-c]-pyridin-4-one compounds of the following formula.

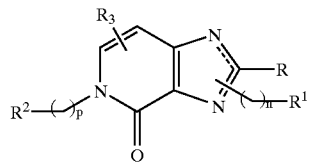

These compounds are stated to be factor Xa inhibitors. Compounds of this type, however, are not considered to be part of the presently claimed invention.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, one object of the present invention is to provide novel heteroaryl-phenyl heterobicyclic compounds that are useful as factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

It is another object of the present invention to provide novel heteroaryl-phenyl heterobicyclic compounds for use in therapy.

It is another object of the present invention to provide the use of novel heteroaryl-phenyl heterobicyclic compounds for the manufacture of a medicament for the treatment of a thromboembolic disorder.

These and other objects, which will become apparent during the following detailed description, have been achieved by the inventors' discovery that the presently claimed heteroaryl-phenyl heterobicyclic compounds, or pharmaceutically acceptable salt or prodrug forms thereof, are effective factor Xa inhibitors.

DETAILED DESCRIPTION OF PREFERRED EMBODIMENTS

[1] Thus, in a first embodiment, the present invention provides a novel compound of formula Ia, Ib, or Ic:

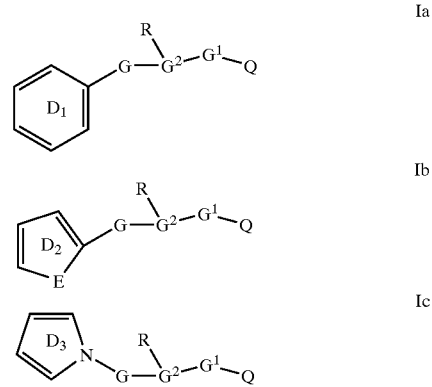

or a stereoisomer or pharmaceutically acceptable salt thereof, wherein;

ring $D_1$ is selected from pyridine, pyrazine, pyridazine, and pyrimidine and is substituted with 1 $R^a$ and 0–1 $R^b$;

ring $D_2$ is a 5-membered heteroaromatic ring system comprising E, carbon atoms, and 0–3 N atoms, wherein E is selected from O, S, and N—$R^c$ and ring $D_2$ is substituted with 1 $R^a$ and 0–1 $R^b$;

ring $D_3$ is a 5-membered heteroaromatic ring system comprising carbon atoms and from 0–3 additional N atoms and ring $D_3$ is substituted with 1 $R^a$ and 0–1 $R^b$;

R is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $NR^8CH(=NR^7)$, $NH_2$, $NH(C_{1-3}$ alkyl$)$, $N(C_{1-3}$ alkyl$)_2$, $C(=NH)NH_2$, $CH_2NH_2$, $CH_2NH(C_{1-3}$ alkyl$)$, $CH_2N(C_{1-3}$ alkyl$)_2$, $CH_2CH_2NH_2$, $CH_2CH_2NH(C_{1-3}$ alkyl$)$, $CH_2CH_2N(C_{1-3}$ alkyl$)_2$, $(CR^8R^9)_rNR^7R^8$, $(CR^8R^9)_rC(O)NR^7R^8$, and $OCF_3$;

$R^a$ is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $NR^8CH(=NR^7)$, $NH_2$, $NH(C_{1-3}$ alkyl$)$, $N(C_{1-3}$ alkyl$)_2$, $C(=NH)NH_2$, $CH_2NH_2$, $CH_2NH(C_{1-3}$ alkyl$)$, $CH_2N(C_{1-3}$ alkyl$)_2$, $CH_2CH_2NH_2$, $CH_2CH_2NH(C_{1-3}$ alkyl$)$, $CH_2CH_2N(C_{1-3}$ alkyl$)_2$, $(CR^8R^9)_rNR^7R^8$, $(CR^8R^9)_rC(O)NR^7R^8$, and $OCF_3$;

$R^b$ is selected from H, $C_{1-4}$ alkyl, F, Cl, Br, I, OH, $OCH_3$, $OCH_2CH_3$, $OCH(CH_3)_2$, $OCH_2CH_2CH_3$, CN, C(=NR⁸)NR⁷R⁹, NHC(=NR⁸)NR⁷R⁹, NR⁸CH
(=NR⁷), NH₂, NH(C₁₋₃ alkyl), N(C₁₋₃ alkyl)₂,
C(=NH)NH₂, CH₂NH₂, CH₂NH(C₁₋₃ alkyl), CH₂N
(C₁₋₃ alkyl)₂, CH₂CH₂NH₂, CH₂CH₂NH(C₁₋₃ alkyl),
CH₂CH₂N(C₁₋₃ alkyl)₂, (CR⁸R⁹)ᵣNR⁷R⁸, (CR⁸R⁹)ᵣC
(O)NR⁷R⁸, and OCF₃;

Rᶜ is selected from H, C₁₋₄ alkyl, OCH₃, OCH₂CH₃,
OCH(CH₃)₂, OCH₂CH₂CH₃, NH₂, NH(C₁₋₃ alkyl),
N(C₁₋₃ alkyl)₂, C(=NH)NH₂, CH₂NH₂, CH₂NH(C₁₋₃
alkyl), CH₂N(C₁₋₃ alkyl)₂, CH₂CH₂NH₂, CH₂CH₂NH
(C₁₋₃ alkyl), CH₂CH₂N(C₁₋₃ alkyl)₂, (CR⁸R⁹)ᵣNR⁷R⁸,
(CR⁸R⁹)ᵣC(O)NR⁷R⁸, and OCF₃;

G is absent or is selected from CH₂, C(O), O, NR³, S(O)ₚ,
CH₂CH₂, C(O)CH₂, CH₂C(O), OCH₂, CH₂O,
NR³CH₂, CH₂NR³, S(O)ₚCH₂, CH₂S(O)ₚ,
CH₂CH₂CH₂, C(O)CH₂CH₂, CH₂C(O)CH₂,
CH₂CH₂C(O), OCH₂CH₂, CH₂OCH₂, CH₂CH₂O,
NR³CH₂CH₂, CH₂NR³_{CH2}, CH₂CH₂NR³,
S(O)ₚCH₂CH₂, CH₂S(O)ₚCH₂, and CH₂CH₂S(O)ₚ;

G₁ is absent or is selected from (CR³R³ᵃ)₁₋₅, (CR³R³ᵃ)₀₋₂CR³=CR³(CR³R³ᵃ)₀₋₂, (CR³R³ᵃ)₀₋₂C≡C
(CR³R³ᵃ)₀₋₂, (CR³R³ᵃ)ᵤC(O)(CR³R³ᵃ)ᵥᵥ, (CR³R³ᵃ)ᵤC
(O)O(CR³R³ᵃ)ᵥᵥ, (CR³R³ᵃ)ᵤOC(O)(CR³R³ᵃ)ᵥᵥ,
(CR³R³ᵃ)ᵤO(CR³R³ᵃ)ᵥᵥ, (CR³R³ᵃ)ᵤNR³(CR³R³ᵃ)ᵥᵥ,
(CR³R³ᵃ)ᵤC(O)NR³(CR³R³ᵃ)ᵥᵥ, (CR³R³ᵃ)ᵤNR³C(O)
(CR³R³ᵃ)ᵥᵥ, (CR³R³ᵃ)ᵤOC(O)NR³(CR³R³ᵃ)ᵥᵥ,
(CR³R³ᵃ)ᵤNR³C(O)O(CR³R³ᵃ)ᵥᵥ, (CR³R³ᵃ)ᵤNR³C(O)
NR³(CR³R³ᵃ)ᵥᵥ, (CR³R³ᵃ)ᵤNR³C(S)NR³(CR³R³ᵃ)ᵥᵥ,
(CR³R³ᵃ)ᵤS(CR³R³ᵃ)ᵥᵥ, (CR³R³ᵃ)ᵤS(O)(CR³R³ᵃ)ᵥᵥ,
(CR³R³ᵃ)ᵤS(O)₂(CR³R³ᵃ)ᵥᵥ, (CR³R³ᵃ)ᵤS(O)NR³
(CR³R³ᵃ)ᵥᵥ, (CR³R³ᵃ)ᵤNR³S(O)₂(CR³R³ᵃ)ᵥᵥ,
(CR³R³ᵃ)ᵤS(O)₂NR³(CR³R³ᵃ)ᵥᵥ, and (CR³R³ᵃ)ᵤNR³S
(O)₂NR³(CR³R³ᵃ)ᵥᵥ, wherein u+w total 0, 1, 2, 3, or 4,
provided that G₁ does not form a N—N, N—O, N—S,
NCH₂N, NCH₂O, or NCH₂S bond with either group to
which it is attached;

G² is phenyl, naphthyl, or a 5–10 membered heteroaryl
consisting of carbon atoms and from 1–3 heteroatoms
selected from N, O, and S;

Q is a group of formula II:

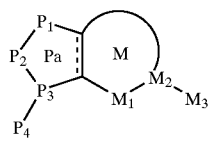

II one of P₄ and M₃ is —Z—A—B and the other is attached to G₁;

ring M, including M₁ and M₂, is a 6 or 7 membered
carbocycle or 6 or 7 membered heterocycle, consisting
of: carbon atoms and 1–3 heteroatoms selected from O,
S(O)ₚ, N, and NZ²;

ring M is substituted with 0–2 R¹ᵃ and 0–2 carbonyl
groups, and, comprises: 0–2 additional double bonds;

ring P, including P₁, P₂, P₃, and P₄ is selected from group:

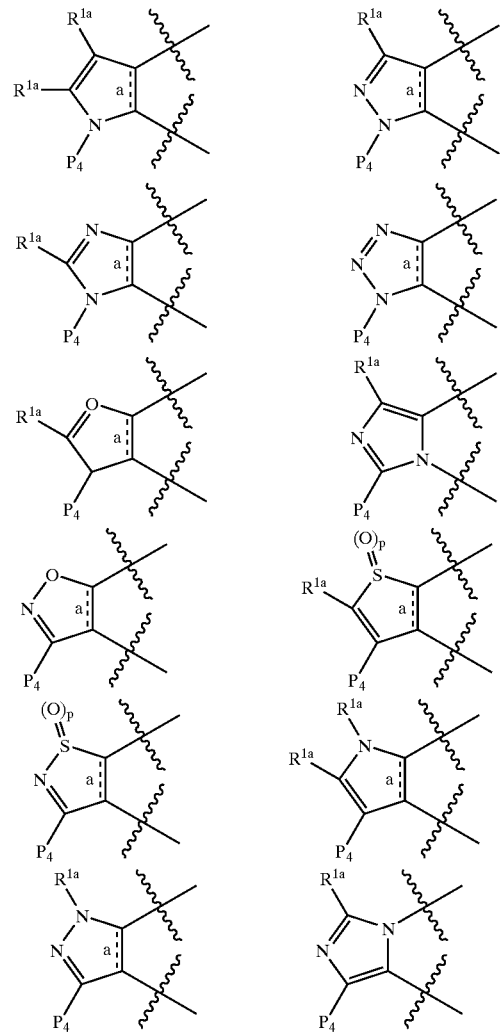

"a" is absent or is a bond
provided that when Q is a dihydroimidazolo[4,5-c]-pyridin-4-one then:
(i) G₁ is present and is other than alkylene;
(ii) Z is present and is other than alkylene;
(iii) Ring D₁—G is present, D₁—G is other than benzyloxy;
(iv) Ring D₃ is present; or
(v) Ring D₂ is present and is other than 5-methyl-1,2,4-oxadiazole or 5-oxo-1,2,4-oxadiazole;

Z is selected from a bond, —(CR²R²ᵃ)₁₋₄—,
(CR²R²ᵃ)ᵩO(CR²R²ᵃ)ᵩ₁, (CR²R²ᵃ)ᵩNR³(CR²R²ᵃ)ᵩ₁,
(CR²R²ᵃ)ᵩC(O)(CR²R²ᵃ)ᵩ₁, (CR²R²ᵃ)ᵩC(O)O
(CR²R²ᵃ)ᵩ₁, (CR²R²ᵃ)ᵩOC(O)(CR²R²ᵃ)ᵩ₁, (CR²R²ᵃ)ᵩC
(O)NR³(CR²R²ᵃ)ᵩ₁, (CR²R²ᵃ)ᵩNR³C(O)(CR²R²ᵃ)ᵩ₁,
(CR²R²ᵃ)ᵩOC(O)O(CR²R²ᵃ)ᵩ₁, (CR²R²ᵃ)ᵩOC(O)NR³
(CR²R²ᵃ)ᵩ₁, (CR²R²ᵃ)ᵩNR³C(O)O(CR²R²ᵃ)ᵩ₁,
(CR²R²ᵃ)ᵩNR³C(O)NR³(CR²R²ᵃ)ᵩ₁, (CR²R²ᵃ)ᵩS
(CR²R²ᵃ)ᵩ₁, (CR²R²ᵃ)ᵩS(O)(CR²R²ᵃ)ᵩ₁, (CR²R²ᵃ)ᵩS
(O)₂(CR²R²ᵃ)ᵩ₁, (CR²R²ᵃ)ᵩSO₂NR³(CR²R²ᵃ)ᵩ₁,
(CR²R²ᵃ)ᵩNR³SO₂(CR²R²ᵃ)ᵩ₁, and
(CR²R²ᵃ)ᵩNR³SO₂NR³(CR²R²ᵃ)ᵩ₁, wherein q+q¹ total
0, 1, or 2, provided that Z does not form a N—N,
N—O, N—S, NCH₂N, NCH₂O, or NCH₂S bond with
either group to which it is attached;

Z² is selected from H, C₁₋₄ alkyl, phenyl, benzyl, C(O)R³,
and S(O)ₚR³ᶜ;

$R^{1a}$ is selected from H, —$(CH_2)_r$—$R^{1b}$, —CH=CH—$R^{1b}$, $NCH_2R^{1c}$, $OCH_2R^{1c}$, $SCH_2R^{1c}$, $NH(CH_2)_2(CH_2)_rR^{1b}$, $O(CH_2)_2(CH_2)_rR^{1b}$, $S(CH_2)_2(CH_2)_rR^{1b}$, $S(O)_p(CH_2)_rR^{1d}$, $O(CH_2)_rR^{1d}$, $NR^3(CH_2)_rR^{1d}$, $OC(O)NR^3(CH_2)_rR^{1b}$, $NR^3C(O)NR^3(CH_2)_rR^{1d}$, $NR^3C(O)O(CH_2)_rR^{1d}$, and $NR^3C(O)(CH_2)_rR^{1d}$, provided that $R^{1a}$ forms other than an N-halo, N—N, N—S, N—O, or N—CN bond;

alternatively, when two $R^{1a}$'s are attached to adjacent atoms, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and comprising: 0–3 double bonds;

$R^{1b}$ is selected from H, $C_{1-3}$ alkyl, F, Cl, Br, I, —CN, —CHO, $(CF_2)_rCF_3$, $(CH_2)_rOR^2$, $NR^2R^{2a}$, $C(O)R^{2c}$, $OC(O)R^2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NHR^{2b}$, $NR^2C(O)_2R^{2a}$, $OC(O)NR^{2a}R^{2b}$, $C(O)NR^2R^{2a}$, $C(O)NR^2(CH_2)_rOR^2$, $SO_2NR^2R^{2a}$, $NR^2SO_2R^{2b}$, $C_{3-6}$ carbocycle substituted with 0–2 $R^{4a}$, and 5–10 membered heterocycle consisting of carbon atoms and from 1–4 heteroatoms selected from the group consisting of N, O, and $S(O)_p$ substituted with 0–2 $R^{4a}$, provided that $R^{1b}$ forms other than an N-halo, N—N, N—S, N—O, or N—CN bond;

$R^{1c}$ is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;

$R^{1d}$ is selected from $C_{3-13}$ carbocycle substituted with 0–2 $R^{4a}$, and 5–13 membered heterocycle consisting of carbon atoms and from 1–4 heteroatoms selected from the group consisting of N, O, and $S(O)_p$ substituted with 0–2 $R^{4a}$, provided that $R^{1d}$ forms other than an N—N, N—S, or N—O bond;

$R^2$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system comprising carbon atoms and from 1–4 heteroatoms selected from the group consisting of N, O, and S substituted with 0–2 $R^{4b}$;

$R^{2a}$, at each occurrence, is selected from H, $CF_3$, $C_{1-6}$ alkyl, benzyl, phenethyl, $C_{3-6}$ carbocyclic residue substituted with 0–2 $R^{4b}$, and 5–6 membered heterocyclic system comprising carbon atoms and from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{3-6}$ carbocyclic residue substituted with 0–2 $R^{4b}$, and 5–6 membered heterocyclic system comprising carbon atoms and from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic residue substituted with 0–2 $R^{4b}$, and 5–6 membered heterocyclic system comprising carbon atoms and from 1–4 heteroatoms selected from the group consisting of N, O, and S substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and comprising carbon atoms and from 0–1 additional heteroatoms selected from the group consisting of N, O, and S;

$R^3$, at each occurrence, is selected from H, $C_{1-4}$ alkyl, and phenyl;

$R^{3a}$, at each occurrence, is selected from H, $C_{1-4}$ alkyl, and phenyl;

$R^{3b}$, at each occurrence, is selected from H, $C_{1-4}$ alkyl, and phenyl;

$R^{3c}$, at each occurrence, is selected from $C_{1-4}$ alkyl, and phenyl;

$R^{3d}$, at each occurrence, is selected from H, $C_{1-4}$ alkyl, $C_{1-4}$ alkyl-phenyl, and $C(O)R^{3c}$;

A is selected from:
$C_{3-10}$ carbocyclic residue substituted with 0–2 $R^4$, and 5–12 membered heterocyclic system comprising carbon atoms and from 1–4 heteroatoms selected from the group consisting of N, O, and S substituted with 0–2 $R^4$;

B is selected from: H, Y, and X—Y, provided that Z and B are attached to different atoms on A;

X is selected from —$(CR^2R^{2a})_{1-4}$—, —$CR^2(CR^2R^{2b})(CH_2)_r$—, —C(O)—, —C(=$NR^{1c}$)—, —$CR^2(NR^{1c}R^2)$—, —$CR^2(OR^2)$—, —$CR^2(SR^2)$—, —$C(O)CR^2R^{2a}$—, —$CR^2R^{2a}C(O)$, —S—, —S(O)—, —$S(O)_2$—, —$SCR^2R^{2a}$—, —$S(O)CR^2R^{2a}$—, —$S(O)_2CR^2R^{2a}$—, —$CR^2R^{2a}S$—, —$CR^2R^{2a}S(O)$—, —$CR^2R^{2a}S(O)_2$—, —$S(O)_2NR^2$—, —$NR^2S(O)_2$—, —$NR^2S(O)_2CR^2R^{2a}$—, —$CR^2R^{2a}S(O)_2NR^2$—, —$NR^2S(O)_2NR^2$—, —$C(O)NR^2$—, —$NR^2C(O)$—, —$C(O)NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)O$—, —$OC(O)NR^2$—, —$NR^2C(O)NR^2$—, —$NR^2$—, —$NR^2CR^2R^{2a}$—, —$CR^2R^{2a}NR^2$—, O, —$CR^2R^{2a}O$—, and —$OCR^2R^{2a}$—;

Y is selected from:
$C_{3-10}$ carbocyclic residue substituted with 0–2 $R^{4a}$, and 5–12 membered heterocyclic system comprising carbon atoms and from 1–4 heteroatoms selected from the group consisting of N, O, and S substituted with 0–2 $R^{4a}$;

$R^4$, at each occurrence, is selected from H, =O, $(CH_2)_rOR^2$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^2R^{2a}$, $(CH_2)_rN(\rightarrow O)R^2R^{2a}$, $(CH_2)_rC(O)R^{2c}$, $(CH_2)_rNR^2C(O)R^{2b}$, $(CH_2)_rC(O)NR^2R^{2a}$, $(CH_2)_rNR^2C(O)NR^2R^{2a}$, $(CH_2)_rC(=NR^2)NR^2R^{2a}$, $(CH_2)_rC(=NS(O)_2R^5)NR^2R^{2a}$, $(CH_2)_rNHC(=NR^2)NR^2R^{2a}$, $(CH_2)_rC(O)NHC(=NR^2)NR^2R^{2a}$, $(CH_2)_rSO_2NR^2R^{2a}$, $(CH_2)_rNR^2SO_2NR^2R^{2a}$, $(CH_2)_rNR^2SO_2$—$C_{1-4}$ alkyl, $(CH_2)_rNR^2SO_2R^5$, $(CH_2)_r$—$NR^2SO_2R^{5a}$, $(CH_2)_rS(O)_pR^5$, $(CH_2)_r$—$S(O)_pR^{5a}$, $(CF_2)_rCF_3$, $(CH_2)_r$—$CF_3$, $(CR^{4c}R^{4d})(CR^{3e}R^{4e})_r$—$NR^{4e}R^{4f}$, $(CR^{4c}R^{4d})(CR^{3e}R^{3e})_r$—$OR^{4e}$, $(CR^{4c}R^{4d})(CR^{3e}R^{3e})_r$—$SR^{4e}$, $(CR^{4c}R^{4d})(CR^{3e}R^{3e})_r$—$N(\rightarrow O)R^{4e}R^{4f}$, $(CH_2)_rNCH_2R^{1c}$, $(CH_2)_rOCH_2R^{1c}$, $(CH_2)_rSCH_2R^{1c}$, $(CH_2)_rN(CH_2)_2(CH_2)_rR^{1b}$, $(CH_2)_rO(CH_2)_2(CH_2)_rR^{1b}$, $(CH_2)_rS(CH_2)_2(CH_2)_rR^{1b}$, $(CH_2)_r$5–6 membered carbocycle substituted with 0–1 $R^5$, and $(CH_2)_r$5–6 membered heterocycle consisting of: carbon atoms and 1–4 heteroatoms selected from the group consisting of N, O, and $S(O)_p$ substituted with 0–1 $R^5$;

$R^4$, at each occurrence, is selected from H, =O, $(CH_2)_rOR^2$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^2R^{2a}$, $C(O)R^{2c}$, $NR^2C(O)R^{2b}$, $C(O)NR^2R^{2a}$, $NR^2C(O)NR^2R^{2a}$, $C(=NR^2)NR^2R^{2a}$, $C(=NS(O)_2R^5)NR^2R^{2a}$, $NHC(=NR^2)NR^2R^{2a}$, $C(O)NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, $(CF_2)_rCF_3$, $(CH_2)_r$—$CF_3$, $NCH_2R^{1c}$, $OCH_2R^{1c}$, $SCH_2R^{1c}$, $N(CH_2)_2(CH_2)_rR^{1b}$, O(CH$_2$)$_2$(CH$_2$)$_r$R$^{1b}$, S(CH$_2$)$_2$(CH$_2$)$_r$R$^{1b}$, 5–6 membered carbocycle substituted with 0–1 R$^5$, and 5–6 membered heterocycle consisting of: carbon atoms and 1–4 heteroatoms selected from the group consisting of N, O, and S(O)$_p$ substituted with 0–1 R$^5$;

R$^{4a}$, at each occurrence, is selected from H, =O, (CH$_2$)$_r$OR$^2$, (CF$_2$)$_r$CF$_3$, (CH$_2$)$_r$—CF$_3$, (CH$_2$)$_r$—F, (CH$_2$)$_r$—Br, (CH$_2$)$_r$—Cl, C$_{1-4}$ alkyl, (CH$_2$)$_r$CN, (CH$_2$)$_r$NO$_2$, (CH$_2$)$_r$NR$^2$R$^{2a}$, (CH$_2$)$_r$C(O)R$^{2c}$, NR$^2$C(O)R$^{2b}$, C(O)NR$^2$R$^{2a}$, (CH$_2$)$_r$N=CHOR$^3$, C(O)NH(CH$_2$)$_2$NR$^2$R$^{2a}$, NR$^2$C(O)NR$^2$R$^{2a}$, C(=NR$^2$)NR$^2$R$^{2a}$, NHC(=NR$^2$)NR$^2$R$^{2a}$, SO$_2$NR$^2$R$^{2a}$, NR$^2$SO$_2$NR$^2$R$^{2a}$, NR$^2$SO$_2$—C$_{1-4}$ alkyl, NR$^2$SO$_2$R$^5$, C(O)NHSO$_2$—C$_{1-4}$ alkyl, S(O)$_p$R$^5$, 5–6 membered carbocycle substituted with 0–1 R$^5$, and 5–6 membered heterocycle consisting of: carbon atoms and 1–4 heteroatoms selected from the group consisting of N, O, and S(O)$_p$ substituted with 0–1 R$^5$;

R$^{4b}$, at each occurrence, is selected from H, =O, (CH$_2$)$_r$OR$^3$, (CH$_2$)$_r$—F, (CH$_2$)$_r$—Cl, (CH$_2$)$_r$—Br, (CH$_2$)$_r$—I, C$_{1-4}$ alkyl, (CH$_2$)$_r$—CN, (CH$_2$)$_r$—NO$_2$, (CH$_2$)$_r$NR$^3$R$^{3a}$, (CH$_2$)$_r$C(O)R$^3$, (CH$_2$)$_r$C(O)OR$^{3c}$, NR$^3$C(O)R$^{3a}$, C(O)NR$^3$R$^{3a}$, NR$^3$C(O)NR$^3$R$^{3a}$, C(=NR$^3$)NR$^3$R$^{3a}$, NR$^3$C(=NR$^3$)NR$^3$R$^{3a}$, SO$_2$NR$^3$R$^{3a}$, NR$^3$SO$_2$NR$^3$R$^{3a}$, NR$^3$SO$_2$—C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, (CH$_2$)$_r$CF$_3$, and (CF$_2$)$_r$CF$_3$;

R$^5$, at each occurrence, is selected from H, C$_{1-6}$ alkyl, =O, (CH$_2$)$_r$OR$^3$, F, Cl, Br, I, —CN, NO$_2$, (CH$_2$)$_r$NR$^3$R$^{3a}$, (CH$_2$)$_r$C(O)R$^3$, (CH$_2$)$_r$C(O)OR$^{3c}$, NR$^3$C(O)R$^{3a}$, C(O)NR$^3$R$^{3a}$, NR$^3$C(O)NR$^3$R$^{3a}$, CH(=NOR$^{3d}$), C(=NR$^3$)NR$^3$R$^{3a}$, NR$^3$C(=NR$^3$)NR$^3$R$^{3a}$, SO$_2$NR$^3$R$^{3a}$, NR$^3$SO$_2$NR$^3$R$^{3a}$, NR$^3$SO$_2$—C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, (CF$_2$)$_r$CF$_3$, phenyl substituted with 0–2 R$^6$, naphthyl substituted with 0–2 R$^6$, and benzyl substituted with 0–2 R$^6$;

R$^6$, at each occurrence, is selected from H, OH, (CH$_2$)$_r$OR$^2$, halo, C$_{1-4}$ alkyl, CN, NO$_2$, (CH$_2$)$_r$NR$^2$R$^{2a}$, (CH$_2$)$_r$C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl;

R$^7$, at each occurrence, is selected from H, OH, C$_{1-4}$ alkoxycarbonyl, C$_{6-10}$ aryloxy, C$_{6-10}$ aryloxycarbonyl, C$_{6-10}$ arylmethylcarbonyl, C$_{1-4}$ alkylcarbonyloxy C$_{1-4}$ alkoxycarbonyl, C$_{6-10}$ arylcarbonyloxy C$_{1-4}$ alkoxycarbonyl, C$_{1-6}$ alkylaminocarbonyl, phenylaminocarbonyl, and phenyl C$_{1-4}$ alkoxycarbonyl;

R$^8$, at each occurrence, is selected from H, C$_{1-6}$ alkyl, and (CH$_2$)$_n$-phenyl; alternatively, R$^7$ and R$^8$, when attached to the same nitrogen, combine to form a 5–6 membered heterocyclic ring consisting of carbon atoms and 0–2 additional heteroatoms selected from the group consisting of N, O, and S(O)$_p$;

R$^9$, at each occurrence, is selected from H, C$_{1-6}$ alkyl, and (CH$_2$)$_n$-phenyl;

n, at each occurrence, is selected from 0, 1, 2, and 3;
m, at each occurrence, is selected from 0, 1, and 2;
p, at each occurrence, is selected from 0, 1, and 2;
r, at each occurrence, is selected from 0, 1, 2, and 3;
s, at each occurrence, is selected from 0, 1, and 2; and,
t, at each occurrence, is selected from 0, 1, 2, and 3.

[2] In a preferred embodiment, the present invention provides a novel compound, wherein the compound is of formula Ia$_1$–Ic$_1$, wherein:

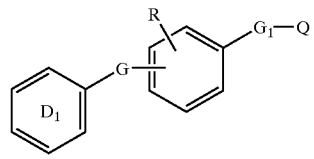

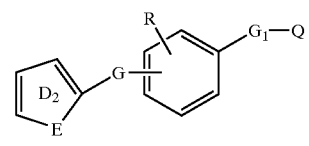

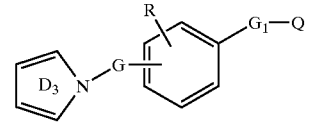

ring D$_2$ is a 5-membered heteroaromatic ring system comprising E, carbon atoms, and 0–2 N atoms, wherein E is selected from O, S, and N—R$^c$ and ring D$_2$ is substituted with 1 R$^a$ and 0–1 R$^b$;

ring D$_3$ is a 5-membered heteroaromatic ring system comprising carbon atoms and from 0–3 additional N atoms and ring D$_3$ is substituted with 1 R$^a$ and 0–1 R$^b$;

R is selected from H, Cl, F, Br, I, OH, C$_{1-3}$ alkoxy, NH$_2$, NH(C$_{1-3}$ alkyl), N(C$_{1-3}$ alkyl)$_2$, CH$_2$NH$_2$, CH$_2$NH(C$_{1-3}$ alkyl), CH$_2$N(C$_{1-3}$ alkyl)$_2$, CH$_2$CH$_2$NH$_2$, CH$_2$CH$_2$NH (C$_{1-3}$ alkyl), and CH$_2$CH$_2$N(C$_{1-3}$ alkyl)$_2$;

R$^a$ is selected from H, OH, SH, C$_{1-3}$ alkoxy, C$_{1-3}$ thioalkoxy, NH$_2$, NH(C$_{1-3}$ alkyl), N(C$_{1-3}$ alkyl)$_2$, CH$_2$NH$_2$, CH$_2$NH(C$_{1-3}$ alkyl), CH$_2$N(C$_{1-3}$ alkyl)$_2$, CH$_2$CH$_2$NH$_2$, CH$_2$CH$_2$NH(C$_{1-3}$ alkyl), and CH$_2$CH$_2$N (C$_{1-3}$ alkyl)$_2$;

R$^b$ is selected from H, C$_{1-4}$ alkyl, Cl, F, Br, I, OH, C$_{1-3}$ alkoxy, NH$_2$, NH(C$_{1-3}$ alkyl), N(C$_{1-3}$ alkyl)$_2$, CH$_2$NH$_2$, CH$_2$NH(C$_{1-3}$ alkyl), CH$_2$N(C$_{1-3}$ alkyl)$_2$, CH$_2$CH$_2$NH$_2$, CH$_2$CH$_2$NH(C$_{1-3}$ alkyl), and CH$_2$CH$_2$N (C$_{1-3}$ alkyl)$_2$;

R$^c$ is selected from H, C$_{1-4}$ alkyl, C$_{1-3}$ alkoxy, NH$_2$, NH(C$_{1-3}$ alkyl), N(C$_{1-3}$ alkyl)$_2$, CH$_2$NH$_2$, CH$_2$NH(C$_{1-3}$ alkyl), CH$_2$N(C$_{1-3}$ alkyl)$_2$, CH$_2$CH$_2$NH$_2$, CH$_2$CH$_2$NH (C$_{1-3}$ alkyl), and CH$_2$CH$_2$N(C$_{1-3}$ alkyl)$_2$;

G$_1$ is absent or is selected from CH$_2$, C(O), O, NR$^3$, S(O)$_p$, CH$_2$CH$_2$, C(O)CH$_2$, CH$_2$C(O), OCH$_2$, CH$_2$O, NR$^3$CH$_2$, CH$_2$NR$^3$, S(O)$_p$CH$_2$, CH$_2$S(O)$_p$, CH$_2$CH$_2$CH$_2$, C(O)CH$_2$CH$_2$, CH$_2$C(O)CH$_2$, CH$_2$CH$_2$C(O), OCH$_2$CH$_2$, CH$_2$OCH$_2$, CH$_2$CH$_2$O, NR$^3$CH$_2$CH$_2$, CH$_2$NR$^3$CH$_2$, CH$_2$CH$_2$NR$^3$, S(O)$_p$CH$_2$CH$_2$, CH$_2$S(O)$_p$CH$_2$, and CH$_2$CH$_2$S(O)$_p$, and provided that G$_1$—Q form other than a N—N, O—N, or S—N bond; ring M is substituted with 0–2 R$^{1a}$ and is selected from the group;

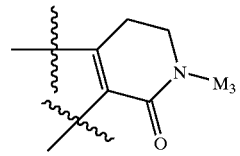 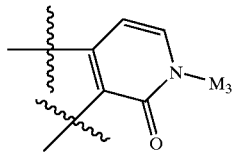

-continued
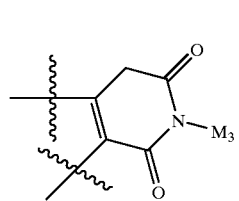
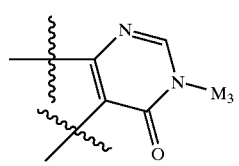
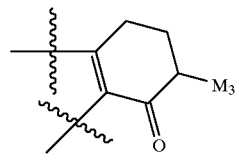
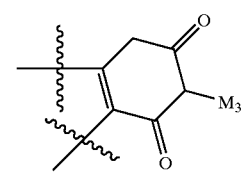
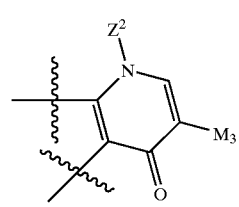
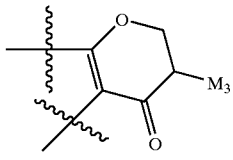
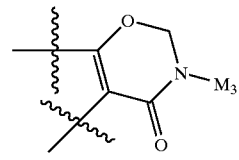
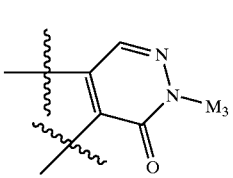
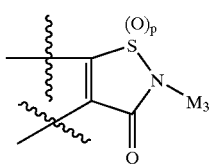
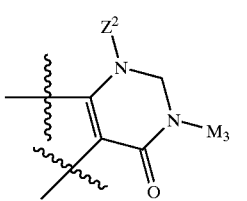
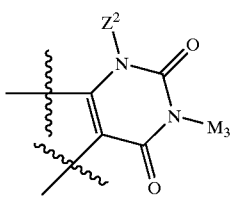
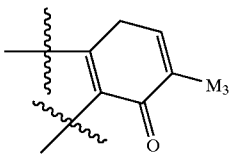
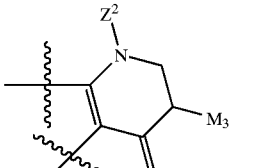
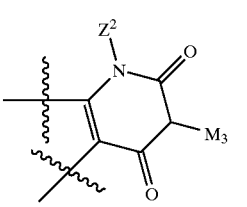
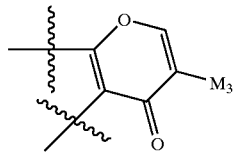
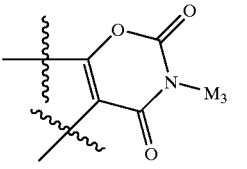
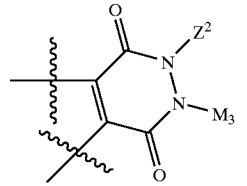
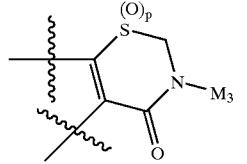
-continued
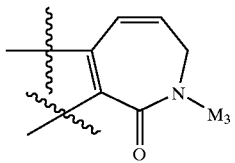
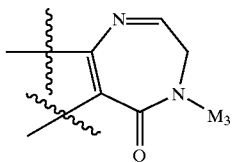
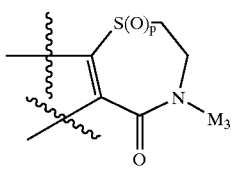
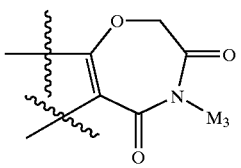
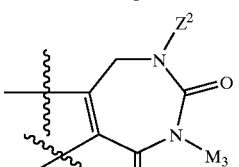
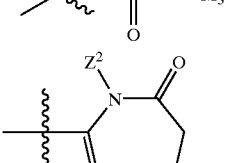
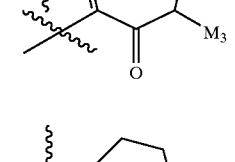
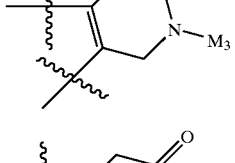
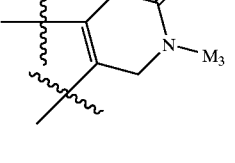
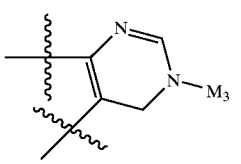

-continued
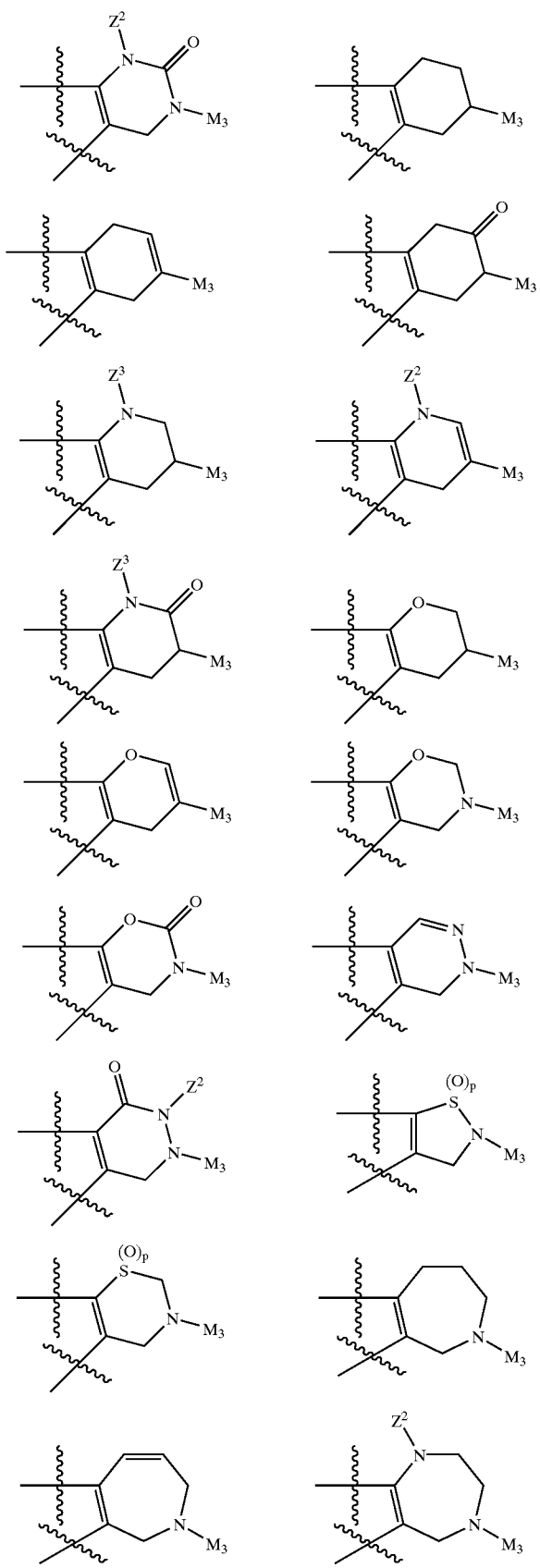
-continued
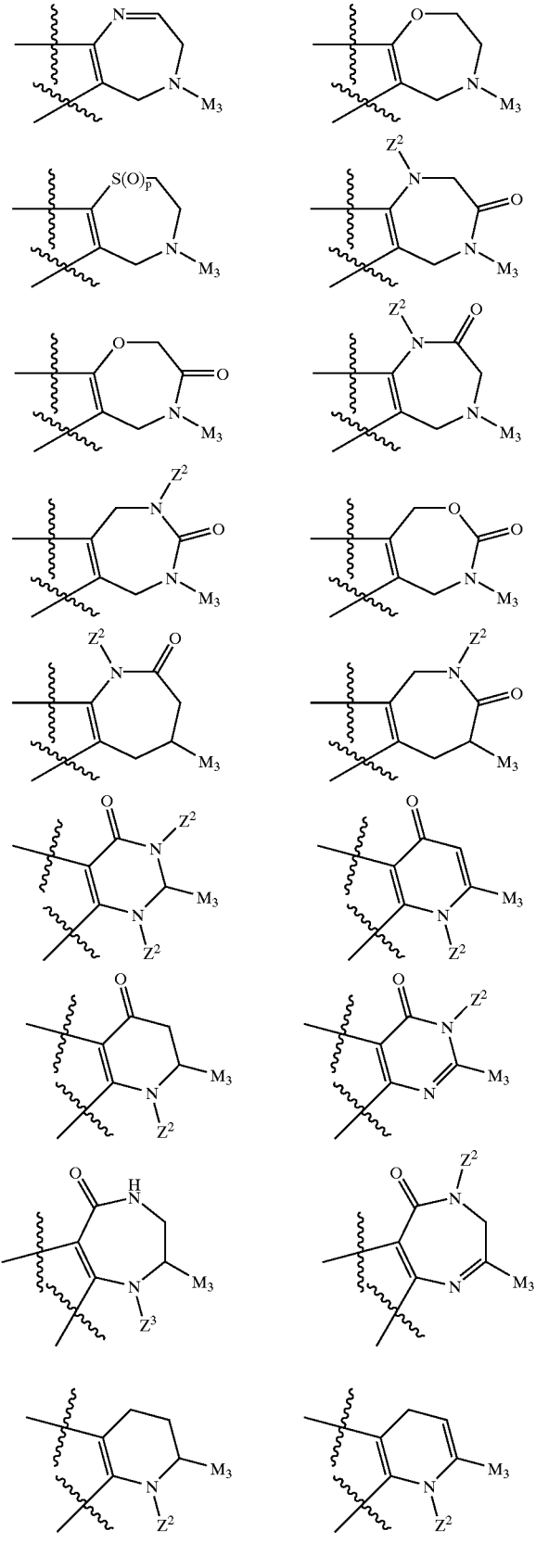

13

$Z^2$ is selected from H, $C_{1-4}$ alkyl, phenyl, benzyl, $C(O)R^3$, and $S(O)_pR^{3c}$;

ring P, including $P_1$, $P_2$, $P_3$, and $P_4$ is selected from group:

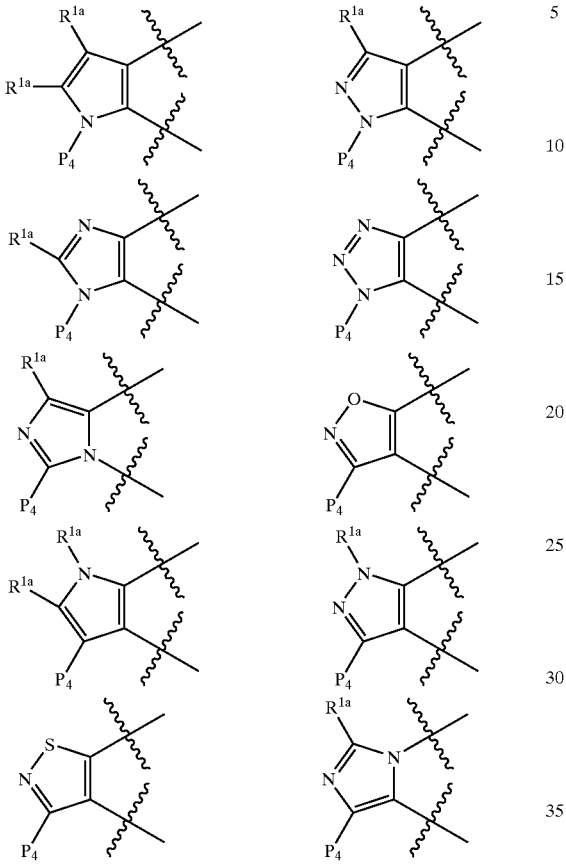

$G^1$ is absent or is selected from $(CR^3R^{3a})_{1-3}$, $(CR^3R^{3a})_uC(O)(CR^3R^{3a})_w$, $(CR^3R^{3a})_uO(CR^3R^{3a})_w$, $(CR^3R^{3a})_uNR^3(CR^3R^{3a})_w$, $(CR^3R^{3a})_uC(O)NR^3(CR^3R^{3a})_w$, $(CR^3R^{3a})_uNR^3C(O)(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^3(CR^3R^{3a})_w$, and $(CR^3R^{3a})_uS(O)_2NR^3(CR^3R^{3a})_w$, wherein u+w total 0, 1, or 2, provided that $G_1$ does not form a N—N, N—O, N—S, $NCH_2N$, $NCH_2O$, or $NCH_2S$ bond with either group to which it is attached;

A is selected from one of the following carbocyclic and heterocyclic systems which are substituted with 0–2 $R^4$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

X is selected from —$(CR^2R^{2a})_{1-4}$—, —C(O)—, (=$NR^{1c}$)—, —$CR^2(NR^{1c}R^2)$—, —$C(O)CR^2R^{2a}$—, —$CR^2R^{2a}C(O)$, —C(O)$NR^2$—, —$NR^2C(O)$—, —C(O)$NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)NR^2$—, —$NR^2$—, —$NR^2CR^2R^{2a}$—, —$CR^2R^{2a}NR^2$—, O, —$CR^2R^{2a}O$—, and —$OCR^2R^{2a}$—;

Y is selected from one of the following carbocyclic and heterocyclic systems that are substituted with 0–2 $R^{4a}$;

cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

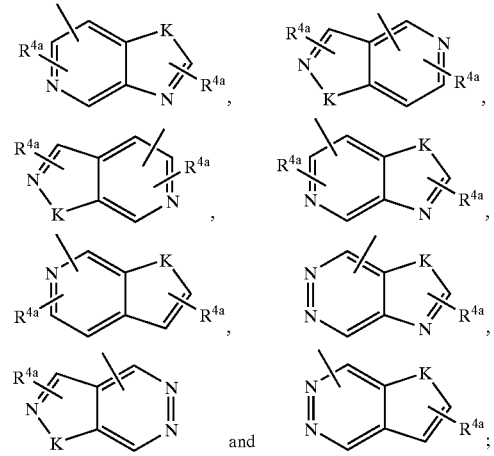

K is selected from O, S, NH, and N;

Z is selected from a bond, $CH_2O$, $OCH_2$, NH, $CH_2NH$, $NHCH_2$, $CH_2C(O)$, $C(O)CH_2$, C(O)NH, NHC(O), $CH_2S(O)_2$, $S(O)_2(CH_2)$, $SO_2NH$, and $NHSO_2$, provided that Z does not form a N—N, N—O, N—S, $NCH_2N$, $NCH_2O$, or $NCH_2S$ bond with either group to which it is attached;

$R^4$, at each occurrence, is selected from H, =O, $(CH_2)_rOR^2$, F, Cl, Br, I, $C_{1-4}$ alkyl, CN, $NO_2$, $(CH_2)_rNR^2R^{2a}$, $C(O)R^{2c}$, $NR^2C(O)R^{2b}$, $C(O)NR^2R^{2a}$, $NR^2C(O)NR^2R^{2a}$, $C(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, $CF_3$, $NCH_2R^{1c}$, $OCH_2R^{1c}$, $SCH_2R^{1c}$, $N(CH_2)_2(CH_2)_rR^{1b}$, $O(CH_2)_2(CH_2)_rR^{1b}$, $S(CH_2)_2(CH_2)_rR^{1b}$, 5–6 membered carbocycle substituted with 0–1 $R^5$, and 5–6 membered heterocycle consisting of: carbon atoms and 1–4 heteroatoms selected from the group consisting of N, O, and $S(O)_p$ substituted with 0–1 $R^5$; and, $R^{4a}$, at each occurrence, is selected from H, =O, $(CH_2)_rOR^2$, $CF_3$, F, Br, Cl, $C_{1-4}$ alkyl, CN, $NO_2$, $(CH_2)_rNR^2R^{2a}$, $(CH_2)_rC(O)R^{2c}$, $NR^2C(O)R^{2b}$, $C(O)NR^2R^{2a}$, $NR^2C(O)NR^2R^{2a}$, $C(=NR^2)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $C(O)NHSO_2$—$C_{1-4}$-alkyl, S(O)

$_pR^5$, 5–6 membered carbocycle substituted with 0–1 $R^5$, and 5–6 membered heterocycle consisting of: carbon atoms and 1–4 heteroatoms selected from the group consisting of N, O, and $S(O)_p$ substituted with 0–1 $R^5$.

[3] In another preferred embodiment, the present invention provides a novel compound, wherein the compound is of formula $Ib_1$, or $Ic_1$, wherein;

ring $D_2$ is a 5-membered heteroaromatic ring system comprising E, carbon atoms, and 0–2 N atoms, wherein E is selected from O, S, and N—$R^c$ and ring $D_2$ is substituted with 1 $R^a$ and 0–1 $R^b$;

R is selected from H, Cl, F, Br, I, OH, $C_{1-3}$ alkoxy, $NH_2$, $NH(C_{1-3}$ alkyl), $N(C_{1-3}$ alkyl)$_2$, $CH_2NH_2$, $CH_2NH(C_{1-3}$ alkyl), and $CH_2N(C_{1-3}$ alkyl)$_2$;

$R^a$ is selected from H, OH, SH, $NH_2$, $NH(C_{1-3}$ alkyl), $N(C_{1-3}$ alkyl)$_2$, $CH_2NH_2$, $CH_2NH(C_{1-3}$ alkyl), and $CH_2N(C_{1-3}$ alkyl)$_2$;

$R^b$ is selected from H, $C_{1-4}$ alkyl, Cl, F, Br, I, OH, $C_{1-3}$ alkoxy, $NH_2$, $NH(C_{1-3}$ alkyl), $N(C_{1-3}$ alkyl)$_2$, $CH_2NH_2$, $CH_2NH(C_{1-3}$ alkyl), and $CH_2N(C_{1-3}$ alkyl)$_2$;

$R^c$ is selected from H, $C_{1-4}$ alkyl, $C_{1-3}$ alkoxy, $NH_2$, $NH(C_{1-3}$ alkyl), $N(C_{1-3}$ alkyl)$_2$, $CH_2NH_2$, $CH_2NH(C_{1-3}$ alkyl), and $CH_2N(C_{1-3}$ alkyl)$_2$;

ring M is substituted with 0–2 $R^{1a}$ and is selected from the group:

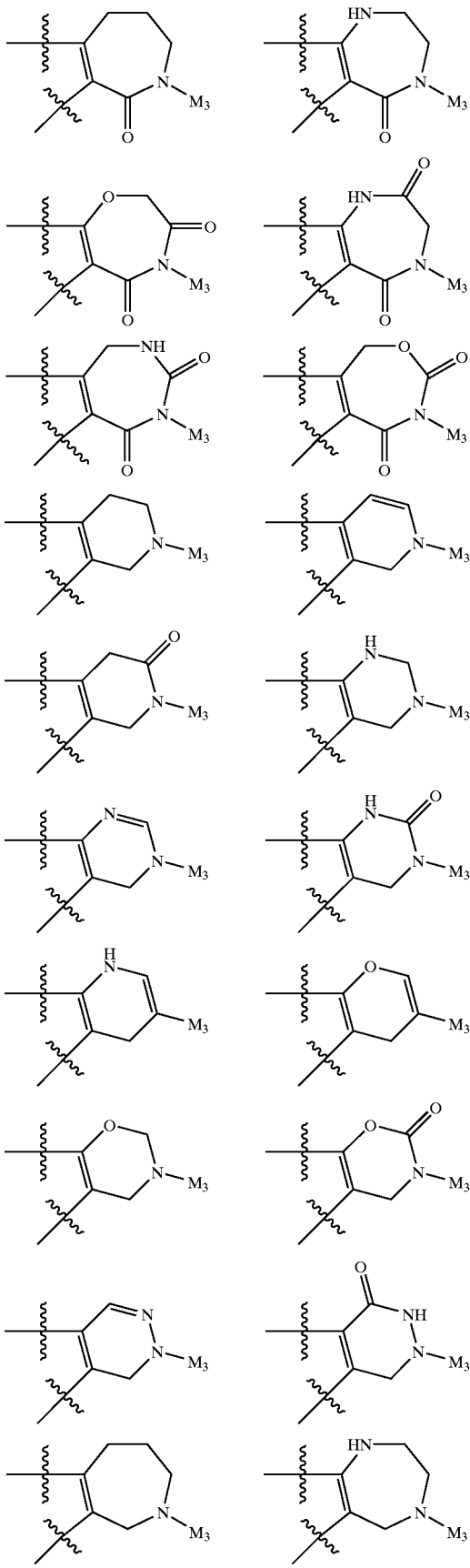

-continued

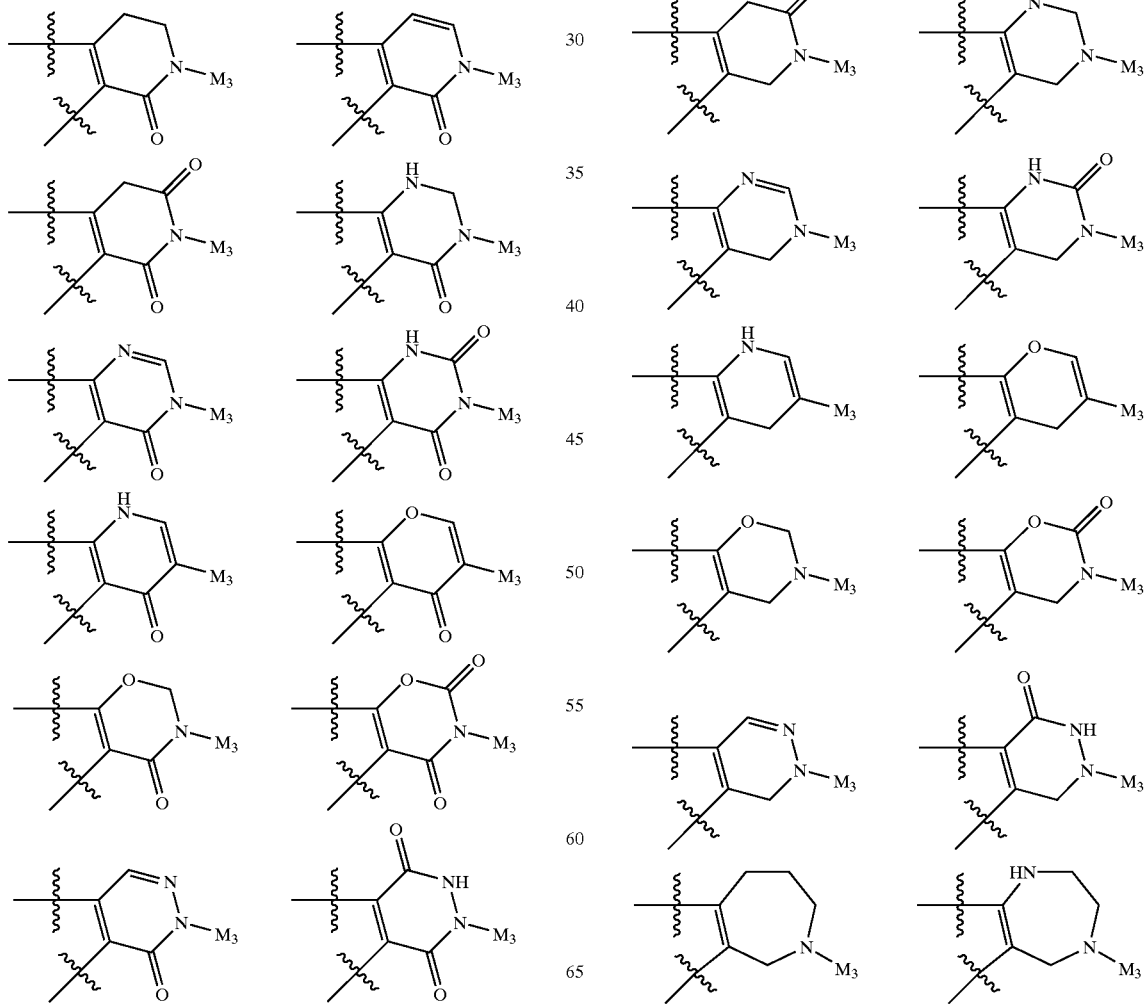

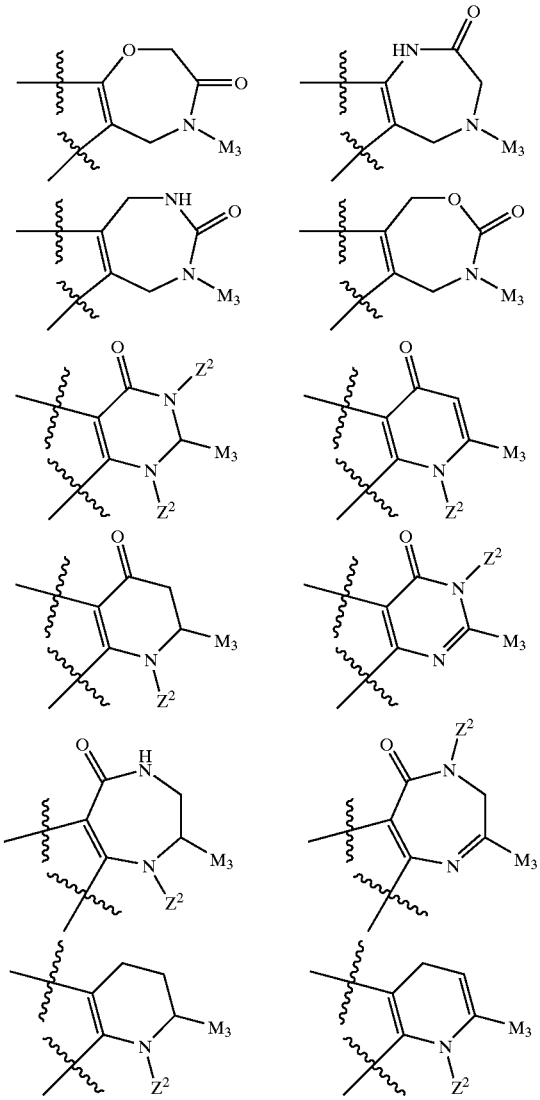

ring P, including $P_1$, $P_2$, $P_3$, and $P_4$ is selected from group:

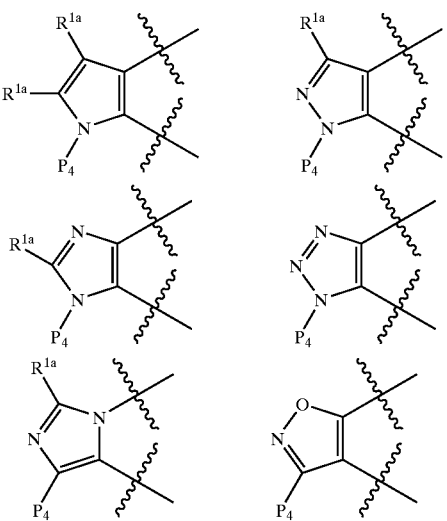

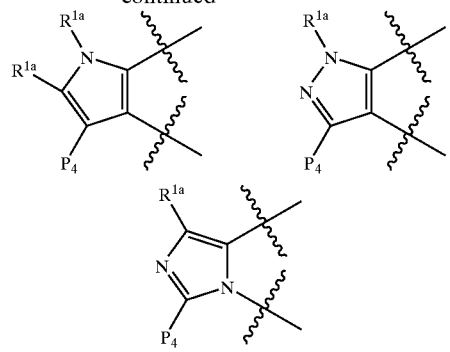

Y is selected from one of the following carbocyclic and heterocyclic systems which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzimidazolone, benzoxazole, benzthiazole, indazole, benzisoxazole, benzisothiazole, and isoindazole;

Z is selected from a bond, $CH_2O$, $OCH_2$, NH, $CH_2NH$, $NHCH_2$, $CH_2C(O)$, $C(O)CH_2$, C(O)NH, NHC(O), $CH_2S(O)_2$, $S(O)_2(CH_2)$, $SO_2NH$, and $NHSO_2$, provided that Z does not form a N—N, N—O, N—S, $NCH_2N$, $NCH_2O$, or $NCH_2S$ bond with either group to which it is attached;

$R^4$, at each occurrence, is selected from H, =O, $(CH_2)_rOR^2$, F, Cl, Br, I, $C_{1-4}$ alkyl, CN, $NO_2$, $(CH_2)_rNR^2R^{2a}$, $C(O)R^{2c}$, $NR^2C(O)R^{2b}$, $C(O)NR^2R^{2a}$, $NR^2C(O)NR^2R^{2a}$, $C(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, $CF_3$, 5–6 membered carbocycle substituted with 0–1 $R^5$, and 5–6 membered heterocycle consisting of: carbon atoms and 1–4 heteroatoms selected from the group consisting of N, O, and $S(O)_p$ substituted with 0–1 $R^5$; and, $R^{4a}$, at each occurrence, is selected from H, =O, $(CH_2)_rOR^2$, $CF_3$, F, Br, Cl, $C_{1-4}$ alkyl, CN, $NO_2$, $(CH_2)_rNR^2R^{2a}$, $(CH_2)_rC(O)R^{2c}$, $NR^2C(O)R^{2b}$, $C(O)NR^2R^{2a}$, $NR^2C(O)NR^2R^{2a}$, $C(=NR^2)NR^2R^{2a}$, $SO_2NR^2R^{2a}$, $C(O)NHSO_2$—$C_{1-4}$ alkyl, $S(O)_pR^5$, 5–6 membered carbocycle substituted with 0–1 $R^5$, and 5–6 membered heterocycle consisting of: carbon atoms and 1–4 heteroatoms selected from the group consisting of N, O, and $S(O)_p$ substituted with 0–1 $R^5$.

[4] In another preferred embodiment, the present invention provides a novel compound, wherein the compound is of formula $Ib_2$:

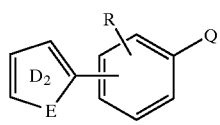

Ib$_2$ or a stereoisomer or pharmaceutically acceptable salt thereof, wherein;

ring D$_2$ is a 5-membered heteroaromatic ring system comprising E, carbon atoms, and 0–2 N atoms, wherein E is selected from O, S, and N—R$^c$ and ring D$_2$ is substituted with 1 R$^a$ and 0–1 R$^b$;

R is selected from H, Cl, F, Br, I, OH, C$_{1-3}$ alkoxy, NH$_2$, NH(C$_{1-3}$ alkyl), N(C$_{1-3}$ alkyl)$_2$, CH$_2$NH$_2$, CH$_2$NH(C$_{1-3}$ alkyl), and CH$_2$N(C$_{1-3}$ alkyl)$_2$;

R$^a$ is selected from H, OH, SH, NH$_2$, NH(C$_{1-3}$ alkyl), and N(C$_{1-3}$ alkyl) 2;

R$^b$ is selected from H, C$_{1-4}$ alkyl, Cl, F, Br, I, OH, C$_{1-3}$ alkoxy, NH$_2$, NH(C$_{1-3}$ alkyl), N(C$_{1-3}$ alkyl)$_2$, CH$_2$NH$_2$, CH$_2$NH(C$_{1-3}$ alkyl), and CH$_2$N(C$_{1-3}$ alkyl)$_2$;

ring M is substituted with 0–1 R$^{1a}$ and is selected from the group:

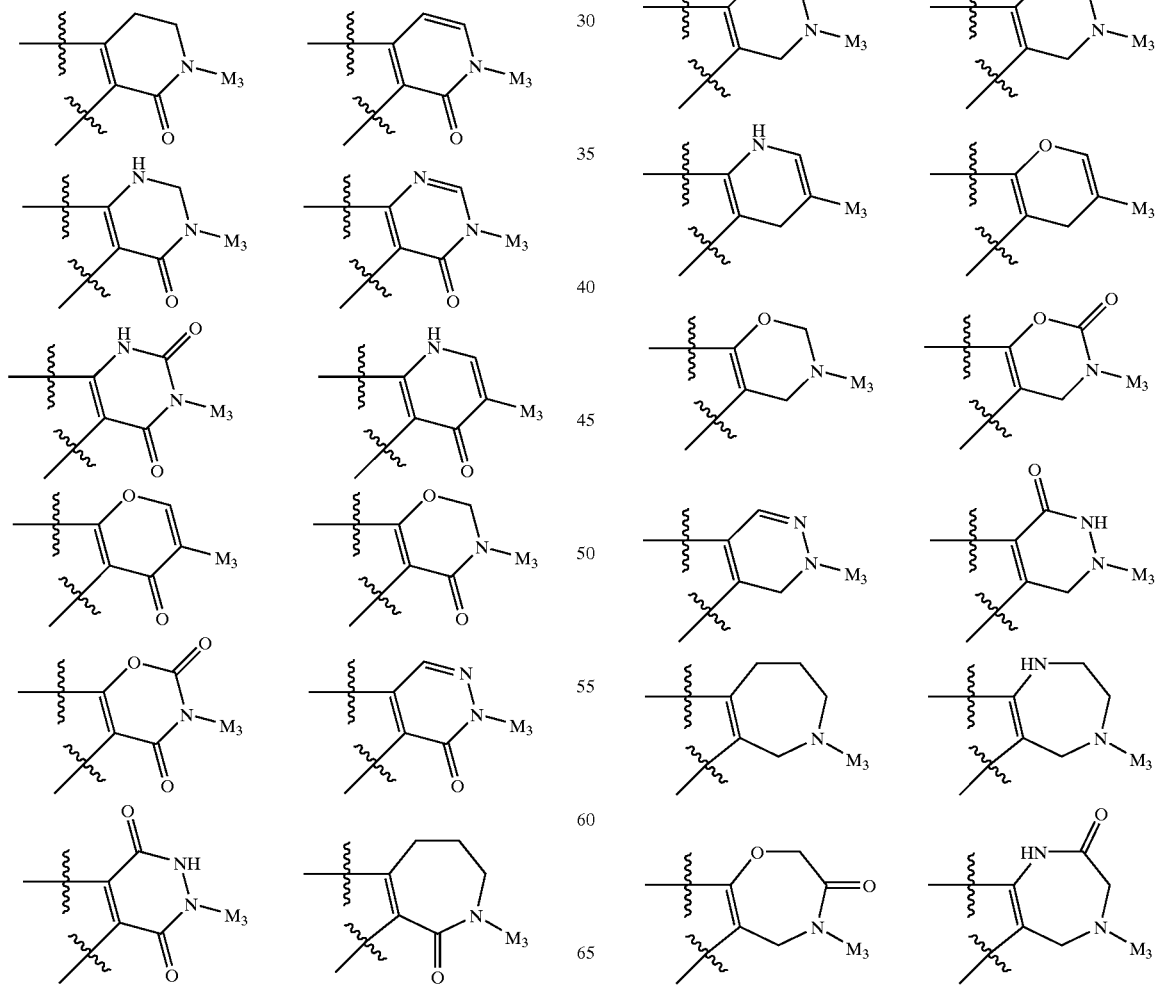

-continued

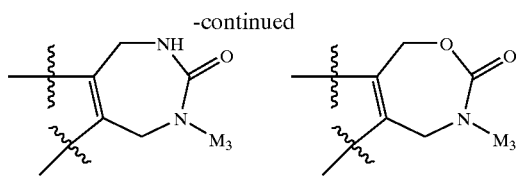

G₁ is absent or is selected from CH₂, CH₂CH₂, CH₂O, OCH₂, NH, CH₂NH, NHCH₂, CH₂C(O), C(O)CH₂, C(O)NH, NHC(O), CH₂S(O)₂, S(O)₂(CH₂), SO₂NH, and NHSO₂, provided that G₁ does not form a N—N, N—O, N—S, NCH₂N, NCH₂O, or NCH₂S bond with either group to which it is attached.

[5] In another preferred embodiment, the present invention provides a novel compound, wherein the compound is selected for one of the formulas:

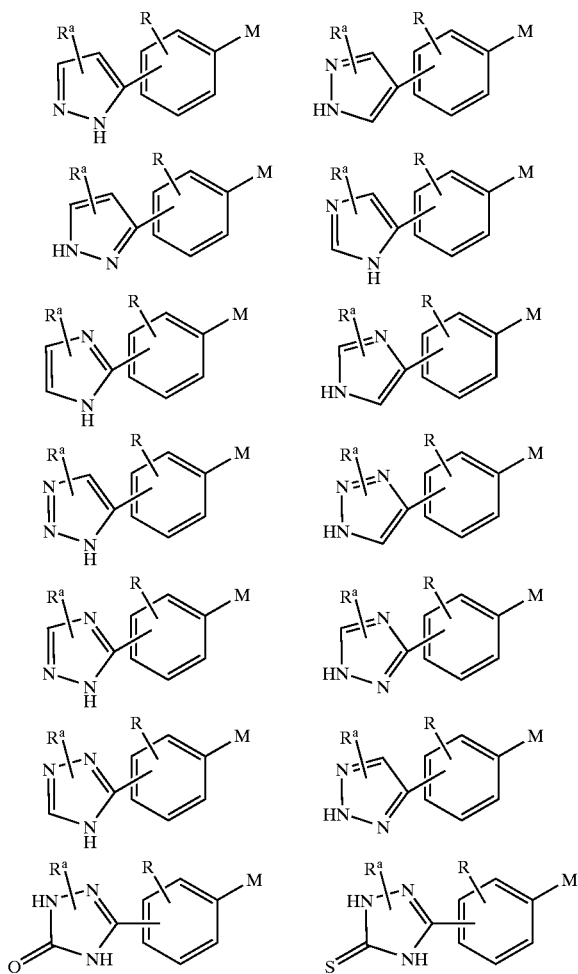

or a stereoisomer or pharmaceutically acceptable salt thereof, wherein;

G₁ is absent;

A is selected from phenyl, piperidinyl, pyridyl, and pyrimidyl, and is substituted with 0–2 $R^4$; and, B is selected from phenyl, pyrrolidino, N-pyrrolidinocarbonyl, morpholino, N-morpholino-carbonyl, 1,2,3-triazolyl, imidazolyl, and benzimidazolyl, and is substituted with 0–1 $R^{4a}$;

$R^2$, at each occurrence, is selected from H, CH₃, CH₂CH₃, cyclopropylmethyl, cyclobutyl, and cyclopentyl;

$R^{2a}$, at each occurrence, is selected from H, CH₃, and CH₂CH₃;

alternatively, $R^2$ and $R^{2a}$, together with the atom to which they are attached, combine to form pyrrolidine substituted with 0–2 $R^{4b}$ or piperidine substituted with 0–2 $R^{4b}$;

$R^4$, at each occurrence, is selected from OH, OR², (CH₂)OR², (CH₂)₂OR², F, Br, Cl, I, $C_{1-4}$ alkyl, NR²R²ᵃ, (CH₂)NR²R²ᵃ, (CH₂)₂NR²R²ᵃ, CF₃, and (CF₂)CF₃;

$R^{4a}$ is selected from $C_{1-4}$ alkyl, CF₃, OR², (CH₂)OR², (CH₂)₂OR², NR²R²ᵃ, (CH₂)NR²R²ᵃ, (CH₂)₂NR²R²ᵃ, SR⁵, S(O)R⁵, S(O)₂R⁵, SO₂NR²R²ᵃ, and 1-CF₃-tetrazol-2-yl;

$R^{4b}$, at each occurrence, is selected from H, CH₃, and OH;

$R^5$, at each occurrence, is selected from CF₃, $C_{1-6}$ alkyl, phenyl, and benzyl; and, r, at each occurrence, is selected from 0, 1, and 2.

[6] In another preferred embodiment, the present invention provides a novel compound, wherein;

A is selected from the group: phenyl, piperidinyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N-methylaminomethyl)phenyl, 2-(N-ethyl-N-methylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(methylaminomethyl)-1-imidazolyl, 2-(N-(cyclopropylmethyl)aminomethyl)phenyl, 2-(N-(cyclobutyl)aminomethyl)phenyl, 2-(N-(cyclopentyl)aminomethyl)phenyl, 2-(N-(4-hydroxypiperidinyl)methyl)phenyl, and 2-(N-(3-hydroxypyrrolidinyl)methyl)phenyl.

[7] In another preferred embodiment, the present invention provides a novel compound selected from the group:

1-[3-(2'-Amino-3',4'-thiadiazol-5'-yl)phenyl]-3-methyl-6-[2'-aminosulfonyl-[1,1']-biphen-4-yl]-1,4,5,6-tetrahydropyrazolo-[3,4-c]-pyridin-7-one trifluoroacetic acid salt;

1-[3-(1',3',4'-Triazol-2'-on-5'-yl)phenyl]-3-cyano-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(1',3',4'-Triazol-2'-on-5'-yl)phenyl]-3-trifluoromethyl-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(1',3',4'-Triazol-2'-on-5'-yl)phenyl]-3-(ethoxycarbonyl)-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(1',3',4'-Triazol-2'-on-5'-yl)phenyl]-3-methyl-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(2'-Amino-3',4'-oxadiazol-5'-yl)phenyl]-3-cyano-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(2'-Amino-3',4'-oxadiazol-5'-yl)phenyl]-3-trifluoromethyl-6-[(2'-N,N-dimethylaminomethyl-[1, 1']-biphen-4-yl)aminocarbonyl]-1,4-dihydropyrazolo-[4,3-d]-pyrimidine-5,7-dione;

1-[3-(2'-Amino-3',4'-oxadiazol-5'-yl)phenyl]-3-(ethoxycarbonyl)-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(2'-Amino-3',4'-oxadiazol-5'-yl)phenyl]-3-methyl-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(2'-Amino-1',3',4'-triazol-5'-yl)phenyl]-3-cyano-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(2'-Amino-1',3',4'-triazol-5'-yl)phenyl]-3-trifluoromethyl-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(2'-Amino-1',3',4'-triazol-5'-yl)phenyl]-3-(ethoxycarbonyl)-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(2'-Amino-1',3',4'-triazol-5'-yl)phenyl]-3-methyl-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(Pyrid-3'-yl)phenyl]-3-cyano-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(Pyrid-3'-yl)phenyl]-3-trifluoromethyl-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(Pyrid-3'-yl)phenyl]-3-(ethoxycarbonyl)-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(Pyrid-3'-yl)phenyl]-3-methyl-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(Pyrid-4'-yl)phenyl]-3-cyano-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(Pyrid-4'-yl)phenyl]-3-trifluoromethyl-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(Pyrid-4'-yl)phenyl]-3-(ethoxycarbonyl)-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(Pyrid-4'-yl)phenyl]-3-methyl-6-[(2'-N,N-dimethylaminomethyl-[1,1']-biphen-4-yl)aminocarbonyl]-1,4-dihydropyrazolo-[4,3-d]-pyrimidine-5,7-dione;

1-[3-(1',3',4'-Triazol-2'-on-5'-yl)phenyl]-3-cyano-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(1',3',4'-Triazol-2'-on-5'-yl)phenyl]-3-trifluoromethyl-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(1',3',4'-Triazol-2'-on-5'-yl)phenyl]-3-(ethoxycarbonyl)-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(1',3',4'-Triazol-2'-on-5'-yl)phenyl]-3-methyl-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(2'-Amino-3',4'-oxadiazol-5'-yl)phenyl]-3-cyano-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(2'-Amino-3',4'-oxadiazol-5'-yl)phenyl]-3-trifluoromethyl-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(2'-Amino-3',4'-oxadiazol-5'-yl)phenyl]-3-(ethoxycarbonyl)-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(2'-Amino-3',4'-oxadiazol-5'-yl)phenyl]-3-methyl-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(2'-Amino-1',3',4'-triazol-5'-yl)phenyl]-3-cyano-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(2'-Amino-1',3',4'-triazol-5'-yl)phenyl]-3-trifluoromethyl-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(2'-Amino-1',3',4'-triazol-5'-yl)phenyl]-3-(ethoxycarbonyl)-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(2'-Amino-1',3',4'-triazol-5'-yl)phenyl]-3-methyl-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(Pyrid-3'-yl)phenyl]-3-cyano-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(Pyrid-3'-yl)phenyl]-3-trifluoromethyl-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(Pyrid-3'-yl)phenyl]-3-(ethoxycarbonyl)-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(Pyrid-3'-yl)phenyl]-3-methyl-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(Pyrid-4'-yl)phenyl]-3-cyano-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(Pyrid-4'-yl)phenyl]-3-trifluoromethyl-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(Pyrid-4'-yl)phenyl]-3-(ethoxycarbonyl)-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(Pyrid-4'-yl)phenyl]-3-methyl-6-[(2'-N-pyrrolidinylmethyl-[1,1']-biphen-4-yl)aminocarbonyl]-1,4-dihydropyrazolo-[4,3-d]-pyrimidine-5,7-dione;

1-[3-(1',3',4'-Triazol-2'-on-5'-yl)phenyl]-3-cyano-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(1',3',4'-Triazol-2'-on-5'-yl)phenyl]-3-trifluoromethyl-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(1',3',4'-Triazol-2'-on-5'-yl)phenyl]-3-(ethoxycarbonyl)-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(1',3',4'-Triazol-2'-on-5'-yl)phenyl]-3-methyl-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(2'-Amino-3',4'-oxadiazol-5'-yl)phenyl]-3-cyano-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(2'-Amino-3',4'-oxadiazol-5'-yl)phenyl]-3-trifluoromethyl-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(2'-Amino-3',4'-oxadiazol-5'-yl)phenyl]-3-(ethoxycarbonyl)-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(2'-Amino-3',4'-oxadiazol-5'-yl)phenyl]-3-methyl-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(2'-Amino-1',3',4'-triazol-5'-yl)phenyl]-3-cyano-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(2'-Amino-1',3',4'-triazol-5'-yl)phenyl]-3-trifluoromethyl-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(2'-Amino-1',3',4'-triazol-5'-yl)phenyl]-3-(ethoxycarbonyl)-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(2'-Amino-1',3',4'-triazol-5'-yl)phenyl]-3-methyl-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(Pyrid-3'-yl)phenyl]-3-cyano-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(Pyrid-3'-yl)phenyl]-3-trifluoromethyl-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(Pyrid-3'-yl)phenyl]-3-(ethoxycarbonyl)-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(Pyrid-3'-yl)phenyl]-3-methyl-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(Pyrid-4'-yl)phenyl]-3-cyano-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(Pyrid-4'-yl)phenyl]-3-trifluoromethyl-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(Pyrid-4'-yl)phenyl]-3-(ethoxycarbonyl)-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(Pyrid-4'-yl)phenyl]-3-methyl-6-[(2'-(3"-hydroxy-N-pyrrolidinylmethyl)-[1,1']-biphen-4-yl)aminocarbonyl]-1,4-dihydropyrazolo-[4,3-d]-pyrimidine-5,7-dione;

1-[3-(1',3',4'-Triazol-2'-on-5'-yl)phenyl]-3-cyano-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(1',3',4'-Triazol-2'-on-5'-yl)phenyl]-3-trifluoromethyl-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(1',3',4'-Triazol-2'-on-5'-yl)phenyl]-3-(ethoxycarbonyl)-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(1',3',4'-Triazol-2'-on-5'-yl)phenyl]-3-methyl-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(2'-Amino-3',4'-oxadiazol-5'-yl)phenyl]-3-cyano-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(2'-Amino-3',4'-oxadiazol-5'-yl)phenyl]-3-trifluoromethyl-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(2'-Amino-3',4'-oxadiazol-5'-yl)phenyl]-3-(ethoxycarbonyl)-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(2'-Amino-3',4'-oxadiazol-5'-yl)phenyl]-3-methyl-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(2'-Amino-1',3',4'-triazol-5'-yl)phenyl]-3-cyano-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(2'-Amino-1',3',4'-triazol-5'-yl)phenyl]-3-trifluoromethyl-6-[4-(21-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(2'-Amino-1',3',4'-triazol-5'-yl)phenyl]-3-(ethoxycarbonyl)-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(2'-Amino-1',3',4'-triazol-5'-yl)phenyl]-3-methyl-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(Pyrid-3'-yl)phenyl]-3-cyano-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(Pyrid-3'-yl)phenyl]-3-trifluoromethyl-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(Pyrid-3'-yl)phenyl]-3-(ethoxycarbonyl)-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(Pyrid-3'-yl)phenyl]-3-methyl-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(Pyrid-4'-yl)phenyl]-3-cyano-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(Pyrid-4'-yl)phenyl]-3-trifluoromethyl-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(Pyrid-4'-yl)phenyl]-3-(ethoxycarbonyl)-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(Pyrid-4'-yl)phenyl]-3-methyl-6-[4-(2'-(N,N-dimethylamino)methylimidazol-1'-yl)-2-fluorophenyl)aminocarbonyl]-1,4-dihydropyrazolo-[4,3-d]-pyrimidine-5,7-dione;

1-[3-(1',3',4'-Triazol-2'-on-5'-yl)phenyl]-3-cyano-6-[4-(2'-methylimidazol-1'-yl)-2-fluorophenyl)aminocarbonyl]-1,4-dihydropyrazolo-[4,3-d]-pyrimidine-5,7-dione;

1-[3-(1',3',4'-Triazol-2'-on-5'-yl)phenyl]-3-trifluoromethyl-6-[4-(2'-methylimidazol-1'-yl)-2-fluorophenyl)aminocarbonyl]-1,4-dihydropyrazolo-[4,3-d]-pyrimidine-5,7-dione;

1-[3-(1',3',41-Triazol-2'-on-5'-yl)phenyl]-3-(ethoxycarbonyl)-6-[4-(2'-methylimidazol-1'-yl)-2-fluorophenyl)aminocarbonyl]-1,4-dihydropyrazolo-[4,3-d]-pyrimidine-5,7-dione;

1-[3-(1',3',4'-Triazol-2'-on-5'-yl)phenyl]-3-methyl-6-[4-(2'-methylimidazol-1'-yl)-2-fluorophenyl)aminocarbonyl]-1,4-dihydropyrazolo-[4,3-d]-pyrimidine-5,7-dione;

1-[3-(2'-Amino-3',4'-oxadiazol-5'-yl)phenyl]-3-cyano-6-[4-(2'-methylimidazol-1'-yl)-2-fluorophenyl)aminocarbonyl]-1,4-dihydropyrazolo-[4,3-d]-pyrimidine-5,7-dione;

1-[3-(2'-Amino-3',4'-oxadiazol-5'-yl)phenyl]-3-trifluoromethyl-6-[4-(2'-methylimidazol-1'-yl)-2-fluorophenyl)aminocarbonyl]-1,4-dihydropyrazolo-[4,3-d]-pyrimidine-5,7-dione;

1-[3-(2'-Amino-3',4'-oxadiazol-5'-yl)phenyl]-3-(ethoxycarbonyl)-6-[4-(2'-methylimidazol-1'-yl)-2-fluorophenyl)aminocarbonyl]-1,4-dihydropyrazolo-[4,3-d]-pyrimidine-5,7-dione;

1-[3-(2'-Amino-3',4'-oxadiazol-5'-yl)phenyl]-3-methyl-6-[4-(2'-methylimidazol-1'-yl)-2-fluorophenyl)aminocarbonyl]-1,4-dihydropyrazolo-[4,3-d]-pyrimidine-5,7-dione;

1-[3-(2'-Amino-1',3',4'-triazol-5'-yl)phenyl]-3-cyano-6-[4-(2'-methylimidazol-1'-yl)-2-fluorophenyl)aminocarbonyl]-1,4-dihydropyrazolo-[4,3-d]-pyrimidine-5,7-dione;

1-[3-(2'-Amino-1',3',4'-triazol-5'-yl)phenyl]-3-trifluoromethyl-6-[4-(2'-methylimidazol-1'-yl)-2-fluorophenyl)aminocarbonyl]-1,4-dihydropyrazolo-[4,3-d]-pyrimidine-5,7-dione;

1-[3-(2'-Amino-1',3',4'-triazol-5'-yl)phenyl]-3-(ethoxycarbonyl)-6-[4-(2'-methylimidazol-1'-yl)-2-fluorophenyl)aminocarbonyl]-1,4-dihydropyrazolo-[4,3-d]-pyrimidine-5,7-dione;

1-[3-(2'-Amino-1',3',4'-triazol-5'-yl)phenyl]-3-methyl-6-[4-(2'-methylimidazol-1'-yl)-2-fluorophenyl)aminocarbonyl]-1,4-dihydropyrazolo-[4,3-d]-pyrimidine-5,7-dione;

1-[3-(Pyrid-3'-yl)phenyl]-3-cyano-6-[4-(2'-methylimidazol-1'-yl)-2-fluorophenyl)aminocarbonyl]-1,4-dihydropyrazolo-[4,3-d]-pyrimidine-5,7-dione;

1-[3-(Pyrid-3'-yl)phenyl]-3-trifluoromethyl-6-[4-(2'-methylimidazol-1'-yl)-2-fluorophenyl)aminocarbonyl]-1,4-dihydropyrazolo-[4,3-d]-pyrimidine-5,7-dione;

1-[3-(Pyrid-3'-yl)phenyl]-3-(ethoxycarbonyl)-6-[4-(2'-methylimidazol-1'-yl)-2-fluorophenyl)aminocarbonyl]-1,4-dihydropyrazolo-[4,3-d]-pyrimidine-5,7-dione;

1-[3-(Pyrid-3'-yl)phenyl]-3-methyl-6-[4-(2'-methylimidazol-1'-yl)-2-fluorophenyl)aminocarbonyl]-1,4-dihydropyrazolo-[4,3-d]-pyrimidine-5,7-dione;

1-[3-(Pyrid-4'-yl)phenyl]-3-cyano-6-[4-(2'-methylimidazol-1'-yl)-2-fluorophenyl)aminocarbonyl]-1,4-dihydropyrazolo-[4,3-d]-pyrimidine-5,7-dione;

1-[3-(Pyrid-4'-yl)phenyl]-3-trifluoromethyl-6-[4-(2'-methylimidazol-1'-yl)-2-fluorophenyl)aminocarbonyl]-1,4-dihydropyrazolo-[4,3-d]-pyrimidine-5,7-dione;

1-[3-(Pyrid-4'-yl)phenyl]-3-(ethoxycarbonyl)-6-[4-(2'-methylimidazol-1'-yl)-2-fluorophenyl)aminocarbonyl]-1,4-dihydropyrazolo-[4,3-d]-pyrimidine-5,7-dione; and, 1-[3-(Pyrid-4'-yl)phenyl]-3-methyl-6-[4-(2'-methylimidazol-1'-yl)-2-fluorophenyl)aminocarbonyl]-1,4-dihydropyrazolo-[4,3-d]-pyrimidine-5,7-dione;

or a pharmaceutically acceptable salt thereof.

[8] In another preferred embodiment, the present invention provides a novel compound selected from the group:

1-[3-(1',3',4'-Triazol-2'-on-5'-yl)phenyl]-3-cyano-6-[(2'-N,N-dimethylaminomethyl-[1,1']-biphen-4-yl)aminocarbonyl]-1,6-dihydropyrazolo-[4,3-d]-pyrimidin-7-one;

1-[3-(1',3',4'-Triazol-2'-on-5'-yl)phenyl]-3-trifluoromethyl-6-[(2'-N,N-dimethylaminomethyl-[1, 1']-biphen-4-yl)aminocarbonyl]-1,6-dihydropyrazolo-[4,3-d]-pyrimidin-7-one;

1-[3-(1',3',4'-Triazol-2'-on-5'-yl)phenyl]-3-(ethoxycarbonyl)-6-[(2'-N,N-dimethylaminomethyl-[1,1']-biphen-4-yl)aminocarbonyl]-1,6-dihydropyrazolo-[4,3-d]-pyrimidin-7-one;

1-[3-(1',3',4'-Triazol-2'-on-5'-yl)phenyl]-3-methyl-6-[(2'-N,N-dimethylaminomethyl-[1,1']-biphen-4-yl)aminocarbonyl]-1,6-dihydropyrazolo-[4,3-d]-pyrimidin-7-one;

1-[3-(2'-Amino-3',4'-oxadiazol-5'-yl)phenyl]-3-cyano-6-[(2'-N,N-dimethylaminomethyl-[1,1']-biphen-4-yl)aminocarbonyl]-1,6-dihydropyrazolo-[4,3-d]-pyrimidin-7-one;

1-[3-(2'-Amino-3',4'-oxadiazol-5'-yl)phenyl]-3-trifluoromethyl-6-[(2'-N,N-dimethylaminomethyl-[1,1']-biphen-4-yl)aminocarbonyl]-1,6-dihydropyrazolo-[4,3-d]-pyrimidin-7-one;

1-[3-(2'-Amino-3',4'-oxadiazol-5'-yl)phenyl]-3-(ethoxycarbonyl)-6-[(2'-N,N-dimethylaminomethyl-[1,1']-biphen-4-yl)aminocarbonyl]-1,6-dihydropyrazolo-[4,3-d]-pyrimidin-7-one;

1-[3-(2'-Amino-3',4'-oxadiazol-5'-yl)phenyl]-3-methyl-6-[(2'-N,N-dimethylaminomethyl-[1,1']-biphen-4-yl)aminocarbonyl]-1,6-dihydropyrazolo-[4,3-d]-pyrimidin-7-one;

1-[3-(2'-Amino-1',3',4'-triazol-5'-yl)phenyl]-3-cyano-6-[(2'-N,N-dimethylaminomethyl-[1,1']-biphen-4-yl)aminocarbonyl]-1,6-dihydropyrazolo-[4,3-d]-pyrimidin-7-one;

1-[3-(2'-Amino-1',3',4'-triazol-5'-yl)phenyl]-3-trifluoromethyl-6-[(2'-N,N-dimethylaminomethyl-[1,1']-biphen-4-yl)aminocarbonyl]-1,6-dihydropyrazolo-[4,3-d]-pyrimidin-7-one;

1-[3-(2'-Amino-1',3',4'-triazol-5'-yl)phenyl]-3-(ethoxycarbonyl)-6-[(2'-N,N-dimethylaminomethyl-[1,1']-biphen-4-yl)aminocarbonyl]-1,6-dihydropyrazolo-[4,3-d]-pyrimidin-7-one;

1-[3-(2'-Amino-1',3',4'-triazol-5'-yl)phenyl]-3-methyl-6-[(2'-N,N-dimethylaminomethyl-[1,1']-biphen-4-yl)aminocarbonyl]-1,6-dihydropyrazolo-[4,3-d]-pyrimidin-7-one;

1-[3-(Pyrid-3'-yl)phenyl]-3-cyano-6-[(2'-N,N-dimethylaminomethyl-[1,1']-biphen-4-yl)aminocarbonyl]-1,6-dihydropyrazolo-[4,3-d]-pyrimidin-7-one;

1-[3-(Pyrid-3'-yl)phenyl]-3-trifluoromethyl-6-[(2'-N,N-dimethylaminomethyl-[1,1']-biphen-4-yl)aminocarbonyl]-1,6-dihydropyrazolo-[4,3-d]-pyrimidin-7-one;

1-[3-(Pyrid-3'-yl)phenyl]-3-(ethoxycarbonyl)-6-[(2'-N,N-dimethylaminomethyl-[1,1']-biphen-4-yl)aminocarbonyl]-1,6-dihydropyrazolo-[4,3-d]-pyrimidin-7-one;

1-[3-(Pyrid-3'-yl)phenyl]-3-methyl-6-[(2'-N,N-dimethylaminomethyl-[1,1']-biphen-4-yl)aminocarbonyl]-1,6-dihydropyrazolo-[4,3-d]-pyrimidin-7-one;

1-[3-(Pyrid-4'-yl)phenyl]-3-cyano-6-[(2'-N,N-dimethylaminomethyl-[1,1']-biphen-4-yl)aminocarbonyl]-1,6-dihydropyrazolo-[4,3-d]-pyrimidin-7-one;

1-[3-(Pyrid-4'-yl)phenyl]-3-trifluoromethyl-6-[(2'-N,N-dimethylaminomethyl-[1,1']-biphen-4-yl)aminocarbonyl]-1,6-dihydropyrazolo-[4,3-d]-pyrimidin-7-one;

1-[3-(Pyrid-4'-yl)phenyl]-3-(ethoxycarbonyl)-6-[(2'-N,N-dimethylaminomethyl-[1,1']-biphen-4-yl)aminocarbonyl]-1,6-dihydropyrazolo-[4,3-d]-pyrimidin-7-one;

1-[3-(Pyrid-4'-yl)phenyl]-3-methyl-6-[(2'-N,N-dimethylaminomethyl-[1,1']-biphen-4-yl)aminocarbonyl]-1,6-dihydropyrazolo-[4,3-d]-pyrimidin-7-one;

1-[3-(1',3',4'-Triazol-2'-on-5'-yl)phenyl]-3-cyano-6-[(2'-N-pyrrolidinylmethyl-[1,1']-biphen-4-yl)aminocarbonyl]-1,6-dihydropyrazolo-[4,3-d]-pyrimidin-7-one;

1-[3-(1',3',4'-Triazol-2'-on-5'-yl)phenyl]-3-trifluoromethyl-6-[(2'-N-pyrrolidinylmethyl-[1,1']-biphen-4-yl)aminocarbonyl]-1,6-dihydropyrazolo-[4,3-d]-pyrimidin-7-one;

1-[3-(1',3',4'-Triazol-2'-on-5'-yl)phenyl]-3-(ethoxycarbonyl)-6-[(2'-N-pyrrolidinylmethyl-[1,1']-biphen-4-yl)aminocarbonyl]-1,6-dihydropyrazolo-[4,3-d]-pyrimidin-7-one;

1-[3-(1',3',4'-Triazol-2'-on-5'-yl)phenyl]-3-methyl-6-[(2'-N-pyrrolidinylmethyl-[1,1']-biphen-4-yl)aminocarbonyl]-1,6-dihydropyrazolo-[4,3-d]-pyrimidin-7-one;

1-[3-(2'-Amino-3',4'-oxadiazol-5'-yl)phenyl]-3-cyano-6-[(2'-N-pyrrolidinylmethyl-[1,1']-biphen-4-yl)aminocarbonyl]-1,6-dihydropyrazolo-[4,3-d]-pyrimidin-7-one;

1-[3-(2'-Amino-3',4'-oxadiazol-5'-yl)phenyl]-3-trifluoromethyl-6-[(2'-N-pyrrolidinylmethyl-[1,1']-biphen-4-yl)aminocarbonyl]-1,6-dihydropyrazolo-[4,3-d]-pyrimidin-7-one;

1-[3-(2'-Amino-3',4'-oxadiazol-5'-yl)phenyl]-3-(ethoxycarbonyl)-6-[(2'-N-pyrrolidinylmethyl-[1,1']-biphen-4-yl)aminocarbonyl]-1,6-dihydropyrazolo-[4,3-d]-pyrimidin-7-one;

1-[3-(2'-Amino-3',4'-oxadiazol-5'-yl)phenyl]-3-methyl-6-[(2'-N-pyrrolidinylmethyl-[1,1']-biphen-4-yl)aminocarbonyl]-1,6-dihydropyrazolo-[4,3-d]-pyrimidin-7-one;

1-[3-(2'-Amino-1',3',4'-triazol-5'-yl)phenyl]-3-cyano-6-[(2'-N-pyrrolidinylmethyl-[1,1']-biphen-4-yl)aminocarbonyl]-1,6-dihydropyrazolo-[4,3-d]-pyrimidin-7-one;

1-[3-(2'-Amino-1',3',4'-triazol-5'-yl)phenyl]-3-trifluoromethyl-6-[(2'-N-pyrrolidinylmethyl-[1,1']-biphen-4-yl)aminocarbonyl]-1,6-dihydropyrazolo-[4,3-d]-pyrimidin-7-one;

1-[3-(2'-Amino-1',3',4'-triazol-5'-yl)phenyl]-3-(ethoxycarbonyl)-6-[(2'-N-pyrrolidinylmethyl-[1,1']-biphen-4-yl)aminocarbonyl]-1,6-dihydropyrazolo-[4,3-d]-pyrimidin-7-one;

1-[3-(2'-Amino-1',3',4'-triazol-5'-yl)phenyl]-3-methyl-6-[(2'-N-pyrrolidinylmethyl-[1,1]-biphen-4-yl)aminocarbonyl]-1,6-dihydropyrazolo-[4,3-d]-pyrimidin-7-one;

1-[3-(Pyrid-3'-yl)phenyl]-3-cyano-6-[(2'-N-pyrrolidinylmethyl-[1,1']-biphen-4-yl)aminocarbonyl]-1,6-dihydropyrazolo-[4,3-d]-pyrimidin-7-one;

1-[3-(Pyrid-3'-yl)phenyl]-3-trifluoromethyl-6-[(2'-N-pyrrolidinylmethyl-[1,1']-biphen-4-yl)aminocarbonyl]-1,6-dihydropyrazolo-[4,3-d]-pyrimidin-7-one;

1-[3-(Pyrid-3'-yl)phenyl]-3-(ethoxycarbonyl)-6-[2'-N-pyrrolidinylmethyl-[1,1']-biphen-4-yl)aminocarbonyl]-1,6-dihydropyrazolo-[4,3-d]-pyrimidin-7-one;

1-[3-(Pyrid-3'-yl)phenyl]-3-methyl-6-[(2'-N-pyrrolidinylmethyl-[1,1']-biphen-4-yl)aminocarbonyl]-1,6-dihydropyrazolo-[4,3-d]-pyrimidin-7-one;

1-[3-(Pyrid-4'-yl)phenyl]-3-cyano-6-[(2'-N-pyrrolidinylmethyl-[1,1']-biphen-4-yl)aminocarbonyl]-1,6-dihydropyrazolo-[4,3-d]-pyrimidin-7-one;

1-[3-(Pyrid-4'-yl)phenyl]-3-trifluoromethyl-6-[(2'-N-pyrrolidinylmethyl-[1,1']-biphen-4-yl)aminocarbonyl]-1,6-dihydropyrazolo-[4,3-d]-pyrimidin-7-one;

1-[3-(Pyrid-4'-yl)phenyl]-3-(ethoxycarbonyl)-6-[(2'-N-pyrrolidinylmethyl-[1,1']-biphen-4-yl)aminocarbonyl]-1,6-dihydropyrazolo-[4,3-d]-pyrimidin-7-one;

1-[3-(Pyrid-4'-yl)phenyl]-3-methyl-6-[(2'-N-pyrrolidinylmethyl-[1,1']-biphen-4-yl)aminocarbonyl]-1,6-dihydropyrazolo-[4,3-d]-pyrimidin-7-one;

1-[3-(1',3',4'-Triazol-2'-on-5'-yl)phenyl]-3-cyano-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(1',3',3'-Triazol-2'-on-5'-yl)phenyl]-3-trifluoromethyl-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(1',3',4'-Triazol-2'-on-5'-yl)phenyl]-3-(ethoxycarbonyl)-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(1',3',4'-Triazol-2'-on-5'-yl)phenyl]-3-methyl-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(2'-Amino-3',4'-oxadiazol-5'-yl)phenyl]-3-cyano-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(2'-Amino-3',4'-oxadiazol-5'-yl)phenyl]-3-trifluoromethyl-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(2'-Amino-3',4'-oxadiazol-5'-yl)phenyl]-3-(ethoxycarbonyl)-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(2'-Amino-3',4'-oxadiazol-5'-yl)phenyl]-3-methyl-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(2'-Amino-1',3',4'-triazol-5'-yl)phenyl]-3-cyano-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(2'-Amino-1',3',4'-triazol-5'-yl)phenyl]-3-trifluoromethyl-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(2'-Amino-1,',3',4'-triazol-5'-yl)phenyl]-3-(ethoxycarbonyl)-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(2'-Amino-1',3',4'-triazol-5'-yl)phenyl]-3-methyl-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(Pyrid-3'-yl)phenyl]-3-cyano-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(Pyrid-3'-yl)phenyl]-3-trifluoromethyl-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(Pyrid-3'-yl)phenyl]-3-(ethoxycarbonyl)-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(Pyrid-3'-yl)phenyl]-3-methyl-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(Pyrid-4'-yl)phenyl]-3-cyano-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(Pyrid-4'-yl)phenyl]-3-trifluoromethyl-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(Pyrid-4'-yl)phenyl]-3-(ethoxycarbonyl)-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(Pyrid-4'-yl)phenyl]-3-methyl-6-[(2'-(3"-hydroxy-N-pyrrolidinylmethyl)-[1,1']-biphen-4-yl)aminocarbonyl]-1,6-dihydropyrazolo-[4,3-d]-pyrimidin-7-one;

1-[3-(1',3',4'-Triazol-2'-on-5'-yl)phenyl]-3-cyano-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(1',3',4'-Triazol-2'-on-5'-yl)phenyl]-3-trifluoromethyl-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(1',3',4'-Triazol-2'-on-5'-yl)phenyl]-3-(ethoxycarbonyl)-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(1',3',4'-Triazol-2'-on-5'-yl)phenyl]-3-methyl-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(2'-Amino-3',4'-oxadiazol-5'-yl)phenyl]-3-cyano-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(2'-Amino-3',4'-oxadiazol-5'-yl)phenyl]-3-trifluoromethyl-6-[4-(2'-(N,N-dimethylamino)methylimidazol-1'-yl)-2-fluorophenyl)

aminocarbonyl]-1,6-dihydropyrazolo-[4,3-d]-pyrimidin-7-one;

1-[3-(2'-Amino-3',4'-oxadiazol-5'-yl)phenyl]-3-(ethoxycarbonyl)-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(2'-Amino-3',4'-oxadiazol-5'-yl)phenyl]-3-methyl-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(2'-Amino-1',3',4'-triazol-5'-yl)phenyl]-3-cyano-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(2'-Amino-1',3',4'-triazol-5'-yl)phenyl]-3-trifluoromethyl-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(2'-Amino-1',3',4'-triazol-5'-yl)phenyl]-3-(ethoxycarbonyl)-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(2'-Amino-1',3',4'-triazol-5'-yl)phenyl]-3-methyl-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(Pyrid-3'-yl)phenyl]-3-cyano-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(Pyrid-3'-yl)phenyl]-3-trifluoromethyl-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(Pyrid-3'-yl)phenyl]-3-(ethoxycarbonyl)-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(Pyrid-3'-yl)phenyl]-3-methyl-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(Pyrid-4'-yl)phenyl]-3-cyano-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(Pyrid-4'-yl)phenyl]-3-trifluoromethyl-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(Pyrid-4'-yl)phenyl]-3-(ethoxycarbonyl)-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(Pyrid-4'-yl)phenyl]-3-methyl-6-[4-(2'-(N,N-dimethylamino)methylimidazol-1'-yl)-2-fluorophenyl)aminocarbonyl]-1,6-dihydropyrazolo-[4,3-d]-pyrimidin-7-one;

1-[3-(1',3',4'-Triazol-2'-on-5'-yl)phenyl]-3-cyano-6-[4-(2'-methylimidazol-1'-yl)-2-fluorophenyl)aminocarbonyl]-1,6-dihydropyrazolo-[4,3-d]-pyrimidin-7-one;

1-[3-(1',3',4'-Triazol-2'-on-5'-yl)phenyl]-3-trifluoromethyl-6-[4-(2'-methylimidazol-1'-yl)-2-fluorophenyl)aminocarbonyl]-1,6-dihydropyrazolo-[4,3-d]-pyrimidin-7-one;

1-[3-(1',3',4'-Triazol-2'-on-5'-yl)phenyl]-3-(ethoxycarbonyl)-6-[4-(2'-methylimidazol-1'-yl)-2-fluorophenyl)aminocarbonyl]-1,6-dihydropyrazolo-[4,3-d]-pyrimidin-7-one;

1-[3-(1',3',4'-Triazol-2'-on-5'-yl)phenyl]-3-methyl-6-[4-(2'-methylimidazol-1'-yl)-2-fluorophenyl)aminocarbonyl]-1,6-dihydropyrazolo-[4,3-d]-pyrimidin-7-one;

1-[3-(2'-Amino-3',4'-oxadiazol-5'-yl)phenyl]-3-cyano-6-[4-(2'-methylimidazol-1'-yl)-2-fluorophenyl)aminocarbonyl]-1,6-dihydropyrazolo-[4,3-d]-pyrimidin-7-one;

1-[3-(2'-Amino-3',4'-oxadiazol-5'-yl)phenyl]-3-trifluoromethyl-6-[4-(2'-methylimidazol-1'-yl)-2-fluorophenyl)aminocarbonyl]-1,6-dihydropyrazolo-[4,3-d]-pyrimidin-7-one;

1-[3-(2'-Amino-3',4'-oxadiazol-5'-yl)phenyl]-3-(ethoxycarbonyl)-6-[4-(2'-methylimidazol-1'-yl)-2-fluorophenyl)aminocarbonyl]-1,6-dihydropyrazolo-[4,3-d]-pyrimidin-7-one;

1-[3-(2'-Amino-3',4'-oxadiazol-5'-yl)phenyl]-3-methyl-6-[4-(2'-methylimidazol-1'-yl)-2-fluorophenyl)aminocarbonyl]-1,6-dihydropyrazolo-[4,3-d]-pyrimidin-7-one;

1-[3-(2'-Amino-1',3',4'-triazol-5'-yl)phenyl]-3-cyano-6-[4-(2'-methylimidazol-1'-yl)-2-fluorophenyl)aminocarbonyl]-1,6-dihydropyrazolo-[4,3-d]-pyrimidin-7-one;

1-[3-(2'-Amino-1',3',4'-triazol-5'-yl)phenyl]-3-trifluoromethyl-6-[4-(2'-methylimidazol-1'-yl)-2-fluorophenyl)aminocarbonyl]-1,6-dihydropyrazolo-[4,3-d]-pyrimidin-7-one;

1-[3-(2'-Amino-1',3',4'-triazol-5'-yl)phenyl]-3-(ethoxycarbonyl)-6-[4-(2'-methylimidazol-1'-yl)-2-fluorophenyl)aminocarbonyl]-1,6-dihydropyrazolo-[4,3-d]-pyrimidin-7-one;

1-[3-(2'-Amino-1',3',4'-triazol-5'-yl)phenyl]-3-methyl-6-[4-(2'-methylimidazol-1'-yl)-2-fluorophenyl)aminocarbonyl]-1,6-dihydropyrazolo-[4,3-d]-pyrimidin-7-one;

1-[3-(Pyrid-3'-yl)phenyl]-3-cyano-6-[4-(2'-methylimidazol-1'-yl)-2-fluorophenyl)aminocarbonyl]-1,6-dihydropyrazolo-[4,3-d]-pyrimidin-7-one;

1-[3-(Pyrid-3'-yl)phenyl]-3-trifluoromethyl-6-[4-(2'-methylimidazol-1'-yl)-2-fluorophenyl)aminocarbonyl]-1,6-dihydropyrazolo-[4,3-d]-pyrimidin-7-one;

1-[3-(Pyrid-3'-yl)phenyl]-3-(ethoxycarbonyl)-6-[4-(2'-methylimidazol-1'-yl)-2-fluorophenyl)aminocarbonyl]-1,6-dihydropyrazolo-[4,3-d]-pyrimidin-7-one;

1-[3-(Pyrid-3'-yl)phenyl]-3-methyl-6-[4-(2'-methylimidazol-1'-yl)-2-fluorophenyl)aminocarbonyl]-1,6-dihydropyrazolo-[4,3-d]-pyrimidin-7-one;

1-[3-(Pyrid-4'-yl)phenyl]-3-cyano-6-[4-(2'-methylimidazol-1'-yl)-2-fluorophenyl)aminocarbonyl]-1,6-dihydropyrazolo-[4,3-d]-pyrimidin-7-one;

1-[3-(Pyrid-4'-yl)phenyl]-3-trifluoromethyl-6-[4-(2'-methylimidazol-1'-yl)-2-fluorophenyl)aminocarbonyl]-1,6-dihydropyrazolo-[4,3-d]-pyrimidin-7-one;

1-[3-(Pyrid-4'-yl)phenyl]-3-(ethoxycarbonyl)-6-[4-(2'-methylimidazol-1'-yl)-2-fluorophenyl)aminocarbonyl]-1,6-dihydropyrazolo-[4,3-d]-pyrimidin-7-one; and, 1-[3-(Pyrid-4'-yl)phenyl]-3-methyl-6-[4-(2'-methylimidazol-1'-yl)-2-fluorophenyl)aminocarbonyl]-1,6-dihydropyrazolo-[4,3-d]-pyrimidin-7-one;

or a pharmaceutically acceptable salt thereof.

[9] In another preferred embodiment, the present invention provides a novel compound selected from the group:

1-[3-(1',3',4'-Triazol-2'-on-5'-yl)phenyl]-3-cyano-6-[(2'-N,N-dimethylaminomethyl-[1,1']-biphen-4-yl)aminocarbonyl]-1,6-dihydropyrazolo-[4,3-d]-pyridazin-7-one;

1-[3-(1',3',4'-Triazol-2'-on-5'-yl)phenyl]-3-trifluoromethyl-6-[(2'-N,N-dimethylaminomethyl-[1,1']-biphen-4-yl)aminocarbonyl]-1,6-dihydropyrazolo-[4,3-d]-pyridazin-7-one;

1-[3-(1',3',4'-Triazol-2'-on-5'-yl)phenyl]-3-(ethoxycarbonyl)-6-[(2'-N,N-dimethylaminomethyl-[1,1']-biphen-4-yl)aminocarbonyl]-1,6-dihydropyrazolo-[4,3-d]-pyridazin-7-one;

1-[3-(1',3',4'-Triazol-2'-on-5'-yl)phenyl]-3-methyl-6-[(2'-N,N-dimethylaminomethyl-[1,1']-biphen-4-yl)aminocarbonyl]-1,6-dihydropyrazolo-[4,3-d]-pyridazin-7-one;

1-[3-(2'-Amino-3',4'-oxadiazol-5'-yl)phenyl]-3-cyano-6-[(2'-N,N-dimethylaminomethyl-[1,1']-biphen-4-yl)aminocarbonyl]-1,6-dihydropyrazolo-[4,3-d]-pyridazin-7-one;

1-[3-(2'-Amino-3',4'-oxadiazol-5'-yl)phenyl]-3-trifluoromethyl-6-[(2'-N,N-dimethylaminomethyl-[1,1']-biphen-4-yl)aminocarbonyl]-1,6-dihydropyrazolo-[4,3-d]-pyridazin-7-one;

1-[3-(2'-Amino-3',4'-oxadiazol-5'-yl)phenyl]-3-(ethoxycarbonyl)-6-[(2'-N,N-dimethylaminomethyl-[1,1']-biphen-4-yl)aminocarbonyl]-1,6-dihydropyrazolo-[4,3-d]-pyridazin-7-one;

1-[3-(2'-Amino-3',4'-oxadiazol-5'-yl)phenyl]-3-methyl-6-[(2'-N,N-dimethylaminomethyl-[1,1']-biphen-4-yl)aminocarbonyl]-1,6-dihydropyrazolo-[4,3-d]-pyridazin-7-one;

1-[3-(2'-Amino-1',3',4'-triazol-5'-yl)phenyl]-3-cyano-6-[(2'-N,N-dimethylaminomethyl-[1,1']-biphen-4-yl)aminocarbonyl]-1,6-dihydropyrazolo-[4,3-d]-pyridazin-7-one;

1-[3-(2'-Amino-1',3',4'-triazol-5'-yl)phenyl]-3-trifluoromethyl-6-[(2'-N,N-dimethylaminomethyl-[1,1']-biphen-4-yl)aminocarbonyl]-1,6-dihydropyrazolo-[4,3-d]-pyridazin-7-one;

1-[3-(2'-Amino-1',3',4'-triazol-5'-yl)phenyl]-3-(ethoxycarbonyl)-6-[(2'-N,N-dimethylaminomethyl-[1,1']-biphen-4-yl)aminocarbonyl]-1,6-dihydropyrazolo-[4,3-d]-pyridazin-7-one;

1-[3-(2'-Amino-1',3',4'-triazol-5'-yl)phenyl]-3-methyl-6-[(2'-N,N-dimethylaminomethyl-[1,1']-biphen-4-yl)aminocarbonyl]-1,6-dihydropyrazolo-[4,3-d]-pyridazin-7-one;

1-[3-(Pyrid-3'-yl)phenyl]-3-cyano-6-[(2'-N,N-dimethylaminomethyl-[1,1']-biphen-4-yl)aminocarbonyl]-1,6-dihydropyrazolo-[4,3-d]-pyridazin-7-one;

1-[3-(Pyrid-3'-yl)phenyl]-3-trifluoromethyl-6-[(2'-N,N-dimethylaminomethyl-[1,1']-biphen-4-yl)aminocarbonyl]-1,6-dihydropyrazolo-[4,3-d]-pyridazin-7-one;

1-[3-(Pyrid-3'-yl)phenyl]-3-(ethoxycarbonyl)-6-[(2'-N,N-dimethylaminomethyl-[1,1']-biphen-4-yl)aminocarbonyl]-1,6-dihydropyrazolo-[4,3-d]-pyridazin-7-one;

1-[3-(Pyrid-3'-yl)phenyl]-3-methyl-6-[(2'-N,N-dimethylaminomethyl-[1,1']-biphen-4-yl)aminocarbonyl]-1,6-dihydropyrazolo-[4,3-d]-pyridazin-7-one;

1-[3-(Pyrid-4'-yl)phenyl]-3-cyano-6-[(2'-N,N-dimethylaminomethyl-[1,1']-biphen-4-yl)aminocarbonyl]-1,6-dihydropyrazolo-[4,3-d]-pyridazin-7-one;

1-[3-(Pyrid-4'-yl)phenyl]-3-trifluoromethyl-6-[(2'-N,N-dimethylaminomethyl-[1,1']-biphen-4-yl)aminocarbonyl]-1,6-dihydropyrazolo-[4,3-d]-pyridazin-7-one;

1-[3-(Pyrid-4'-yl)phenyl]-3-(ethoxycarbonyl)-6-[(2'-N,N-dimethylaminomethyl-[1,1']-biphen-4-yl)aminocarbonyl]-1,6-dihydropyrazolo-[4,3-d]-pyridazin-7-one;

1-[3-(Pyrid-4'-yl)phenyl]-3-methyl-6-[(2'-N,N-dimethylaminomethyl-[1,1']-biphen-4-yl)aminocarbonyl]-1,6-dihydropyrazolo-[4,3-d]-pyridazin-7-one;

1-[3-(1',3',4'-Triazol-2'-on-5'-yl)phenyl]-3-cyano-6-[(2'-N-pyrrolidinylmethyl-[1,1']-biphen-4-yl)aminocarbonyl]-1,6-dihydropyrazolo-[4,3-d]-pyridazin-7-one;

1-[3-(1',3',4'-Triazol-2'-on-5'-yl)phenyl]-3-trifluoromethyl-6-[(2'-N-pyrrolidinylmethyl-[1,1']-biphen-4-yl)aminocarbonyl]-1,6-dihydropyrazolo-[4,3-d]-pyridazin-7-one;

1-[3-(1',3',4'-Triazol-2'-on-5'-yl)phenyl]-3-(ethoxycarbonyl)-6-[(2'-N-pyrrolidinylmethyl-[1,1']-biphen-4-yl)aminocarbonyl]-1,6-dihydropyrazolo-[4,3-d]-pyridazin-7-one;

1-[3-(1',3',4'-Triazol-2'-on-5'-yl)phenyl]-3-methyl-6-[(2'-N-pyrrolidinylmethyl-[1,1']-biphen-4-yl)aminocarbonyl]-1,6-dihydropyrazolo-[4,3-d]-pyridazin-7-one;

1-[3-(2'-Amino-3',4'-oxadiazol-5'-yl)phenyl]-3-cyano-6-[(2'-N-pyrrolidinylmethyl-[1,1']-biphen-4-yl)aminocarbonyl]-1,6-dihydropyrazolo-[4,3-d]-pyridazin-7-one;

1-[3-(2'-Amino-3',4'-oxadiazol-5'-yl)phenyl]-3-trifluoromethyl-6-[(2'-N-pyrrolidinylmethyl-[1,1']-biphen-4-yl)aminocarbonyl]-1,6-dihydropyrazolo-[4,3-d]-pyridazin-7-one;

1-[3-(2'-Amino-3',4'-oxadiazol-5'-yl)phenyl]-3-(ethoxycarbonyl)-6-[(2'-N-pyrrolidinylmethyl-[1,1']-biphen-4-yl)aminocarbonyl]-1,6-dihydropyrazolo-[4,3-d]-pyridazin-7-one;

1-[3-(2'-Amino-3',4'-oxadiazol-5'-yl)phenyl]-3-methyl-6-[(2'-N-pyrrolidinylmethyl-[1,1']-biphen-4-yl)aminocarbonyl]-1,6-dihydropyrazolo-[4,3-d]-pyridazin-7-one;

1-[3-(2'-Amino-1',3',4'-triazol-5'-yl)phenyl]-3-cyano-6-[(2'-N-pyrrolidinylmethyl-[1,1']-biphen-4-yl)

aminocarbonyl]-1,6-dihydropyrazolo-[4,3-d]-pyridazin-7-one;

1-[3-(2'-Amino-1',3',4'-triazol-5'-yl)phenyl]-3-trifluoromethyl-6-[(2'-N-pyrrolidinylmethyl-[1,1']-biphen-4-yl)aminocarbonyl]-1,6-dihydropyrazolo-[4,3-d]-pyridazin-7-one;

1-[3-(2'-Amino-1',3',4'-triazol-5'-yl)phenyl]-3-(ethoxycarbonyl)-6-[(2'-N-pyrrolidinylmethyl-[1,1']-biphen-4-yl)aminocarbonyl]-1,6-dihydropyrazolo-[4,3-d]-pyridazin-7-one;

1-[3-(2'-Amino-1',3',4'-triazol-5'-yl)phenyl]-3-methyl-6-[(2'-N-pyrrolidinylmethyl-[1,1']-biphen-4-yl)aminocarbonyl]-1,6-dihydropyrazolo-[4,3-d]-pyridazin-7-one;

1-[3-(Pyrid-3'-yl)phenyl]-3-cyano-6-[(2'-N-pyrrolidinylmethyl-[1,1']-biphen-4-yl)aminocarbonyl]-1,6-dihydropyrazolo-[4,3-d]-pyridazin-7-one;

1-[3-(Pyrid-3'-yl)phenyl]-3-trifluoromethyl-6-[(2'-N-pyrrolidinylmethyl-[1,1']-biphen-4-yl)aminocarbonyl]-1,6-dihydropyrazolo-[4,3-d]-pyridazin-7-one;

1-[3-(Pyrid-3'-yl)phenyl]-3-(ethoxycarbonyl)-6-[(2'-N-pyrrolidinylmethyl-[1,1']-biphen-4-yl)aminocarbonyl]-1,6-dihydropyrazolo-[4,3-d]-pyridazin-7-one;

1-[3-(Pyrid-3'-yl)phenyl]-3-methyl-6-[(2'-N-pyrrolidinylmethyl-[1,1']-biphen-4-yl)aminocarbonyl]-1,6-dihydropyrazolo-[4,3-d]-pyridazin-7-one;

1-[3-(Pyrid-4'-yl)phenyl]-3-cyano-6-[(2'-N-pyrrolidinylmethyl-[1,1']-biphen-4-yl)aminocarbonyl]-1,6-dihydropyrazolo-[4,3-d]-pyridazin-7-one;

1-[3-(Pyrid-4'-yl)phenyl]-3-trifluoromethyl-6-[(2'-N-pyrrolidinylmethyl-[1,1']-biphen-4-yl)aminocarbonyl]-1,6-dihydropyrazolo-[4,3-d]-pyridazin-7-one;

1-[3-(Pyrid-4'-yl)phenyl]-3-(ethoxycarbonyl)-6-[(2'-N-pyrrolidinylmethyl-[1,1']-biphen-4-yl)aminocarbonyl]-1,6-dihydropyrazolo-[4,3-d]-pyridazin-7-one;

1-[3-(Pyrid-4'-yl)phenyl]-3-methyl-6-[(2'-N-pyrrolidinylmethyl-[1,1']-biphen-4-yl)aminocarbonyl]-1,6-dihydropyrazolo-[4,3-d]-pyridazin-7-one;

1-[3-(1',3',4'-Triazol-2'-on-5'-yl)phenyl]-3-cyano-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(1',3',4'-Triazol-2'-on-5'-yl)phenyl]-3-trifluoromethyl-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(1',3',4'-Triazol-2'-on-5'-yl)phenyl]-3-(ethoxycarbonyl)-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(1',3',4'-Triazol-2'-on-5'-yl)phenyl]-3-methyl-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(2'-Amino-3',4'-oxadiazol-5'-yl)phenyl]-3-cyano-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(2'-Amino-3',4'-oxadiazol-5'-yl)phenyl]-3-trifluoromethyl-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(2'-Amino-3',4'-oxadiazol-5'-yl)phenyl]-3-(ethoxycarbonyl)-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(2'-Amino-3',4'-oxadiazol-5'-yl)phenyl]-3-methyl-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(2'-Amino-1',3',4'-triazol-5'-yl)phenyl]-3-cyano-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(2'-Amino-1',3',4'-triazol-5'-yl)phenyl]-3-trifluoromethyl-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(2'-Amino-1',3',4'-triazol-5'-yl)phenyl]-3-(ethoxycarbonyl)-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(2'-Amino-1',3',4'-triazol-5'-yl)phenyl]-3-methyl-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(Pyrid-3'-yl)phenyl]-3-cyano-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(Pyrid-3'-yl)phenyl]-3-trifluoromethyl-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(Pyrid-3'-yl)phenyl]-3-(ethoxycarbonyl)-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(Pyrid-3'-yl)phenyl]-3-methyl-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(Pyrid-4'-yl)phenyl]-3-cyano-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(Pyrid-4'-yl)phenyl]-3-trifluoromethyl-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(Pyrid-4'-yl)phenyl]-3-(ethoxycarbonyl)-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(Pyrid-4'-yl)phenyl]-3-methyl-6-[(2'-(3"-hydroxy-N-pyrrolidinylmethyl)-[1,1']-biphen-4-yl)aminocarbonyl]-1,6-dihydropyrazolo-[4,3-d]-pyridazin-7-one;

1-[3-(1',3',4'-Triazol-2'-on-5'-yl)phenyl]-3-cyano-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(1',3',4'-Triazol-2'-on-5'-yl)phenyl]-3-trifluoromethyl-6-[4-(2'-(N,N-dimethylamino)

methylimidazol-1'-yl)-2-fluorophenyl)aminocarbonyl]-1,6-dihydropyrazolo-[4,3-d]-pyridazin-7-one;

1-[3-(1',3',4'-Triazol-2'-on-5'-yl)phenyl]-3-(ethoxycarbonyl)-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(1',3',4'-Triazol-2'-on-5'-yl)phenyl]-3-methyl-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(2'-Amino-3',4'-oxadiazol-5'-yl)phenyl]-3-cyano-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(2'-Amino-3',4'-oxadiazol-5'-yl)phenyl]-3-trifluoromethyl-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(2'-Amino-3',4'-oxadiazol-5'-yl)phenyl]-3-(ethoxycarbonyl)-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(2'-Amino-3',4'-oxadiazol-5'-yl)phenyl]-3-methyl-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(2'-Amino-1',3',4'-triazol-5'-yl)phenyl]-3-cyano-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(2'-Amino-1',3',4'-triazol-5'-yl)phenyl]-3-trifluoromethyl-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(2'-Amino-1',3',4'-triazol-5'-yl)phenyl]-3-(ethoxycarbonyl)-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(2'-Amino-1',3',4'-triazol-5'-yl)phenyl]-3-methyl-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(Pyrid-3'-yl)phenyl]-3-cyano-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(Pyrid-3'-yl)phenyl]-3-trifluoromethyl-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(Pyrid-3'-yl)phenyl]-3-(ethoxycarbonyl)-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(Pyrid-3'-yl)phenyl]-3-methyl-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(Pyrid-4'-yl)phenyl]-3-cyano-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(Pyrid-4'-yl)phenyl]-3-trifluoromethyl-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(Pyrid-4'-yl)phenyl]-3-(ethoxycarbonyl)-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(Pyrid-4'-yl)phenyl]-3-methyl-6-[4-(2'-(N,N-dimethylamino)methylimidazol-1'-yl)-2-fluorophenyl)aminocarbonyl]-1,6-dihydropyrazolo-[4,3-d]-pyridazin-7-one;

1-[3-(1',3',4'-Triazol-2'-on-5'-yl)phenyl]-3-cyano-6-[4-(2'-methylimidazol-1'-yl)-2-fluorophenyl)aminocarbonyl]-1,6-dihydropyrazolo-[4,3-d]-pyridazin-7-one;

1-[3-(1',3',4'-Triazol-2'-on-5'-yl)phenyl]-3-trifluoromethyl-6-[4-(2'-methylimidazol-1'-yl)-2-fluorophenyl)aminocarbonyl]-1,6-dihydropyrazolo-[4,3-d]-pyridazin-7-one;

1-[3-(1',3',4'-Triazol-2'-on-5'-yl)phenyl]-3-(ethoxycarbonyl)-6-[4-(2'-methylimidazol-1'-yl)-2-fluorophenyl)aminocarbonyl]-1,6-dihydropyrazolo-[4,3-d]-pyridazin-7-one;

1-[3-(1',3',4'-Triazol-2'-on-5'-yl)phenyl]-3-methyl-6-[4-(2'-methylimidazol-1'-yl)-2-fluorophenyl)aminocarbonyl]-1,6-dihydropyrazolo-[4,3-d]-pyridazin-7-one;

1-[3-(2'-Amino-3',4'-oxadiazol-5'-yl)phenyl]-3-cyano-6-[4-(2'-methylimidazol-1'-yl)-2-fluorophenyl)aminocarbonyl]-1,6-dihydropyrazolo-[4,3-d]-pyridazin-7-one;

1-[3-(2'-Amino-3',4'-oxadiazol-5'-yl)phenyl]-3-trifluoromethyl-6-[4-(2'-methylimidazol-1'-yl)-2-fluorophenyl)aminocarbonyl]-1,6-dihydropyrazolo-[4,3-d]-pyridazin-7-one;

1-[3-(2'-Amino-3',4'-oxadiazol-5'-yl)phenyl]-3-(ethoxycarbonyl)-6-[4-(2'-methylimidazol-1'-yl)-2-fluorophenyl)aminocarbonyl]-1,6-dihydropyrazolo-[4,3-d]-pyridazin-7-one;

1-[3-(2'-Amino-3',4'-oxadiazol-5'-yl)phenyl]-3-methyl-6-[4-(2'-methylimidazol-1'-yl)-2-fluorophenyl)aminocarbonyl]-1,6-dihydropyrazolo-[4,3-d]-pyridazin-7-one;

1-[3-(2'-Amino-1',3',4'-triazol-5'-yl)phenyl]-3-cyano-6-[4-(2'-methylimidazol-1'-yl)-2-fluorophenyl)aminocarbonyl]-1,6-dihydropyrazolo-[4,3-d]-pyridazin-7-one;

1-[3-(2'-Amino-1',3',4'-triazol-5'-yl)phenyl]-3-trifluoromethyl-6-[4-(2'-methylimidazol-1'-yl)-2-fluorophenyl)aminocarbonyl]-1,6-dihydropyrazolo-[4,3-d]-pyridazin-7-one;

1-[3-(2'-Amino-1',3',4'-triazol-5'-yl)phenyl]-3-(ethoxycarbonyl)-6-[4-(2'-methylimidazol-1'-yl)-2-fluorophenyl)aminocarbonyl]-1,6-dihydropyrazolo-[4,3-d]-pyridazin-7-one;

1-[3-(2'-Amino-1',3',4'-triazol-5'-yl)phenyl]-3-methyl-6-[4-(2'-methylimidazol-1'-yl)-2-fluorophenyl)aminocarbonyl]-1,6-dihydropyrazolo-[4,3-d]-pyridazin-7-one;

1-[3-(Pyrid-3'-yl)phenyl]-3-cyano-6-[4-(2'-methylimidazol-1'-yl)-2-fluorophenyl)

aminocarbonyl]-1,6-dihydropyrazolo-[4,3-d]-pyridazin-7-one;

1-[3-(Pyrid-3'-yl)phenyl]-3-trifluoromethyl-6-[4-(2'-methylimidazol-1'-yl)-2-fluorophenyl)aminocarbonyl]-1,6-dihydropyrazolo-[4,3-d]-pyridazin-7-one;

1-[3-(Pyrid-3'-yl)phenyl]-3-(ethoxycarbonyl)-6-[4-(2'-methylimidazol-1'-yl)-2-fluorophenyl)aminocarbonyl]-1,6-dihydropyrazolo-[4,3-d]-pyridazin-7-one;

1-[3-(Pyrid-3'-yl)phenyl]-3-methyl-6-[4-(2'-methylimidazol-1'-yl)-2-fluorophenyl)aminocarbonyl]-1,6-dihydropyrazolo-[4,3-d]-pyridazin-7-one;

1-[3-(Pyrid-4'-yl)phenyl]-3-cyano-6-[4-(2'-methylimidazol-1'-yl)-2-fluorophenyl)aminocarbonyl]-1,6-dihydropyrazolo-[4,3-d]-pyridazin-7-one;

1-[3-(Pyrid-4'-yl)phenyl]-3-trifluoromethyl-6-[4-(2'-methylimidazol-1'-yl)-2-fluorophenyl)aminocarbonyl]-1,6-dihydropyrazolo-[4,3-d]-pyridazin-7-one;

1-[3-(Pyrid-4'-yl)phenyl]-3-(ethoxycarbonyl)-6-[4-(2'-methylimidazol-1'-yl)-2-fluorophenyl)aminocarbonyl]-1,6-dihydropyrazolo-[4,3-d]-pyridazin-7-one; and, 1-[3-(Pyrid-4'-yl)phenyl]-3-methyl-6-[4-(2'-methylimidazol-1'-yl)-2-fluorophenyl)aminocarbonyl]-1,6-dihydropyrazolo-[4,3-d]-pyridazin-7-one;

or a pharmaceutically acceptable salt thereof.

[10] In another preferred embodiment, the present invention provides a novel compound selected from the group:

1-[3-(1',3',4'-Triazol-2'-on-5'-yl)phenyl]-3-cyano-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-trifluoromethyl-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-(ethoxycarbonyl)-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-methyl-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-cyano-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-trifluoromethyl-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-(ethoxycarbonyl)-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-methyl-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-cyano-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-trifluoromethyl-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-(ethoxycarbonyl)-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-methyl-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-cyano-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-trifluoromethyl-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-(ethoxycarbonyl)-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-methyl-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-cyano-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-trifluoromethyl-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-(ethoxycarbonyl)-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-methyl-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-cyano-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-trifluoromethyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-(ethoxycarbonyl)-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-methyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-cyano-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-trifluoromethyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-(ethoxycarbonyl)-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-methyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-cyano-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-trifluoromethyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-(ethoxycarbonyl)-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-methyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-cyano-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-trifluoromethyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-(ethoxycarbonyl)-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-methyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-cyano-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-trifluoromethyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-(ethoxycarbonyl)-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-methyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-cyano-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-trifluoromethyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-(ethoxycarbonyl)-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-methyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-cyano-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-trifluoromethyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-(ethoxycarbonyl)-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-methyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-cyano-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-trifluoromethyl-6-[(2'-(3'-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-(ethoxycarbonyl)-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-methyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-cyano-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-trifluoromethyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-(ethoxycarbonyl)-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-methyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-cyano-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-trifluoromethyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-(ethoxycarbonyl)-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-methyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-cyano-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(1,3,4'-Triazol-2'-on-5'-yl)phenyl]-3-trifluoromethyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(1',3',4'-Triazol-2'-on-5'-yl)phenyl]-3-(ethoxycarbonyl)-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(1',3',4'-Triazol-2'-on-5'-yl)phenyl]-3-methyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(2'-Amino-3',4'-oxadiazol-5'-yl)phenyl]-3-cyano-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(2'-Amino-3',4'-oxadiazol-5'-yl)phenyl]-3-trifluoromethyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(2'-Amino-3',4'-oxadiazol-5'-yl)phenyl]-3-(ethoxycarbonyl)-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(2'-Amino-3',4'-oxadiazol-5'-yl)phenyl]-3-methyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(2'-Amino-1',3',4'-triazol-5'-yl)phenyl]-3-cyano-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(2'-Amino-1',3',4'-triazol-5'-yl)phenyl]-3-trifluoromethyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(2'-Amino-1',3',4'-triazol-5'-yl)phenyl]-3-(ethoxycarbonyl)-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(2'-Amino-1',3',4'-triazol-5'-yl)phenyl]-3-methyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(Pyrid-3'-yl)phenyl]-3-cyano-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(Pyrid-3'-yl)phenyl]-3-trifluoromethyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(Pyrid-3'-yl)phenyl]-3-(ethoxycarbonyl)-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(Pyrid-3'-yl)phenyl]-3-methyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(Pyrid-4'-yl)phenyl]-3-cyano-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(Pyrid-4'-yl)phenyl]-3-trifluoromethyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(Pyrid-4'-yl)phenyl]-3-(ethoxycarbonyl)-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(Pyrid-4'-yl)phenyl]-3-methyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(1',3',4'-Triazol-2'-on-5'-yl)phenyl]-3-cyano-6-[4-(2'-methylimidazol-1'-yl)-2-fluorophenyl)aminocarbonyl]-1,4,5,6-tetrahydropyrazolo-[3,4-c]-pyridin-7-one;

1-[3-(1',3',4'-Triazol-2'-on-5'-yl)phenyl]-3-trifluoromethyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(1',3',4'-Triazol-2'-on-5'-yl)phenyl]-3-(ethoxycarbonyl)-6-[4-(2'-methylimidazol-1'-yl)-2-fluorophenyl)aminocarbonyl]-1,4,5,6-tetrahydropyrazolo-[3,4-c]-pyridin-7-one;

1-[3-(1',3',4'-Triazol-2'-on-5'-yl)phenyl]-3-methyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(2'-Amino-3',4'-oxadiazol-5'-yl)phenyl]-3-cyano-6-[4-(2'-methylimidazol-1'-yl)-2-fluorophenyl)aminocarbonyl]-1,4,5,6-tetrahydropyrazolo-[3,4-c]-pyridin-7-one;

1-[3-(2'-Amino-3',4'-oxadiazol-5'-yl)phenyl]-3-trifluoromethyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(2'-Amino-3',4'-oxadiazol-5'-yl)phenyl]-3-(ethoxycarbonyl)-6-[4-(2'-methylimidazol-1'-yl)-2-fluorophenyl)aminocarbonyl]-1,4,5,6-tetrahydropyrazolo-[3,4-c]-pyridin-7-one;

1-[3-(2'-Amino-3',4'-oxadiazol-5'-yl)phenyl]-3-methyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(2'-Amino-1',3',4'-triazol-5'-yl)phenyl]-3-cyano-6-[4-(2'-methylimidazol-1'-yl)-2-fluorophenyl)aminocarbonyl]-1,4,5,6-tetrahydropyrazolo-[3,4-c]-pyridin-7-one;

1-[3-(2'-Amino-1',3',4'-triazol-5'-yl)phenyl]-3-trifluoromethyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(2'-Amino-1',3',4'-triazol-5'-yl)phenyl]-3-(ethoxycarbonyl)-6-[4-(2'-methylimidazol-1'-yl)-2-fluorophenyl)aminocarbonyl]-1,4,5,6-tetrahydropyrazolo-[3,4-c]-pyridin-7-one;

1-[3-(2'-Amino-1',3',4'-triazol-5'-yl)phenyl]-3-methyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(Pyrid-3'-yl)phenyl]-3-cyano-6-[4-(2'-methylimidazol-1'-yl)-2-fluorophenyl)aminocarbonyl]-1,4,5,6-tetrahydropyrazolo-[3,4-c]-pyridin-7-one;

1-[3-(Pyrid-3'-yl)phenyl]-3-trifluoromethyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(Pyrid-3'-yl)phenyl]-3-(ethoxycarbonyl)-6-[4-(2'-methylimidazol-1'-yl)-2-fluorophenyl)aminocarbonyl]-1,4,5,6-tetrahydropyrazolo-[3,4-c]-pyridin-7-one;

1-[3-(Pyrid-3'-yl)phenyl]-3-methyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(Pyrid-4'-yl)phenyl]-3-cyano-6-[4-(2'-methylimidazol-1'-yl)-2-fluorophenyl)aminocarbonyl]-1,4,5,6-tetrahydropyrazolo-[3,4-c]-pyridin-7-one;

1-[3-(Pyrid-4'-yl)phenyl]-3-trifluoromethyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(Pyrid-4'-yl)phenyl]-3-(ethoxycarbonyl)-6-[4-(2'-methylimidazol-1'-yl)-2-fluorophenyl)aminocarbonyl]-1,4,5,6-tetrahydropyrazolo-[3,4-c]-pyridin-7-one; and, 1-[3-(Pyrid-4'-yl)phenyl]-3-methyl-6-[4-(2'-methylimidazol-1'-yl)-2-fluorophenyl)aminocarbonyl]-1,4,5,6-tetrahydropyrazolo-[3,4-c]-pyridin-7-one;

or a pharmaceutically acceptable salt thereof.

[11] In another preferred embodiment, the present invention provides a novel compound selected from the group:

1-[3-(5-oxo-4,5-Dihydro-1H-1,2,4-triazol-3-yl)phenyl]-6-[2'-(1-pyrrolidinylmethyl)-1,1'-biphenyl-4-yl]-3-(trifluoromethyl)-1,4,5,6-tetrahydro-7H-pyrazolo[3,4-c]pyridin-7-one;

6-(2'-{[(3S)-3-Hydroxy-1-pyrrolidinyl]methyl}-1,1'-biphenyl-4-yl)-1-[3-(5-oxo-4,5-dihydro-1H-1,2,4-triazol-3-yl)phenyl]-3-(trifluoromethyl)-1,4,5,6-tetrahydro-7H-pyrazolo[3,4-c]pyridin-7-one;

6-{2'-[(Dimethylamino)methyl]-1,1'-biphenyl-4-yl}-1-[3-(5-oxo-4,5-dihydro-1H-1,2,4-triazol-3-yl)phenyl]-3-(trifluoromethyl)-1,4,5,6-tetrahydro-7H-pyrazolo[3,4-c]pyridin-7-one;

6-[2'-(Methylsulfonyl)-1,1'-biphenyl-4-yl]-1-[3-(5-oxo-4,5-dihydro-1H-1,2,4-triazol-3-yl)phenyl]-3-(trifluoromethyl)-1,4,5,6-tetrahydro-7H-pyrazolo[3,4-c]pyridin-7-one;

1-[3-(5-Amino-1,3,4-oxadiazol-2-yl)phenyl]-6-{2'-[(dimethylamino)methyl]-1,1'-biphenyl-4-yl}-3-(trifluoromethyl)-1,4,5,6-tetrahydro-7H-pyrazolo[3,4-c]pyridin-7-one;

1-[3-(5-Amino-1,3,4-thiadiazol-2-yl)phenyl]-6-{2'-[(dimethylamino)methyl]-1,1'-biphenyl-4-yl}-3-(trifluoromethyl)-1,4,5,6-tetrahydro-7H-pyrazolo[3,4-c]pyridin-7-one;

1-[3-(5-Amino-1,3,4-thiadiazol-2-yl)phenyl]-6-[2'-(1-pyrrolidinylmethyl)-1,1'-biphenyl-4-yl]-3-(trifluoromethyl)-1,4,5,6-tetrahydro-7H-pyrazolo[3,4-c]pyridin-7-one;

1-[3-(5-Amino-1,3,4-thiadiazol-2-yl)phenyl]-6-(4-{2-[(dimethylamino)methyl]-1H-imidazol-1-yl}phenyl)-3-(trifluoromethyl)-1,4,5,6-tetrahydro-7H-pyrazolo[3,4-c]pyridin-7-one;

1-[3-(5-Amino-1,3,4-thiadiazol-2-yl)phenyl]-6-{4-[2-(1-pyrrolidinylmethyl)-1H-imidazol-1-yl]phenyl}-3-(trifluoromethyl)-1,4,5,6-tetrahydro-7H-pyrazolo[3,4-c]pyridin-7-one;

6-(4-{2-[(Dimethylamino)methyl]-1H-imidazol-1-yl}phenyl)-1-[3-(5-oxo-4,5-dihydro-1H-1,2,4-triazol-3-yl)phenyl]-3-(trifluoromethyl)-1,4,5,6-tetrahydro-7H-pyrazolo[3,4-c]pyridin-7-one;

3-Methyl-1-[3-(5-oxo-4,5-dihydro-1H-1,2,4-triazol-3-yl)phenyl]-6-{4-[2-(1-pyrrolidinylmethyl)-1H-imidazol-1-yl]phenyl}-1,4,5,6-tetrahydro-7H-pyrazolo[3,4-c]pyridin-7-one;

7-Oxo-1-[3-(5-oxo-4,5-dihydro-1H-1,2,4-triazol-3-yl)phenyl]-6-[2'-(1-pyrrolidinylmethyl)-1,1'-biphenyl-4-yl]-4,5,6,7-tetrahydro-1H-pyrazolo[3,4-c]pyridine-3-carboxamide;

1-[3-(5-Oxo-4,5-dihydro-1H-1,2,4-triazol-3-yl)phenyl]-7-[2'-(1-pyrrolidinylmethyl)-1,1'-biphenyl-4-yl]-3-(trifluoromethyl)-4,5,6,7-tetrahydropyrazolo[3,4-c]azepin-8(1H)-one; and, 1-[2-(5-Oxo-4,5-dihydro-1H-1,2,4-triazol-3-yl)phenyl]-6-[2'-(1-pyrrolidinylmethyl)-1,1'-biphenyl-4-yl]-3-(trifluoromethyl)-1,4,5,6-tetrahydro-7H-pyrazolo[3,4-c]pyridin-7-one;

or a pharmaceutically acceptable salt thereof.

In another embodiment, the present invention provides a novel compound, wherein the compound is of formula $Ia_1$–$Ic_1$, wherein:

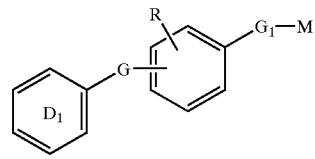

$Ia_1$

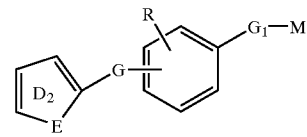

$Ib_1$

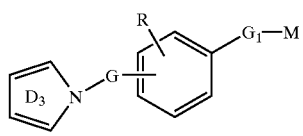

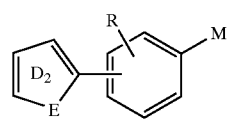

ring $D_2$ is a 5-membered heteroaromatic ring system comprising E, carbon atoms, and 0–2 N atoms, wherein E is selected from O, S, and N—$R^c$ and ring $D_2$ is substituted with 1 $R^a$ and 0–1 $R^b$;

ring $D_3$ is a 5-membered heteroaromatic ring system comprising carbon atoms and from 0–3 additional N atoms and ring $D_3$ is substituted with 1 $R^a$ and 0–1 $R^b$;

R is selected from H, Cl, F, Br, I, OH, $C_{1-3}$ alkoxy, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), and $CH_2CH_2N(C_{1-3}$ alkyl$)_2$;

$R^a$ is selected from H, OH, SH, $C_{1-3}$ alkoxy, $C_{1-3}$ thioalkoxy, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), and $CH_2CH_2N(C_{1-3}$ alkyl$)_2$;

$R^b$ is selected from H, $C_{1-4}$ alkyl, Cl, F, Br, I, OH, $C_{1-3}$ alkoxy, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), and $CH_2CH_2N(C_{1-3}$ alkyl$)_2$;

$R^c$ is selected from H, $C_{1-4}$ alkyl, $C_{1-3}$ alkoxy, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), and $CH_2CH_2N(C_{1-3}$ alkyl$)_2$; and, $G_1$ is absent or is selected from $CH_2$, C(O), O, $NR^3$, $S(O)_p$, $CH_2CH_2$, $C(O)CH_2$, $CH_2C(O)$, $OCH_2$, $CH_2O$, $NR^3CH_2$, $CH_2NR^3$, $S(O)_pCH_2$, $CH_2S(O)_p$, $CH_2CH_2CH_2$, $C(O)CH_2CH_2$, $CH_2C(O)CH_2$, $CH_2CH_2C(O)$, $OCH_2CH_2$, $CH_2OCH_2$, $CH_2CH_2O$, $NR^3CH_2CH_2$, $CH_2NR^3CH_2$, $CH_2CH_2NR^3$, $S(O)_pCH_2CH_2$, $CH_2S(O)_pCH_2$, and $CH_2CH_2S(O)_p$, and provided that $G_1$—M form other than a N—N, O—N, or S—N bond.

In another embodiment, the present invention provides a novel compound, wherein the compound is of formula $Ib_1$ or $Ic_1$, wherein;

ring $D_2$ is a 5-membered heteroaromatic ring system comprising E, carbon atoms, and 0–2 N atoms, wherein E is selected from O, S, and N—$R^c$ and ring $D_2$ is substituted with 1 $R^a$ and 0–1 $R^b$;

R is selected from H, Cl, F, Br, I, OH, $C_{1-3}$ alkoxy, $NH_2$, $NH(C_{1-3}$ alkyl), $N(C_{1-3}$ alkyl$)_2$, $CH_2NH_2$, $CH_2NH(C_{1-3}$ alkyl), and $CH_2N(C_{1-3}$ alkyl$)_2$;

$R^a$ is selected from H, OH, SH, $NH_2$, $NH(C_{1-3}$ alkyl), $N(C_{1-3}$ alkyl$)_2$, $CH_2NH_2$, $CH_2NH(C_{1-3}$ alkyl), and $CH_2N(C_{1-3}$ alkyl$)_2$;

$R_b$ is selected from H, $C_{1-4}$ alkyl, Cl, F, Br, I, OH, $C_{1-3}$ alkoxy, $NH_2$, NH ($C_{1-3}$ alkyl), $N(C_{1-3}$ alkyl$)_2$, $CH_2NH_2$, $CH_2NH(C_{1-3}$ alkyl), and $CH_2N(C_{1-3}$ alkyl$)_2$; and, $R^c$ is selected from H, $C_{1-4}$ alkyl, $C_{1-3}$ alkoxy, $NH_2$, $NH(C_{1-3}$ alkyl), $N(C_{1-3}$ alkyl$)_2$, $CH_2NH_2$, $CH_2NH(C_{1-3}$ alkyl), and $CH_2N(C_{1-3}$ alkyl$)_2$.

In another embodiment, the present invention provides a novel compound, wherein the compound is of formula $Ib_2$:

or a stereoisomer or pharmaceutically acceptable salt thereof, wherein;

ring $D_2$ is a 5-membered heteroaromatic ring system comprising E, carbon atoms, and 0–2 N atoms, wherein E is selected from O, S, and N—$R^c$ and ring $D_2$ is substituted with 1 $R^a$ and 0–1 $R^b$;

R is selected from H, Cl, F, Br, I, OH, $C_{1-3}$ alkoxy, $NH_2$, $NH(C_{1-3}$ alkyl), $N(C_{1-3}$ alkyl$)_2$, $CH_2NH_2$, $CH_2NH(C_{1-3}$ alkyl), and $CH_2N(C_{1-3}$ alkyl$)_2$;

$R^a$ is selected from H, OH, SH, $NH_2$, $NH(C_{1-3}$ alkyl), and $N(C_{1-3}$ alkyl$)_2$; and, $R^b$ is selected from H, $C_{1-4}$ alkyl, Cl, F, Br, I, OH, $C_{1-3}$ alkoxy, $NH_2$, $NH(C_{1-3}$ alkyl), $N(C_{1-3}$ alkyl$)_2$, $CH_2NH_2$, $CH_2NH(C_{1-3}$ alkyl), and $CH_2N(C_{1-3}$ alkyl$)_2$.

In another embodiment, the present invention provides a novel compound selected from one of the formulas:

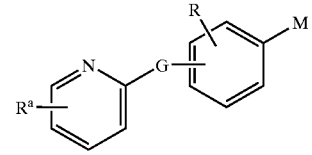

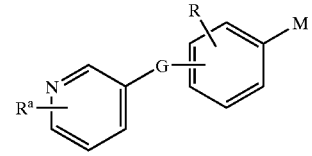

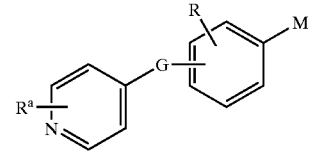

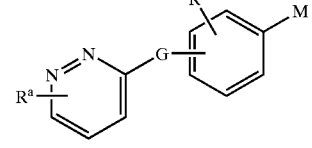

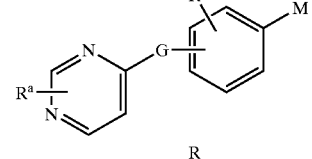

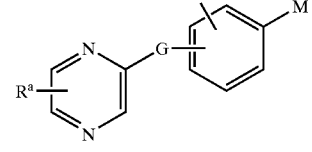

-continued
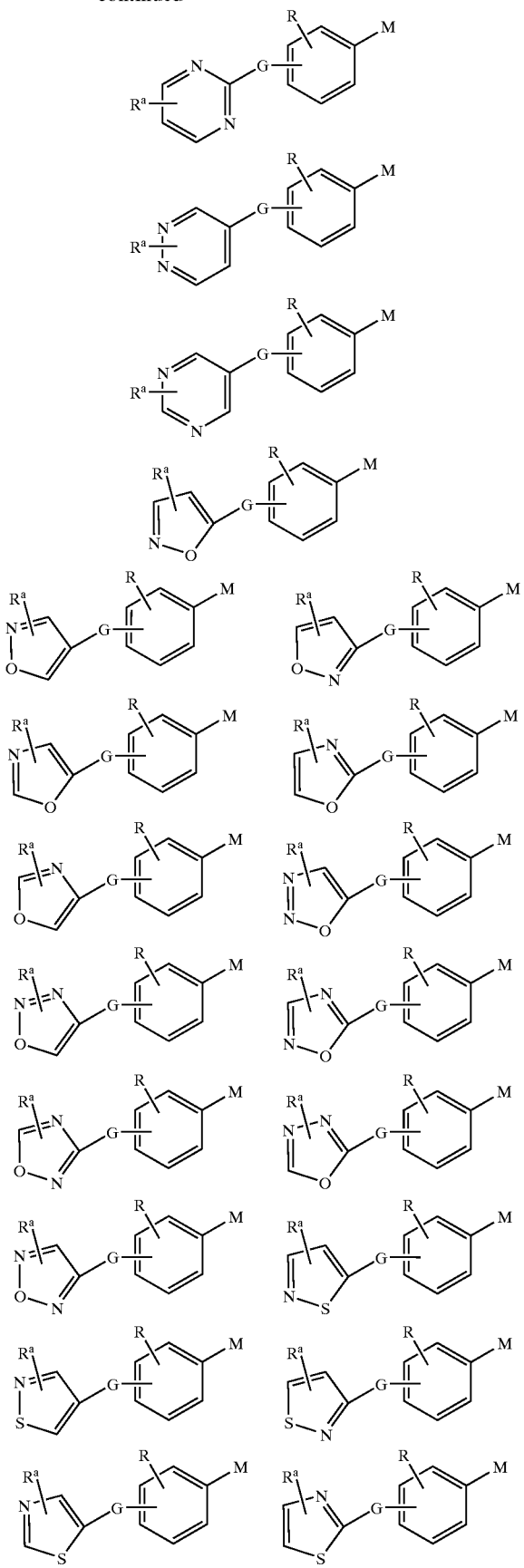
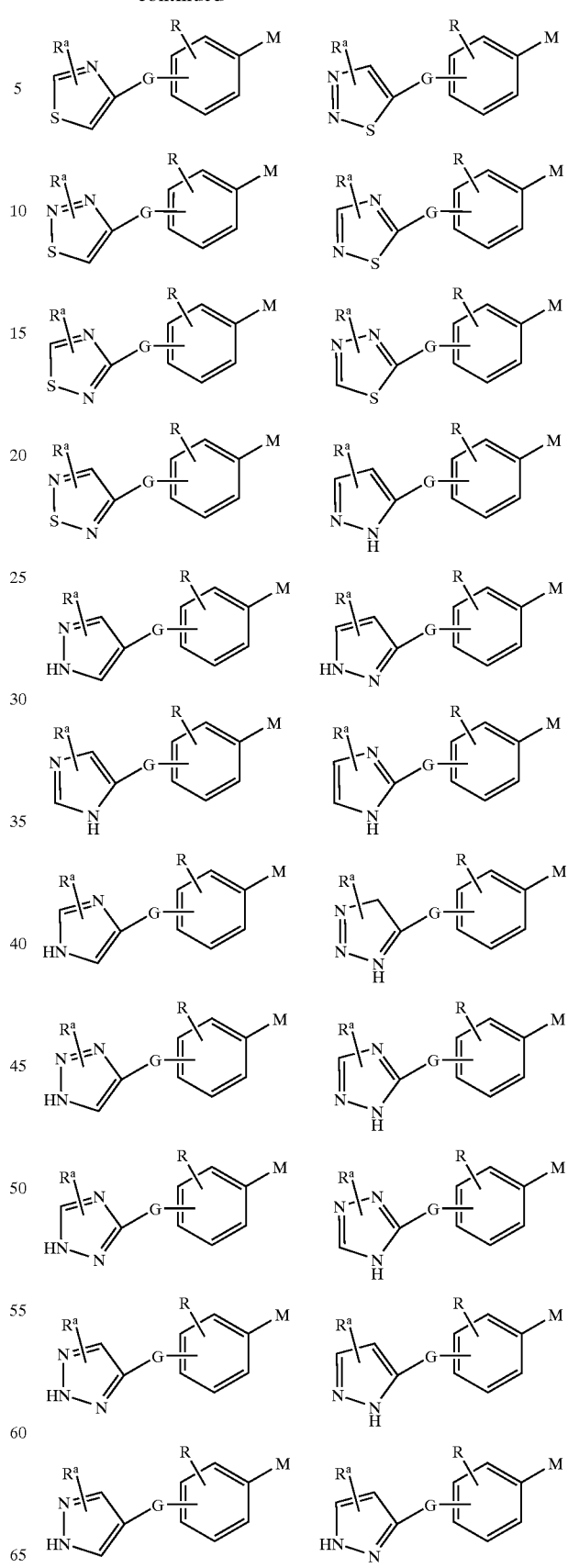

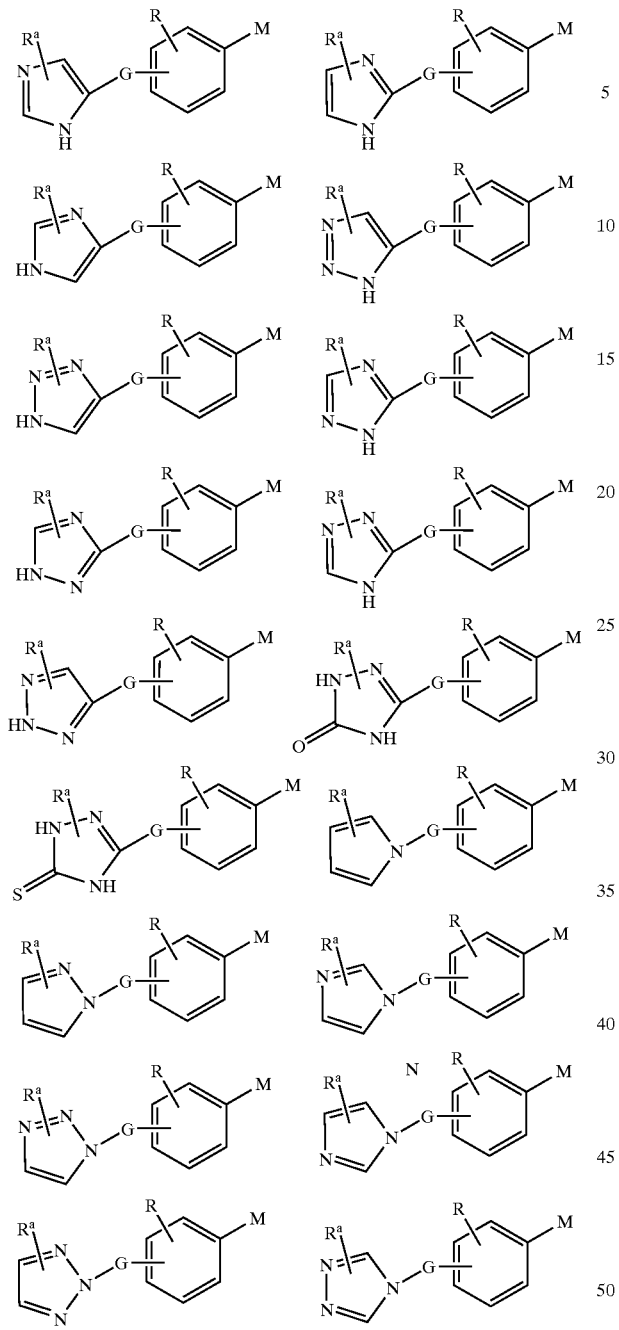
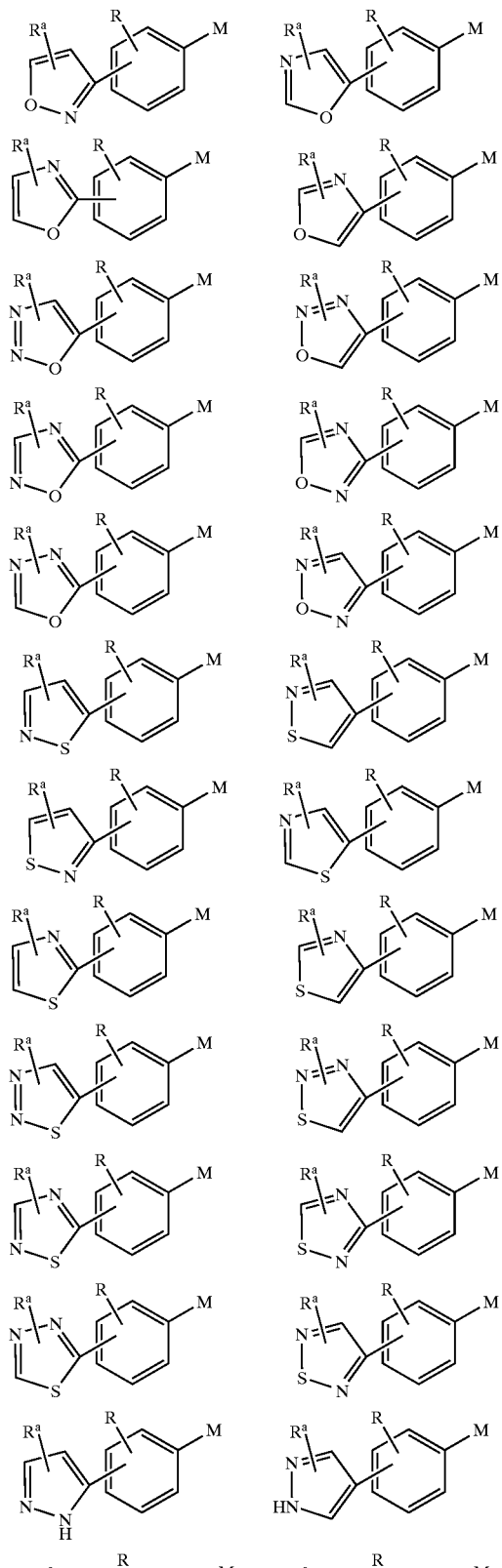
or a stereoisomer or pharmaceutically acceptable salt thereof.
In another embodiment, the present invention provides a novel compound selected from one of the formulas:
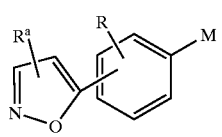
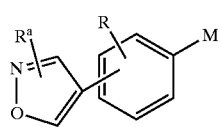
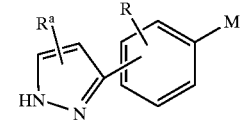
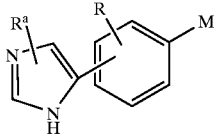

-continued

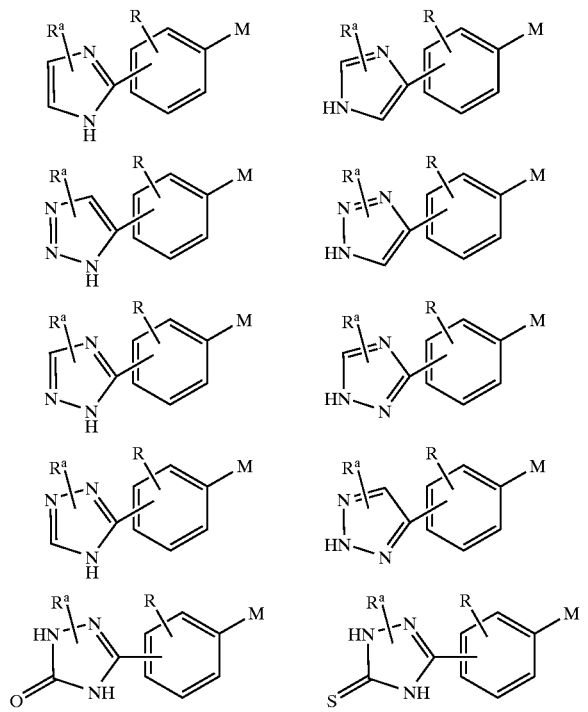
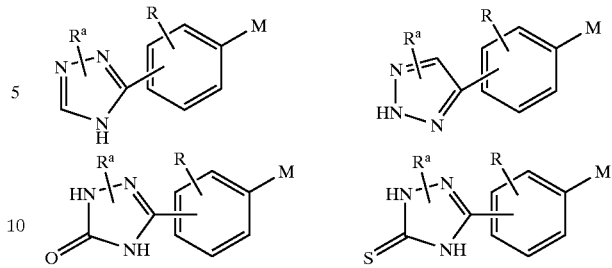
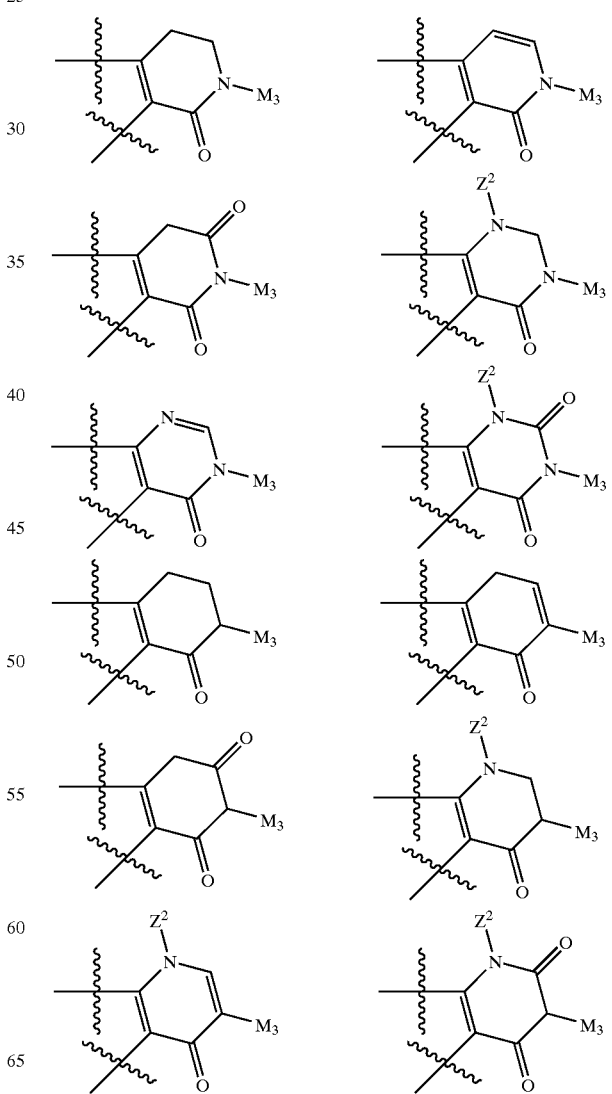

or a stereoisomer or pharmaceutically acceptable salt thereof.

In another embodiment, the present invention provides a novel compound wherein:

ring M is substituted with 0–2 $R^{1a}$ and is selected from the group:

or a stereoisomer or pharmaceutically acceptable salt thereof.

In another embodiment, the present invention provides a novel compound selected from one of the formulas:

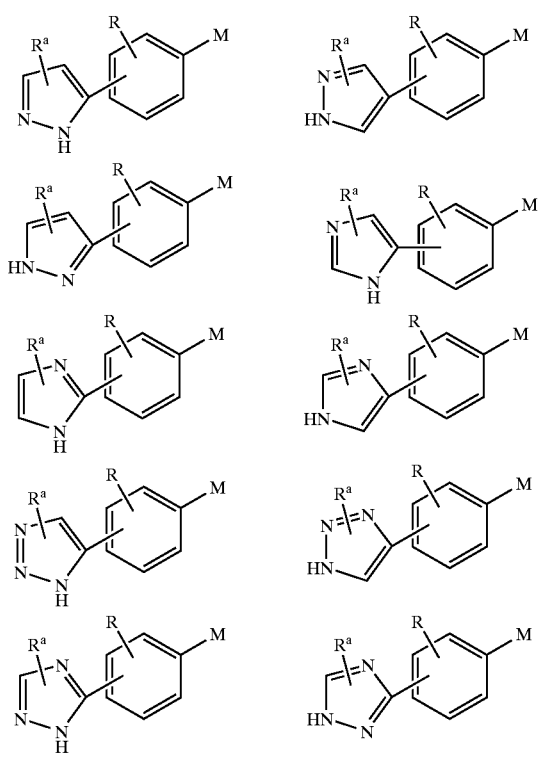

-continued
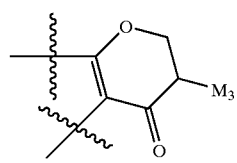
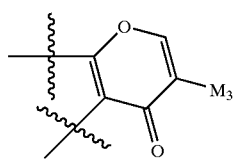
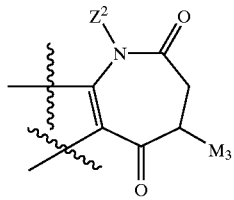
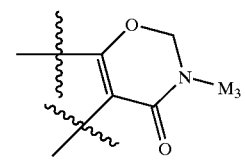
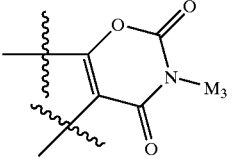
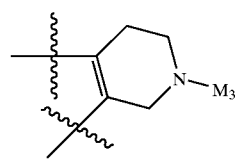
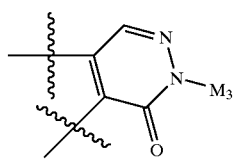
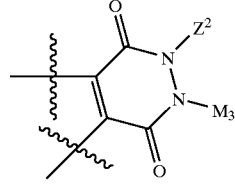
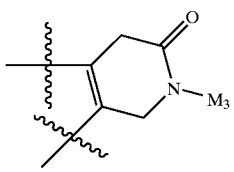
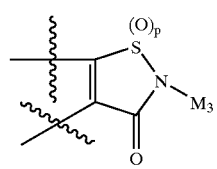
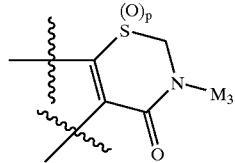
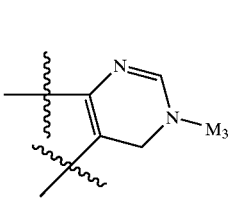
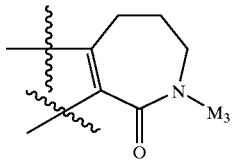
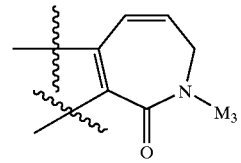
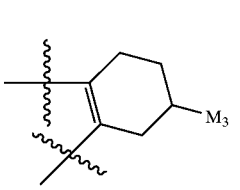
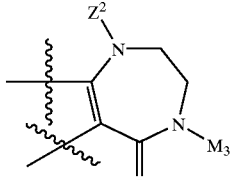
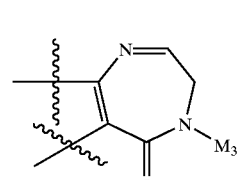
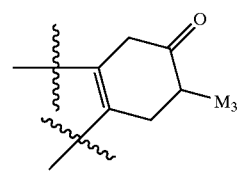
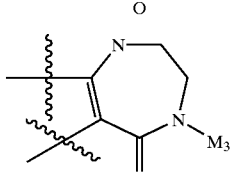
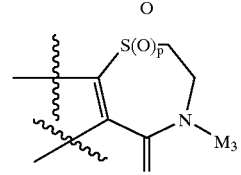
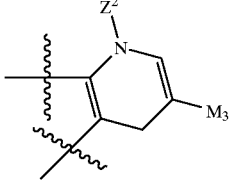
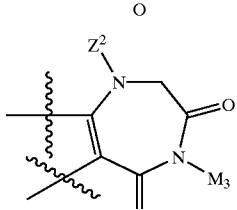
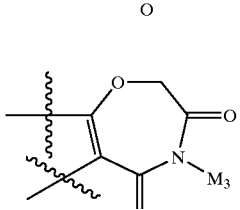
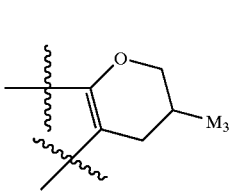
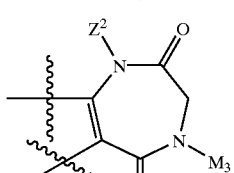
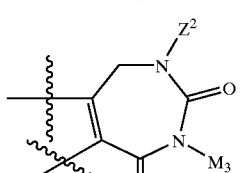
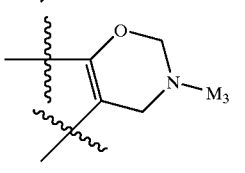

-continued
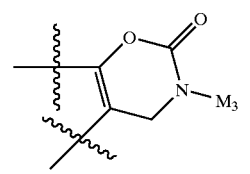 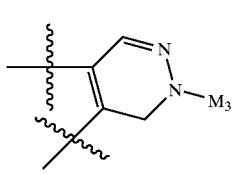 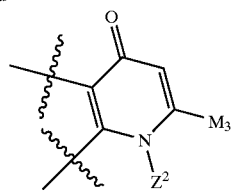
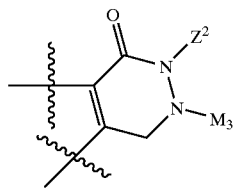 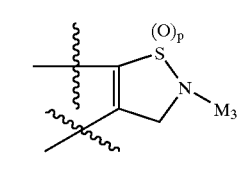 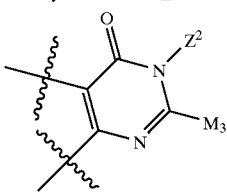
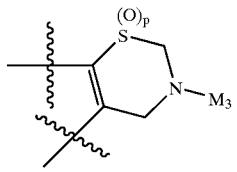 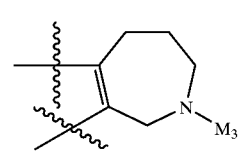 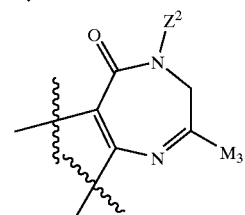
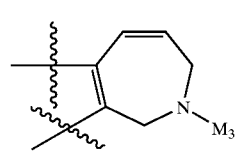 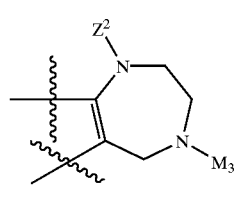 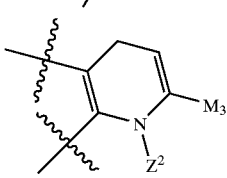
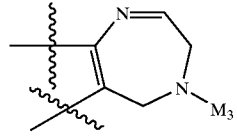 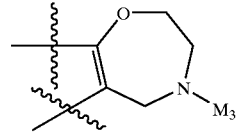
$Z^2$ is selected from H, $C_{1-4}$ alkyl, phenyl, benzyl, $C(O)R^3$, and $S(O)_pR^{3c}$;
ring P, including $P_1$, $P_2$, $P_3$, and $P_4$ is selected from group:
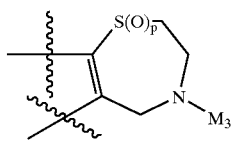 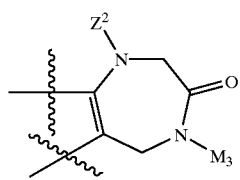 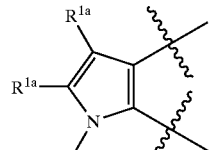 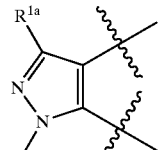
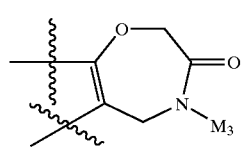 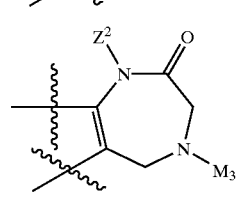 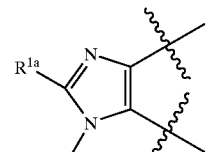 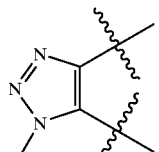
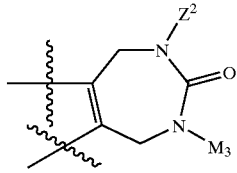 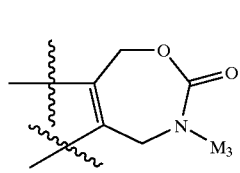 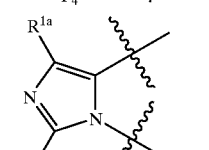 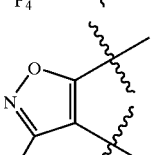
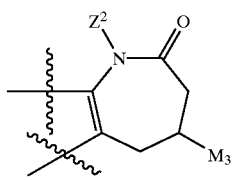 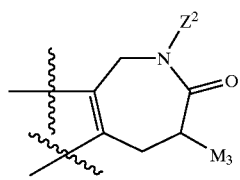 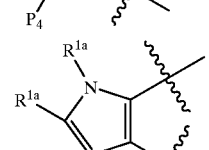 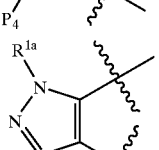

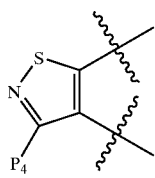 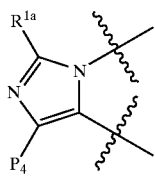
In another embodiment, the present invention provides a novel compound wherein:
ring M is substituted with 0–2 $R^{1a}$ and is selected from the group:
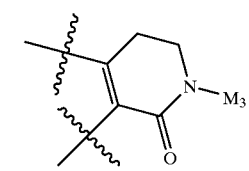 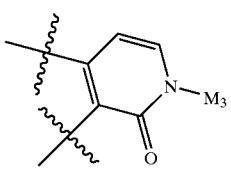 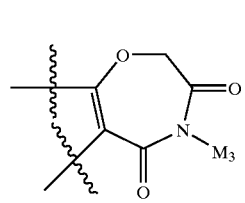 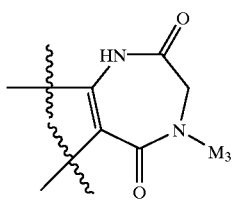
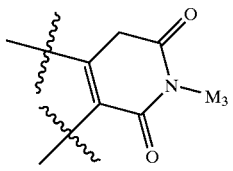 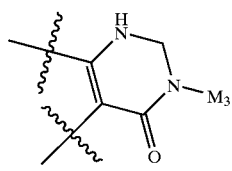 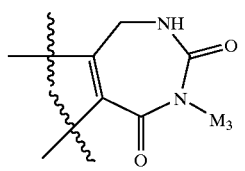 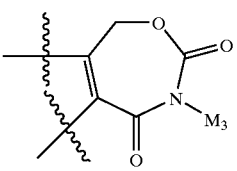
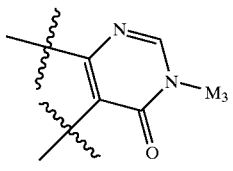 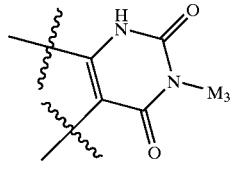 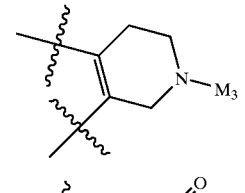 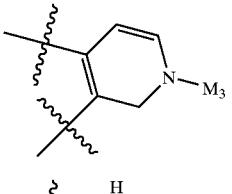
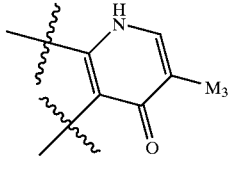 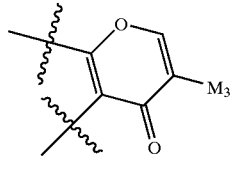 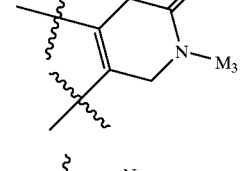 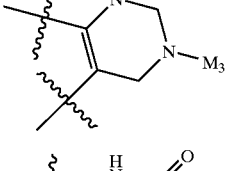
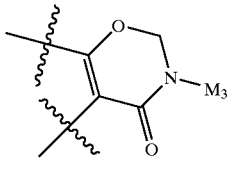 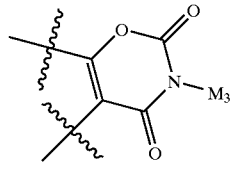 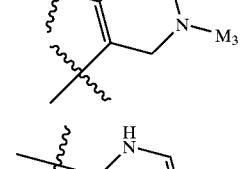 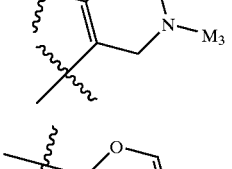
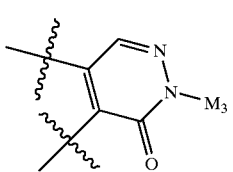 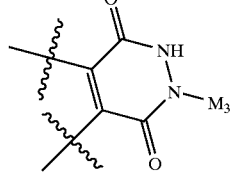 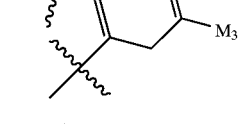 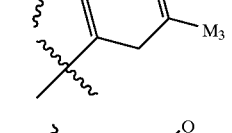
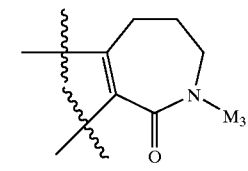 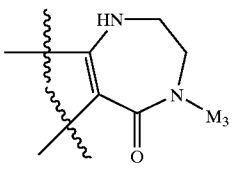 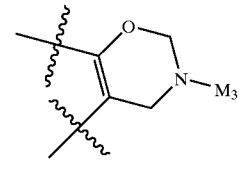 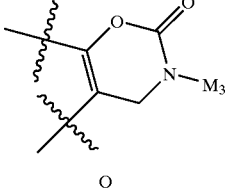
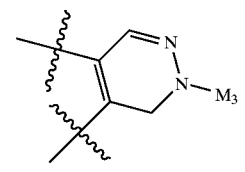 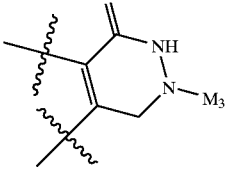
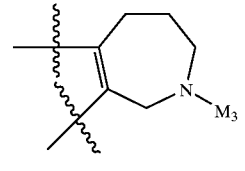 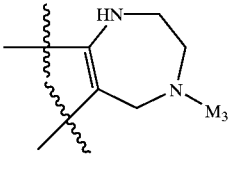

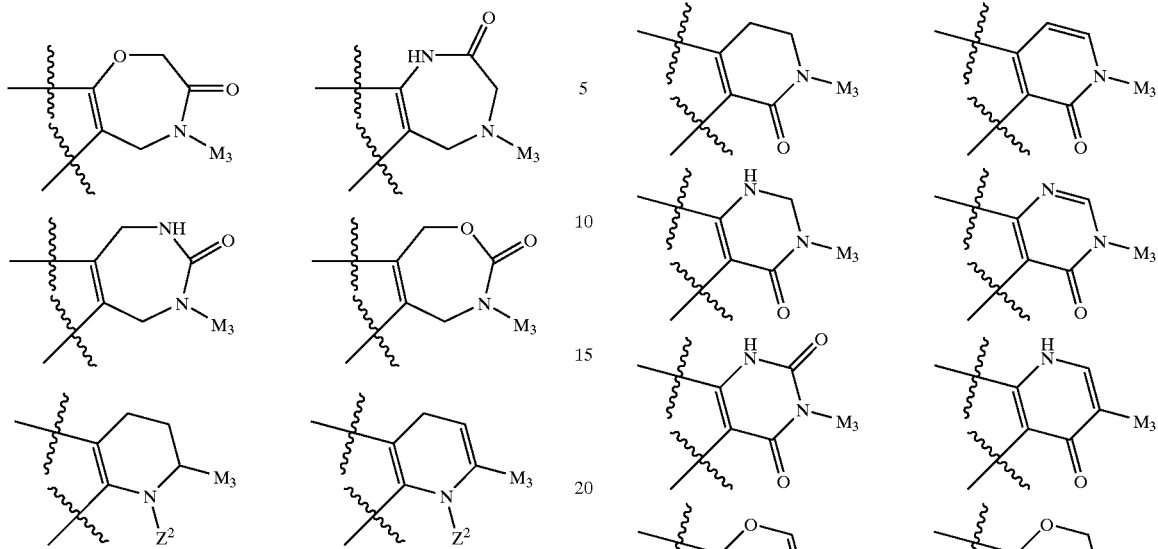
ring P, including $P_1$, $P_2$, $P_3$, and $P_4$ is selected from group:
In another embodiment, the present invention provides a novel compound wherein:
ring M is substituted with 0–1 $R^{1a}$ and is selected from the group:
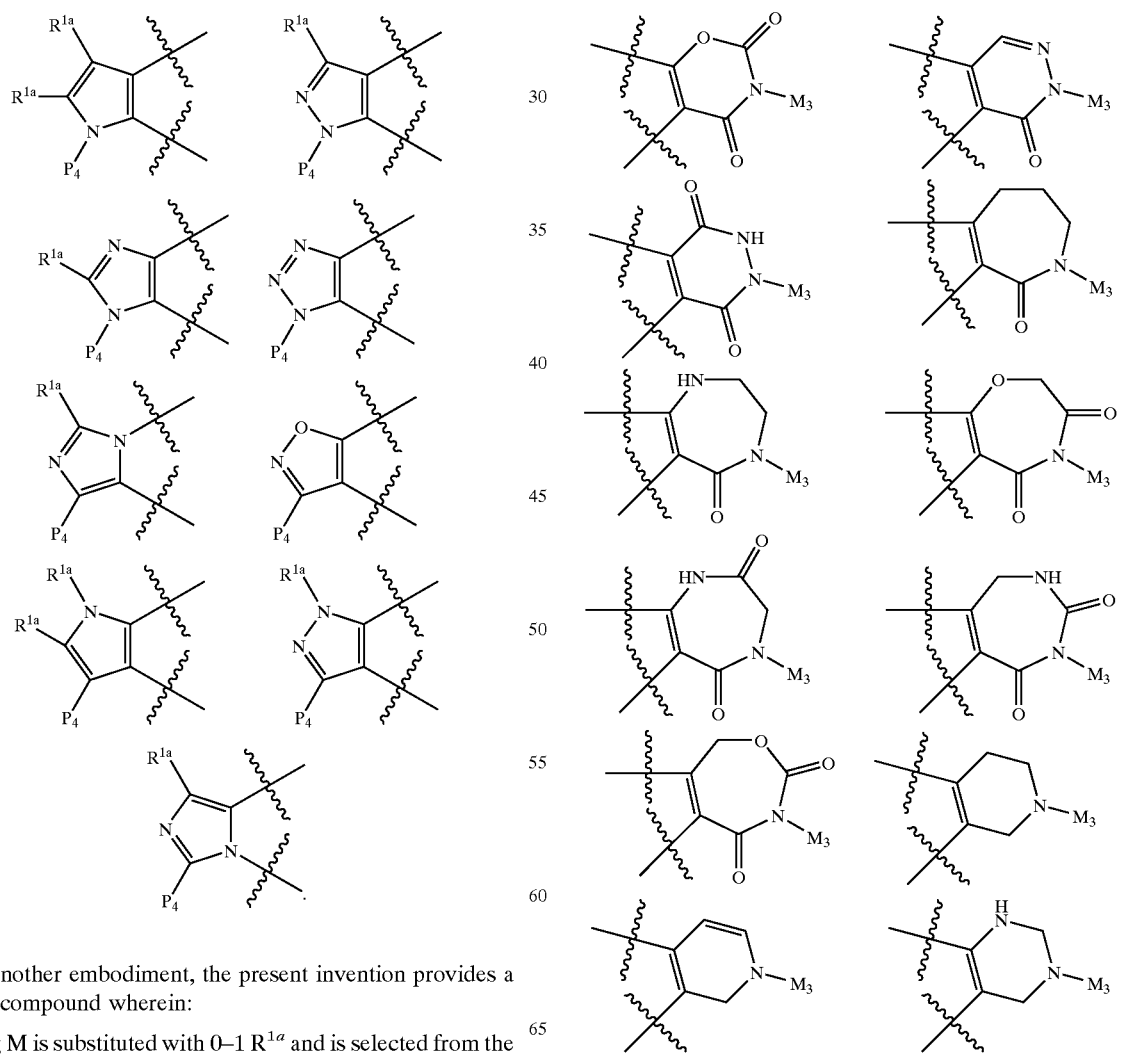

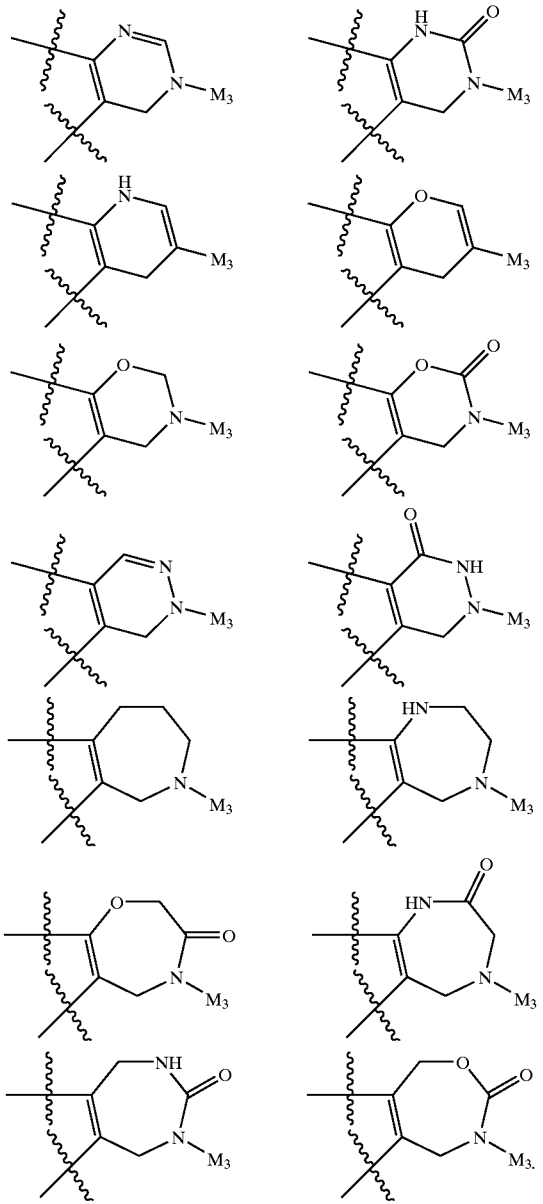

In another embodiment, the present invention provides a novel compound wherein A is selected from one of the following carbocyclic and heterocyclic systems that are substituted with 0–2 $R^4$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

In another embodiment, the present invention provides a novel compound wherein A is selected from phenyl, piperidinyl, pyridyl, and pyrimidyl, and is substituted with 0–2 $R^4$.

In another embodiment, the present invention provides a novel compound wherein A is selected from the group: phenyl, piperidinyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl.

In another embodiment, the present invention provides a novel compound wherein:

B is selected from: H, Y, and X—Y, provided that Z and B are attached to different atoms on A;

X is selected from $-(CR^2R^{2a})_{1-4}-$, $-C(O)-$, $-C(=NR^{1c})-$, $-CR^2(NR^{1c}R^2)-$, $-C(O)CR^2R^{2a}-$, $-CR^2R^{2a}C(O)$, $-C(O)NR^2-$, $-NR^2C(O)-$, $-C(O)NR^2CR^2R^{2a}-$, $-NR^2C(O)CR^2R^{2a}-$, $-CR^2R^{2a}C(O)NR^2-$, $-CR^2R^{2a}NR^2C(O)-$, $-NR^2C(O)NR^2-$, $-NR^2-$, $-NR^2CR^2R^{2a}-$, $-CR^2R^{2a}NR^2-$, O, $-CR^2R^{2a}O-$, and $-OCR^2R^{2a}-$;

Y is selected from one of the following carbocyclic and heterocyclic systems that are substituted with 0–2 $R^{4a}$;
cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

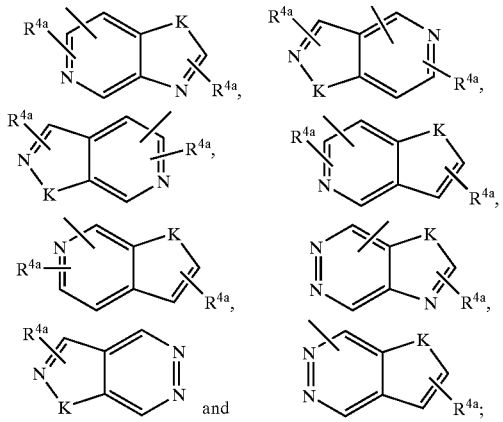

K is selected from O, S, NH, and N.

In another embodiment, the present invention provides a novel compound wherein:

Y is selected from one of the following carbocyclic and heterocyclic systems which are substituted with 0–2 $R^{4a}$; phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-25 oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzimidazolone, benzoxazole, benzthiazole, indazole, benzisoxazole, benzisothiazole, and isoindazole.

In another embodiment, the present invention provides a novel compound wherein B is selected from phenyl, pyrrolidino, N-pyrrolidino-carbonyl, morpholino, N-morpholino-carbonyl, 1,2,3-triazolyl, imidazolyl, and benzimidazolyl, and is substituted with 0–1 $R^{4a}$.

In another embodiment, the present invention provides a novel compound wherein B is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N-methylaminomethyl)phenyl, 2-(N-ethyl-N-methylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(methylaminomethyl)-1-imidazolyl, 2-(N-(cyclopropylmethyl)aminomethyl)phenyl, 2-(N-(cyclobutyl)aminomethyl)phenyl, 2-(N-(cyclopentyl)aminomethyl)phenyl, 2-(N-(4-hydroxypiperidinyl)methyl)phenyl, and 2-(N-(3-hydroxypyrrolidinyl)methyl)phenyl.

In another embodiment, the present invention provides novel pharmaceutical compositions, comprising: a pharmaceutically acceptable carrier and a therapeutically effective amount of a compound of formula Ia, Ib, or Ic or a pharmaceutically acceptable salt form thereof.

In another embodiment, the present invention provides a novel method for treating or preventing a thromboembolic disorder, comprising: administering to a patient in need thereof a therapeutically effective amount of a compound of formula Ia, Ib, or Ic or a pharmaceutically acceptable salt form thereof.

In another embodiment, the present invention provides a compound of formula Ia, Ib, or Ic as described above for use in therapy.

In another embodiment, the present invention provides the use of a compound formula Ia, Ib, or Ic as described above for the manufacture of a medicament for the treatment of a thromboembolic disorder.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. $C_{1-6}$ alkyl, is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-6}$ alkenyl is intended to include $C_2$, $C_3$, $C_4$, $C_5$, and $C_6$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-6}$ Alkynyl is intended to include $C_2$, $C_3$, $C_4$, $C_5$, and $C_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amount" is intended to include an amount of a compound of the present invention or an amount of the combination of compounds claimed effective to inhibit factor Xa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

The compounds of the present invention represented by Formulas Ia, Ib, and Ic consist of a group "Ring D—G—$G^2$—$G^1$" (i.e., $P_4$ or $M_3$) and a group "Z—A—B" (i.e., the remaining of $P_4$ or $M_3$) attached to a [5,6]- or [5,7]-heterobicyclic core structure of varying composition. The five-membered ring can be pyrazole, triazole, isoxazole or isothiazole and this ring can be fused to a variety of six- or seven membered rings including but not limited to piperidinone, pyridinone, pyrimidinone, pyrimidinedione, pyranone, diazepinone, diazepinedione. The following discussion and schemes will describe methods for the syntheses of the heterobicyclic cores and attachment of the groups "Ring D—G—$G^2$—$G^{12}$" and "Z—A—B".

The 4-aminopyrazole-5-carboxylate V is a useful intermediate for the preparation of many of the pyrazole fused compounds of Formulas Ia, Ib, and Ic wherein the $P_4$ residue is attached to a nitrogen atom of the pyrazole (Scheme I). This intermediate can be prepared in a variety of ways from aromatic hydrazines I. Hydrazines I are readily available starting materials. Specifically, they are conveniently prepared from the corresponding aniline by diazotization with $NaNO_2$ in acidic media followed by reduction of the resulting diazonium ion with a suitable reducing agent, with $SnCl_2$ being a preferred reagent. Non-aromatic hydrazines represented by I are readily prepared by a variety of methods, such as by displacement of a suitable halogen compound with hydrazine or with a protected hydrazine followed by deprotection.

Condensation of hydrazines I with a suitable hemiacetal or aldehyde followed by halogenation with NBS or NCS leads to hydrazidoyl halides II. Alternatively, the hydrazines I can be acylated with an acid chloride and converted to hydrazidoyl halides II by carbon tetrahalide/triphenylphosphine. The hydrazidoyl halides II are versatile intermediates for pyrazole synthesis (Shawali, A. S.; et. al. *J. Het. Chem.* 1980, 17, 833). The halide can be displaced with cyanide ion to afford cyanide III. Cyano compounds of this type can also be prepared more directly by diazotization of aniline IV followed by direct reaction with a cyano-containing active methylene compound, where $R^{1a}$ can include a variety of groups such as ester, ketone, cyano, trifluoromethyl, sulfone, aryl, etc. (Butler, R. N.; et. al. *J. Chem. Soc. Chem. Commun.* 1992, 20, 1481).

Treatment of III with a bromoacetate in the presence of a suitable base such as carbonate or trialkylamine results in N-alkylation followed by ring closure to give the 4-aminopyrazole-5-carboxylate V. Alternatively, treatment of II with a nitropyruvate in the presence of a base such as alkoxide provides a 4-nitropyrazole by displacement of the halide followed by ring closure of the nitrogen onto the carbonyl group. Reduction of the nitro group can be accomplished by a variety of reducing agents, a preferred one of which is $SnCl_2$, to give the 4-aminopyrazole-5-carboxylate V.

The hyrazidoyl halide II can also be reacted with a ketoester where R' represents a masked ester, preferably a 2-furyl residue, to give a pyrazole-4-carboxylate VI. Ester hydrolysis, conversion to an acyl azide, either via the acid chloride or anhydride, heating to generate an isocyanate via Curtius rearrangement, and finally treatment with water affords the 4-aminopyrazole VII. Alternatively, the amino can be masked as an appropriate carbamate by using an alcohol instead of water in the Curtius rearrangement. When R'=2-furyl, the furan can be oxidatively cleaved under a variety of conditions, such as sodium periodate with catalytic ruthenium trichloride, or $KMnO_4$, to afford a carboxylic acid which can be esterified to afford the 4-aminopyrazole-5-carboxylate V.

Another route to the 4-aminopyrazole V involves condensation of the hydrazine I with an appropriate diketone or monoprotected diketone to form a 3,5-disubstituted pyrazole in which the 5-substituent is a carboxylic ester. Usually, this pyrazole can be selectively nitrated at the 4-position with nitrating agents such as nitric acid or ammonium nitrate/trifluoroacetic anhydride. Reduction of the nitro group under a variety of conditions, such as with tin (II) chloride or catalytic hydrogenation, affords the 4-aminopyrazole V. This route can also be carried out using a diketone with a 2-furyl group as a latent carboxylate, giving initially a 3,5-disubstituted pyrazole in which the 5-substituent is the 2-furyl group. Oxidative cleavage of the furyl group to a carboxylate, nitration of the pyrazole 4-position, esterifica tion and nitro reduction then affords 4-aminopyrazole V. It will be recognized by those skilled in the art that the synthetic route chosen to V will depend on additional functionality present in the molecule of interest and the route may require additional protection/deprotection sequences as well as modifications in the order of synthetic steps.

Scheme I

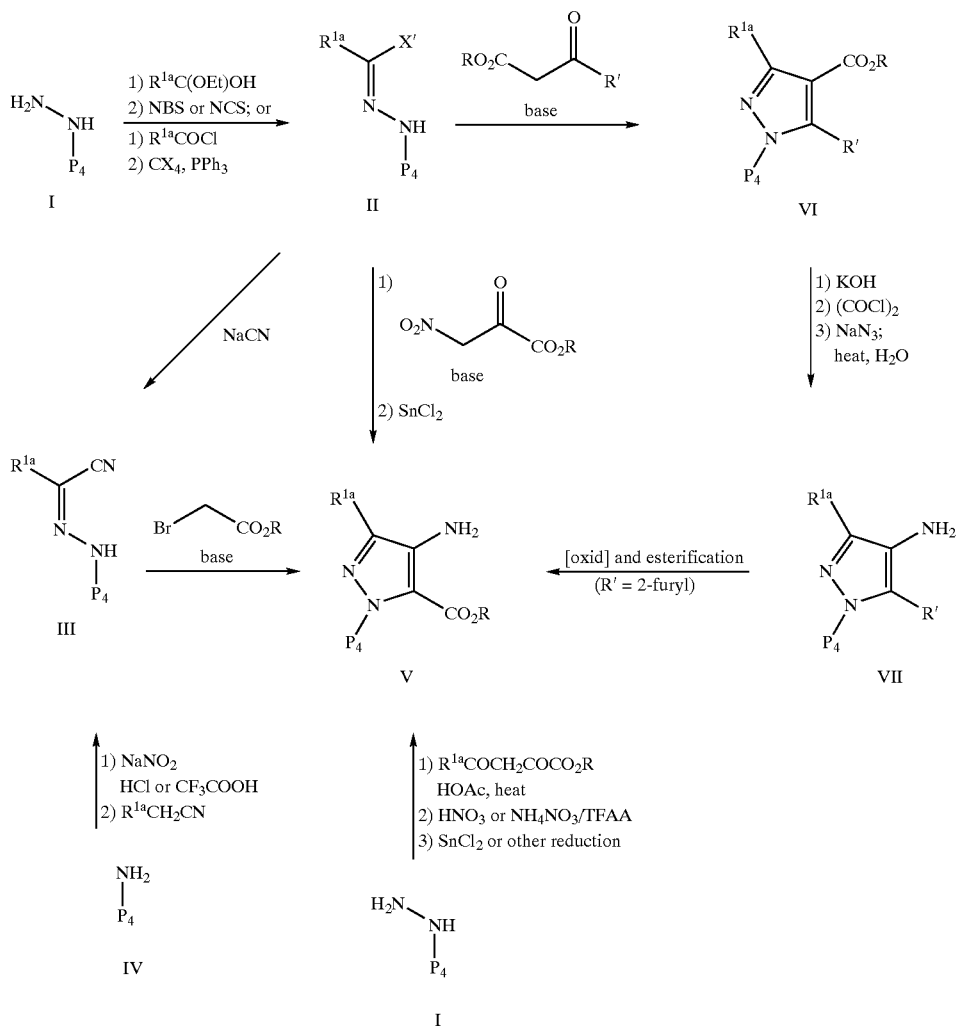

In Scheme II is shown how the 4-aminopyrazole-5-carboxylate V can be utilized to prepare a variety of structures described by Formulas Ia, Ib, and Ic where the A—B residue is connected to a nitrogen atom of the bicyclic core. The 4-amino group can be protected as a suitable carbamate (see Greene and Wuts, *Protective Groups in Organic Synthesis*, Wiley and Sons, 1991) or as an azide group ($NaNO_2$, acid, $NaN_3$). In some cases it may not be necessary to protect the amino functionality, as will be recognized by those skilled in the art. Unmasking of the ester residue involves either basic hydrolysis (R=Me, Et), hydrogenolysis (R=Bn) or trifluoroacetic acid (R=t-Bu). Coupling of the resulting acid with the appropriate amine $H_2N$—A—B can be accomplished by a wide variety of methods known to those skilled in the art, including dicyclohexylcarbodiimide and N,N-dimethylaminopyridine, the mixed anhydride method, and the BOP reagent. Alternatively, the amide bond can be formed directly from the ester (R=Me, Et) by reacting the ester with an aluminum reagent prepared from the amine $H_2N$—A—B and trimethylaluminum. Deprotection of the amino group, if required, provides compounds VIII. Treating this amino amide with carbonyl diimidazole or other phosgene equivalent, such as triphosgene, provides pyrazolopyrimidinediones IX. Alternatively, aminocarboxylate V can be converted to pyrazolopyrimidinediones IX in a single step by heating with an appropriate isocyanate OCN—A—B in the presence of a base such as sodium hydride.

Treating VIII with a substituted bromoacetyl chloride or bromide in the presence of a base such as triethylamine affords the pyrazolodiazepinediones X. Refluxing VIII in the presence of formic acid provides the pyrazolopyrimidinones XI ($R^3$=H). Substituted derivatives XI can be obtained by refluxing VIII in the presence of triethylorthoacetate ($R^3$= Me) or other orthoesters. Reduction of XI with catalytic hydrogenation, sodium borohydride in acidic medium or other reducing agent can provide compounds of type XII.

Additionally, V can be treated with a bromoacetate in the presence of a base such as carbonate or sodium hydride to provide XIII. Selective hydrolysis of either ester of XIII followed by standard coupling with $H_2N$—A—B and subsequent heating affords compounds XIV, which are regioisomeric with X.

Oxygen analogs of XIV are prepared by converting the amino group of v to a hydroxy group via a diazonium ion. Coupling with the amine $H_2N$—A—B by any of a wide variety of procedures yields XV. O-alkylation of XV with a bromoacetate in the presence of a base such as sodium hydride leads to XVI, the oxygen analogs of XIV.

In the cases of compounds IX, X, XII and XIV the nitrogen atom can be further functionalized to provide additional analogs, such as by treating with methyl iodide in the presence of a base to afford the N-methyl derivatives.

carbamate protected nitrogen or can represent conversion of the amino group to an azide group as described previously,

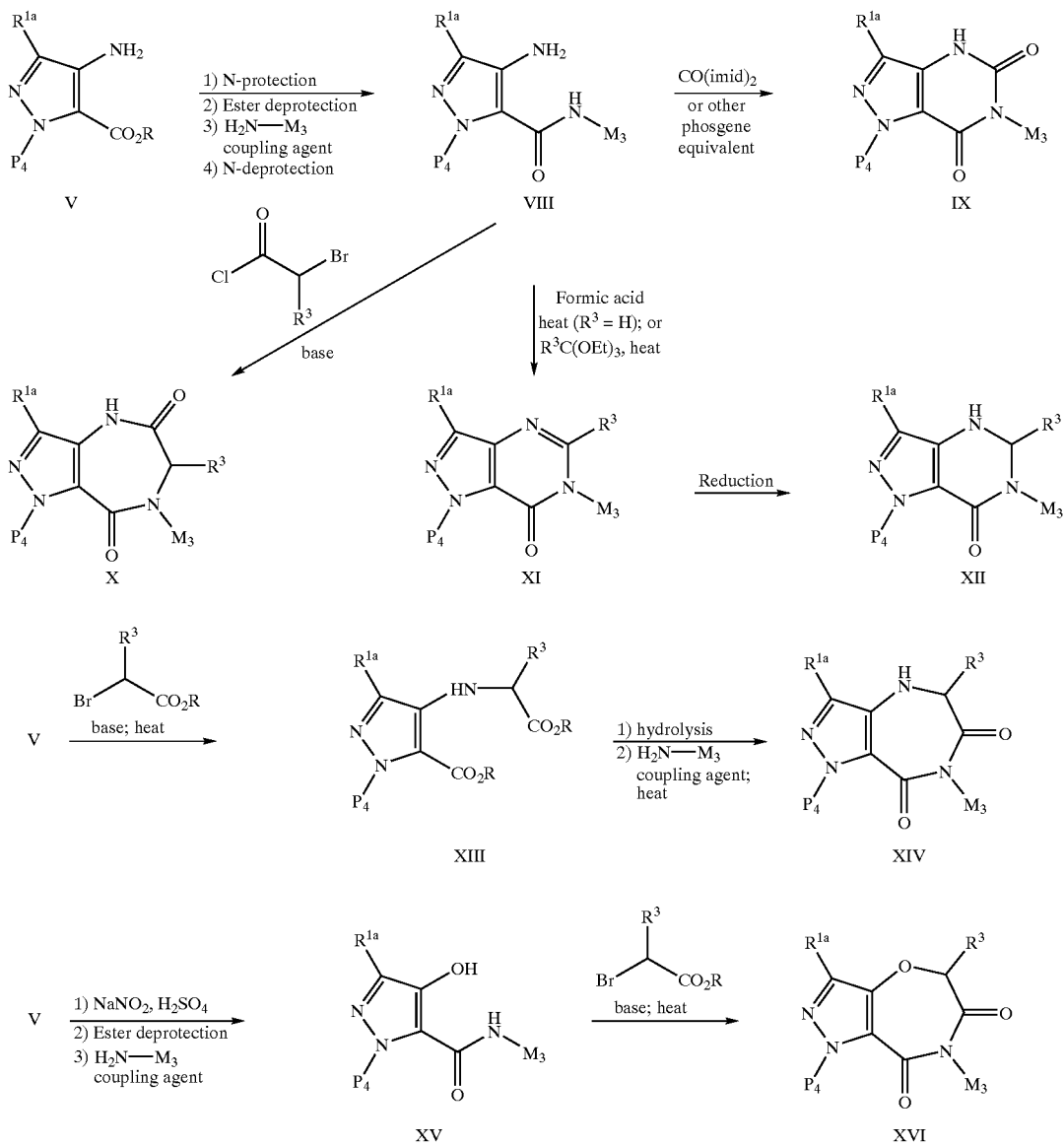

Scheme II

The 4-aminopyrazole-5-carboxylate can be used to prepare pyrazolopyranone and pyrazolopyridinone derivatives, in which the A—B residue is attached to a carbon atom of the bicyclic core, as shown in Scheme III. N-protection of V as described previously can be followed by straightforward conversion of the ester residue to an acid chloride. Treatment of this acid chloride with a zinc cuprate reagent derived from Br—CH$_2$—M$_3$ (the connecting portion of M$_3$ being aryl) will afford the ketone XVII after N-deprotection. Heating XVII with dimethylformamide dimethylacetal or with an orthoester can provide the pyrazolopyridinone compounds XVIII. Conversion of the 4-amino residue of XVII to a hydroxyl group via the diazonium ion will lead to XIX, which will provide the pyrazolopyranone derivatives XX under similar cyclization conditions.

Alternatively, treatment of the acid chloride XXI, obtained as described above where N—PG can represent a with a suitable enamine in the presence of a base such as triethylamine can afford the ketone XXII. N-deprotection followed by heating will afford the pyrazolopyridinones XXIII (XVIII where R$^3$=H).

Also, the ketone XVII can be prepared from the cyano compound III by treatment with a suitable bromoketone in the presence of a base such as carbonate or triethylamine. The required bromoketone is readily available by treating an appropriate acid chloride with diazomethane followed by HBr. It will be recognized by those skilled in the art that the syntheses of the compounds described in Scheme III may require additional protection/deprotection steps or modifications in the order of carrying out the steps, depending on additional functionality present in the compounds of interest.

Scheme III

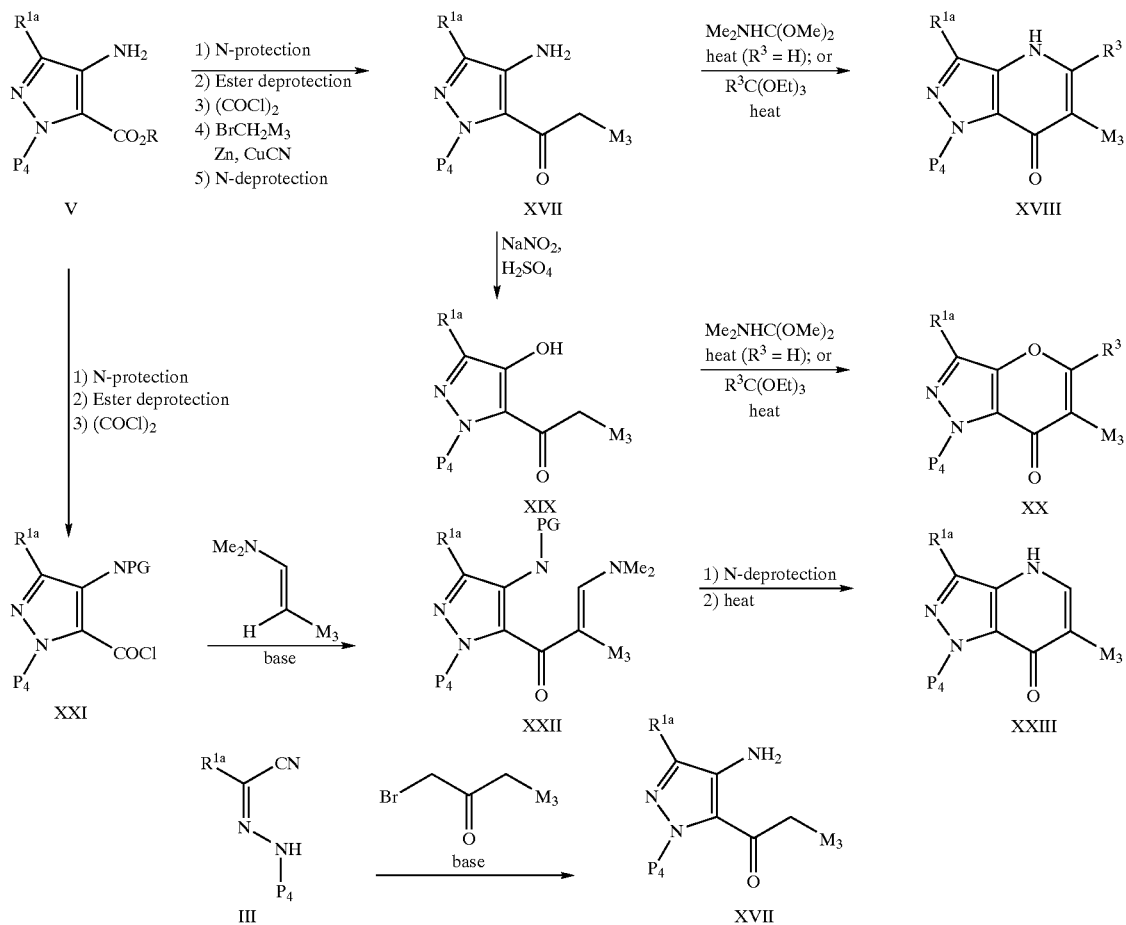

Additional oxygen-containing bicyclic systems can be prepared as shown in Scheme IV. The 4-amino-5-carboxylate V can be converted to its 4-hydroxy derivative via the diazonium ion to give XXIV. Ester deprotection and amide bond formation with an appropriate $H_2N-M_3$ as described in Scheme II will afford the amide XXV. Alternatively, the amide bond can be formed directly from the ester by addition of the aluminum reagent derived from $H_2N-M_3$ and trimethylaluminum. The 4-hydroxy substituent can be easily protected if required by any of a number of protecting groups, such as with t-butyldimethylsilyl ether (TBS), and then deprotected following amide bond formation. Treating the hydroxy amide XXV with carbonyl diimidazole or other phosgene equivalent, such as triphosgene, can provide the bicyclic core XXVI. Heating XXV in the presence of paraformaldehyde in the presence of a suitable acid such as p-toluenesulfonic acid will provide XXVII ($R^3$=H). Alternatively, XXV can be treated with dibromomethane in the presence of a suitable base such as carbonate to afford XXVII ($R^3$=H). Other aldehydes and substituted dibromomethanes can provide substituted derivatives of XXVII where $R^3$ is not hydrogen.

Scheme IV

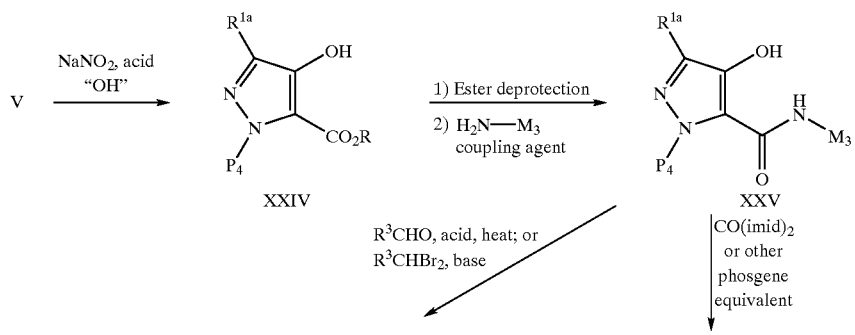

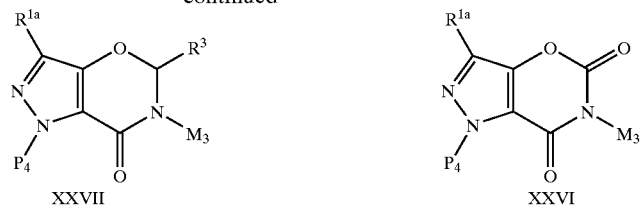

XXVII            XXVI

Additional bicyclic systems in which the $M_3$ residue is substituted on a carbon atom can be prepared as shown in Scheme V. N-protection of 4-aminopyrazole-5-carboxylate V can be followed by manipulation of the ester to afford an acid chloride or an N-methoxy-N-methyl amide. Addition of an enolate derived from $RO_2CCH_2$—$M_3$ and a base such as lithium diisopropylamide or lithium hexamethyldisilazide provides XXVIII. The N-methoxy-N-methyl amide is the preferred reaction partner for this addition, as this functionality prevents the formation of overaddition products. Alternatively, the enolate addition reaction could be done on the ester as well. N-Deprotection of the 4-amino substituent allows it to close onto the ester residue and provides the pyrazolopiperidinedione XXIX.

Manipulation of the ester residue of XXVIII can lead to XXX where X represents a suitable leaving group such as a bromide or mesylate residue. A variety of methods can be utilized for the transformation of XXVIII to XXX, such as ketone protection, reduction of the ester to a primary alcohol, ketone deprotection and conversion of the primary alcohol to a bromide using $CBr_4/PPh_3$ or to a mesylate using methanesulfonyl chloride and a base such as triethylamine. Alternatively, the ester can be hydrolyzed to the acid that can be reduced to the primary alcohol with borane and converted to a leaving group as just described. N-deprotection liberates the 4-amino group, which provides compounds of structure XXXI upon heating or treatment with base.

The corresponding oxygen derivative is also available from XXVIII. N-deprotection, diazotization with $NaNO_2$ in acidic medium and treatment with sulfuric acid produces the 4-hydroxy derivative XXXII. Protection of the alcohol functionality, for example as the TBS ether, followed by ester manipulation as described above and subsequent alcohol deprotection, produces XXXIII. Treatment of XXXIII with a suitable base such as carbonate leads to ring closure to afford compounds XXXIV. Alternatively, compounds XXXIII where X=OH can be closed to XXXIV via a Mitsunobu reaction by treatment with diethylazodicarboxylate and triphenylphosphine.

Scheme V

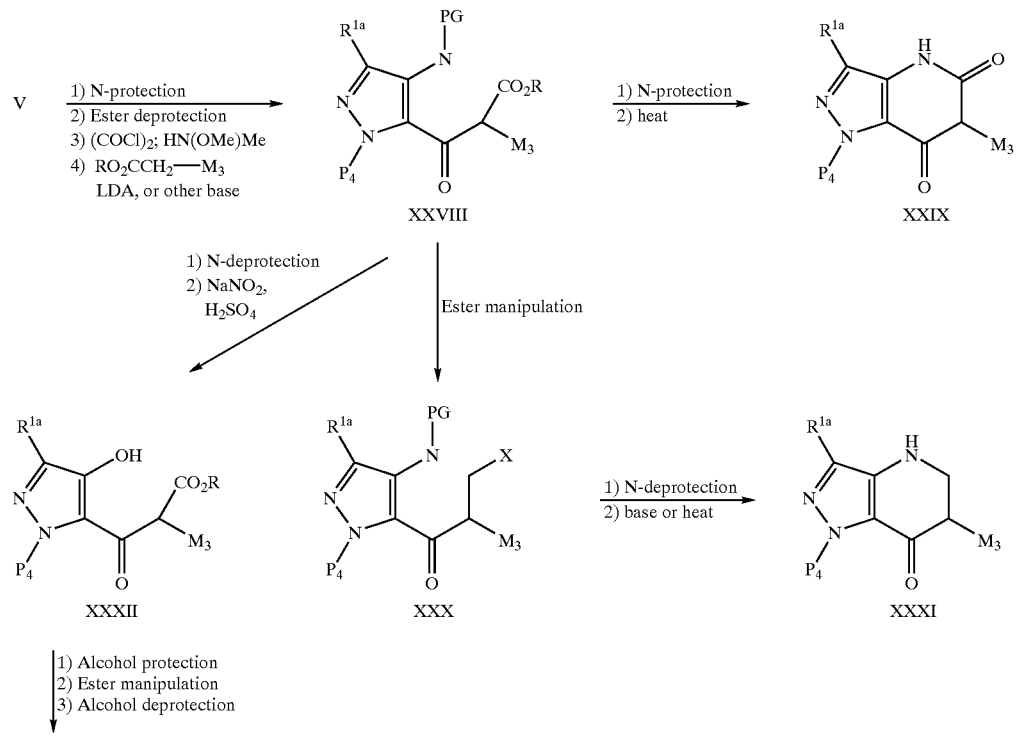

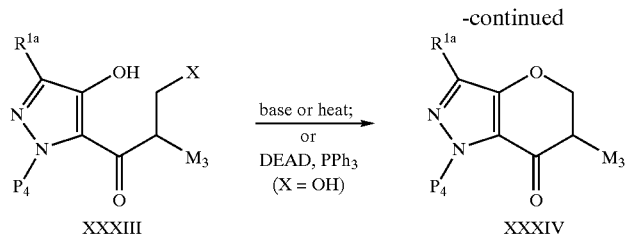

In scheme VI it is shown how to make additional bicyclic systems in which the $M_3$ residue is substituted on a carbon atom and the ring is substituted with an $R^3$ group. Ester XXVIII can be converted under standard conditions to the N-methoxy-N-methyl amide XXXV. Addition of an appropriate Grignard reagent $R^3MgBr$ produces a ketone, which upon N-deprotection and heating in acidic conditions leads to the substituted pyridones XXXVI. Hydride reduction, with REDAL for example, will produce the piperidone XXXVII.

Alternatively, diisobutylaluminum hydride reduction of the N-methoxy-N-methyl amide gives an aldehyde which will add a suitable Grignard reagent $R^3MgBr$ to afford XXXVIII. Conversion of the alcohol to a leaving group, for example by making the mesylate with methanesulfonyl chloride and a trialkylamine base, followed by N-deprotection leads to ring closure to piperidones XXXVII. The alcohol XXXVIII can also be prepared from enamine XXII from Scheme III by hydrolysis to the corresponding aldehyde followed by addition of the appropriate Grignard reagent $R^3MgBr$.

Preparation of a bicyclic system containing a seven-membered ring in which the $M_3$ residue is attached to a carbon atom is described in Scheme VII. N-protection of aminoketone XVII, where N—PG represents preferably an N-protected nitrogen wherein both N—H groups are masked, such as by conversion to an azide group, is followed by formation of a ketone enolate, with a base such as lithium diisopropylamide, and reaction with a bromoacetate to afford XXXIX. N-deprotection followed by heating of the resulting amino ester affords XL.

Alternatively, the ester can be converted by straightforward means to a more reactive species prior to ring closure, such as a mixed anhydride or acid chloride. Treatment of XVII with bromoacetyl bromide and a base such as triethylamine gives the acylamine XLI that can be cyclized by formation of the ketone enolate with a base such as lithium diisopropylamide.

Scheme VI

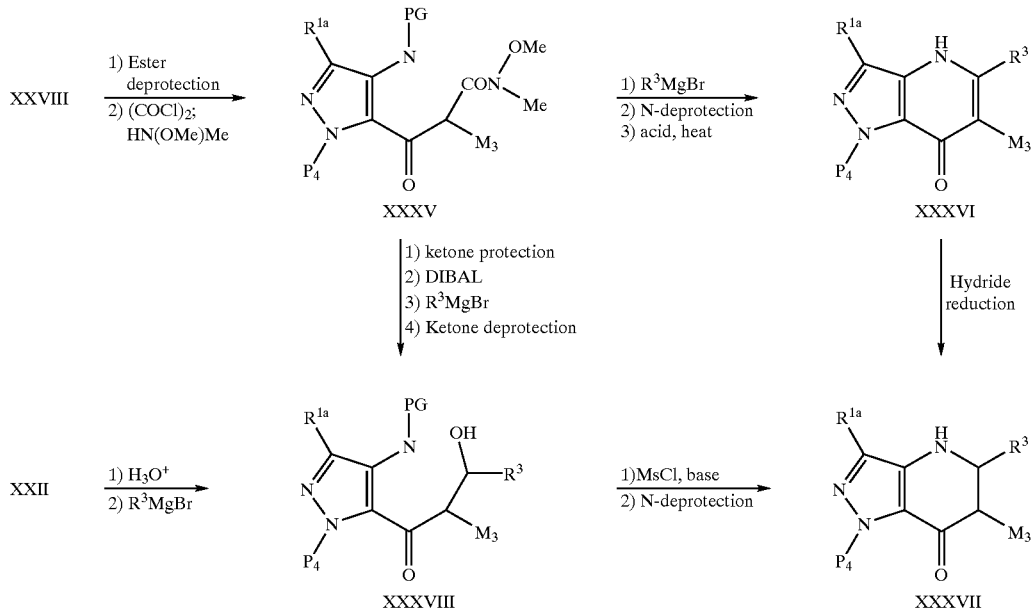

Scheme VII

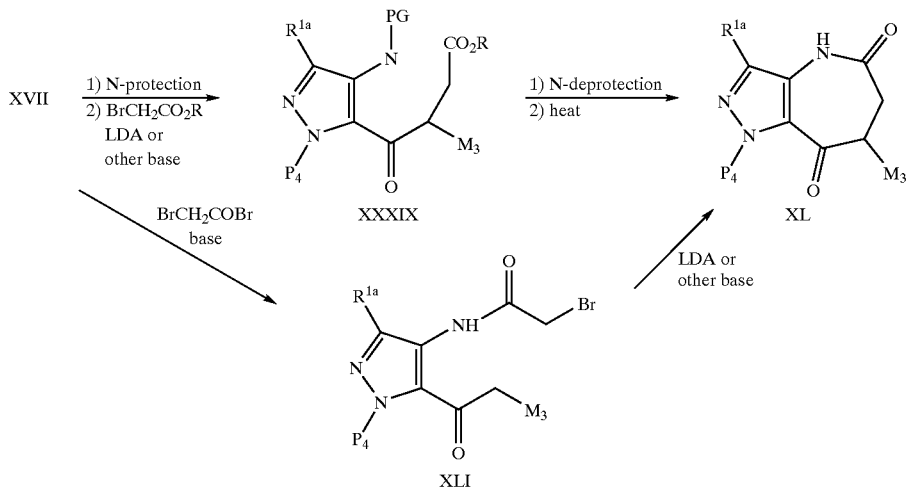

Additional seven-membered ring-containing bicyclic systems can be prepared as shown in Scheme VIII. The hydrazidoyl halide II, prepared as shown in Scheme I, can be cyclized with a cyanopyruvate in the presence of a base such as alkoxide to afford 4-cyanopyrazole XLII. Ester deprotection and coupling with $H_2N—M_3$ as described in previous schemes yields cyanoamide XLIII. Reduction of the nitrile can be accomplished by various methods, such as by catalytic hydrogenation or by reduction with sodium borohydride in the presence of cobalt chloride. Cyclization of the resulting aminoamide using carbonyl diimidazole or other phosgene equivalent as described previously affords compounds XLIV.

For the corresponding compound wherein the $M_3$ residue is attached to carbon, the ester XLII can be converted to the N-methoxy-N-methyl amide as described previously. Treatment of this amide with the enolate derived from $RO_2CH_2—M_3$ yields the ketone XLV. Catalytic hydrogenation of the nitrile affords an amine that upon heating undergoes cyclization to afford XLVI.

The oxygen containing analog corresponding to XLIV is Ad obtained from ester VI, prepared as described in Scheme I. The group R' represents preferably a 2-furyl residue as a masked carboxylic acid. Reduction of the ester group of VI with a hydride reducing agent such as diisobutylaluminum hydride is followed by protection of the resulting primary alcohol, such as by a TBS ether. When R' is 2-furyl, the carboxylic acid can be unmasked by oxidation by a variety of reagents, including ozone, potassium permanganate, and sodium periodate in the presence of ruthenium trichloride. Coupling with a suitable with $H_2N—M_3$ as described in previous schemes yields the amide XLVII. Deprotection of the alcohol affords a hydroxy amide, which can be cyclized using carbonyl diimidazole as described previously to afford compounds XLVIII.

Scheme VIII

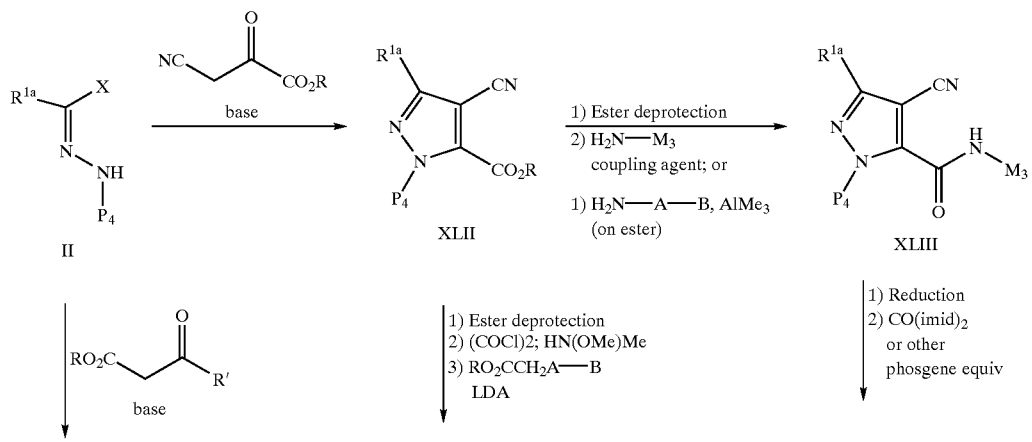

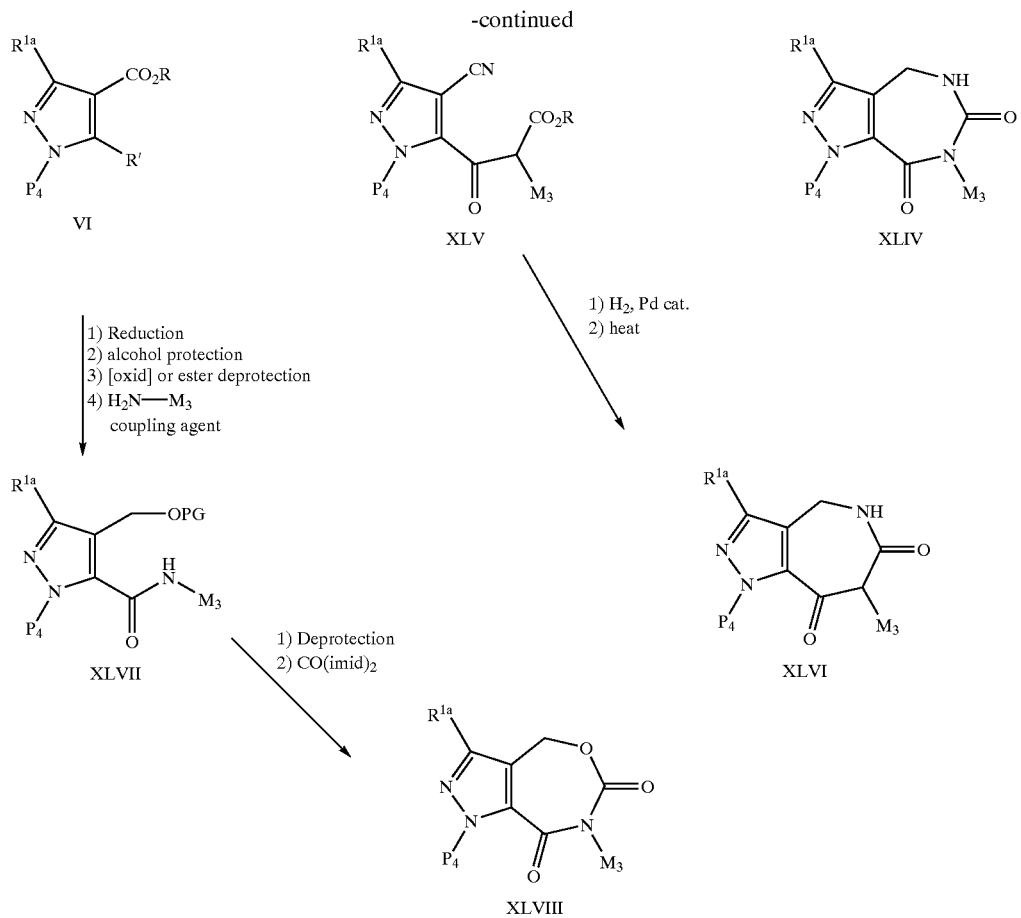

Bicyclic compounds of Formulas Ia, Ib, and Ic containing a carbon atom at the pyrazole 4-position can be prepared by a [3+2] cycloaddition strategy as shown in Scheme IX (for a review of [3+2] cycloadditions, see 1,3-Dipolar Cycloaddition Chemistry (Padwa, ed.), Wiley, New York, 1984).

Treatment of unsaturated lactone XLIX, which is readily available by standard procedures known to those skilled in the art, with an aluminum reagent prepared from an appropriate amine $H_2N$—$M_3$ and trimethylaluminum affords the ring-opened amide L. Conversion of the primary alcohol under standard conditions to a suitable leaving group, such as a bromide or mesylate, and subjection to basic conditions affords the required unsaturated lactam LI. Treatment of hydrazidoyl halide II, prepared as shown in Scheme I where X=Cl or Br, with triethylamine generates a 1,3-dipolar intermediate LII, which can undergo a [3+2] cycloaddition with the olefin LI to produce the bicyclic pyrazolidine LIII as the predominant regioisomer. Mild oxidation with reagents such as chloranil or nickel peroxide will produce the pyrazolopiperidones LIV. Further oxidation, such as with DDQ, can produce the unsaturated derivatives LV. These steps can be reversed such that initial complete oxidation to LV can be followed by reduction, such as by catalytic hydrogenation, to produce LIV. The ketone derivatives can be prepared by condensation of an appropriate amine $H_2N$—$M_3$ with the cyclic anhydride LVI to give LVII. Alternatively, a saturated derivative of LVI can be condensed with an appropriate amine $H_2N$—$M_3$ followed by oxidation to the unsaturated derivative LVII, such as by treatment with LDA/PhSeSePh and subsequent oxidative selenoxide elimination. The olefin LVII undergoes similar [3+2] cycloaddition to give a pyrazolidine intermediate that is readily oxidized to the pyrazolopiperidinedione derivatives LVIII by a variety of oxidizing agents.

An alternative preparation of compound LIV is also described. A standard alkylation/acylation sequence on the amine $H_2N$—$M_3$ affords amide ester LIX, which contains a protected ketone functionality. A variety of reaction conditions can be employed for these transformations, which are known to those skilled in the art. Deprotection of the ketone followed by Dieckmann condensation under basic conditions affords the cyclic diketoamides LX. Condensation of LX with an appropriate hydrazine is readily accomplished by heating in a solvent such as acetic acid or ethanol to afford the previously described LIV.

Pyrazolopiperidone compounds LXVI (where n=1) wherein the pyrazole 4-substituent $R^{1a}$ is a trifluoromethyl group can be prepared via the method outlined in Scheme X. Coupling of the acid LXI with amines $H_2N$—$M_3$ can be accomplished under a variety of conditions, such as via the acid chloride, giving amide LXII. A straightforward sequence involving cleavage of the tetrahydrofuran ring and intramolecular cyclization on the amide nitrogen affords the ketolactam LXIII. This compound can also be prepared from the lactam LXIV by introduction of sulfur substituents and subsequent oxidation to the ketolactam LXIII. Formation of the morpholine or related enamine followed by reaction with trifluoroacetic anhydride leads to the trifluoroacetylated intermediate LXV. Alternatively, dichlorination of lactam LXIV with PCl₅ or analogous reagents, heating with excess morpholine or related amine, and reacting the enamine derived in this way with trifluoroacetic anhydride also yields the trifluoroacetylated intermediate LXV. This compound can be readily condensed with an appropriate hydrazine to afford the pyrazolopiperidone compounds LXVI. Analogous chemistry can be utilized to afford [5,7]-fused ring systems (where n=2).

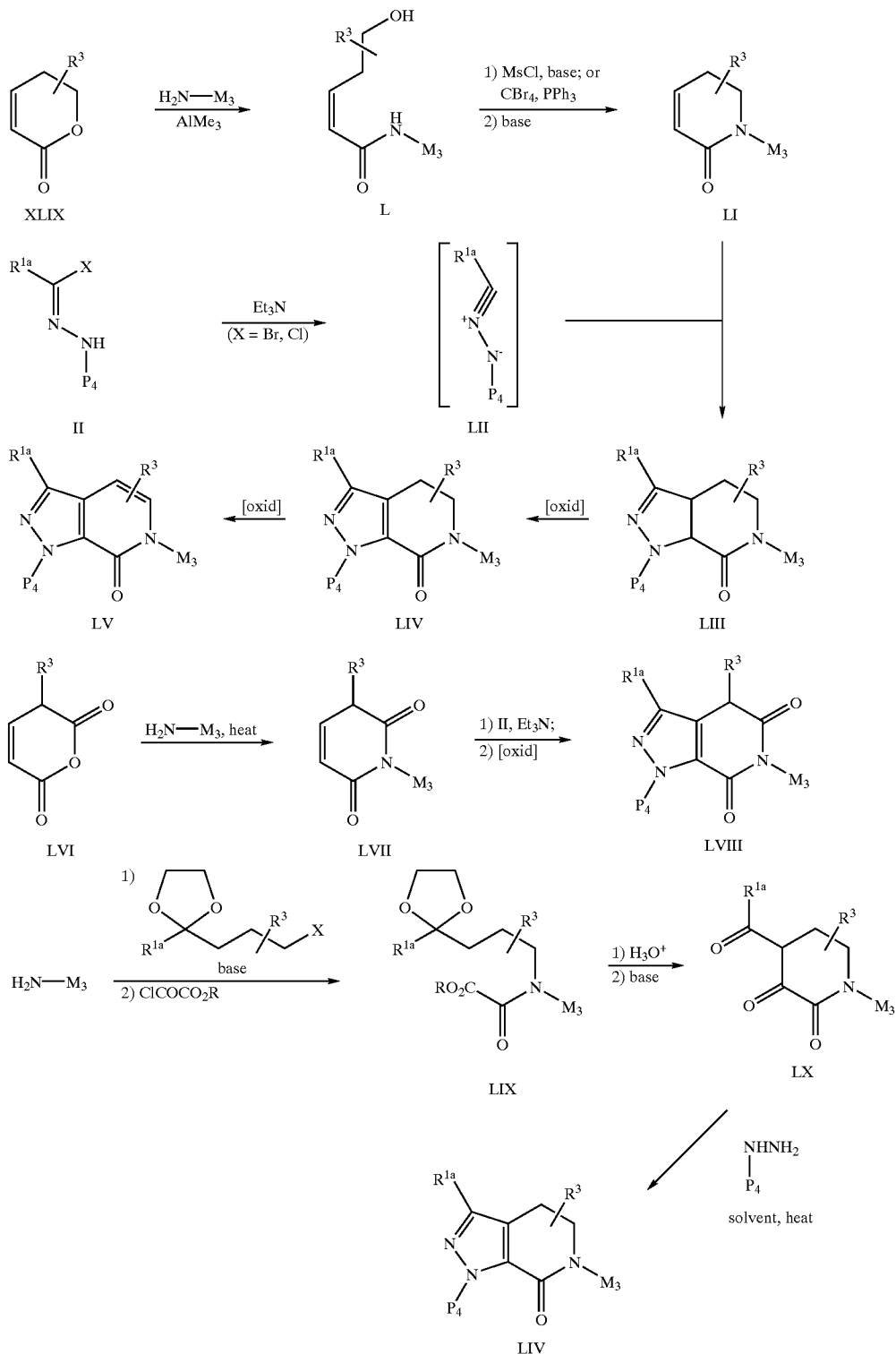

Unsaturated analogs of the above compounds can be prepared as shown in the bottom of Scheme X. Bromination of LXVII, prepared as described in Scheme IX and the top of Scheme X, affords bromo analog LXVIII. Elimination of HBr by treatment with any of a variety of bases, such as DBU, will afford the unsaturated bicylic analogs LXIX. Additional analogs can be prepared by displacement of the bromide LXVIII by any of a wide variety of nitrogen-, oxygen- and sulfur-based nucleophiles.

4H-pyran-4-one and tetrahydrothiopyran-4-one, provides tetrahydro-1,4-oxazepin-5(2H)-one and tetrahydro-1,4-thiazepin-5(2H)-one. Compounds LXXI where X is NH or NR can be prepared by Schmidt rearrangement of 4-piperidone monohydrate hydrochloride or protected 4-piperidone (Groves, J. T. and Chambers, R. R. Jr. *J. Am. Chem. Soc.* 1984, 106, 630–638). Ullmann coupling of the lactam with I(Br)—$M_3$ provides the lactam LXXII with an

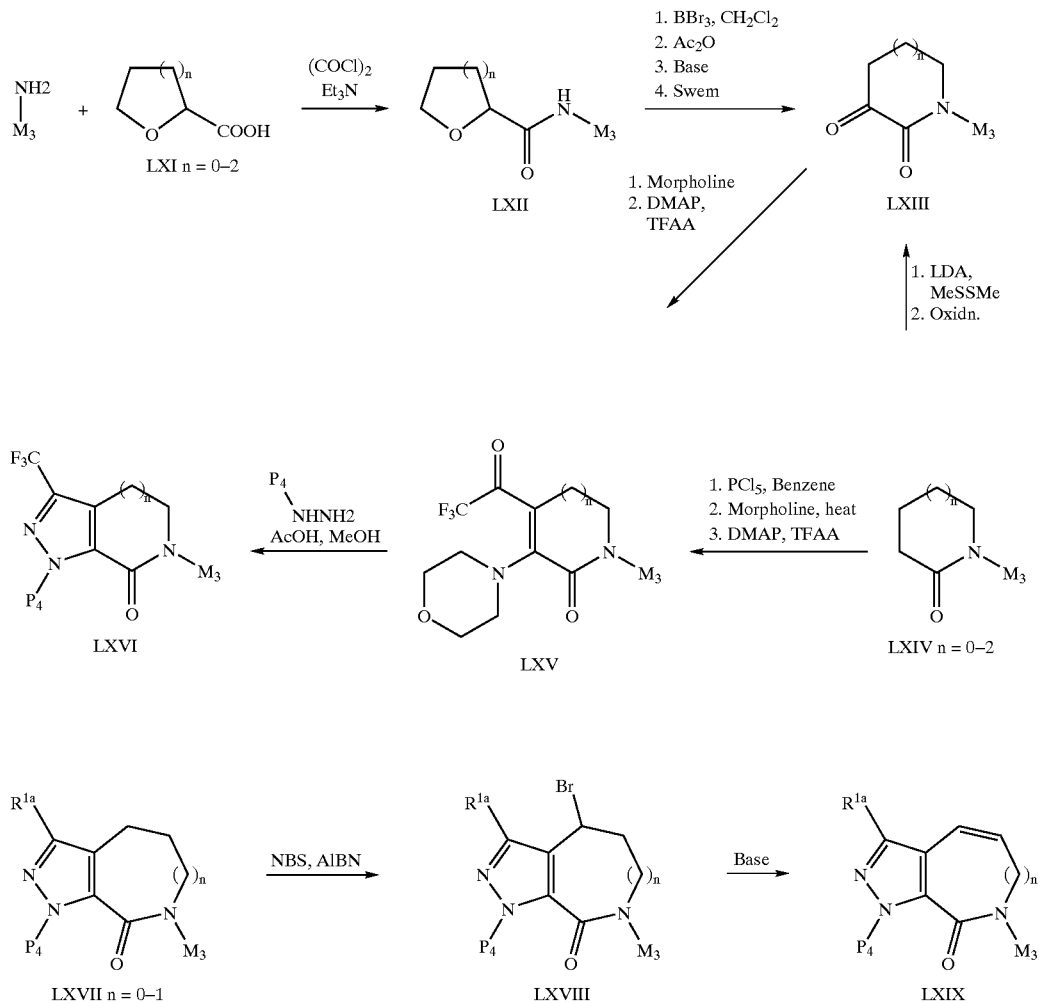

Additional [5,7]-fused bicyclic systems which contain an additional heteroatom in the seven-membered ring can be prepared as shown in Scheme XI. Compounds LXXI where X is O or S can be prepared from commercially available tetrahydro-4H-pyran-4-one and tetrahydrothiopyran-4-one. Photoinduced Schmidt rearrangement of (triisopropylsilyl) azidohydrin (Evans, P. A. and Modi, D. P. *J. Org. Chem.* 1995, 60, 6662–6663), which is formed from tetrahydro- $M_3$ residue. Dichloronation with phosphorus pentachloride or related reagent affords a dichlorinated intermediate which can react with morpholine to give the enamine LXXIII. Reaction of LXXIII with DMAP and an appropriate acid chloride or acid anhydride provides the acylenamine intermediate LXXIV which can be condensed with an appropriate hydrazine in acetic acid to afford the [5,7]-fused bicyclic compounds LXXV.

Scheme XI

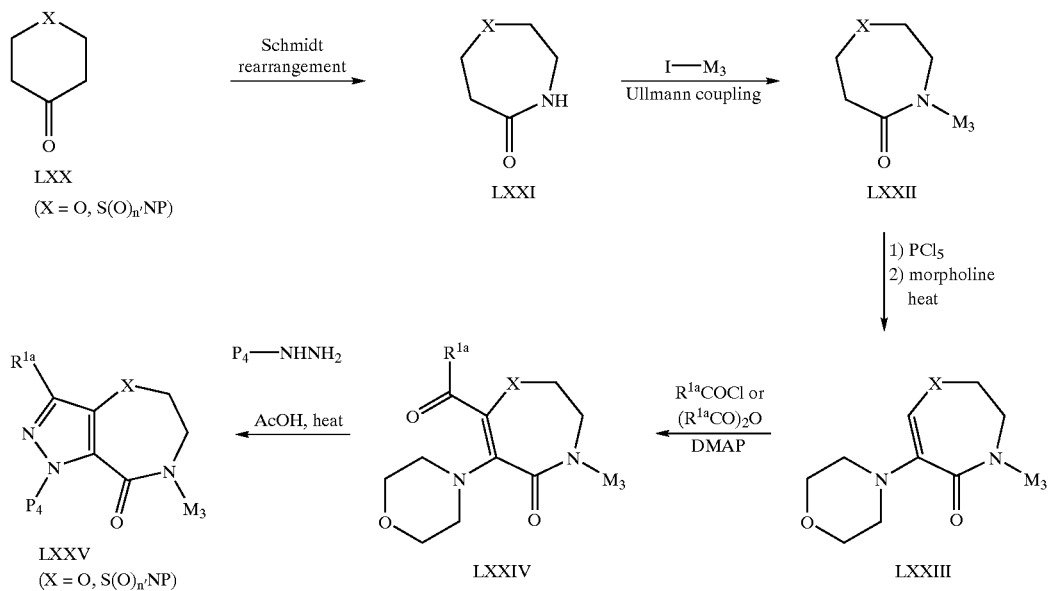

Bicyclic compounds of Formulas Ia, Ib, and Ic which contain a carbon atom at the pyrazole 4-position and wherein the $M_3$ residue is attached to a carbon atom are also prepared by a [3+2] cycloaddition strategy as shown in Scheme XII. Unsaturated cyclic ketones LXXVI are readily available by standard synthetic methods known to those skilled in the art. The [3+2] cycloaddition with the 1,3-dipole generated from II as described previously gives a pyrazolidine intermediate that can be readily oxidized to the pyrazolocyclohexanone LXXVII. Introduction of a double bond, such as by treating with LDA and PhSeSePh followed by oxidative selenoxide elimination, gives the unsaturated derivative LXXVIII. Incorporation of a residue such as a protected alcohol into the unsaturated ketone, represented by LXXIX, leads to pyrazolocyclohexanone LXXX following [3+2] cycloaddition and subsequent oxidation. Deprotection of the alcohol and oxidation by a variety of reagents affords the pyrazolocyclohexanedione LXXXI.

Scheme XII

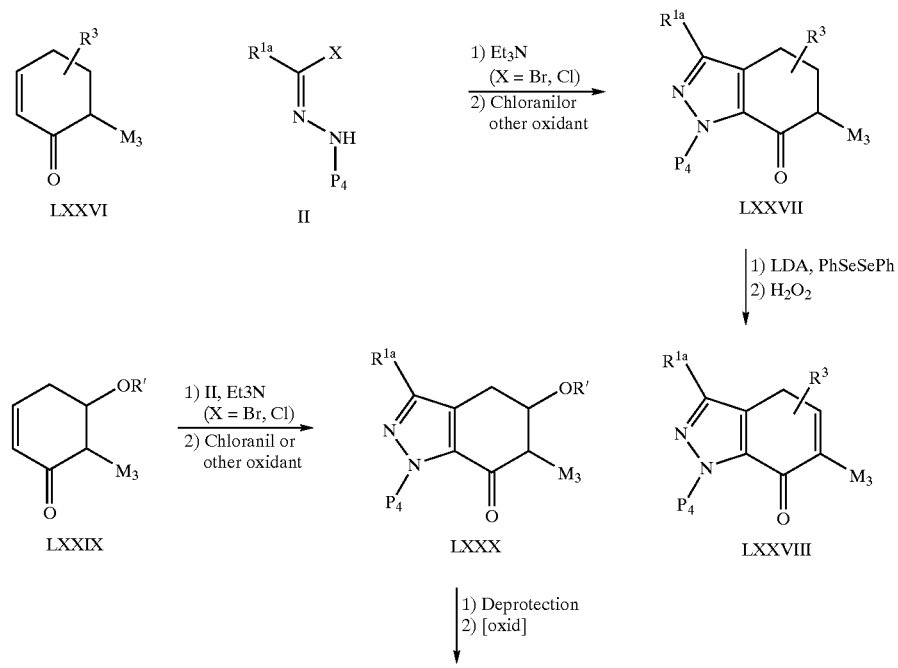

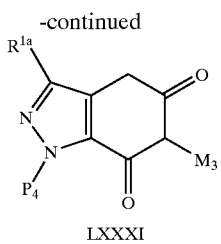

LXXXI

Additional bicyclic compounds of Formulas Ia, Ib, and Ic containing a carbon atom at the pyrazole 4-position are described in Scheme XIII. Condensation of hydrazidoyl halide II with a diketoester in the presence of a base such as alkoxide affords pyrazoles LXXXII. Heating this ketoester in the presence of readily available hydrazines $M_3$—NHNH$_2$ affords the pyrazolopyridazinones LXXXIII.

For preparation of pyrazolopyridazinones where $R^3$ is hydrogen, the hydrazidoyl halide II can be cyclized with a furyl ketoester in the presence of alkoxide base to afford LXXXIV. Standard functional group manipulations, involving ester reduction and protection, furyl oxidation and esterification leads to LXXXV, although not necessarily in that order. Those skilled in the art will be able to determine a proper order and appropriate reagents for achieving these transformations. Alcohol deprotection and oxidation, such as by manganese dioxide, affords an aldehyde ester which readily produces LXXXVI upon heating in the presence of a hydrazine $M_3$—NHNH$_2$. Appropriate functional group manipulation of LXXXIV, of which many methods are available, can also afford ester acids LXXXVII. Activation of the carboxylic acid, such as by formation of the acid chloride with oxalyl chloride, followed by heating in the presence of a hydrazine $M_3$—NHNH$_2$ affords the pyrazolopyridazinedione LXXXVIII.

Scheme XIII

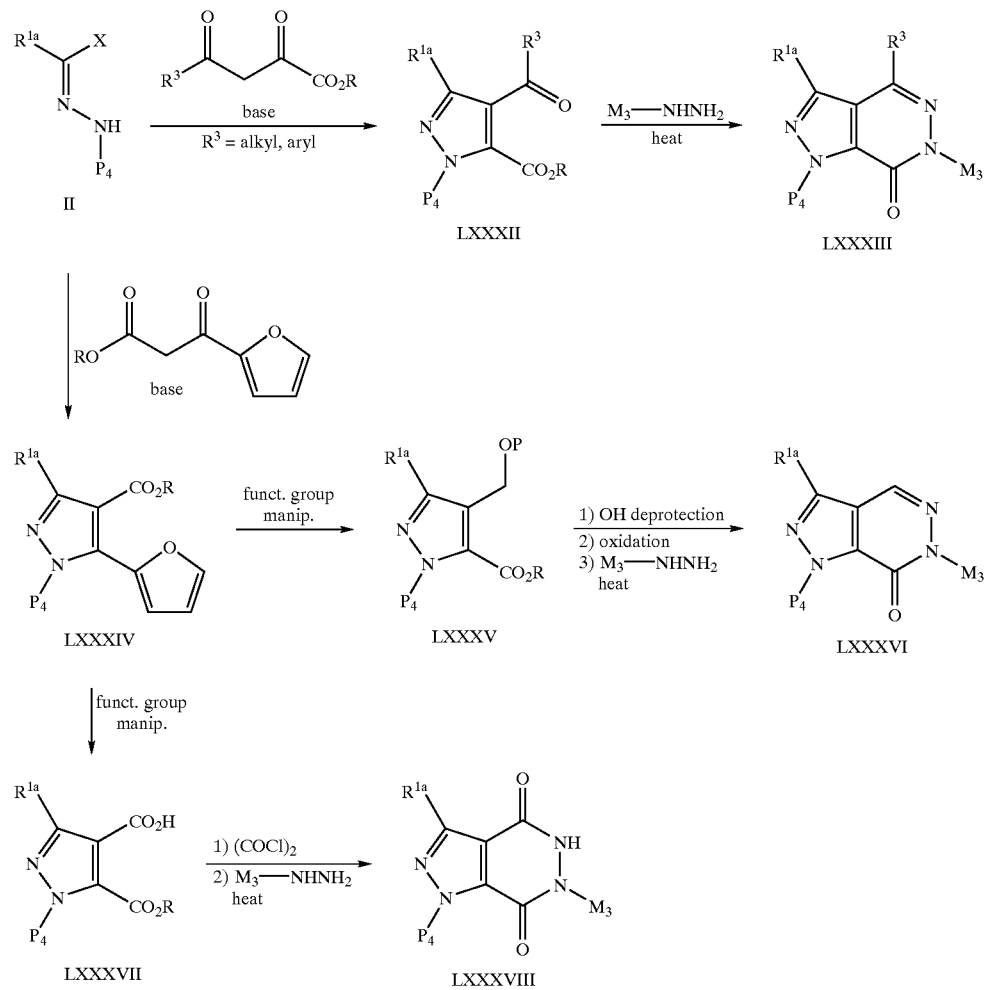

The preparation of the compounds of Formulas Ia, Ib, and Ic where the five-membered ring is triazole is accomplished using azide intermediates. Azides readily undergo [3+2] cycloaddition reactions with a variety of olefins and alkynes, and the application of this reaction to the synthesis of the triazole-fused bicyclic compounds of Formulas Ia, Ib, and Ic is shown in Scheme XIV. As described for the pyrazole-fused compounds previously, the 4-amino-1,2,3-triazole-5-carboxylate XCII is a particularly useful intermediate for the preparation of many of the triazole-fused bicyclic systems. The required azides LXXXIX are readily available. Aliphatic azides are easily prepared from the corresponding bromide by displacement with sodium azide in solvents such as dimethylformamide and dimethyl sulfoxide. $P_4$ represents an aryl azide. These types of azides are readily available from the corresponding aniline by diazotization with $NaNO_2$ in acidic medium followed by displacement of the diazonium ion with sodium azide. The [3+2] cycloaddition of azides LXXXIX with nitroolefins XC (R'=Me, 2-furyl) affords the triazoles XCI as the major product, in which initial cyclization to a triazoline intermediate is followed by autooxidation to the triazole products (Cailleux, P.; et. al. *Bull. Soc. Chim. Belg.* 1996, 105, 45). These reactions can be performed in refluxing benzene or similar solvents at similar temperatures. Conversion of XCI to the 4-amino-1,2,3-triazole-5-carboxylate XCII is straightforward. When R' is methyl, oxidation of the methyl group with an oxidant such as $KMnO_4$ gives the carboxylic acid which can be esterified to an appropriate ester. Reduction of the nitro group by any of a variety of reducing agents, preferably $SnCl_2$ or catalytic hydrogenation, gives XCII. When R' is 2-furyl, the carboxylic acid can be unmasked by a variety of oxidizing agents, including ozone, $KMnO_4$ and sodium periodate/ruthenium trichloride, to give the carboxylic acid which can be esterified and reduced as described above to afford XCII. The 4-hydroxy-1,2,3-triazole-5-carboxylates can be obtained via the diazonium ion of XCII as described for the pyrazole series to afford XCIV.

The reaction of azides LXXXIX with active methylene compounds is also illustrated in Scheme XIV. Treating LXXXIX with cyano- or nitropyruvates in the presence of a base such as alkoxide affords triazoles XCIII. The triazole-4-carboxylate derivatives can be prepared by treating LXXXIX with a furyl ketoester in the presence of alkoxide base to afford XCV. These reactions are analogous to those described in Scheme I for the pyrazole derivatives. The triazole-containing bicyclic systems having a carbon atom at the 4-position of the triazole can be prepared by [3+2] cycloaddition of an appropriate azide LXXXIX with an unsaturated lactam LI or an unsaturated cyclic ketone LXXVI. These cycloadditions are performed by heating in an appropriate solvent, such as benzene or toluene. The resulting triazoline intermediates are readily oxidized to the fused triazoles using chloroanil, nickel peroxide or other mild oxidant to give XCVI and XCVII, respectively.

The triazole intermediates XCI, XCII, XCIII, XCIV, XCV, XCVI and XCVII can be transformed into the final triazole-containing bicyclic compounds described by Formulas Ia, Ib, and Ic following the procedures described for the corresponding pyrazole derivatives in Schemes II–XI. The nitro group present in XCI and XCIII can correspond to the "N—PG" residue described in Schemes II–VIII, or alternatively, the nitro group can be reduced at an appropriate time and further protected as a suitable carbamate derivative or as an azido group.

Scheme XIV

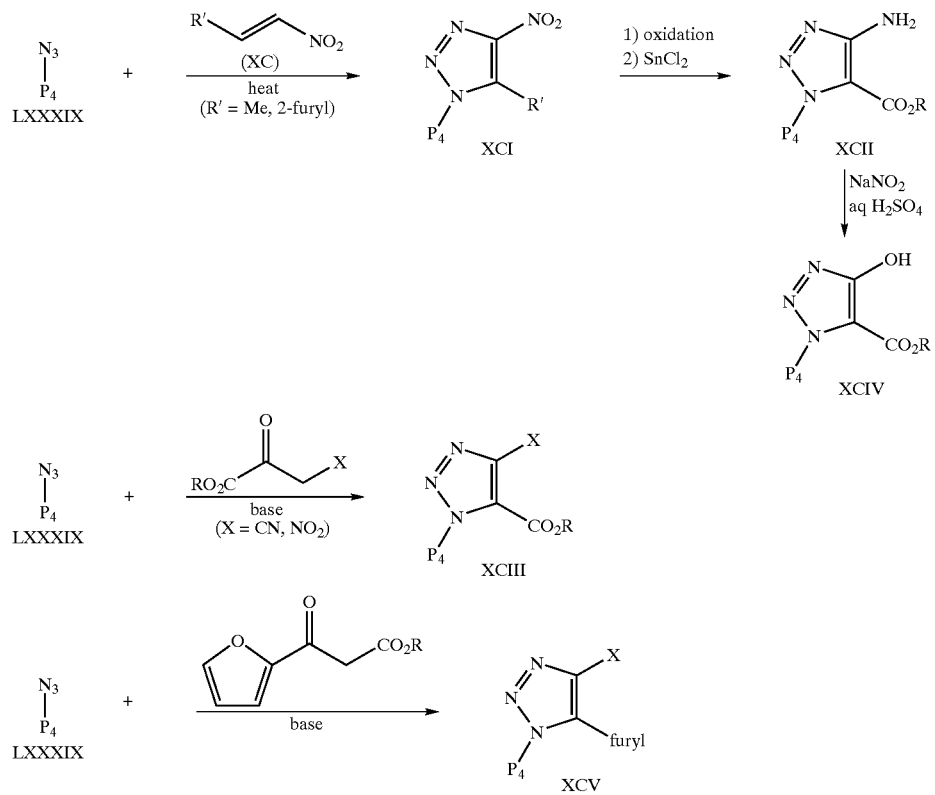

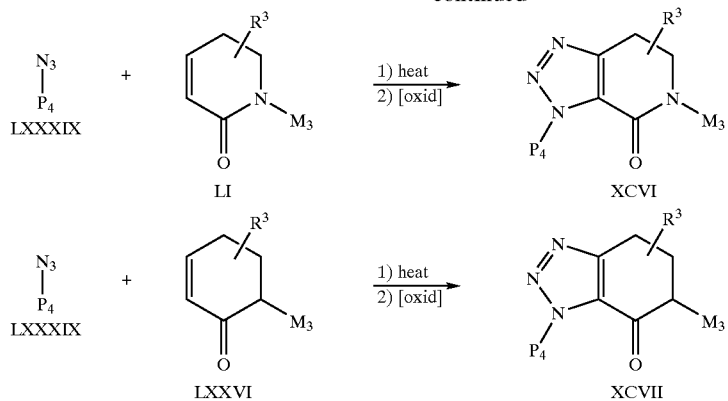

The preparation of the compounds of Formulas Ia, Ib, and Ic where the five-membered ring is isoxazole is accomplished as shown in Scheme XV. The hydroximinoyl chloride XCIX is a useful intermediate for the preparation of isoxazole-fused compounds. This intermediate is readily available from appropriate aldehydes XCVIII by oxime formation with hydroxylamine followed by chlorination with N-chlorosuccinimide. Treatment of XCIX with a cyanoacetate in the presence of a base such as carbonate results in cyclization to give a 5-aminoisoxazole-4-carboxylate C. The amino residue of C can be readily converted into the corresponding hydroxy or cyano derivatives CI and CII, respectively, via the diazonium ion, as described earlier for the pyrazole and triazole compounds.

The isoxazole-5-carboxylates are available from cyclization of XCIX with a furan ketoester to give CIII. Oxidation of the furan to a carboxylic acid residue is accomplished by a variety of oxidizing agents as described earlier.

The hydroxyiminoyl chloride XCIX can also be treated with a base such as triethylamine to generate a nitrile oxide intermediate, which can undergo [3+2] cycloaddition reactions with appropriate olefins or alkynes. This is a convenient method by which to prepare bicyclic compounds containing a carbon atom at the 5-position of the isoxazole ring. For example, cycloaddition with the unsaturated lactam LI leads to formation of a fused isoxazoline intermediate which is readily oxidized with reagents such as nickel peroxide, chloranil or DDQ to afford CIV. Cycloaddition with unsaturated cyclic ketone and oxidation under the same conditions affords the ketone analog CV. The isoxazole-fused intermediates C, CI, CII, CIII, CIV and CV can be transformed into the final isoxazole-containing bicyclic compounds described by Formulas Ia, Ib, and Ic following the procedures described for the corresponding pyrazole derivatives in Schemes II–XI.

Scheme XV

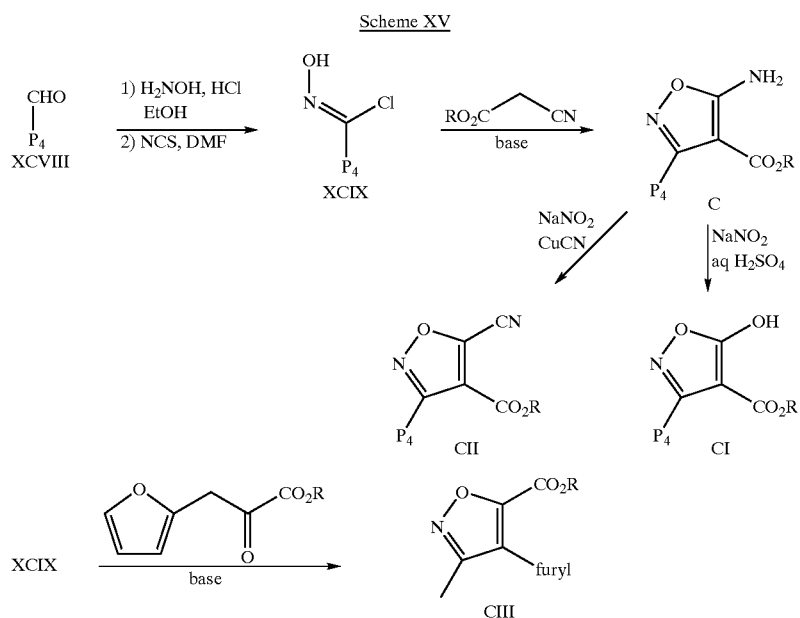

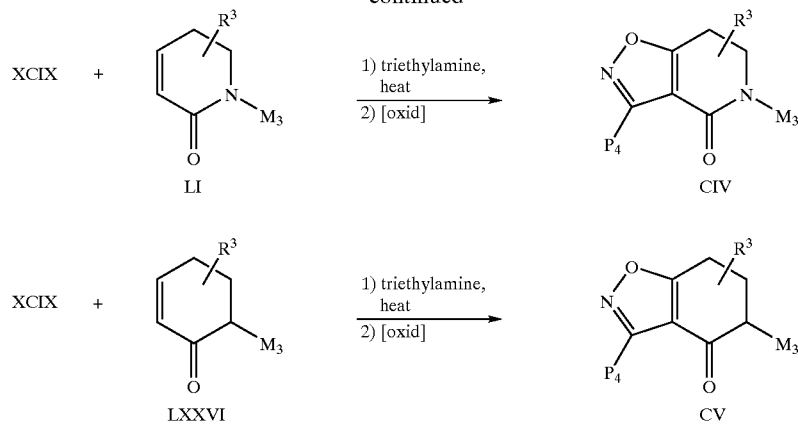

The preparation of the compounds of Formulas Ia, Ib, and Ic where the five-membered ring is isothiazole is accomplished as shown in Scheme XVI. One method for preparing the 5-aminoisothiazole-4-carboxylate intermediate CVIII proceeds from readily available acid chloride CVI. Condensation of CVI with a cyanoacetate in the presence of a base such as a magnesium alkoxide followed by treatment with ammonia in an alcoholic solvent gives an aminonitrile CVII. Treatment with hydrogen sulfide in the presence of a base such as triethylamine affords a thioamide that can undergo an oxidative cyclization to CVIII upon treatment with hydrogen peroxide or bromine. As described in previous schemes, the amino residue can easily be converted into the corresponding hydroxyl or cyano derivatives CIX or CX, respectively.

Another useful intermediate for the preparation of isothiazole compounds of the present invention is the nitrile sulfide CXIII. This intermediate can be generated conveniently from heterocycle CXII, which itself can be prepared from amides CXI either by treating with chlorocarbonylsulfenyl chloride or by treating with trichloromethanesulfenyl chloride followed by aqueous sodium hydroxide. Thermolysis of heterocycle CXII affords the nitrile sulfide CXIII, which can undergo many of the same reactions as the corresponding nitrile oxide intermediates. For example, [3+2] cycloaddition of CXIII with olefins LI and LXXVI can afford, after subsequent mild oxidation as described previously, the isothiazole-fused compounds CXIV and CXV, respectively. Isothiazole intermediates CVIII, CIX, CX, CXIV and CXV can be transformed into the final isothiazole-containing bicyclic compounds described by Formulas Ia, Ib, and Ic following the procedures described for the corresponding pyrazole derivatives in Schemes II–XI.

Scheme XVI

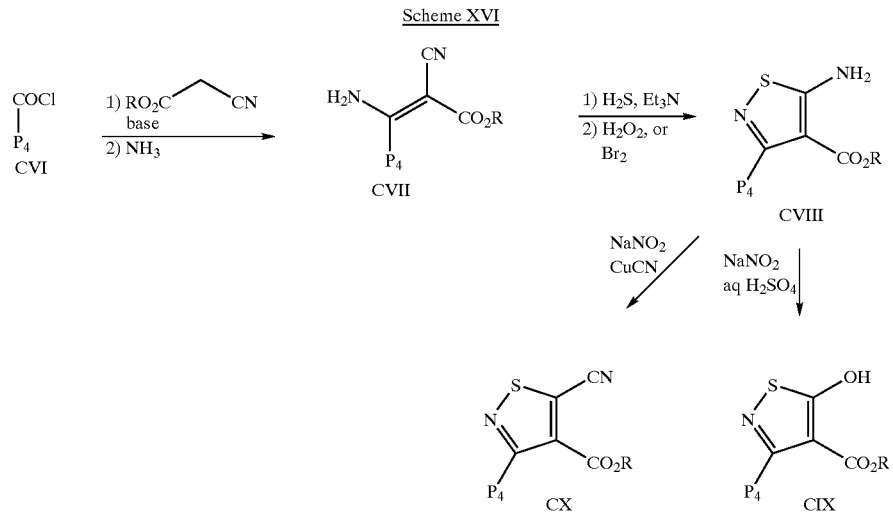

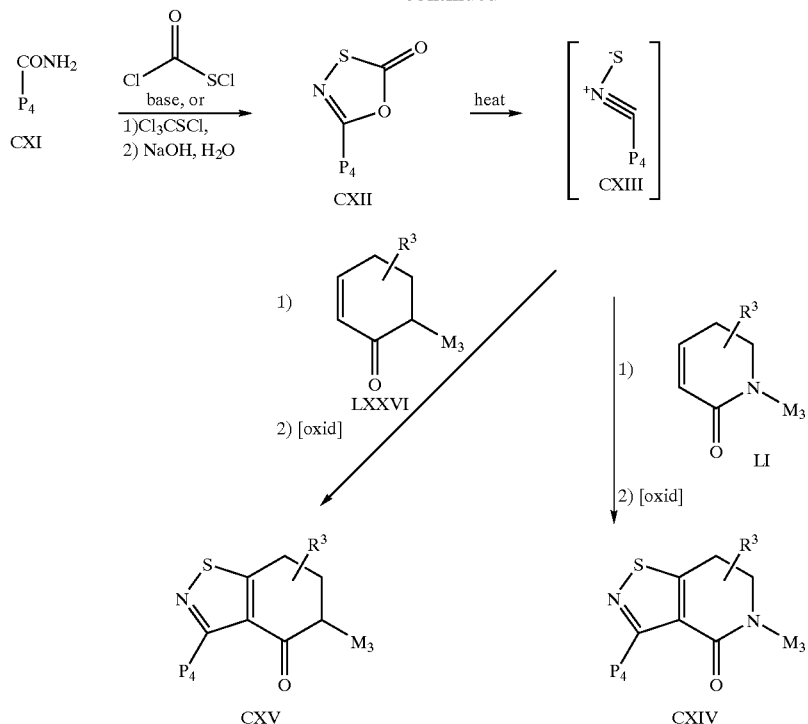

Formulas Ia, Ib, and Ic also describes pyrazole-fused bicyclic compounds in which the $P_4$ group resides on a carbon atom of the pyrazole ring. These compounds can be prepared as shown in Scheme XVII. Condensation of acid chlorides CVI with cyanoacetates in the presence of a base such as magnesium methoxide affords an enol derivative that is converted to the enol ether CXVI (X=OMe) with diazomethane or to the chloro derivative CXVI (X=Cl) with $POCl_3$. Heating with hydrazine (R'=H) or a substituted hydrazine affords 5-amino-4-carboxylate CXVII. The amino residue of CXVII can be converted to the hydroxyl or cyano derivative CXVIII or CXIX, respectively via the diazonium ion as described previously.

The 5-carboxylate derivatives can be prepared by condensing a substituted hydrazine with a hemiacetal or related derivative represented by CXX. Chlorination or bromination with NCS or NBS, respectively, affords the hydrazidoyl halides CXXI. Reaction of CXXI with the anion of a furyl ketoester affords the 5-carboxylate CXXII, the furan residue of which can be oxidized to a carboxylic acid residue by methods described previously.

The hydrazidoyl halides CXXI can also participate in [3+2] cycloadditions as described previously to afford, after oxidation of the intermediate pyrazolines, the pyrazole-fused compounds CXXIII and CXXIV. The intermediates CXVII, CXVIII, CXIX, CXXII, CXXIII and CXXIV can be transformed into the final C-linked pyrazole-containing bicyclic compounds described by Formulas Ia, Ib, and Ic following the procedures described for the corresponding N-linked pyrazole derivatives in Schemes II–XI.

Scheme XVII

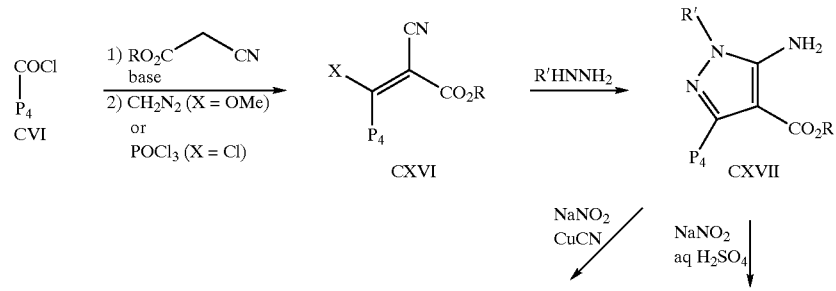

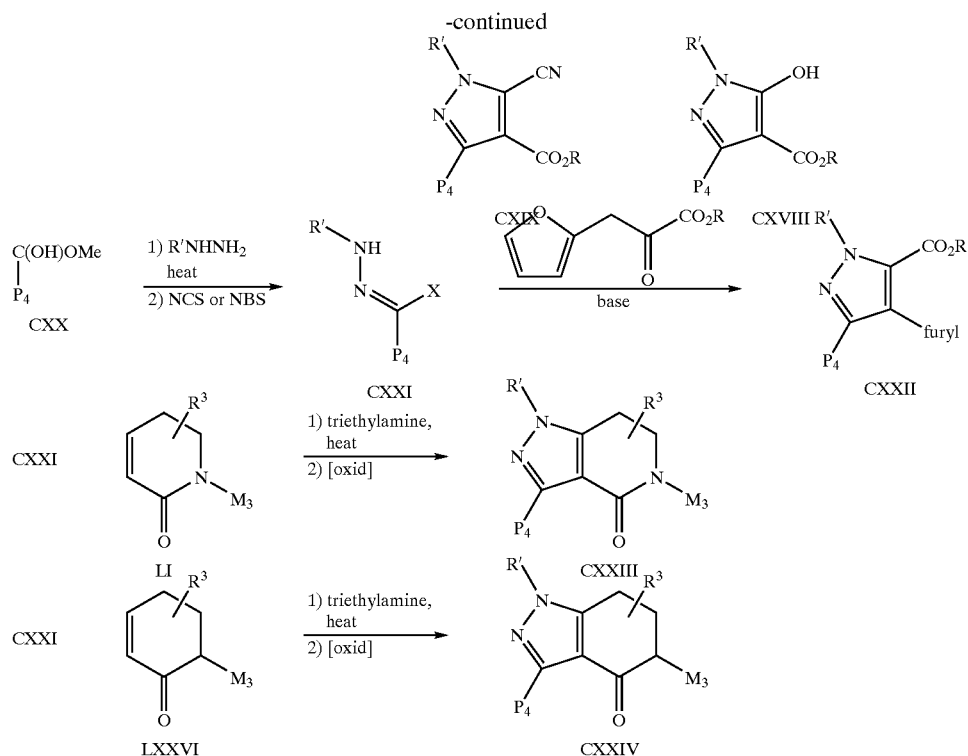

Bicyclic compounds of the present invention in which the five membered ring is pyrrole and the $P_4$ group is attached to a carbon atom can be prepared as shown in Scheme XVIII. For compounds of this type wherein a nitrogen atom is required at the pyrrolo 2-position, the 2-aminopyrrole CXXVI is a useful intermediate. This compound can be prepared by condensation of readily obtained aminocarbonyl compounds CXXV with an appropriate cyanoacetate. This condensation can be carried out under basic conditions or by heating with azeotropic removal of water. The 2-aminopyrroles CXXVI can be diazotized and subsequently converted into the 2-cyano- and 2-hydroxypyrroles CXXVII, which are suitable intermediates for a variety of the bicyclic compounds of this invention.

Pyrrole 2,3-dicarboxylates can also be prepared from aminocarbonyl compounds CXXV. Michael addition under basic conditions with acetylenedicarboxylate esters is followed by in situ ring closure to afford the pyrrole 2,3-dicarboxylate diester. Selective hydrolysis of one of the esters, typically the 2-ester, affords the pyrrole 2-carboxylic acid CXXVIII. Curtius rearrangement of CXXVIII affords another route to the 2-aminopyrrole CXXVI. Also, the carboxylic acid can be reduced to the alcohol CXXIX using borane or by sodium borohydride reduction of the derived mixed anhydride. Following procedures described in Schemes II–VIII and Scheme XIII, the intermediates CXXVI, CXXVII, CXXVIII and CXXIX can be converted to the final pyrrolo-fused bicyclic compounds of Formulas Ia, Ib, and Ic. Other procedures not described here are also known to those skilled in the art and can be used to prepare the pyrrolo-fused bicyclic compounds of Formulas Ia, Ib, and Ic.

Scheme XVIII

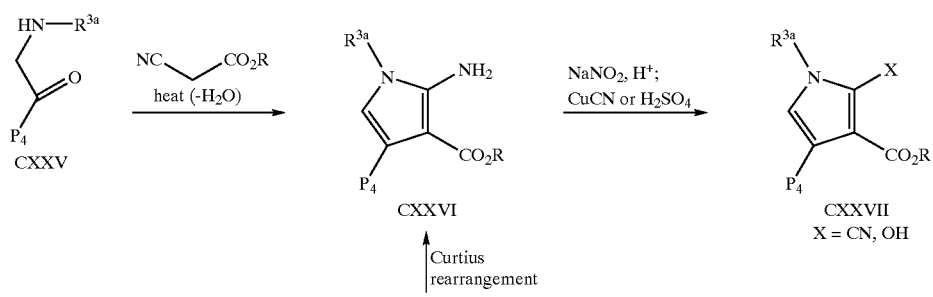

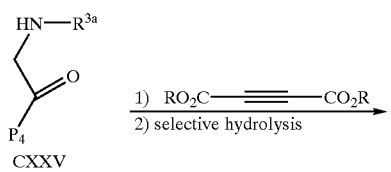
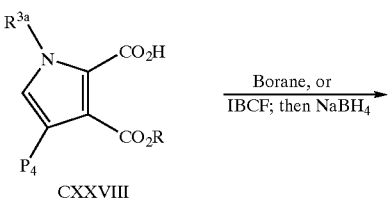

Bicyclic compounds of the present invention in which the five membered ring is furan and the P$_4$ is attached to a carbon atom can be prepared as shown in Scheme XIX. For compounds of this type wherein a nitrogen atom is required at the furyl 2-position, the 2-aminofuran CXXXI is a useful intermediate. These compounds can be prepared analogously to the pyrrole analogs described in Scheme XVIII. Thus, condensation of readily obtained hydroxycarbonyl compounds CXXX with an appropriate cyanoacetate affords the 2-aminofurans CXXXI. This condensation can be carried out under basic conditions or by heating with azeotropic removal of water. The 2-aminofurans CXXXI can be diazotized and subsequently converted into the 2-cyano- and 2-hydroxyfurans CXXXII, which are suitable intermediates for a variety of the bicyclic compounds of this invention.

Furan 2,3-dicarboxylates can also be prepared from hydroxycarbonyl compounds CXXX, analogously to the pyrrole analogs described in Scheme XVIII. Michael addition of CXXX under basic conditions with acetylenedicarboxylate esters is followed by in situ ring closure to afford the furan 2,3-dicarboxylate diester. Selective hydrolysis of one of the esters, typically the 2-ester, affords the furan 2-carboxylic acid CXXXIII. Curtius rearrangement of CXXXIII affords another route to the 2-aminofurans CXXXI. Also, the carboxylic acid can be reduced to the alcohol CXXXIV using borane or by sodium borohydride reduction of the derived mixed anhydride. Following procedures described in Schemes II–VIII and Scheme XIII, the intermediates CXXXI, CXXXII, CXXXIII and CXXXIV can be converted to the final furan-fused bicyclic compounds of Formulas Ia, Ib, and Ic. Other procedures not described here are also known to those skilled in the art and can be used to prepare the furan-fused bicyclic compounds of Formulas Ia, Ib, and Ic.

Scheme XIX

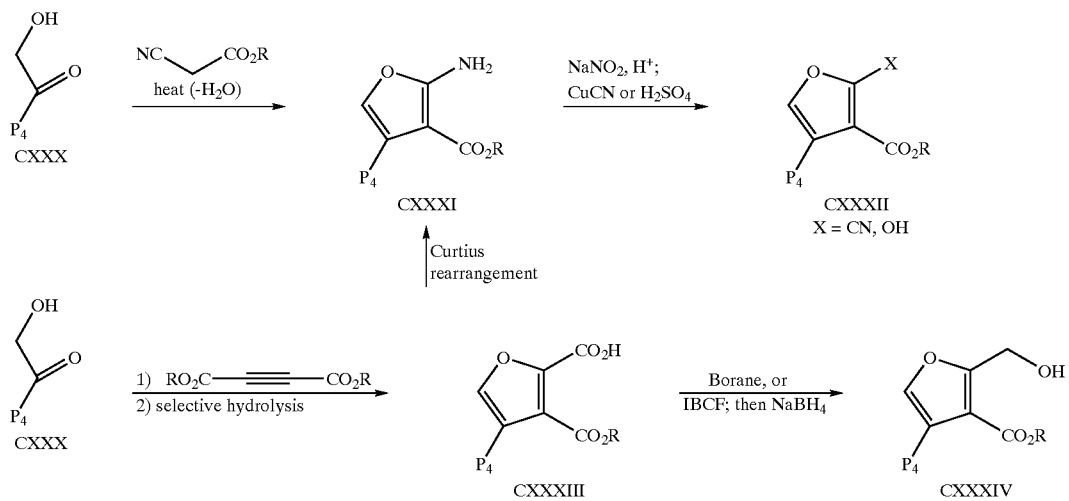

Bicyclic compounds of the present invention in which the five membered ring is thiophene and the P$_4$ is attached to a carbon atom can be prepared as shown in Scheme XX. For compounds of this type wherein a nitrogen atom is required at the thiophene 2-position, the 2-aminothiophene CXXXVI is a useful intermediate. These compounds can be prepared analogously to the pyrrole analogs described in Scheme XVIII. Thus, condensation of readily obtained mercaptocarbonyl compounds CXXXV with an appropriate cyanoacetate affords the 2-aminothiophenes CXXXVI. This condensation can be carried out under basic conditions or by heating with azeotropic removal of water. Alternatively, condensation of the cyanoacetate with ketone CXXXVIII affords olefin CXXXIX. In a subsequent step, CXXXIX can be converted into 2-aminothiophenes CXXXVI by treatment with S$_8$ and a base such as triethylamine. The 2-aminothiophenes CXXXVI can be diazotized and subsequently converted into the 2-cyano- and 2-hydroxythiophenes CXXXVII, which are suitable intermediates for a variety of the bicyclic compounds of this invention.

Thiophene 2,3-dicarboxylates can be prepared from alkali-metal acetylenethiolates CXL. These compounds react with acetylenedicarboxylate esters in a [3+2] cycloaddition to afford thiophene 2,3-dicarboxylate diesters. Selective hydrolysis of one of the esters, typically the 2-ester, affords the thiophene 2-carboxylic acid CXLI. Curtius rearrangement of CXLI affords another route to the 2-aminothiophenes CXXXVI. Also, the carboxylic acid can be reduced to the alcohols CXLII using borane or by sodium borohydride reduction of the derived mixed anhydride. Following procedures described in Schemes II–VIII and Scheme XIII, the intermediates CXXXVI, CXXXVII, CXLI and CXLII can be converted to the final thiophene-fused bicyclic compounds of Formulas Ia, Ib, and Ic. Other procedures not described here are also known to those skilled in the art and can be used to prepare the thiophene-fused bicyclic compounds of Formulas Ia, Ib, and Ic.

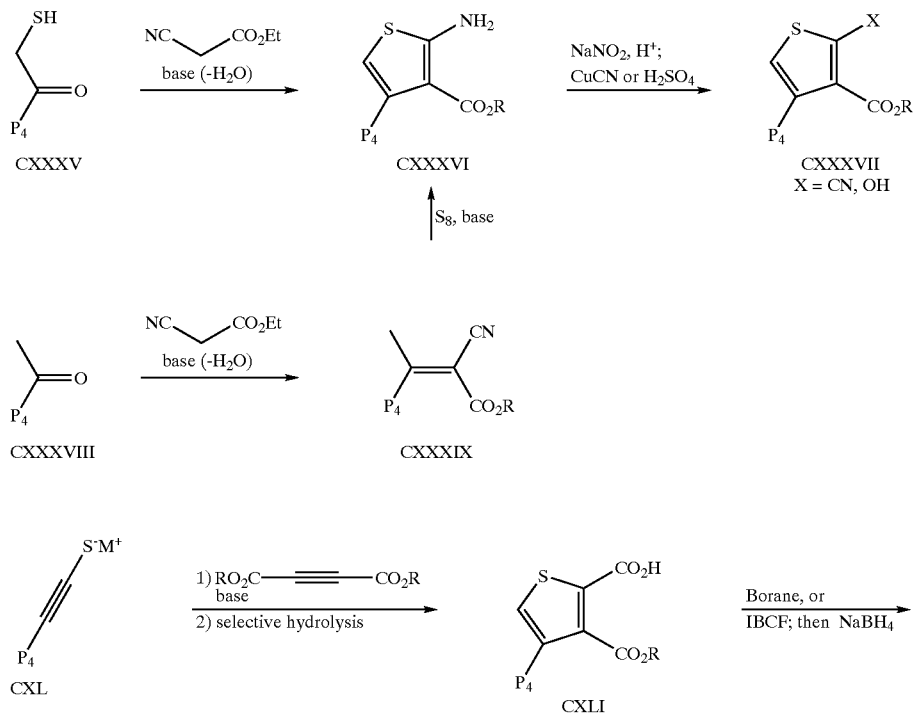

Bicyclic compounds of the present invention in which the five membered ring is imidazole and $P_4$ is attached to a nitrogen atom can be prepared as shown in Scheme XXI. These compounds CXLIII through CLXIV, where the R group may be alkyl, aryl or a protecting group PG, are available either from commercial sources or through known prior art and can be represented generically by CLXV. Suitable protection of the imidazole nitrogen affords compounds of the type CLXVI, which are further elaborated via a cupric mediated coupling of appropriate $M_3$ containing boronic acid to yield CLXVII. Subsequent removal of the imidazole-protecting group PG affords compounds such as CLXVIII. The introduction of a $P_4$ substituent is accomplished as before by the coupling of a $P_4$ containing boronic acid in a manner such that the $P_4$ group is transferred to the imidazole nitrogen as depicted by CLVIX.

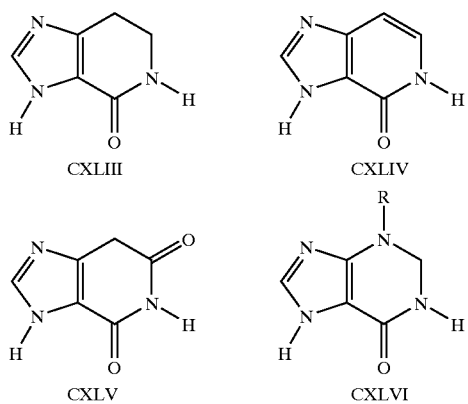

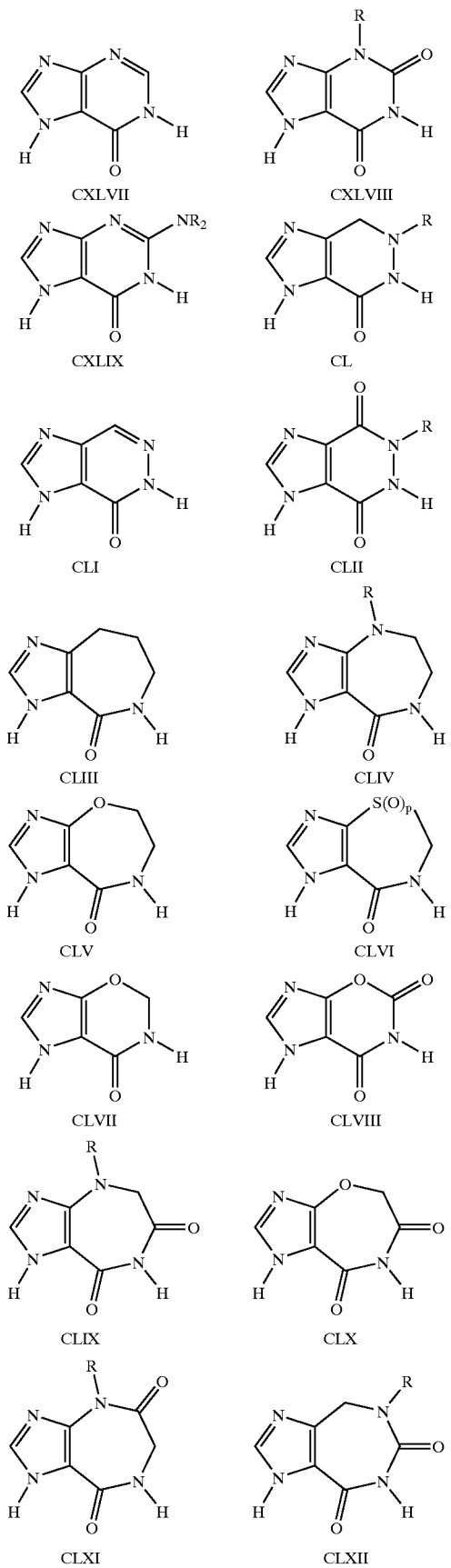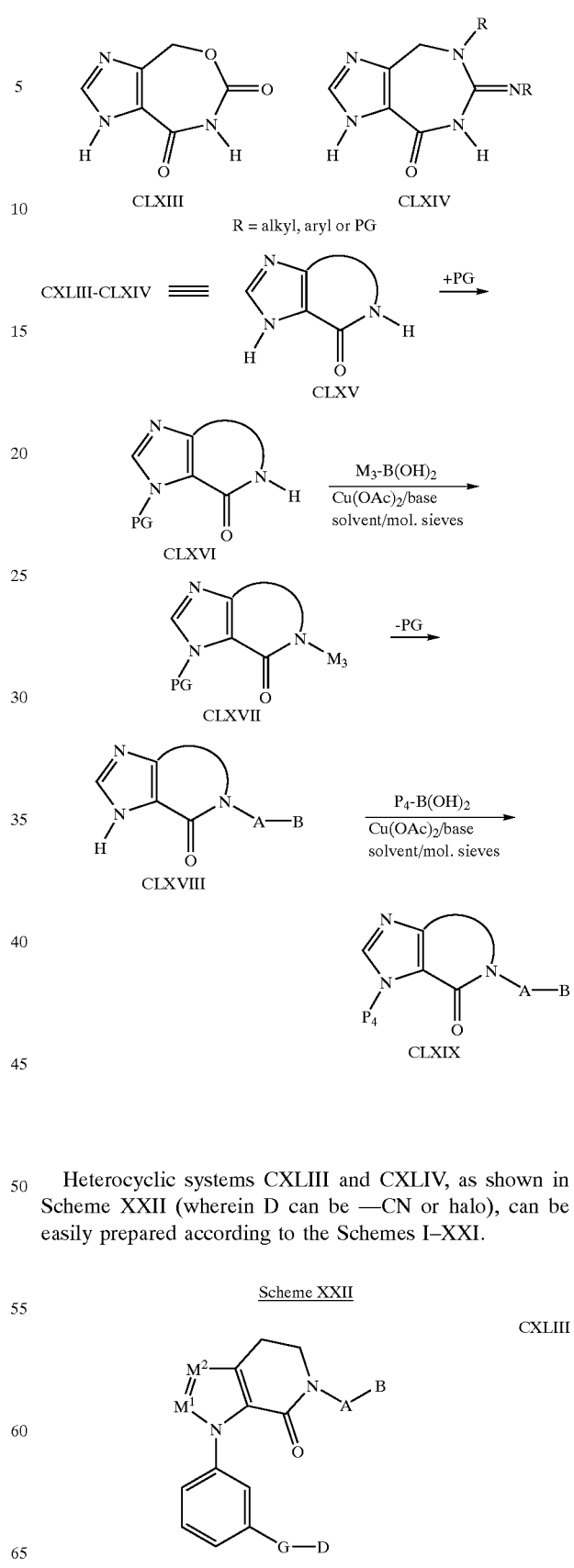
Heterocyclic systems CXLIII and CXLIV, as shown in Scheme XXII (wherein D can be —CN or halo), can be easily prepared according to the Schemes I–XXI.
Scheme XXII
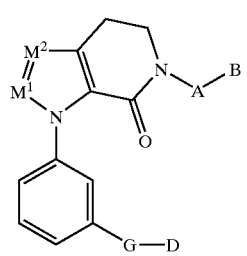
CXLIII

CXLIV

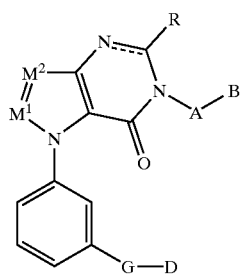

The compounds of the present invention have a group "A—B" and a group "G—D" attached to ring Q. Preparations of some of the "A—B" moieties can follow the same methods described in WO97/23212, WO97/30971, WO97/38984, WO98/01428, WO98/06694, WO98/28269, WO98/28282, WO98/57934, WO98/57937, and WO98/57951, the contents of which are incorporated herein by reference.

Compounds of this invention wherein G is absent and D is a cyano group CXLV can be easily manipulated to afford thiadiazoles CXLVI, oxadiazoles CXLVII, triazoles CXLVIII, pyrazoles CXLIX-CL, and triazolones CLI-CLII as outlined in Scheme XXIII.

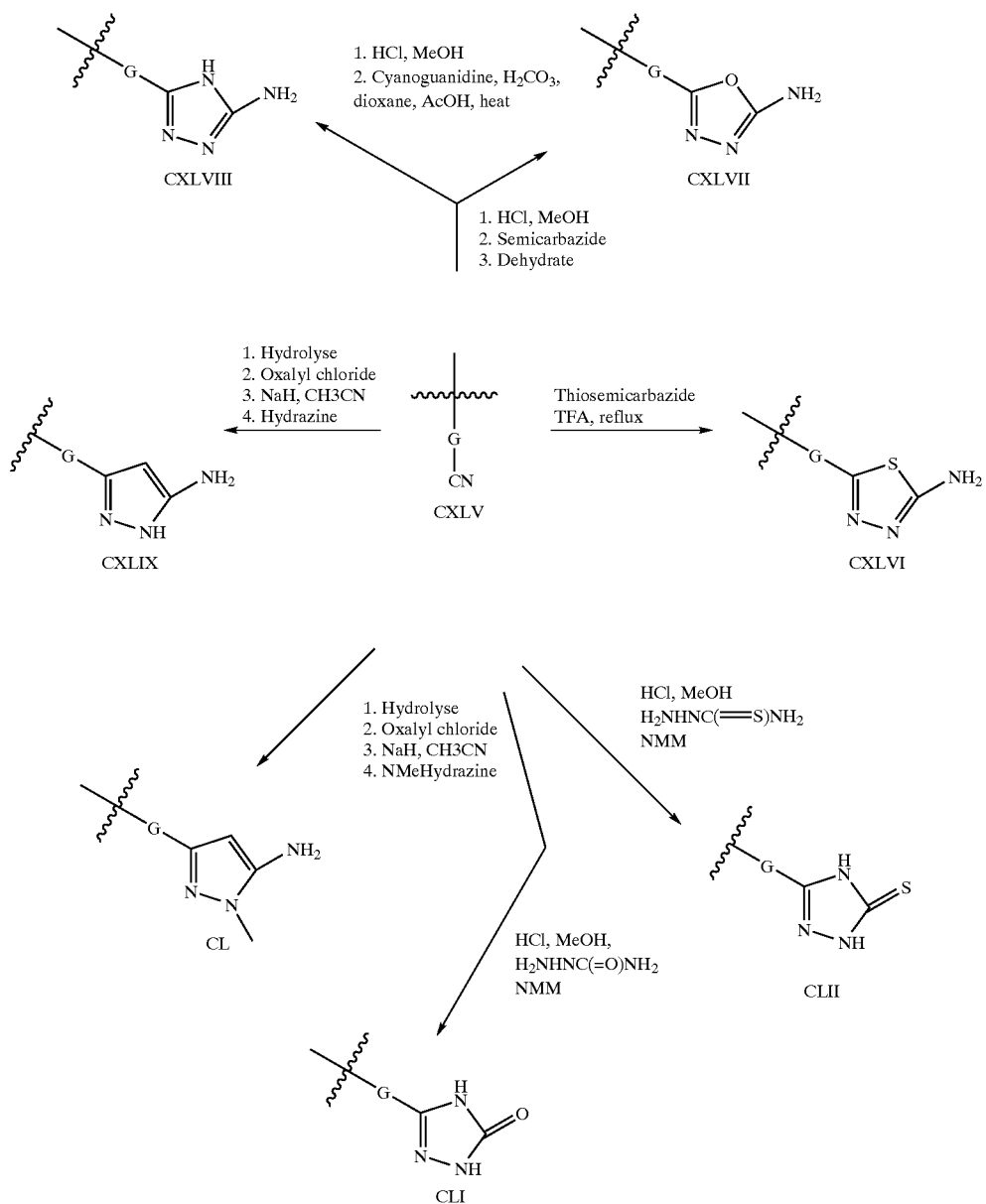

Other heterocycles contained in this invention can also be obtained via methods shown in Scheme XXIV

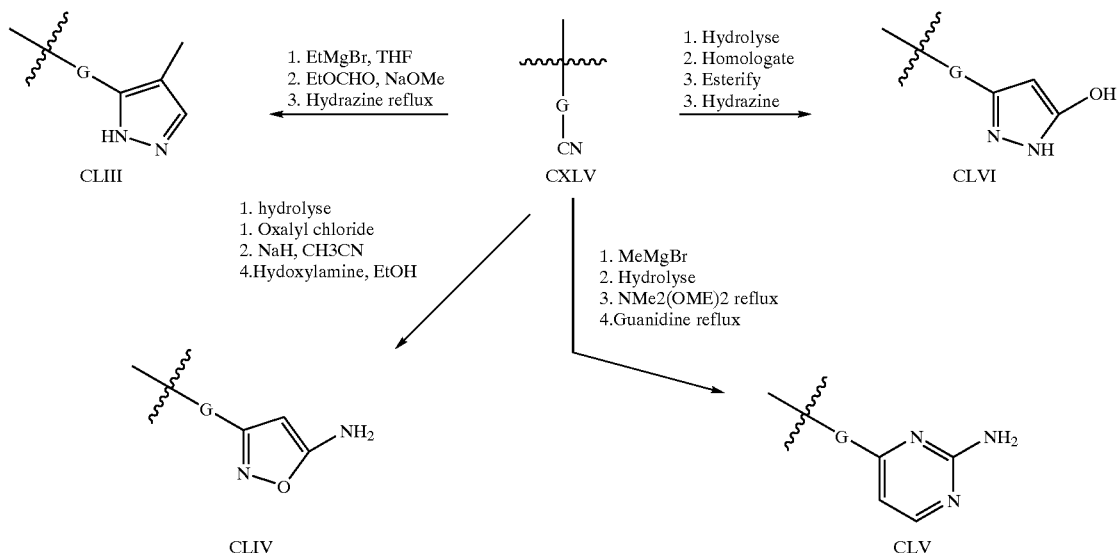

Scheme XXIV

The des-carbonyl compounds of this invention where $M_1$ is $CH_2$ can be prepared from the corresponding carbonyl intermediate A such as LIII (Scheme IX) by reduction as shown in Scheme XX. Further manipulation of the R1 and R2 groups would lead to the final compounds of this invention.

Scheme XXV

CLVI → Reduction → CLVII

UTILITY

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, Ohio.) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o-v_s)/v_s=I/(K_i(1+S/K_m))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Using the methodology described above, some compounds of the present invention were found to exhibit a $K_i$ of $\leq 10$ μM, thereby confirming the utility of the compounds of the present invention as effective Xa inhibitors.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM.

Even more preferred compounds of the present invention have $K_i$'s of $\leq 0.01$ μM. Still more preferred compounds of the present invention have $K_i$'s of $\leq 0.001$ μM.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of the present invention may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 1990, 265, 18289–18297, herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to prevent or ameliorate the thromboembolic disease condition or the progression of the disease.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Administration of the compounds of the present invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of anti-platelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 70–80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Other features of the invention will become apparent in the course of the following descriptions of exemplary embodiments that are given for illustration of the invention and are not intended to be limiting thereof.

EXAMPLES

Example 1

1-[3-(2'-Amino-3',4'-thiadiazol-5'-yl)phenyl]-3-methyl-6-[2'-aminosulfonyl-[1,1']-biphen-4-yl]-1,4,5,6-tetrahydropyrazolo-[3,4-c]-pyridin-7-one Trifluoroacetic

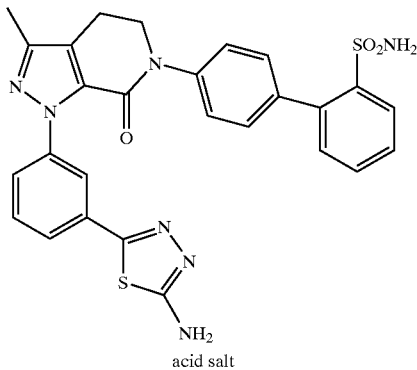

acid salt

Part A: 1-[4-bromophenyl]-4-acetyl-2,3-dioxopiperidine was prepared in four steps in 10% overall yield by the following sequence of reactions. Commercially available 4-bromoaniline was treated with commercially available 5-chloro-2-pentanone ethylene ketal in dimethylformamide in the presence of potassium carbonate for three days. The crude alkylated aniline was treated with ethyloxalyl chloride in THF the presence of triethylamine. Hydrolysis of the ketal was accomplished by treating with aqueous HCl and the resulting material was subjected to Dieckmann cyclization conditions (NaOMe, methanol). The crude dioxopiperidine was purified by flash chromatography (elution with 4:1 hexanes/ethylacetate) to afford the title compound. $^1$H NMR (dmso d6): δ 7.56 (d, 2H, J =8 Hz), 7.26 (d, 2H, J =8 Hz), 3.60 (t, 2H), 3.28 (t, 2H), 2.30 (s, 3H). LRMS (ES+): 281.0 (M+H)$^+$.

Part B: 1-[3-Cyanophenyl]-3-methyl-6-[2'-aminosulfonyl-[1,1']-biphen-4-yl]-1,4,5,6-tetrahydropyrazolo-[3,4-c]-pyridin-7-one was prepared by addition of 3-cyanophenyl hydrazine to a solution of 1-[4-bromophenyl]-4-acetyl-2,3-dioxopiperidine in glacial acetic acid was added. The reaction mixture was stirred at reflux for 3 h and then was cooled to ambient temperature. The volatiles were removed and the residue was taken up in ethyl acetate. The organics were washed with saturated aq sodium bicarbonate and brine, dried (MgSO$_4$) and concentrated.

The residue was dissolved in benzene and then there was added tetrabutylammonium bromide, aqueous Na$_2$CO$_3$ and 2-(tert-butylaminosulfonyl)phenylboronic. This solution was degassed with a stream of nitrogen for 30 minutes. Following the purge, tetrakis(triphenylphosphine)palladium (0) was added and the solution was stirred overnight at reflux. The solution was diluted with EtOAc and washed twice with brine and the organics dried over MgSO$_4$, filtered and the volatiles removed under reduced pressure. The residue was purified by column chromatography (elution with 1:1 hexane/EtOAc) to afford an intermediate biphenyl compound.

Part C: 1-[3-Cyanophenyl]-3-methyl-6-[2'-aminosulfonyl-[1,1']-biphen-4-yl]-1,4,5,6-tetrahydropyrazolo-[3,4-c]-pyridin-7-one was (0.12 g, 0.22 mmol) was treated with thiosemicarbazide (0.02 g, 0.22 mmol) in 10 mL refluxing TFA for 4H. The reaction mixture was concentrated under reduced pressure and purified by HPLC to give the aminothiadiazole. $^1$H NMR (DMSO-d$_6$, 300MHz) δ: 8.04 (d, 2H, J=7 Hz), 7.72–7.51 (m, 7H), 7.33 (d, 1H, J=7 Hz), 7.26 (s, 2H), 4.15–4.13 (m, 2H), 2.96 (bt, 2H, J=6 Hz), 2.31 (s, 3H) ppm; LRMS: m/z 558 (M+H); HRMS: calc'd for C$_{27}$H$_{24}$S$_2$O$_3$N$_7$=558.4216.

Example 2

1-[3-(5-oxo-4,5-Dihydro-1H-1,2,4-triazol-3-yl)phenyl]-6-[2'-(1-pyrrolidinylmethyl)-1,1'-biphenyl-4-yl]-3-(trifluoromethyl)-1,4,5,6-tetrahydro-7H-pyrazolo[3,4-c]pyridin-7-one, Trifluoroacetic Acid Salt Part A: Preparation of 1-(4-Iodophenyl)-4-(2,2,2-trifluoropropanoyl)-2,3-piperidinedione 4-Iodoaniline (45.82 g, 209.2 m mol) and triethylamine (65.61 mL, 470.7 m mol) were dissolved into THF (800 mL) and cooled to 0° C. 5-Bromovaleryl chloride (50.0 g, 251.1 m mol) dissolved in THF (200 mL) was added dropwise to the reaction. The reaction was warmed to room temperature and stirred overnight. Reaction was cooled to 0° C. and potassium tert-butoxide (70.43 g, 627.6 m mol) was slowly added. The reaction was warmed to room temperature and stirred overnight. The reaction was concentrated and then redissolved in ethyl acetate (500 mL) and 3N HCl (500 mL), extracted with ethyl acetate (2×250 mL), washed with 1N HCl (3×250 mL), washed with brine (1×250 mL), and dried (Na$_2$SO$_4$). Purification by silica gel chromatography using 0%–100% ethyl acetate/hexane gradient as eluent to afford 51.03 g (81%): $^1$H NMR (CDCl$_3$)δ 7.70 (d, J=8.4 Hz, 2H), 7.03 (d, J=8.8 Hz, 2H), 3.62 (t, J=5.9 Hz, 2H), 2.56 (t, J=5.7 Hz, 2H), 2.50–1.88 (m, 4H)ppm.

The product from the above reaction (85.17 g, 282.8 mmol) and phosphorus pentachloride (205.91 g, 990.0 mmol) was dissolved into CHCl$_3$ (750 mL) and refluxed for 3½ hours. The reaction was poured over ice and then quenched further with water, extracted with CHCl$_3$ (3×400 mL), washed with brine (1×400 mL), dried (MgSO$_4$), and concentrated. This residue was dissolved in morpholine (400 mL) and refluxed overnight. The reaction was concentrated and purified by silica gel chromatography using 0%–100% ethyl acetate/hexane gradient as eluent to afford 68 g (63%) of desired morpholine adduct: $^1$H NMR (CDCl$_3$) δ 7.68 (d, J=8.8 Hz, 2H), 7.11 (d, J=8.8 Hz, 2H), 5.66 (t, J=4.8 Hz, 1H), 3.82 (t, J=4.8 Hz, 4H), 3.77 (t, J=6.8 Hz, 2H), 2.89 (t, J=4.8 Hz, 4H), 2.53–2.47 (m, 2H)ppm.

4-Dimethylaminopyridine (3.92 g, 32.01 m mol) was dissolved into CH$_2$Cl$_2$ (130 mL) and cooled to 0° C.

Trifluoroacetic anhydride (4.54 g, 32.01 m mol) was added and the mixture was stirred at 0° C. for 30 min. The above morpholine-enamine (10.25 g, 26.68 m mol) dissolved in CH$_2$Cl$_2$ (370 mL) was added slowly and the reaction was warmed to room temperature and stirred overnight. Reaction was concentrated and purified by silica gel chromatography using 0%–50% ethylacetate/hexane gradient to isolate the intermediate. The intermediate was dissolved in 20% HCl (50 mL) and diethyl ether (200 mL) and stirred at room temperature overnight. Reaction was quenched with water, extracted with ether (3×100 mL), washed with brine (1×100 mL), and dried (Na$_2$SO$_4$). The residue was redissolved in petroleum ether and the solids were filtered away. Concentrated filtrate afforded 9.99 g (78%) of the desired compound: $^1$H NMR (CDCl$_3$) δ 7.77 (d, J=8.8 Hz, 2H), 7.11 (d, J=8.8 Hz, 2H), 3.93 (t, J=6.8 Hz, 2H), 2.92 (t, J=6.8 Hz, 2H)ppm.

Part B: Preparation of 1-(3-Cyanophenyl)-3-(trifluoromethyl)-6-(4-iodophenyl)-1,4,5,6-tetrahydropyrazolo-[3,4-c]-pyridin-7-one 1-(4-iodophenyl)-4-(2,2,2-trifluoroacetyl)-2,3-piperidinedione prepared by the same methods described in WO 00/39131 (5.02 g, 12.2 mmol) and 3-cyanophenylhydrazine chloride (3.44 g, 20.4 mmol) were added together with 75 mL of Acetic acid. The mixture was refluxed for 4 hours. The mixture was cooled and the solvent was removed. The residue was partitioned between EtOAc and H$_2$O. The EtOAc layer was washed with H$_2$O, brine, dried over MgSO$_4$, concentrated, and chromatographed with 1:5 EtOAc:hexane to afford 3.8 g of 1-(3-cyanophenyl)-3-(trifluoromethyl)-6-(4-iodophenyl)-1,4,5,6-tetrahydropyrazolo-[3,4-c]-pyridin-7-one as a yellow solid (61.3%). $^1$H NMR (CDCl$_3$, 300 MHz) δ 7.91–7.90 (m, 1H), 7.87–7.83 (m, 1H), 7.75–7.69 (m, 3H), 7.56 (t, 1H), 7.09–7.04 (m, 2H), 4.15 (t, 2H), 3.19 (t, 2H).

Part C: Preparation of 1-[3-(5-oxo-4,5-Dihydro-1H-1,2,4-triazol-3-yl)phenyl]-6-[(4-iodophenyl)]-3-(trifluoromethyl)-1,4,5,6-tetrahydro-7H-pyrazolo[3,4-c]pyridin-7-one 1-(3-Cyanophenyl)-3-(trifluoromethyl)-6-(4-iodophenyl)-1,4,5,6-tetrahydropyrazolo-[3,4-c]-pyridin-7-one (3.75 g, 7.38 mmol) was suspended in 100 mL of anhydrous MeOH and 50 mL of chloroform and cooled in a 0° C. ice-bath. HCl gas was then bubbled in the mixture for 30 minutes resulting in a clear solution. The reaction vessel was sealed and stored at 0° C. for 18 hours. The mixture was concentrated in vacuo and dried. The resulting yellow was suspended in 75 mL of anhydrous 1,4-dioxane. Semicarbazide hydrochloride (1.41 g, 12.6 mmol) was then added, followed by N-methylmorpholine (5.83 mL, 53 mmol). The mixture was refluxed for 48 hours. The precipitate was filtered and washed with 1,4-dioxane, water, and ether. The solid was pumped dry to afford 1.7 g of the title compound as a yellow solid (40.7%). MS (ES$^-$): 565.2, (M–H)$^-$.

Part D: Preparation of 1-[3-(5-oxo-4,5-Dihydro-1H-1,2,4-triazol-3-yl)phenyl]-6-[2'-formyl-1,1'-biphenyl-4-yl]-3-(trifluoromethyl)-1,4,5,6-tetrahydro-7H-pyrazolo[3,4-c]pyridin-7-one 1-[3-(5-Oxo-4,5-Dihydro-1H-1,2,4-triazol-3-yl)phenyl]-6-[(4-iodophenyl)]-3-(trifluoromethyl)-1,4,5,6-tetrahydro-7H-pyrazolo[3,4-c]pyridin-7-one (300 mg, 0.53 mmol), 2-Formylbenzeneboronic acid (159 mg, 1.06 mmol), K$_2$CO$_3$ (293 mg, 2.12 mmol), were dissolved in 15 mL of 1:2 EtOH:Toluene. The system was evacuated and flushed with N$_2$ three times. Pd(PPh$_3$)$_4$ (61 mg, 0.053 mmol) was then added and the system was evacuated and flushed with N$_2$ three times. The mixture was refluxed for seven hours. The mixture was concentrated in vacuo and the residue partitioned between ethyl acetate and H$_2$O. The aqueous layer was extracted with more ethyl acetate (2×50 mL). The ethyl acetate layers were combined and washed with brine. The aqueous layer was extracted with CH$_2$Cl$_2$. All organic layers were combined and dried over MgSO$_4$, concentrated and chromatographed with 1% to 4% MeOH:CHCl$_3$ to afford 170 mg of the title compound as an off-white solid (58.9%). MS (ES$^+$): 545.3, (M+H)$^+$.

Part E: Preparation of 1-[3-(5-Oxo-4,5-Dihydro-1H-1,2,4-triazol-3-yl)phenyl]-6-[2'-(1-pyrrolidinylmethyl)-1,1'-biphenyl-4-yl]-3-(trifluoromethyl)-1,4,5,6-tetrahydro-7H-pyrazolo[3,4-c]pyridin-7-one, Trifluoroacetic Acid Salt 1-[3-(5-Oxo-4,5-Dihydro-1H-1,2,4-triazol-3-yl)phenyl]-6-[2'-formyl-1,1'-biphenyl-4-yl]-3-(trifluoromethyl)-1,4,5,6-tetrahydro-7H-pyrazolo[3,4-c]pyridin-7-one (82 mg, 0.15 mmol) and pyrrolidine (32 mg, 0.45 mmol) were dissolved in 10 mL of methanol and stirred at room temperature for 18 hours. Sodium cyanoborohydride (19 mg, 0.3 mmol) was then added and the mixture was stirred at room temperature for 3 hours. The mixture was concentrated in vacuo and purified by reverse phase HPLC (C18 reverse phase column, eluted with a H$_2$O/CH$_3$CN gradient with 0.05% TFA) to give 40 mg of the title compound as a white solid (37.4% yield). LRMS (ES$^+$), 600.4 (M+H)$^+$. $^1$H NMR (DMSO-d$_6$, 300 MHz) δ 12.11 (s, 1H), 11.77 (s, 1H), 7.99 (s, 1H), 7.85 (d, 1H), 7.69–7.66 (m, 2H), 7.61–7.55 (m, 1H), 7.48–7.46 (m, 4H), 7.37 (d, 2H), 7.32–7.29 (m, 1H), 4.35 (s, 1H), 4.17 (t, 2H), 3.35–3.25 (m, 2H), 3.14 (t, 2H), 2.85–2.75 (m, 2H), 1.8–1.7 (m, 4H).

Example 3

6-(2'-{[(3S)-3-Hydroxy-1-pyrrolidinyl]methyl}-1,1'-biphenyl-4-yl)-1-[3-(5-oxo-4,5-dihydro-1H-1,2,4-triazol-3-yl)phenyl]-3-(trifluoromethyl)-1,4,5,6-tetrahydro-7H-pyrazolo[3,4-c]pyridin-7-one, Trifluoroacetic Acid Salt

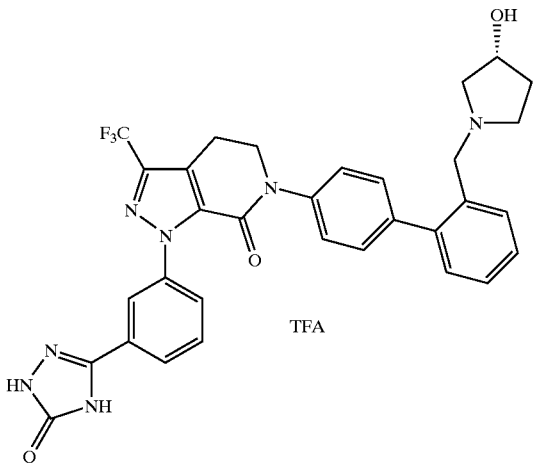

This compound was prepared by the methods described in Example 2. LRMS (ES$^+$), 616.5 (M+H)$^+$. $^1$H NMR (DMSO-d$_6$, 300 MHz) δ 12.1 (s, 1H), 11.75 (s, 1H), 7.99 (s, 1H), 7.85–7.83 (m, 1H), 7.75–7.67 (m, 2H), 7.58–7.42 (m, 5H), 7.37–7.25 (m, 3H), 4.45–4.2 (m, 3H), 4.2–4.15 (m, 2H), 3.2–3.1 (m, 2H), 2.9–2.75 (m, 4H), 1.87–1.65 (m, 2H).

Example 4

6-{2'-[(Dimethylamino)methyl]-1,1'-biphenyl-4-yl}-1-[3-(5-oxo-4,5-dihydro-1H-1,2,4-triazol-3-yl)phenyl]-3-(trifluoromethyl)-1,4,5,6-tetrahydro-7H-pyrazolo[3,4-c]pyridin-7-one, Bistrifluoroacetic Acid Salt

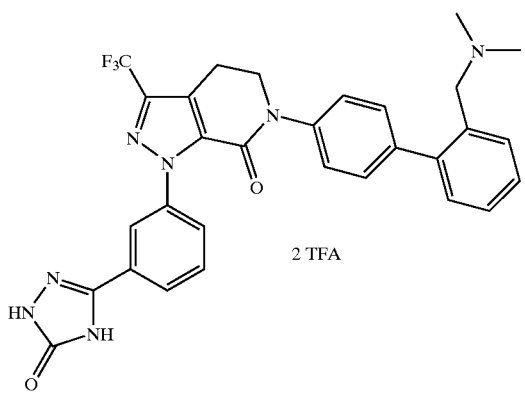

This compound was prepared by the methods described in Example 2. LRMS (ES+), 574.4 (M+H)+. 1H NMR (DMSO-d6, 300 MHz) δ 12.11 (s, 1H), 11.77 (s, 1H), 7.99 (s, 1H), 7.85 (d, 1H), 7.70–7.65 (m, 2H), 7.61–7.56 (m, 1H), 7.51–7.45 (m, 4H), 7.37–7.29 (m, 3H), 4.27 (bs, 2H), 4.18 (t, 2H), 3.14 (t, 2H), 2.45 (s, 6H).

Example 5

6-[2'-(Methylsulfonyl)-1,1'-biphenyl-4-yl]-1-[3-(5-oxo-4,5-dihydro-1H-1,2,4-triazol-3-yl)phenyl]-3-(trifluoromethyl)-1,4,5,6-tetrahydro-7H-pyrazolo[3,4-c]pyridin-7-one

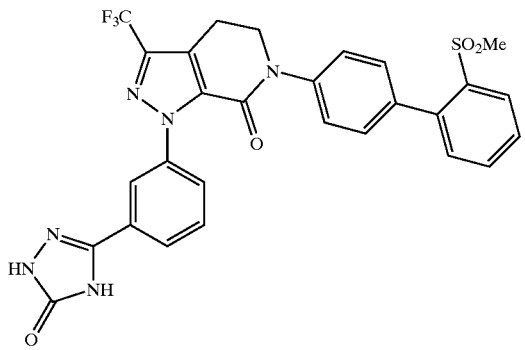

This compound was prepared by the methods described in Example 2. LRMS (ES+), 617.5 (M+H)+. 1H NMR (DMSO-d6, 300 MHz) δ 12.1 (s, 1H), 11.76 (s, 1H), 8.07–8.05 (m, 1H), 7.99 (s, 1H), 7.85 (d, 1H), 7.75–7.58 (m, 4H), 7.41–7.35 (m, 5H), 4.18 (t, 2H), 3.14 (t, 2H), 2.81 (s, 3H).

Example 6

1-[3-(5-Amino-1,3,4-oxadiazol-2-yl)phenyl]-6-{2'-[(dimethylamino)methyl]-1,1'-biphenyl-4-yl}-3-(trifluoromethyl)-1,4,5,6-tetrahydro-7H-pyrazolo[3,4-c]pyridin-7-one, Bistrifluoroacetic Acid Salt

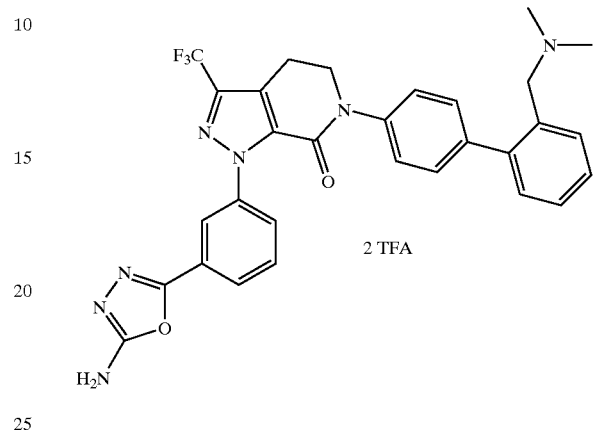

This compound was prepared by the methods described in Example 2. LRMS (ES+), 574.4 (M+H)+. 1H NMR (CD3OD, 300 MHz) δ 8.12 (s, 1H), 7.97 (d, 1H), 7.78–7.75 (m, 1H), 7.66–7.39 (m, 6H), 7.42–7.36 (m, 3H), 4.34 (s, 2H), 4.24 (t, 2H), 3.30–3.21 (m, 2H), 2.60 (s, 6H).

Example 7

1-[3-(5-Amino-1,3,4-thiadiazol-2-yl)phenyl]-6-{2'-[(dimethylamino)methyl]-1,1'-biphenyl-4-yl}-3-(trifluoromethyl)-1,4,5,6-tetrahydro-7H-pyrazolo[3,4-c]pyridin-7-one, Bistrifluoroacetic Acid Salt

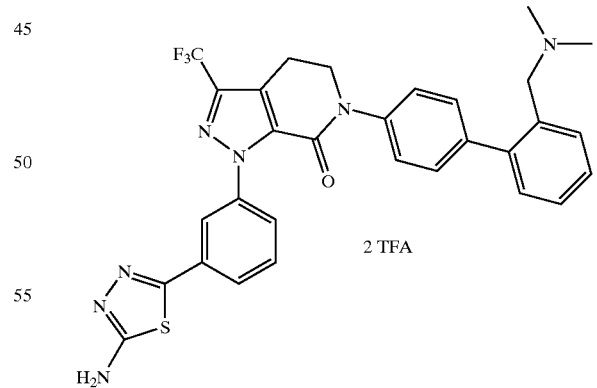

This compound was prepared by the methods described in Example 2. LRMS (ES+), 590.5 (M+H)+. 1H NMR (CD3OD, 300 MHz) δ 8.09 (s, 1H), 7.9–7.85 (m, 1H), 7.75–7.7 (m, 1H), 7.65–7.5 (m, 6H), 7.4–7.35 (m, 3H), 4.36 (s, 2H), 4.26 (t, 2H), 3.25 (t, 2H), 2.62 (s, 6H).

Example 8

1-[3-(5-Amino-1,3,4-thiadiazol-2-yl)phenyl]-6-[2'-(1-pyrrolidinylmethyl)-1,1'-biphenyl-4-yl]-3-(trifluoromethyl)-1,4,5,6-tetrahydro-7H-pyrazolo[3,4-c]pyridin-7-one, Bistrifluoroacetic Acid Salt

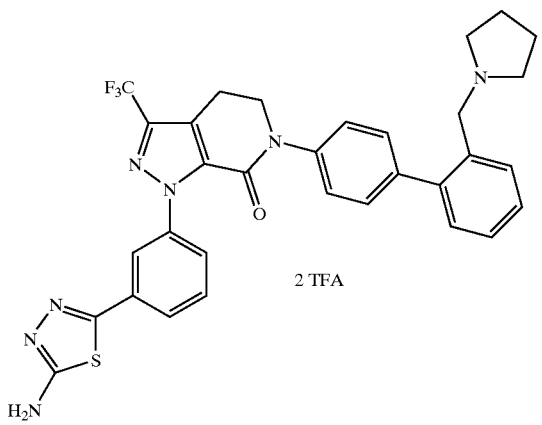

This compound was prepared by the methods described in Example 2. LRMS (ES+), 616.5 (M+H)+. $^1$H NMR (DMSO-$d_6$, 300 MHz) δ 8.01 (t, 1H), 7.81–7.78 (m, 1H), 7.69–7.63 (m, 2H), 7.59–7.45 (m, 5H), 7.38–7.29 (m, 3H), 4.35–4.33 (m, 2H), 4.18 (t, 2H), 3.35–3.22 (m, 2H), 3.14 (t, 2H), 2.81–2.72 (m, 2H), 1.8–1.68 (m, 4H).

Example 9

1-[3-(5-Amino-1,3,4-thiadiazol-2-yl)phenyl]-6-(4-{2-[(dimethylamino)methyl]-1H-imidazol-1-yl}phenyl)-3-(trifluoromethyl)-1,4,5,6-tetrahydro-7H-pyrazolo[3,4-c]pyridin-7-one, Bistrifluoroacetic Acid Salt

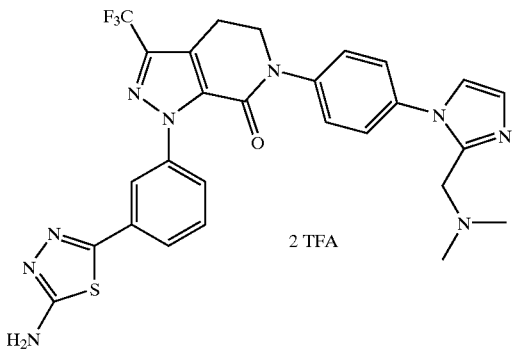

This compound was prepared by the methods described in Example 2. LRMS (ES+), 580.4 (M+H)+. $^1$H NMR (DMSO-$d_6$, 300 MHz) δ 8.02–8.01 (m, 1H), 7.79–7.76 (m, 1H), 7.66–7.64 (m, 1H), 7.58–7.48 (m, 6H), 7.21–7.20 (m, 1H), 4.39 (s, 2H), 4.16 (t, 2H), 3.14 (t, 2H), 2.75 (s, 6H).

Example 10

1-[3-(5-Amino-1,3,4-thiadiazol-2-yl)phenyl]-6-{4-[2-(1-pyrrolidinylmethyl)-1H-imidazol-1-yl]phenyl}-3-(trifluoromethyl)-1,4,5,6-tetrahydro-7H-pyrazolo[3,4-c]pyridin-7-one, Bistrifluoroacetic Acid Salt

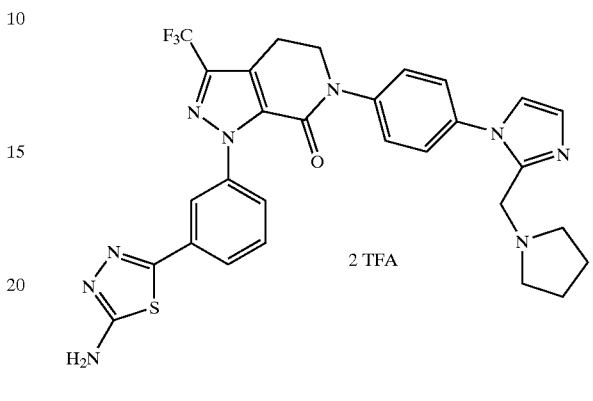

This compound was prepared by the methods described in Example 2. LRMS (ES+), 606.6 (M+H)+. $^1$H NMR (CD$_3$OD, 300 MHz) δ 8.06 (s, 1H), 7.88–7.82 (m, 1H), 7.7–7.65 (m, 1H), 7.61–7.58 (m, 3H), 7.49 (d, 2H), 7.40 (d, 1H), 7.22 (s, 1H), 4.46 (s, 2H), 4.23 (t, 2H), 3.4–3.3 (m, 4H), 3.22 (t, 2H), 2.03–1.98 (m, 4H).

Example 11

6-(4-{2-[(Dimethylamino)methyl]-1H-imidazol-1-yl}phenyl)-1-[3-(5-oxo-4,5-dihydro-1H-1,2,4-triazol-3-yl)phenyl]-3-(trifluoromethyl)-1,4,5,6-tetrahydro-7H-pyrazolo[3,4-c]pyridin-7-one, Bistrifluoroacetic Acid Salt

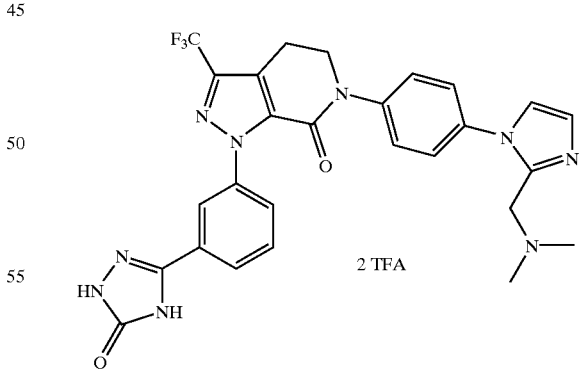

This compound was prepared by the methods described in Example 2. LRMS (ES+), 546.5 (M+H)+. $^1$H NMR (DMSO-$d_6$, 300 MHz) δ 8.0 (s, 1H), 7.85–7.81 (m, 1H), 7.7–7.65 (m, 1H), 7.6–7.5 (m, 6H), 7.2 (s, 1H), 4.4 (s, 2H), 4.19–4.15 (m, 2H), 3.18–3.13 (m, 2H), 2.76 (s, 6H).

Example 12

3-Methyl-1-[3-(5-oxo-4,5-dihydro-1H-1,2,4-triazol-3-yl)phenyl]-6-{4-[2-(1-pyrrolidinylmethyl)-1H-imidazol-1-yl]phenyl}-1,4,5,6-tetrahydro-7H-pyrazolo[3,4-c]pyridin-7-one, Trifluoroacetic Acid Salt

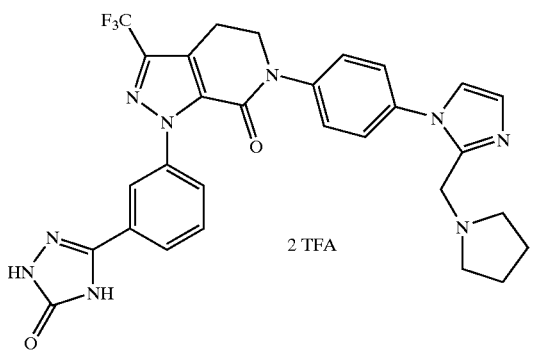

This compound was prepared by the methods described in Example 2. LRMS (ES+), 546.5 (M+H)+. $^1$H NMR (CD$_3$OD, 300 MHz) δ 7.98 (t, 1H), 7.81 (d, 1H), 7.68–7.64 (m, 2H), 7.56–7.49 (m, 5H), 7.41–7.38 (m, 3H), 4.42 (s, 2H), 4.21 (t, 2H), 3.4–3.3 (m, 2H), 3.05 (t, 2H), 2.88–2.78 (m, 2H), 2.37 (s, 3H), 1.93–1.84 (m, 4H).

Example 13

7-Oxo-1-[3-(5-oxo-4,5-dihydro-1H-1,2,4-triazol-3-yl)phenyl]-6-[2'-(1-pyrrolidinylmethyl)-1,1'-biphenyl-4-yl]-4,5,6,7-tetrahydro-1H-pyrazolo[3,4-c]pyridine-3-carboxamide, Trifluoroacetic Acid Salt

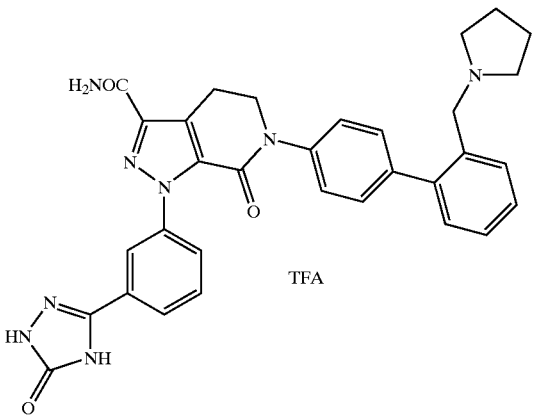

This compound was prepared by the methods described in Example 2. LRMS (ES+), 575.6 (M+H)+. $^1$H NMR (CD$_3$OD, 300 MHz) δ 8.06–8.05 (m, 1H), 7.88–7.84 (m, 1H), 7.78–7.74 (m, 1H), 7.61–7.45 (m, 6H), 7.4–7.35 (m, 3H), 4.41 (s, 2H), 4.21 (t, 2H), 3.4–3.3 (m, 4H), 2.82–2.78 (m, 2H), 1.9–1.82 (m, 4H).

Example 14

1-[3-(5-oxo-4,5-Dihydro-1H-1,2,4-triazol-3-yl)phenyl]-7-[2'-(1-pyrrolidinylmethyl)-1,1'-biphenyl-4-yl]-3-(trifluoromethyl)-4,5,6,7-tetrahydropyrazolo[3,4-c]azepin-8(1H)-one, Trifluoroacetic Acid Salt

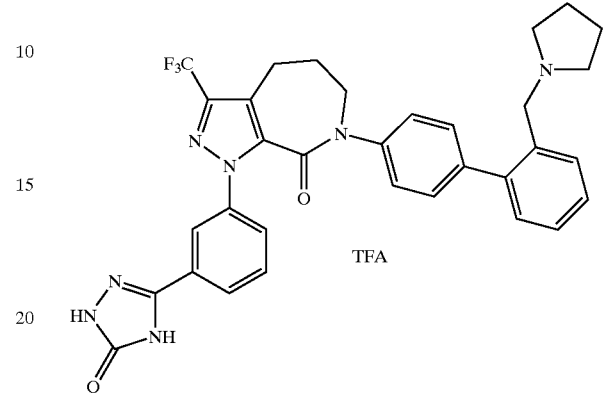

This compound was prepared by the methods described in Example 2. LRMS (ES+), 632.6 (M+H)+. $^1$H NMR (CD$_3$OD, 300 MHz) δ 7.96–7.95 (m, 1H), 7.88–7.84 (m, 1H), 7.65–7.53 (m, 6H), 7.41–7.38 (m, 1H), 7.31–7.23 (m, 2H), 4.4 (s, 2H), 4.05–4.01 (m, 2H), 3.35–3.29 (m, 2H), 3.13 (t, 2H), 2.84–2.81 (m, 2H), 2.33–2.30 (m, 2H), 1.93–1.85 (m, 4H).

Example 15

1-[2-(5-oxo-4,5-Dihydro-1H-1,2,4-triazol-3-yl)phenyl]-6-[2'-(1-pyrrolidinylmethyl)-1,1'-biphenyl-4-yl]-3-(trifluoromethyl)-1,4,5,6-tetrahydro-7H-pyrazolo[3,4-c]pyridin-7-one, Trifluoroacetic Acid Salt

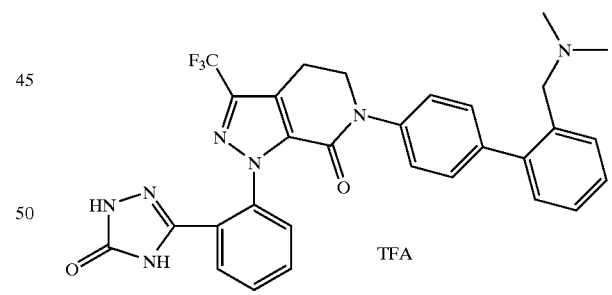

This compound was prepared by the methods described in Example 2. LRMS (ES+), 574.5 (M+H)+. $^1$H NMR (CD$_3$OD, 300 MHz) δ 7.71–7.53 (m, 6H), 7.43–7.35 (m, 6H), 4.34 (s, 2H), 4.16 (t, 2H), 3.21 (t, 2H), 2.61 (s, 6H).

The following tables contain representative examples of the present invention. Each entry in each table is intended to be paired with each formulas at the start of the table. For example, in Table 1, Example 1 is intended to be paired with each of the formulas.

The following nomenclature is intended for group A in the following tables.

131
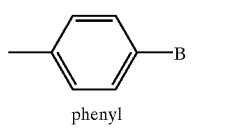
phenyl
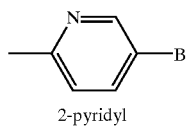
2-pyridyl
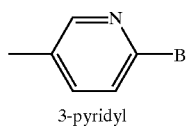
3-pyridyl
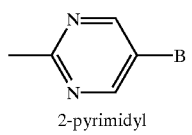
2-pyrimidyl
132
-continued
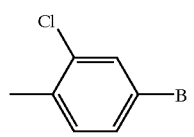
2-Cl-phenyl
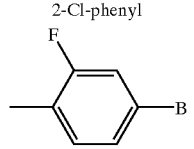
2-F-phenyl
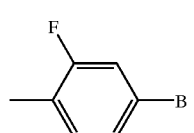
2,6-diF-phenyl
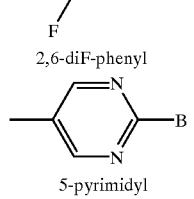
5-pyrimidyl
TABLE 1
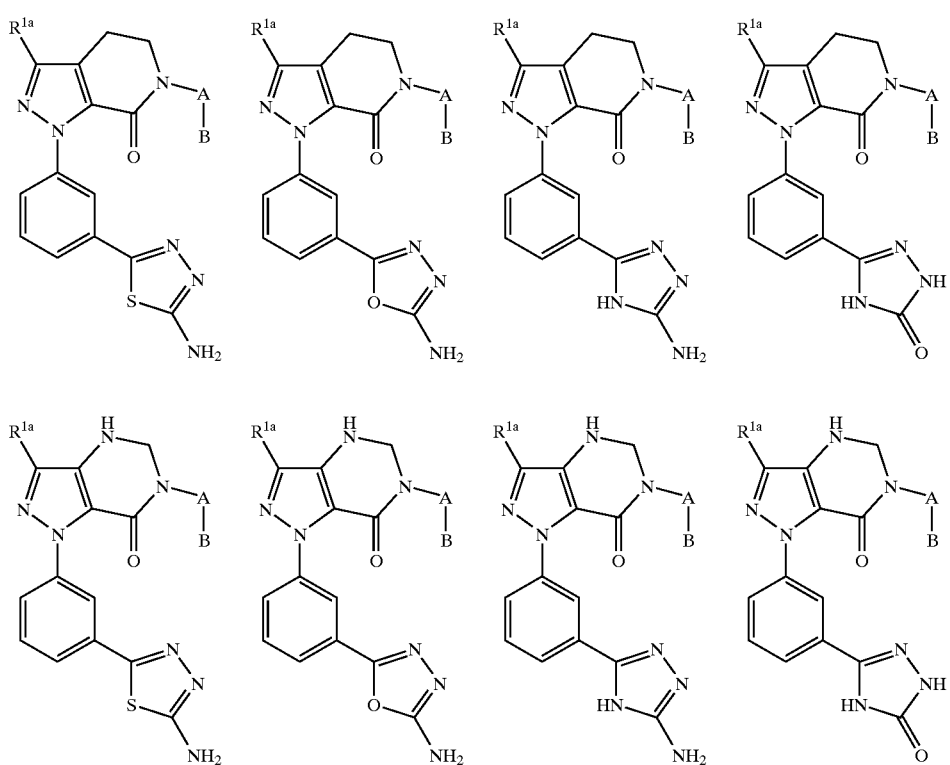

TABLE 1-continued
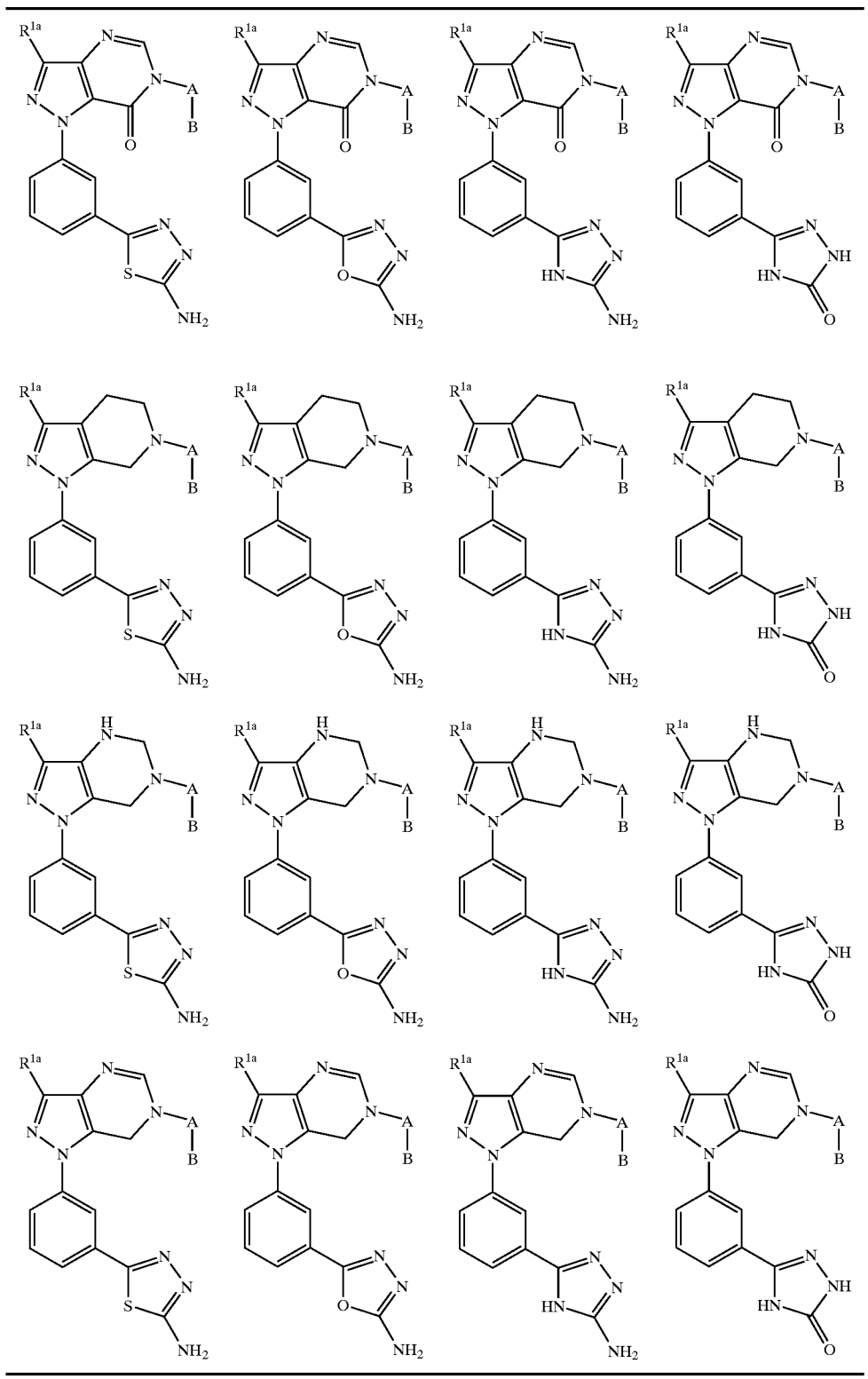

$R^{1a}$ is $CH_3$;

| Ex# | A | B |
|---|---|---|
| 1. | phenyl | 2-($NH_2SO_2$)phenyl |
| 2. | phenyl | 2-($CH_3SO_2$)phenyl |
| 3. | phenyl | 3-$NH_2SO_2$-4-pyridyl |
| 4. | phenyl | 3-$CH_3SO_2$-4-pyridyl |
| 5. | phenyl | 2-($CH_3NH$)phenyl |
| 6. | phenyl | 3-(($CH_3$)$_2NCH_2$)-4-pyridyl |
| 7. | phenyl | 2-(N-(3-R-HO-pyrrolidinyl)$CH_2$)phenyl |
| 8. | phenyl | 2-(N-(4-HO-piperidinyl) $CH_2$)phenyl |
| 9. | phenyl | 2-(($CH_3$)$_2NCH_2$)phenyl |
| 10. | phenyl | 2-(($CH_3$)$NHCH_2$)phenyl |
| 11. | phenyl | 2-(($CH_3CH_2$)$NHCH_2$)phenyl |
| 12. | phenyl | 2-(($CH_3CH_2$)$_2NCH_2$)phenyl |
| 13. | phenyl | 2-(($CH_3CH_2$)$N(CH_3)CH_2$)phenyl |
| 14. | phenyl | 2-((($CH_3$)$_2CH)NHCH_2$)phenyl |
| 15. | phenyl | 2-((($CH_3$)$_2CH)_2NCH_2$)phenyl |
| 16. | phenyl | 2-((cyclopropyl)$NHCH_2$)phenyl |
| 17. | phenyl | 2-((cyclopropyl)$_2NCH_2$)phenyl |
| 18. | phenyl | 2-((cyclobutyl)$NHCH_2$)phenyl |
| 19. | phenyl | 2-((cyclobutyl)$_2NCH_2$)phenyl |
| 20. | phenyl | 2-((cyclopentyl)$NHCH_2$)phenyl |
| 21. | phenyl | 2-((cyclopentyl)$_2NCH_2$)phenyl |
| 22. | phenyl | 2-((cyclohexyl)$NHCH_2$)phenyl |
| 23. | phenyl | 2-((cyclohexyl)$_2NCH_2$)phenyl |
| 24. | phenyl | 1-$CH_3$-2-imidazolyl |
| 25. | phenyl | 2-$CH_3$-1-imidazolyl |
| 26. | phenyl | 2-(($CH_3$)$_2NCH_2$)-1-imidazolyl |
| 27. | phenyl | 2-(($CH_3$)$NHCH_2$)-1-imidazolyl |
| 28. | phenyl | 2-(($CH_3CH_2$)$NHCH_2$)-1-imidazolyl |
| 29. | phenyl | 2-(($CH_3CH_2$)$_2NCH_2$)-1-imidazolyl |
| 30. | phenyl | 2-(($CH_3CH_2$)$N(CH_3)CH_2$)-1-imidazolyl |
| 31. | phenyl | 2-((($CH_3$)$_2CH)NHCH_2$)-1-imidazolyl |
| 32. | phenyl | 2-((($CH_3$)$_2CH)_2NCH_2$)-1-imidazolyl |
| 33. | phenyl | 2-((cyclopropyl)$NHCH_2$)-1-imidazolyl |
| 34. | phenyl | 2-((cyclopropyl)$_2NCH_2$)-1-imidazolyl |
| 35. | phenyl | 2-((cyclobutyl)$NHCH_2$)-1-imidazolyl |
| 36. | phenyl | 2-((cyclobutyl)$_2NCH_2$)-1-imidazolyl |
| 37. | phenyl | 2-((cyclopentyl)$NHCH_2$)-1-imidazolyl |
| 38. | phenyl | 2-((cyclopentyl)$_2NCH_2$)-1-imidazolyl |
| 39. | phenyl | 2-((cyclohexyl)$NHCH_2$)-1-imidazolyl |
| 40. | phenyl | 2-((cyclohexyl)$_2NCH_2$)-1-imidazolyl |
| 41. | 2-pyridyl | 2-($NH_2SO_2$)phenyl |
| 42. | 2-pyridyl | 2-($CH_3SO_2$)phenyl |
| 43. | 2-pyridyl | 3-$NH_2SO_2$-4-pyridyl |
| 44. | 2-pyridyl | 3-$CH_3SO_2$-4-pyridyl |
| 45. | 2-pyridyl | 2-($CH_3NH$)phenyl |
| 46. | 2-pyridyl | 3-(($CH_3$)$_2NCH_2$)-4-pyridyl |
| 47. | 2-pyridyl | 2-(N-(3-R-HO-pyrrolidinyl)$CH_2$)phenyl |
| 48. | 2-pyridyl | 2-(N-(4-HO-piperidinyl)$CH_2$)phenyl |
| 49. | 2-pyridyl | 2-(($CH_3$)$_2NCH_2$)phenyl |
| 50. | 2-pyridyl | 2-(($CH_3$)$NHCH_2$)phenyl |
| 51. | 2-pyridyl | 2-(($CH_3CH_2$)$NHCH_2$)phenyl |
| 52. | 2-pyridyl | 2-(($CH_3CH_2$)$_2NCH_2$)phenyl |
| 53. | 2-pyridyl | 2-(($CH_3CH_2$)$N(CH_3)CH_2$)phenyl |
| 54. | 2-pyridyl | 2-((($CH_3$)$_2CH)NHCH_2$)phenyl |
| 55. | 2-pyridyl | 2-((($CH_3$)$_2CH)_2NCH_2$)phenyl |
| 56. | 2-pyridyl | 2-((cyclopropyl)$NHCH_2$)phenyl |
| 57. | 2-pyridyl | 2-((cyclopropyl)$_2NCH_2$)phenyl |
| 58. | 2-pyridyl | 2-((cyclobutyl)$NHCH_2$)phenyl |
| 59. | 2-pyridyl | 2-((cyclobutyl)$_2NCH_2$)phenyl |
| 60. | 2-pyridyl | 2-((cyclopentyl)$NHCH_2$)phenyl |
| 61. | 2-pyridyl | 2-((cyclopentyl)$_2NCH_2$)phenyl |
| 62. | 2-pyridyl | 2-((cyclohexyl)$NHCH_2$)phenyl |
| 63. | 2-pyridyl | 2-((cyclohexyl)$_2NCH_2$)phenyl |
| 64. | 2-pyridyl | 1-$CH_3$-2-imidazolyl |
| 65. | 2-pyridyl | 2-$CH_3$-1-imidazolyl |
| 66. | 2-pyridyl | 2-(($CH_3$)$_2NCH_2$)-1-imidazolyl |
| 67. | 2-pyridyl | 2-(($CH_3$)$NHCH_2$)-1-imidazolyl |
| 68. | 2-pyridyl | 2-(($CH_3CH_2$)$NHCH_2$)-1-imidazolyl |
| 69. | 2-pyridyl | 2-(($CH_3CH_2$)$_2NCH_2$)-1-imidazolyl |
| 70. | 2-pyridyl | 2-(($CH_3CH_2$)$N(CH_3)CH_2$)-1-imidazolyl |
| 71. | 2-pyridyl | 2-((($CH_3$)$_2CH)NHCH_2$)-1-imidazolyl |
| 72. | 2-pyridyl | 2-((($CH_3$)$_2CH)_2NCH_2$)-1-imidazolyl |
| 73. | 2-pyridyl | 2-((cyclopropyl)$NHCH_2$)-1-imidazolyl |
| 74. | 2-pyridyl | 2-((cyclopropyl)$_2NCH_2$)-1-imidazolyl |
| 75. | 2-pyridyl | 2-((cyclobutyl)$NHCH_2$)-1-imidazolyl |
| 76. | 2-pyridyl | 2-((cyclobutyl)$_2NCH_2$)-1-imidazolyl |
| 77. | 2-pyridyl | 2-((cyclopentyl)$NHCH_2$)-1-imidazolyl |
| 78. | 2-pyridyl | 2-((cyclopentyl)$_2NCH_2$)-1-imidazolyl |
| 79. | 2-pyridyl | 2-((cyclohexyl)$NHCH_2$)-1-imidazolyl |
| 80. | 2-pyridyl | 2-((cyclohexyl)$_2NCH_2$)-1-imidazolyl |
| 81. | 3-pyridyl | 2-($NH_2SO_2$)phenyl |
| 82. | 3-pyridyl | 2-($CH_3SO_2$)phenyl |
| 83. | 3-pyridyl | 3-$NH_2SO_2$-4-pyridyl |
| 84. | 3-pyridyl | 3-$CH_3SO_2$-4-pyridyl |
| 85. | 3-pyridyl | 2-($CH_3NH$)phenyl |
| 86. | 3-pyridyl | 3-(($CH_3$)$_2NCH_2$)-4-pyridyl |
| 87. | 3-pyridyl | 2-(N-(3-R-HO-pyrrolidinyl)$CH_2$)phenyl |
| 88. | 3-pyridyl | 2-(N-(4-HO-piperidinyl)$CH_2$)phenyl |
| 89. | 3-pyridyl | 2-(($CH_3$)$_2NCH_2$)phenyl |
| 90. | 3-pyridyl | 2-(($CH_3$)$NHCH_2$)phenyl |
| 91. | 3-pyridyl | 2-(($CH_3CH_2$)$NHCH_2$)phenyl |
| 92. | 3-pyridyl | 2-(($CH_3CH_2$)$_2NCH_2$)phenyl |
| 93. | 3-pyridyl | 2-(($CH_3CH_2$)$N(CH_3)CH_2$)phenyl |
| 94. | 3-pyridyl | 2-((($CH_3$)$_2CH)NHCH_2$)phenyl |
| 95. | 3-pyridyl | 2-((($CH_3$)$_2CH)_2NCH_2$)phenyl |
| 96. | 3-pyridyl | 2-((cyctopropyl)$NHCH_2$)phenyl |
| 97. | 3-pyridyl | 2-((cyclopropyl)$_2NCH_2$)phenyl |
| 98. | 3-pyridyl | 2-((cyclobutyl)$NHCH_2$)phenyl |
| 99. | 3-pyridyl | 2-((cyclobutyl)$_2NCH_2$)phenyl |
| 100. | 3-pyridyl | 2-((cyclopentyl)$NHCH_2$)phenyl |
| 101. | 3-pyridyl | 2-((cyclopentyl)$_2NCH_2$)phenyl |
| 102. | 3-pyridyl | 2-((cyclohexyl)$NHCH_2$)phenyl |
| 103. | 3-pyridyl | 2-((cyclohexyl)$_2NCH_2$)phenyl |
| 104. | 3-pyridyl | 1-$CH_3$-2-imidazolyl |
| 105. | 3-pyridyl | 2-$CH_3$-1-imidazolyl |
| 106. | 3-pyridyl | 2-(($CH_3$)$_2NCH_2$)-1-imidazolyl |
| 107. | 3-pyridyl | 2-(($CH_3$)$NHCH_2$)-1-imidazolyl |
| 108. | 3-pyridyl | 2-(($CH_3CH_2$)$NHCH_2$)-1-imidazolyl |
| 109. | 3-pyridyl | 2-(($CH_3CH_2$)$_2NCH_2$)-1-imidazolyl |
| 110. | 3-pyridyl | 2-(($CH_3CH_2$)$N(CH_3)CH_2$)-1-imidazolyl |
| 111. | 3-pyridyl | 2-((($CH_3$)$_2CH)NHCH_2$)-1-imidazolyl |
| 112. | 3-pyridyl | 2-((($CH_3$)$_2CH)_2NCH_2$)-1-imidazolyl |
| 113. | 3-pyridyl | 2-((cyclopropyl)$NHCH_2$)-1-imidazolyl |
| 114. | 3-pyridyl | 2-((cyclopropyl)$_2NCH_2$)-1-imidazolyl |
| 115. | 3-pyridyl | 2-((cyclobutyl)$NHCH_2$)-1-imidazolyl |
| 116. | 3-pyridyl | 2-((cyclobutyl)$_2NCH_2$)-1-imidazolyl |
| 117. | 3-pyridyl | 2-((cyclopentyl)$NHCH_2$)-1-imidazolyl |
| 118. | 3-pyridyl | 2-((cyclopentyl)$_2NCH_2$)-1-imidazolyl |
| 119. | 3-pyridyl | 2-((cyclohexyl)$NHCH_2$)-1-imidazolyl |
| 120. | 3-pyridyl | 2-((cyclohexyl)$_2NCH_2$)-1-imidazolyl |
| 121. | 2-pyrimidyl | 2-($NH_2SO_2$)phenyl |
| 122. | 2-pyrimidyl | 2-($CH_3SO_2$)phenyl |
| 123. | 2-pyrimidyl | 3-$NH_2SO_2$-4-pyridyl |
| 124. | 2-pyrimidyl | 3-$CH_3SO_2$-4-pyridyl |
| 125. | 2-pyrimidyl | 2-($CH_3NH$)phenyl |
| 126. | 2-pyrimidyl | 3-(($CH_3$)$_2NCH_2$)-4-pyridyl |
| 127. | 2-pyrimidyl | 2-(N-(3-R-HO-pyrrolidinyl)$CH_2$)phenyl |
| 128. | 2-pyrimidyl | 2-(N-(4-HO-piperidinyl)$CH_2$)phenyl |
| 129. | 2-pyrimidyl | 2-(($CH_3$)$_2NCH_2$)phenyl |
| 130. | 2-pyrimidyl | 2-(($CH_3$)$NHCH_2$)phenyl |
| 131. | 2-pyrimidyl | 2-(($CH_3CH_2$)$NHCH_2$)phenyl |
| 132. | 2-pyrimidyl | 2-(($CH_3CH_2$)$_2NCH_2$)phenyl |
| 133. | 2-pyrimidyl | 2-(($CH_3CH_2$)$N(CH_3)CH_2$)phenyl |
| 134. | 2-pyrimidyl | 2-((($CH_3$)$_2CH)NHCH_2$)phenyl |
| 135. | 2-pyrimidyl | 2-((($CH_3$)$_2CH)_2NCH_2$)phenyl |
| 136. | 2-pyrimidyl | 2-((cyclopropyl)$NHCH_2$)phenyl |
| 137. | 2-pyrimidyl | 2-((cyclopropyl)$_2NCH_2$)phenyl |
| 138. | 2-pyrimidyl | 2-((cyclobutyl)$NHCH_2$)phenyl |
| 139. | 2-pyrimidyl | 2-((cyclobutyl)$_2NCH_2$)phenyl |
| 140. | 2-pyrimidyl | 2-((cyclopentyl)$NHCH_2$)phenyl |
| 141. | 2-pyrimidyl | 2-((cyclopentyl)$_2NCH_2$)phenyl |
| 142. | 2-pyrimidyl | 2-((cyclohexyl)$NHCH_2$)phenyl |
| 143. | 2-pyrimidyl | 2-((cyclohexyl)$_2NCH_2$)phenyl |
| 144. | 2-pyrimidyl | 1-$CH_3$-2-imidazolyl |
| 145. | 2-pyrimidyl | 2-$CH_3$-1-imidazolyl |
| 146. | 2-pyrimidyl | 2-(($CH_3$)$_2NCH_2$)-1-imidazolyl |
| 147. | 2-pyrimidyl | 2-(($CH_3$)$NHCH_2$)-1-imidazolyl |
| 148. | 2-pyrimidyl | 2-(($CH_3CH_2$)$NHCH_2$)-1-imidazolyl |
| 149. | 2-pyrimidyl | 2-(($CH_3CH_2$)$_2NCH_2$)-1-imidazolyl |
| 150. | 2-pyrimidyl | 2-(($CH_3CH_2$)$N(CH_3)CH_2$)-1-imidazolyl |
| 151. | 2-pyrimidyl | 2-((($CH_3$)$_2CH)NHCH_2$)-1-imidazolyl |
| 152. | 2-pyrimidyl | 2-((($CH_3$)$_2CH)_2NCH_2$)-1-imidazolyl |

-continued

| Ex# | A | B |
| --- | --- | --- |
| 153. | 2-pyrimidyl | 2-((cyclopropyl)NHCH$_2$)-1-imidazolyl |
| 154. | 2-pyrimidyl | 2-((cyclopropyl)$_2$NCH$_2$)-1-imidazolyl |
| 155. | 2-pyrimidyl | 2-((cyclobutyl)NHCH$_2$)-1-imidazolyl |
| 156. | 2-pyrimidyl | 2-((cyclobutyl)$_2$NCH$_2$)-1-imidazolyl |
| 157. | 2-pyrimidyl | 2-((cyclopentyl)NHCH$_2$)-1-imidazolyl |
| 158. | 2-pyrimidyl | 2-((cyclopentyl)$_2$NCH$_2$)-1-imidazolyl |
| 159. | 2-pyrimidyl | 2-((cyclohexyl)NHCH$_2$)-1-imidazolyl |
| 160. | 2-pyrimidyl | 2-((cyclohexyl)$_2$NCH$_2$)-1-imidazolyl |
| 161. | 5-pyrimidyl | 2-(NH$_2$SO$_2$)phenyl |
| 162. | 5-pyrimidyl | 2-(CH$_3$SO$_2$)phenyl |
| 163. | 5-pyrimidyl | 3-NH$_2$SO$_2$-4-pyridyl |
| 164. | 5-pyrimidyl | 3-CH$_3$SO$_2$-4-pyridyl |
| 165. | 5-pyrimidyl | 2-(CH$_3$NH)phenyl |
| 166. | 5-pyrimidyl | 3-((CH$_3$)$_2$NCH$_2$)-4-pyridyl |
| 167. | 5-pyrimidyl | 2-(N-(3-R-HO-pyrrolidinyl) CH$_2$)phenyl |
| 168. | 5-pyrimidyl | 2-(N-(4-HO-piperidinyl)CH$_2$)phenyl |
| 169. | 5-pyrimidyl | 2-((CH$_3$)$_2$NCH$_2$)phenyl |
| 170. | 5-pyrimidyl | 2-((CH$_3$)NHCH$_2$)phenyl |
| 171. | 5-pyrimidyl | 2-((CH$_3$CH$_2$)NHCH$_2$)phenyl |
| 172. | 5-pyrimidyl | 2-((CH$_3$CH$_2$)$_2$NCH$_2$)phenyl |
| 173. | 5-pyrimidyl | 2-((CH$_3$CH$_2$)N(CH$_3$)CH$_2$)phenyl |
| 174. | 5-pyrimidyl | 2-(((CH$_3$)$_2$CH)NHCH$_2$)phenyl |
| 175. | 5-pyrimidyl | 2-(((CH$_3$)$_2$CH)$_2$NCH$_2$)phenyl |
| 176. | 5-pyrimidyl | 2-((cyclopropyl)NHCH$_2$) phenyl |
| 177. | 5-pyrimidyl | 2-((cyclopropyl)$_2$NCH$_2$)phenyl |
| 178. | 5-pyrimidyl | 2-((cyclobutyl)NHCH$_2$)phenyl |
| 179. | 5-pyrimidyl | 2-((cyclobutyl)$_2$NCH$_2$)phenyl |
| 180. | 5-pyrimidyl | 2-((cyclopentyl)NHCH$_2$)phenyl |
| 181. | 5-pyrimidyl | 2-((cyclopentyl)$_2$NCH$_2$)phenyl |
| 182. | 5-pyrimidyl | 2-((cyclohexyl)NHCH$_2$)phenyl |
| 183. | 5-pyrimidyl | 2-((cyclohexyl)$_2$NCH$_2$)phenyl |
| 184. | 5-pyrimidyl | 1-CH$_3$-2-imidazolyl |
| 185. | 5-pyrimidyl | 2-CH$_3$-1-imidazolyl |
| 186. | 5-pyrimidyl | 2-((CH$_3$)$_2$NCH$_2$)-1-imidazolyl |
| 187. | 5-pyrimidyl | 2-((CH$_3$)NHCH$_2$)-1-imidazolyl |
| 188. | 5-pyrimidyl | 2-((CH$_3$CH$_2$)NHCH$_2$)-1-imidazolyl |
| 189. | 5-pyrimidyl | 2-((CH$_3$CH$_2$)$_2$NCH$_2$)-1-imidazolyl |
| 190. | 5-pyrimidyl | 2-((CH$_3$CH$_2$)N(CH$_3$)CH$_2$)-1-imidazolyl |
| 191. | 5-pyrimidyl | 2-(((CH$_3$)$_2$CH)NHCH$_2$)-1-imidazolyl |
| 192. | 5-pyrimidyl | 2-(((CH$_3$)$_2$CH)$_2$NCH$_2$)-1-imidazolyl |
| 193. | 5-pyrimidyl | 2-((cyclopropyl)NHCH$_2$)-1-imidazolyl |
| 194. | 5-pyrimidyl | 2-((cyclopropyl)$_2$NCH$_2$)-1-imidazolyl |
| 195. | 5-pyrimidyl | 2-((cyclobutyl)NHCH$_2$)-1-imidazolyl |
| 196. | 5-pyrimidyl | 2-((cyclobutyl)$_2$NCH$_2$)-1-imidazolyl |
| 197. | 5-pyrimidyl | 2-((cyclopentyl)NHCH$_2$)-1-imidazolyl |
| 198. | 5-pyrimidyl | 2-((cyclopentyl)$_2$NCH$_2$)-1-imidazolyl |
| 199. | 5-pyrimidyl | 2-((cyclohexyl)NHCH$_2$)-1-imidazolyl |
| 200. | 5-pyrimidyl | 2-((cyclohexyl)$_2$NCH$_2$)-1-imidazolyl |
| 201. | 2-Cl-phenyl | 2-(NH$_2$SO$_2$)phenyl |
| 202. | 2-Cl-phenyl | 2-(CH$_3$SO$_2$)phenyl |
| 203. | 2-Cl-phenyl | 3-NH$_2$SO$_2$-4-pyridyl |
| 204. | 2-Cl-phenyl | 3-CH$_3$SO$_2$-4-pyridyl |
| 205. | 2-Cl-phenyl | 2-(CH$_3$NH)phenyl |
| 206. | 2-Cl-phenyl | 3-((CH$_3$)$_2$NCH$_2$)-4-pyridyl |
| 207. | 2-Cl-phenyl | 2-(N-(3-R-HO-pyrrolidinyl)CH$_2$)phenyl |
| 208. | 2-Cl-phenyl | 2-(N-(4-HO-piperidinyl)CH$_2$)phenyl |
| 209. | 2-Cl-phenyl | 2-((CH$_3$)$_2$NCH$_2$)phenyl |
| 210. | 2-Cl-phenyl | 2-((CH$_3$)NHCH$_2$)phenyl |
| 211. | 2-Cl-phenyl | 2-((CH$_3$CH$_2$)NHCH$_2$)phenyl |
| 212. | 2-Cl-phenyl | 2-((CH$_3$CH$_2$)$_2$NCH$_2$)phenyl |
| 213. | 2-Cl-phenyl | 2-((CH$_3$CH$_2$)N(CH$_3$)CH$_2$)phenyl |
| 214. | 2-Cl-phenyl | 2-(((CH$_3$)$_2$CH)NHCH$_2$)phenyl |
| 215. | 2-Cl-phenyl | 2-(((CH$_3$)$_2$CH)$_2$NCH$_2$)phenyl |
| 216. | 2-Cl-phenyl | 2-((cyclopropyl)NHCH$_2$)phenyl |
| 217. | 2-Cl-phenyl | 2-((cyclopropyl)$_2$NCH$_2$)phenyl |
| 218. | 2-Cl-phenyl | 2-((cyclobutyl)NHCH$_2$)phenyl |
| 219. | 2-Cl-phenyl | 2-((cyclobutyl)$_2$NCH$_2$)phenyl |
| 220. | 2-Cl-phenyl | 2-((cyclopentyl)NHCH$_2$)phenyl |
| 221. | 2-Cl-phenyl | 2-((cyclopentyl)$_2$NCH$_2$)phenyl |
| 222. | 2-Cl-phenyl | 2-((cyclohexyl)NHCH$_2$)phenyl |
| 223. | 2-Cl-phenyl | 2-((cyclohexyl)$_2$NCH$_2$)phenyl |
| 224. | 2-Cl-phenyl | 1-CH$_3$-2-imidazolyl |
| 225. | 2-Cl-phenyl | 2-CH$_3$-1-imidazolyl |
| 226. | 2-Cl-phenyl | 2-((CH$_3$)$_2$NCH$_2$)-1-imidazolyl |
| 227. | 2-Cl-phenyl | 2-((CH$_3$)NHCH$_2$)-1-imidazolyl |
| 228. | 2-Cl-phenyl | 2-((CH$_3$CH$_2$)NHCH$_2$)-1-imidazolyl |
| 229. | 2-Cl-phenyl | 2-((CH$_3$CH$_2$)$_2$NCH$_2$)-1-imidazolyl |
| 230. | 2-Cl-phenyl | 2-((CH$_3$CH$_2$)N(CH$_3$)CH$_2$)-1-imidazolyl |
| 231. | 2-Cl-phenyl | 2-(((CH$_3$)$_2$CH)NHCH$_2$)-1-imidazolyl |
| 232. | 2-Cl-phenyl | 2-(((CH$_3$)$_2$CH)$_2$NCH$_2$)-1-imidazolyl |
| 233. | 2-Cl-phenyl | 2-((cyclopropyl)NHCH$_2$)-1-imidazolyl |
| 234. | 2-Cl-phenyl | 2-((cyclopropyl)$_2$NCH$_2$)-1-imidazolyl |
| 235. | 2-Cl-phenyl | 2-((cyclobutyl)NHCH$_2$)-1-imidazolyl |
| 236. | 2-Cl-phenyl | 2-((cyclobutyl)$_2$NCH$_2$)-1-imidazolyl |
| 237. | 2-Cl-phenyl | 2-((cyclopentyl)NHCH$_2$)-1-imidazolyl |
| 238. | 2-Cl-phenyl | 2-((cyclopentyl)$_2$NCH$_2$)-1-imidazolyl |
| 239. | 2-Cl-phenyl | 2-((cyclohexyl)NHCH$_2$)-1-imidazolyl |
| 240. | 2-Cl-phenyl | 2-((cyclohexyl)$_2$NCH$_2$)-1-imidazolyl |
| 241. | 2-F-phenyl | 2-(NH$_2$SO$_2$)phenyl |
| 242. | 2-F-phenyl | 2-(CH$_3$SO$_2$)phenyl |
| 243. | 2-F-phenyl | 3-NH$_2$SO$_2$-4-pyridyl |
| 244. | 2-F-phenyl | 3-CH$_3$SO$_2$-4-pyridyl |
| 245. | 2-F-phenyl | 2-(CH$_3$NH)phenyl |
| 246. | 2-F-phenyl | 3-((CH$_3$)$_2$NCH$_2$)-4-pyridyl |
| 247. | 2-F-phenyl | 2-(N-(3-R-HO-pyrrolidinyl)CH$_2$)phenyl |
| 248. | 2-F-phenyl | 2-(N-(4-HO-piperidinyl)CH$_2$)phenyl |
| 249. | 2-F-phenyl | 2-((CH$_3$)$_2$NCH$_2$)phenyl |
| 250. | 2-F-phenyl | 2-((CH$_3$)NHCH$_2$)phenyl |
| 251. | 2-F-phenyl | 2-((CH$_3$CH$_2$)NHCH$_2$)phenyl |
| 252. | 2-F-phenyl | 2-((CH$_3$CH$_2$)$_2$NCH$_2$)phenyl |
| 253. | 2-F-phenyl | 2-((CH$_3$CH$_2$)N(CH$_3$)CH$_2$)phenyl |
| 254. | 2-F-phenyl | 2-(((CH$_3$)$_2$CH)NHCH$_2$)phenyl |
| 255. | 2-F-phenyl | 2-(((CH$_3$)$_2$CH)$_2$NCH$_2$)phenyl |
| 256. | 2-F-phenyl | 2-(cyclopropyl)NHCH$_2$)phenyl |
| 257. | 2-F-phenyl | 2-((cyclopropyl)$_2$NCH$_2$)phenyl |
| 258. | 2-F-phenyl | 2-((cyclobutyl)NHCH$_2$)phenyl |
| 259. | 2-F-phenyl | 2-((cyclobutyl)$_2$NCH$_2$)phenyl |
| 260. | 2-F-phenyl | 2-((cyclopentyl)NHCH$_2$)phenyl |
| 261. | 2-F-phenyl | 2-((cyclopenty1)$_2$NCH$_2$)phenyl |
| 262. | 2-F-phenyl | 2-((cyclohexyl)NHCH$_2$)phenyl |
| 263. | 2-F-phenyl | 2-((cyclohexyl)$_2$NCH$_2$)phenyl |
| 264. | 2-F-phenyl | 1-CH$_3$-2-imidazolyl |
| 265. | 2-F-phenyl | 2-CH$_3$-1-imidazolyl |
| 266. | 2-F-phenyl | 2-((CH$_3$)$_2$NCH$_2$)-1-imidazolyl |
| 267. | 2-F-phenyl | 2-((CH$_3$)NHCH$_2$)-1-imidazolyl |
| 268. | 2-F-phenyl | 2-((CH$_3$CH$_2$)NHCH$_2$)-1-imidazolyl |
| 269. | 2-F-phenyl | 2-((CH$_3$CH$_2$)$_2$NCH$_2$)-1-imidazolyl |
| 270. | 2-F-phenyl | 2-((CH$_3$CH$_2$)N(CH$_3$)CH$_2$)-1-imidazolyl |
| 271. | 2-F-phenyl | 2-(((CH$_3$)$_2$CH)NHCH$_2$)-1-imidazolyl |
| 272. | 2-F-phenyl | 2-(((CH$_3$)$_2$CH)$_2$NCH$_2$)-1-imidazolyl |
| 273. | 2-F-phenyl | 2-((cyclopropyl)NHCH$_2$)-1-imidazolyl |
| 274. | 2-F-phenyl | 2-((cyclopropyl)$_2$NCH$_2$)-1-imidazolyl |
| 275. | 2-F-phenyl | 2-((cyclobutyl)NHCH$_2$)-1-imidazolyl |
| 276. | 2-F-phenyl | 2-((cyclobutyl)$_2$NCH$_2$)-1-imidazolyl |
| 277. | 2-F-phenyl | 2-((cyclopentyl)NHCH$_2$)-1-imidazolyl |
| 278. | 2-F-phenyl | 2-((cyclopentyl)$_2$NCH$_2$)-1-imidazolyl |
| 279. | 2-F-phenyl | 2-((cyclohexyl)NHCH$_2$)-1-imidazolyl |
| 280. | 2-F-phenyl | 2-((cyclohexyl)$_2$NCH$_2$)-1-imidazolyl |
| 281. | 2,6-diF-phenyl | 2-(NH$_2$SO$_2$)phenyl |
| 282. | 2,6-diF-phenyl | 2-(CH$_3$SO$_2$)phenyl |
| 283. | 2,6-diF-phenyl | 3-NH$_2$SO$_2$-4-pyridyl |
| 284. | 2,6-diF-phenyl | 3-CH$_3$SO$_2$-4-pyridyl |
| 285. | 2,6-diF-phenyl | 2-(CH$_3$NH)phenyl |
| 286. | 2,6-diF-phenyl | 3-((CH$_3$)$_2$NCH$_2$)-4-pyridyl |
| 287. | 2,6-diF-phenyl | 2-(N-(3-R-HO-pyrrolidinyl)CH$_2$)phenyl |
| 288. | 2,6-diF-phenyl | 2-(N-(4-HO-piperidinyl)CH$_2$)phenyl |
| 289. | 2,6-diF-phenyl | 2-((CH$_3$)$_2$NCH$_2$)phenyl |
| 290. | 2,6-diF-phenyl | 2-((CH$_3$)NHCH$_2$)phenyl |
| 291. | 2,6-diF-phenyl | 2-((CH$_3$CH$_2$)NHCH$_2$)phenyl |
| 292. | 2,6-diF-phenyl | 2-((CH$_3$CH$_2$)$_2$NCH$_2$)phenyl |
| 293. | 2,6-diF-phenyl | 2-((CH$_3$CH$_2$)N(CH$_3$)CH$_2$)phenyl |
| 294. | 2,6-diF-phenyl | 2-(((CH$_3$)$_2$CH)NHCH$_2$)phenyl |
| 295. | 2,6-diF-phenyl | 2-(((CH$_3$)$_2$CH)$_2$NCH$_2$)phenyl |
| 296. | 2,6-diF-phenyl | 2-((cyclopropyl)NHCH$_2$)phenyl |
| 297. | 2,6-diF-phenyl | 2-((cyclopropyl)$_2$NCH$_2$)phenyl |
| 298. | 2,6-diF-phenyl | 2-((cyclobutyl)NHCH$_2$)phenyl |
| 299. | 2,6-diF-phenyl | 2-((cyclobutyl)$_2$NCH$_2$)phenyl |
| 300. | 2,6-diF-phenyl | 2-((cyclopentyl)NHCH$_2$)phenyl |
| 301. | 2,6-diF-phenyl | 2-((cyclopentyl)$_2$NCH$_2$)phenyl |
| 302. | 2,6-diF-phenyl | 2-((cyclohexyl)NHCH$_2$)phenyl |
| 303. | 2,6-diF-phenyl | 2-((cyclohexyl)$_2$NCH$_2$)phenyl |
| 304. | 2,6-diF-phenyl | 1-CH$_3$-2-imidazolyl |
| 305. | 2,6-diF-phenyl | 2-CH$_3$-1-imidazolyl |
| 306. | 2,6-diF-phenyl | 2-((CH$_3$)$_2$NCH$_2$)-1-imidazolyl |

-continued

| Ex# | A | B |
|---|---|---|
| 307. | 2,6-diF-phenyl | 2-(($CH_3$)NHOH2)-1-imidazolyl |
| 308. | 2,6-diF-phenyl | 2-(($CH_3CH_2$)NHCH$_2$)-1-imidazolyl |
| 309. | 2,6-diF-phenyl | 2-(($CH_3CH_2$)$_2$NCH$_2$)-1-imidazolyl |
| 310. | 2,6-diF-phenyl | 2-(($CH_3CH_2$)N($CH_3$)CH$_2$)-1-imidazolyl |
| 311. | 2,6-diF-phenyl | 2-((($CH_3$)$_2$CH)NHCH$_2$)-1-imidazolyl |
| 312. | 2,6-diF-phenyl | 2-((($CH_3$)$_2$CH)$_2$NCH$_2$)-1-imidazolyl |
| 313. | 2,6-diF-phenyl | 2-((cyclopropyl)NHCH$_2$)-1-imidazolyl |
| 314. | 2,6-diF-phenyl | 2-((cyclopropyl)$_2$NCH$_2$)-1-imidazolyl |
| 315. | 2,6-diF-phenyl | 2-((cyclobutyl)NHCH$_2$)-1-imidazolyl |
| 316. | 2,6-diF-phenyl | 2-((cyclobutyl)$_2$NCH$_2$)-1-imidazolyl |
| 317. | 2,6-diF-phenyl | 2-((cyclopentyl)NHCH$_2$)-1-imidazolyl |
| 318. | 2,6-diF-phenyl | 2-((cyclopentyl)$_2$NCH$_2$)-1-imidazolyl |
| 319. | 2,6-diF-phenyl | 2-((cyclohexyl)NHCH$_2$)-1-imidazolyl |
| 320. | 2,6-diF-phenyl | 2-((cyclohexyl)$_2$NCH$_2$)-1-imidazolyl |
| 321. | piperidinyl | 2-(NH$_2$SO$_2$)phenyl |
| 322. | piperidinyl | 2-(CH$_3$SO$_2$)phenyl |
| 323. | piperidinyl | 3-NH$_2$SO$_2$-4-pyridyl |
| 324. | piperidinyl | 3-CH$_3$SO$_2$-4-pyridyl |
| 325. | piperidinyl | 2-(CH$_3$NH)phenyl |
| 326. | piperidinyl | 3-(($CH_3$)$_2$NCH$_2$)-4-pyridyl |
| 327. | piperidinyl | 2-(N-(3-R-HO-pyrrolidinyl)CH$_2$)phenyl |
| 328. | piperidinyl | 2-(N-(4-HO-piperidinyl)CH$_2$)phenyl |
| 329. | piperidinyl | 2-(($CH_3$)$_2$NCH$_2$)phenyl |
| 330. | piperidinyl | 2-(($CH_3$)NHCH$_2$)phenyl |
| 331. | piperidinyl | 2-(($CH_3CH_2$)NHCH$_2$)phenyl |
| 332. | piperidinyl | 2-(($CH_3CH_2$)$_2$NCH$_2$)phenyl |
| 333. | piperidinyl | 2-(($CH_3CH_2$)N($CH_3$)CH$_2$)phenyl |
| 334. | piperidinyl | 2-((($CH_3$)$_2$CH)NHCH$_2$)phenyl |
| 335. | piperidinyl | 2-((($CH_3$)$_2$CH)$_2$NCH$_2$)phenyl |
| 336. | piperidinyl | 2-((cyclopropyl)NHCH$_2$)phenyl |
| 337. | piperidinyl | 2-((cyclopropyl)$_2$NCH$_2$)phenyl |
| 338. | piperidinyl | 2-((cyclobutyl)NHCH$_2$)phenyl |
| 339. | piperidinyl | 2-((cyclobutyl)$_2$NCH$_2$)phenyl |
| 340. | piperidinyl | 2-((cyclopentyl)NHCH$_2$)phenyl |
| 341. | piperidinyl | 2-((cyclopentyl)$_2$NCH$_2$)phenyl |
| 342. | piperidinyl | 2-((cyclohexyl)NHCH$_2$)phenyl |
| 343. | piperidinyl | 2-((cyclohexyl)$_2$NCH$_2$)phenyl |
| 344. | piperidinyl | 1-CH$_3$-2-imidazolyl |
| 345. | piperidinyl | 2-CH$_3$-1-imidazolyl |
| 346. | piperidinyl | 2-(($CH_3$)$_2$NCH$_2$)-1-imidazolyl |
| 347. | piperidinyl | 2-(($CH_3$)NHCH$_2$)-1-imidazolyl |
| 348. | piperidinyl | 2-(($CH_3CH_2$)NHCH$_2$)-1-imidazolyl |
| 349. | piperidinyl | 2-(($CH_3CH_2$)$_2$NCH$_2$)-1-imidazolyl |
| 350. | piperidinyl | 2-(($CH_3CH_2$)N($CH_3$)CH$_2$)-1-imidazolyl |
| 351. | piperidinyl | 2-((($CH_3$)$_2$CH)NHCH$_2$)-1-imidazolyl |
| 352. | piperidinyl | 2-((($CH_3$)$_2$CH)$_2$NCH$_2$)-1-imidazolyl |
| 353. | piperidinyl | 2-((cyclopropyl)NHCH$_2$)-1-imidazolyl |
| 354. | piperidinyl | 2-((cyclopropyl)$_2$NCH$_2$)-1-imidazolyl |
| 355. | piperidinyl | 2-((cyclobutyl)NHCH$_2$)-1-imidazolyl |
| 356. | piperidinyl | 2-((cyclobutyl)$_2$NCH$_2$)-1-imidazolyl |
| 357. | piperidinyl | 2-((cyclopentyl)NHCH$_2$)-1-imidazolyl |
| 358. | piperidinyl | 2-((cyclopentyl)$_2$NCH$_2$)-1-imidazolyl |
| 359. | piperidinyl | 2-((cyclohexyl)NHCH$_2$)-1-imidazolyl |
| 360. | piperidinyl | 2-((cyclohexyl)$_2$NCH$_2$)-1-imidazolyl |

Table 2

Examples 1–360 use the structures from Table 1 and the corresponding A and B groups from Examples 1–360 of Table 1, and:

$R^{1a}$ is $CH_2CH_3$.

Table 3

Examples 1–360 use the structures from Table 1 and the corresponding A and B groups from Examples 1–360 of Table 1, and:

$R^{1a}$ is $CF_3$.

Table 4

Examples 1–360 use the structures from Table 1 and the corresponding A and B groups from Examples 1–360 of Table 1, and:

$R^{1a}$ is $SCH_3$.

Table 5

Examples 1–360 use the structures from Table 1 and the corresponding A and B groups from Examples 1–360 of Table 1, and:

$R^{1a}$ is $SOCH_3$.

Table 6

Examples 1–360 use the structures from Table 1 and the corresponding A and B groups from Examples 1–360 of Table 1, and:

$R^{1a}$ is $SO_2CH_3$.

Table 7

Examples 1–360 use the structures from Table 1 and the corresponding A and B groups from Examples 1–360 of Table 1, and:

$R^{1a}$ is Cl.

Table 8

Examples 1–360 use the structures from Table 1 and the corresponding A and B groups from Examples 1–360 of Table 1, and:

$R^{1a}$ is F.

Table 9

Examples 1–360 use the structures from Table 1 and the corresponding A and B groups from Examples 1–360 of Table 1, and:

$R^{1a}$ is $CO_2CH_3$.

Table 10

Examples 1–360 use the structures from Table 1 and the corresponding A and B groups from Examples 1–360 of Table 1, and:

$R^{1a}$ is $CH_2OCH_3$.

Table 11

Examples 1–360 use the structures from Table 1 and the corresponding A and B groups from Examples 1–360 of Table 1, and:

$R^{1a}$ is $CONH_2$.

Table 12

Examples 1–360 use the structures from Table 1 and the corresponding A and B groups from Examples 1–360 of Table 1, and:

$R^{1a}$ is CN.

Table 13

Examples 1–360 use the structures from Table 1 and the corresponding A and B groups from Examples 1–360 of Table 1, and:

$R^{1a}$ is $CH_2NH_2$.

Table 14

Examples 1–360 use the structures from Table 1 and the corresponding A and B groups from Examples 1–360 of Table 1, and:

$R^{1a}$ is $CH_2NHSO_2CH_3$.

141
Table 15
Examples 1–360 use the structures from Table 1 and the corresponding A and B groups from Examples 1–360 of Table 1, and:
$R^{1a}$ is 1-imidazolyl-$CH_2$.
142
Table 16
Examples 1–360 use the structures from Table 1 and the corresponding A and B groups from Examples 1–360 of Table 1, and:
$R^{1a}$ is 1-tetrazolyl-$CH_2$—.
TABLE 17
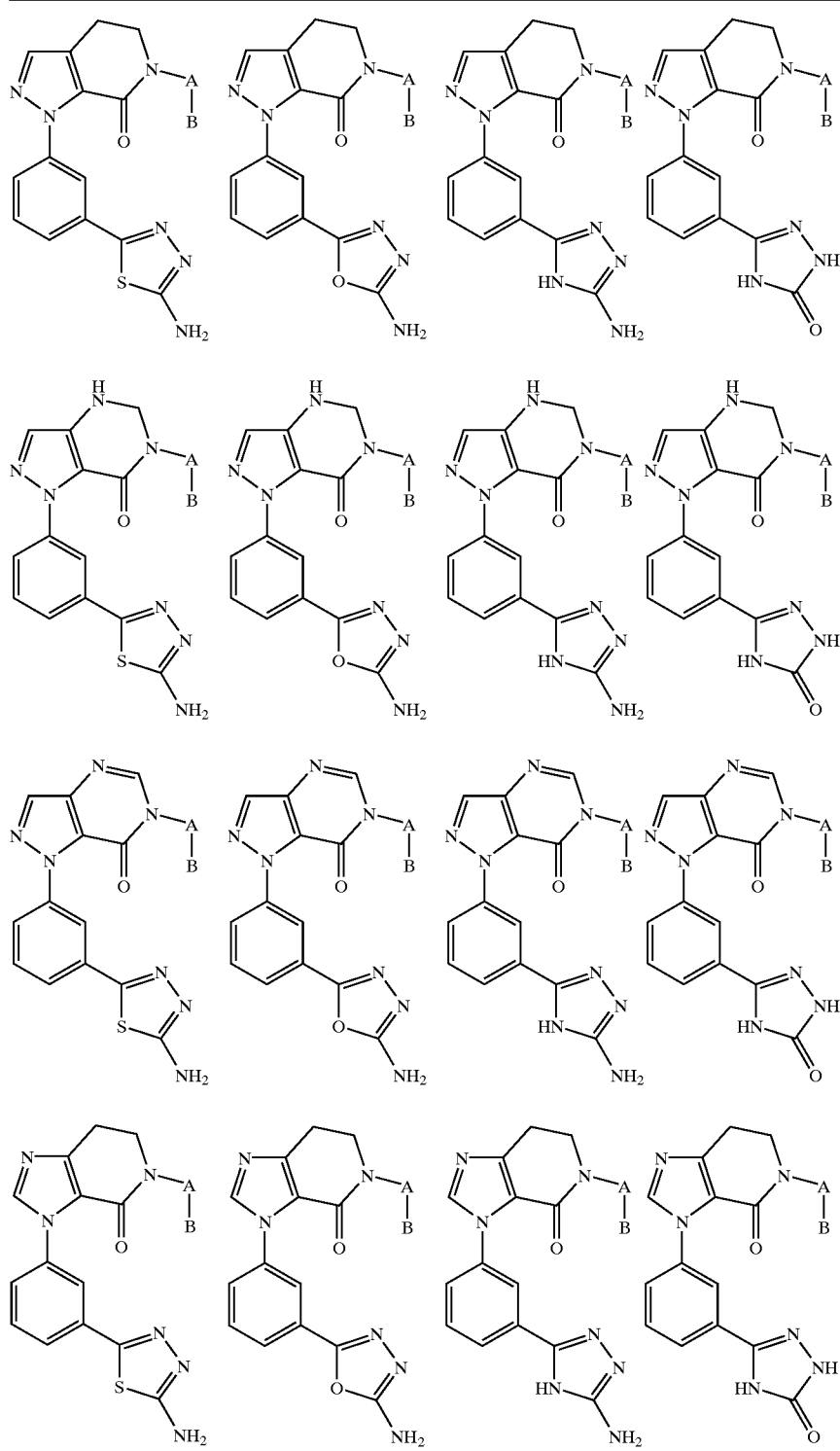

TABLE 17-continued
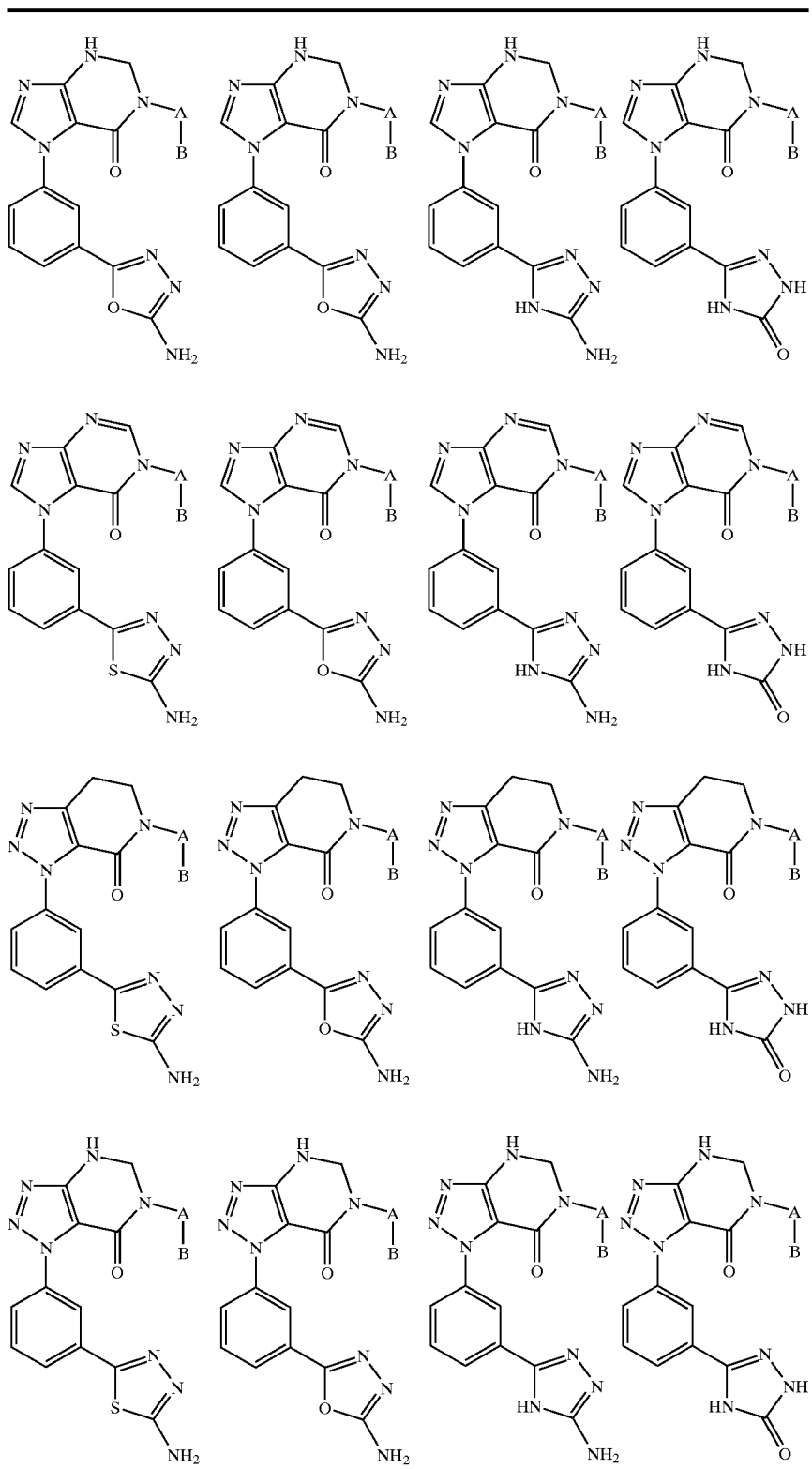

TABLE 17-continued
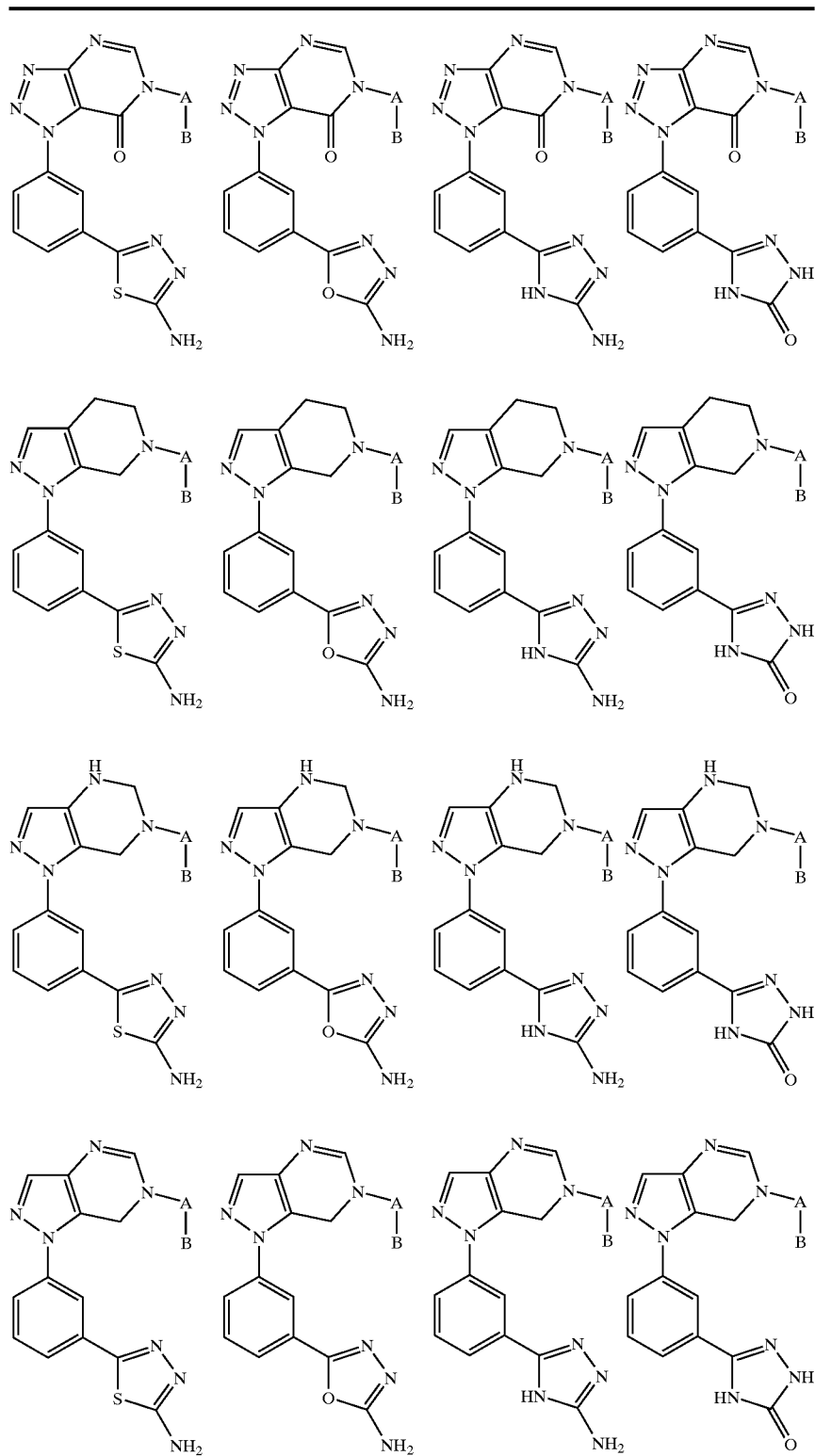

TABLE 17-continued
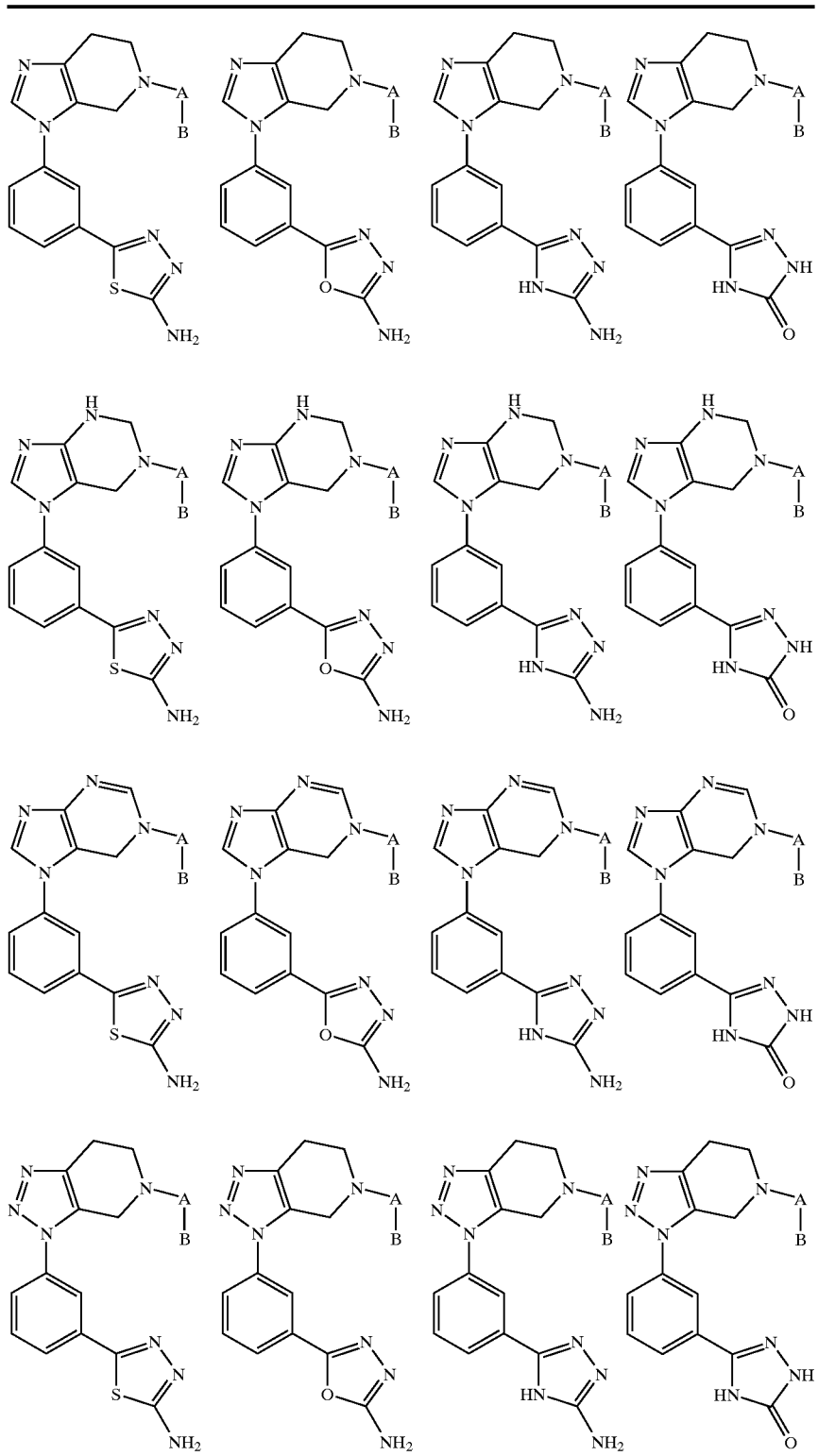

TABLE 17-continued

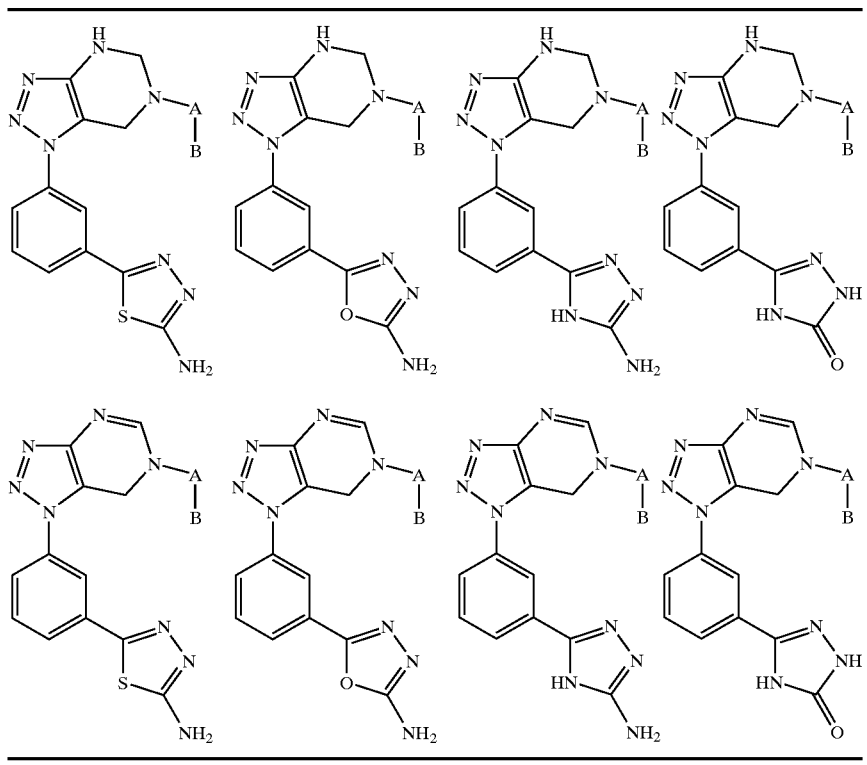

| EX# | A | B |
|---|---|---|
| 1. | phenyl | 2-(NH$_2$SO$_2$)phenyl |
| 2. | phenyl | 2-(CH$_3$SO$_2$)phenyl |
| 3. | phenyl | 3-NH$_2$SO$_2$-4-pyridyl |
| 4. | phenyl | 3-CH$_3$SO$_2$-4-pyridyl |
| 5. | phenyl | 2-(CH$_3$NH)phenyl |
| 6. | phenyl | 3-((CH$_3$)$_2$NCH$_2$)-4-pyridyl |
| 7. | phenyl | 2- (N-(3-R-HO-pyrrolidinyl)CH$_2$)phenyl |
| 8. | phenyl | 2-(N-(4-HO-piperidinyl) CH$_2$)phenyl |
| 9. | phenyl | 2-((CH$_3$)$_2$NCH$_2$)phenyl |
| 10. | phenyl | 2-((CH$_3$)NHCH$_2$)phenyl |
| 11. | phenyl | 2-((CH$_3$CH$_2$)NHCH$_2$)phenyl |
| 12. | phenyl | 2-((CH$_3$CH$_2$)$_2$NCH$_2$)phenyl |
| 13. | phenyl | 2-((CH$_3$CH$_2$)N(CH$_3$)CH$_2$)phenyl |
| 14. | phenyl | 2-(((CH$_3$)$_2$CH)NHCH$_2$)phenyl |
| 15. | phenyl | 2-(((CH$_3$)$_2$CH)$_2$NCH$_2$)phenyl |
| 16. | phenyl | 2-((cyclopropyl)NHCH$_2$)phenyl |
| 17. | phenyl | 2-((cyclopropyl)$_2$NCH$_2$)phenyl |
| 18. | phenyl | 2-((cyclobutyl)NHCH$_2$)phenyl |
| 19. | phenyl | 2-((cyclobutyl)$_2$NCH$_2$)phenyl |
| 20. | phenyl | 2-((cyclopentyl)NHCH$_2$)phenyl |
| 21. | phenyl | 2-((cyclopentyl)$_2$NCH$_2$)phenyl |
| 22. | phenyl | 2-((cyclohexyl)NHCH$_2$)phenyl |
| 23. | phenyl | 2-((cyclohexyl)$_2$NCH$_2$)phenyl |
| 24. | phenyl | 1-CH$_3$-2-imidazolyl |
| 25. | phenyl | 2-CH$_3$-1-imidazolyl |
| 26. | phenyl | 2-((CH$_3$)$_2$NCH$_2$)-1-imidazolyl |
| 27. | phenyl | 2-((CH$_3$)NHCH$_2$)-1-imidazolyl |
| 28. | phenyl | 2-((CH$_3$CH$_2$)NHCH$_2$)-1-imidazolyl |
| 29. | phenyl | 2-((CH$_3$CH$_2$)$_2$NCH$_2$)-1-imidazolyl |
| 30. | phenyl | 2-((CH$_3$CH$_2$)N(CH$_3$)CH$_2$)-1-imidazolyl |
| 31. | phenyl | 2-(((CH$_3$)$_2$CH)NHCH$_2$)-1-imidazolyl |
| 32. | phenyl | 2-(((CH$_3$)$_2$CH)$_2$NCH$_2$)-1-iinidazolyl |
| 33. | phenyl | 2-((cyclopropyl)NHCH$_2$)-1-imidazolyl |
| 34. | phenyl | 2-((cyclopropyl)$_2$NCH$_2$)-1-imidazolyl |
| 35. | phenyl | 2-((cyclobutyl)NHCH$_2$)-1-imidazolyl |
| 36. | phenyl | 2-((cyclobutyl)$_2$NCH$_2$)-1-imidazolyl |
| 37. | phenyl | 2-((cyclopentyl)NHCH$_2$)-1-imidazolyl |
| 38. | phenyl | 2-((cyclopentyl)$_2$NCH$_2$)-1-imidazolyl |
| 39. | phenyl | 2-((cyclohexyl)NHCH$_2$)-1-imidazolyl |
| 40. | phenyl | 2-((cyclohexyl)$_2$NCH$_2$)-1-imidazolyl |
| 41. | 2-pyridyl | 2-(NH$_2$SO$_2$)phenyl |
| 42. | 2-pyridyl | 2-(CH$_3$SO$_2$)phenyl |
| 43. | 2-pyridyl | 3-NH$_2$SO$_2$-4-pyridyl |
| 44. | 2-pyridyl | 3-CH$_3$SO$_2$-4-pyridyl |
| 45. | 2-pyridyl | 2-(CH$_3$NH)phenyl |
| 46. | 2-pyridyl | 3-((CH$_3$)$_2$NCH$_2$)-4-pyridyl |
| 47. | 2-pyridyl | 2-(N-(3-R-HO-pyrrolidinyl)CH$_2$)phenyl |
| 48. | 2-pyridyl | 2-(N-(4-HO-piperidinyl)CH$_2$)phenyl |
| 49. | 2-pyridyl | 2-((CH$_3$)$_2$NCH$_2$)phenyl |
| 50. | 2-pyridyl | 2-((CH$_3$)NHCH$_2$)phenyl |
| 51. | 2-pyridyl | 2-((CH$_3$CH$_2$)NHCH$_2$)phenyl |
| 52. | 2-pyridyl | 2-((CH$_3$CH$_2$)$_2$NCH$_2$)phenyl |
| 53. | 2-pyridyl | 2-((CH$_3$CH$_2$)N(CH$_3$)CH$_2$)phenyl |
| 54. | 2-pyridyl | 2-(((CH$_3$)$_2$CH)NHCH$_2$)phenyl |
| 55. | 2-pyridyl | 2-(((CH$_3$)$_2$CH)$_2$NCH$_2$)phenyl |
| 56. | 2-pyridyl | 2-((cyclopropyl)NHCH$_2$)phenyl |
| 57. | 2-pyridyl | 2-((cyclopropyl)$_2$NCH$_2$)phenyl |
| 58. | 2-pyridyl | 2-((cyclobutyl)NHCH$_2$)phenyl |
| 59. | 2-pyridyl | 2-((cyclobutyl)$_2$NCH$_2$)phenyl |
| 60. | 2-pyridyl | 2-((cyclopentyl)NHCH$_2$)phenyl |
| 61. | 2-pyridyl | 2-((cyclopentyl)$_2$NCH$_2$)phenyl |
| 62. | 2-pyridyl | 2-((cyclohexyl)NHCH$_2$)phenyl |
| 63. | 2-pyridyl | 2-((cyclohexyl)$_2$NCH$_2$)phenyl |
| 64. | 2-pyridyl | 1-CH$_3$-2-imidazolyl |
| 65. | 2-pyridyl | 2-CH$_3$-1-imidazolyl |
| 66. | 2-pyridyl | 2-((CH$_3$)$_2$NCH$_2$)-1-imidazolyl |
| 67. | 2-pyridyl | 2-((CH$_3$)NHCH$_2$)-1-imidazolyl |
| 68. | 2-pyridyl | 2-((CH$_3$CH$_2$)NHCH$_2$)-1-imidazolyl |
| 69. | 2-pyridyl | 2-((CH$_3$CH$_2$)$_2$NCH$_2$)-1-imidazolyl |
| 70. | 2-pyridyl | 2-((CH$_3$CH$_2$)N(CH$_3$)CH$_2$)-1-imidazolyl |
| 71. | 2-pyridyl | 2-(((CH$_3$)$_2$CH)NHCH$_2$)-1-imidazolyl |
| 72. | 2-pyridyl | 2-(((CH$_3$)$_2$CH)$_2$NCH$_2$)-1-imidazolyl |

-continued

| EX# | A | B |
|---|---|---|
| 73. | 2-pyridyl | 2-((cyclopropyl)NHCH$_2$)-1-imidazolyl |
| 74. | 2-pyridyl | 2-((cyclopropyl)$_2$NCH$_2$)-1-imidazolyl |
| 75. | 2-pyridyl | 2-((cyclobutyl)NHCH$_2$)-1-imidazolyl |
| 76. | 2-pyridyl | 2-((cyclobutyl)$_2$NCH$_2$)-1-imidazolyl |
| 77. | 2-pyridyl | 2-((cyclopentyl)NHCH$_2$)-1-imidazolyl |
| 78. | 2-pyridyl | 2-((cyclopentyl)$_2$NCH$_2$)-1-imidazolyl |
| 79. | 2-pyridyl | 2-((cyclohexyl)NHCH$_2$)-1-imidazolyl |
| 80. | 2-pyridyl | 2-((cyclohexyl)$_2$NCH$_2$)-1-imidazolyl |
| 81. | 3-pyridyl | 2-(NH$_2$SO$_2$)phenyl |
| 82. | 3-pyridyl | 2-(CH$_3$SO$_2$)phenyl |
| 83. | 3-pyridyl | 3-NH$_2$SO$_2$-4-pyridyl |
| 84. | 3-pyridyl | 3-CH$_3$SO$_2$-4-pyridyl |
| 85. | 3-pyridyl | 2-(CH$_3$NH)phenyl |
| 86. | 3-pyridyl | 3-((CH$_3$)$_2$NCH$_2$)-4-pyridyl |
| 87. | 3-pyridyl | 2-(N-(3-R-HO-pyrrolidinyl)CH$_2$)phenyl |
| 88. | 3-pyridyl | 2-(N-(4-HO-piperidinyl)CH$_2$)phenyl |
| 89. | 3-pyridyl | 2-((CH$_3$)$_2$NCH$_2$)phenyl |
| 90. | 3-pyridyl | 2-((CH$_3$)NHCH$_2$)phenyl |
| 91. | 3-pyridyl | 2-((CH$_3$CH$_2$)NHCH$_2$)phenyl |
| 92. | 3-pyridyl | 2-((CH$_3$CH$_2$)$_2$NCH$_2$)phenyl |
| 93. | 3-pyridyl | 2-((CH$_3$CH$_2$)N(CH$_3$)CH$_2$)phenyl |
| 94. | 3-pyridyl | 2-(((CH$_3$)$_2$CH)NHCH$_2$)phenyl |
| 95. | 3-pyridyl | 2-(((CH$_3$)$_2$CH)$_2$NCH$_2$)phenyl |
| 96. | 3-pyridyl | 2-((cyclopropyl)NHCH$_2$)phenyl |
| 97. | 3-pyridyl | 2-((cyclopropyl)$_2$NCH$_2$)phenyl |
| 98. | 3-pyridyl | 2-((cyclobutyl)NHCH$_2$)phenyl |
| 99. | 3-pyridyl | 2-((cyclobutyl)$_2$NCH$_2$)phenyl |
| 100. | 3-pyridyl | 2-((cyclopentyl)NHCH$_2$)phenyl |
| 101. | 3-pyridyl | 2-((cyclopentyl)$_2$NCH$_2$)phenyl |
| 102. | 3-pyridyl | 2-((cyclohexyl)NHCH$_2$)phenyl |
| 103. | 3-pyridyl | 2-((cyclohexyl)$_2$NCH$_2$)phenyl |
| 104. | 3-pyridyl | 1-CH$_3$-2-imidazolyl |
| 105. | 3-pyridyl | 2-CH$_3$-1-imidazolyl |
| 106. | 3-pyridyl | 2-((CH$_3$)$_2$NCH$_2$)-1-imidazolyl |
| 107. | 3-pyridyl | 2-((CH$_3$)NHCH$_2$)-1-imidazolyl |
| 108. | 3-pyridyl | 2-((CH$_3$CH$_2$)NHCH$_2$)-1-imidazolyl |
| 109. | 3-pyridyl | 2-((CH$_3$CH$_2$)$_2$NCH$_2$)-1-imidazolyl |
| 110. | 3-pyridyl | 2-((CH$_3$CH$_2$)N(CH$_3$)CH$_2$)-1-imidazolyl |
| 111. | 3-pyridyl | 2-(((CH$_3$)$_2$CH)NHCH$_2$)-1-imidazolyl |
| 112. | 3-pyridyl | 2-(((CH$_3$)$_2$CH)$_2$NCH$_2$)-1-imidazolyl |
| 113. | 3-pyridyl | 2-((cyclopropyl)NHCH$_2$)-1-imidazolyl |
| 114. | 3-pyridyl | 2-((cyclopropyl)$_2$NCH$_2$)-1-imidazolyl |
| 115. | 3-pyridyl | 2-((cyclobutyl)NHCH$_2$)-1-imidazolyl |
| 116. | 3-pyridyl | 2-((cyclobutyl)$_2$NCH$_2$)-1-imidazolyl |
| 117. | 3-pyridyl | 2-((cyclopentyl)NHCH$_2$)-1-imidazolyl |
| 118. | 3-pyridyl | 2-((cyclopentyl)$_2$NCH$_2$)-1-imidazolyl |
| 119. | 3-pyridyl | 2-((cyclohexyl)NHCH$_2$)-1-imidazolyl |
| 120. | 3-pyridyl | 2-((cyclohexyl)$_2$NCH$_2$)-1-imidazolyl |
| 121. | 2-pyrimidyl | 2-(NH$_2$SO$_2$)phenyl |
| 122. | 2-pyrimidyl | 2-(CH$_3$SO$_2$)phenyl |
| 123. | 2-pyrimidyl | 3-NH$_2$SO$_2$-4-pyridyl |
| 124. | 2-pyrimidyl | 3-CH$_3$SO$_2$-4-pyridyl |
| 125. | 2-pyrimidyl | 2-(CH$_3$NH)phenyl |
| 126. | 2-pyrimidyl | 3-((CH$_3$)$_2$NCH$_2$)-4-pyridyl |
| 127. | 2-pyrimidyl | 2-(N-(3-R-HO-pyrrolidinyl)CH$_2$)phenyl |
| 128. | 2-pyrimidyl | 2-(N-(4-HO-piperidinyl)CH$_2$)phenyl |
| 129. | 2-pyrimidyl | 2-((CH$_3$)$_2$NCH$_2$)phenyl |
| 130. | 2-pyrimidyl | 2-((CH$_3$)NHCH$_2$)phenyl |
| 131. | 2-pyrimidyl | 2-((CH$_3$CH$_2$)NHCH$_2$)phenyl |
| 132. | 2-pyrimidyl | 2-((CH$_3$CH$_2$)$_2$NCH$_2$)phenyl |
| 133. | 2-pyrimidyl | 2-((CH$_3$CH$_2$)N(CH$_3$)CH$_2$)phenyl |
| 134. | 2-pyrimidyl | 2-(((CH$_3$)$_2$CH)NHCH$_2$)phenyl |
| 135. | 2-pyrimidyl | 2-(((CH$_3$)$_2$CH)$_2$NCH$_2$)phenyl |
| 136. | 2-pyrimidyl | 2-((cyclopropyl)NHCH$_2$)phenyl |
| 137. | 2-pyrimidyl | 2-((cyclopropyl)$_2$NCH$_2$)phenyl |
| 138. | 2-pyrimidyl | 2-((cyclobutyl)NHCH$_2$)phenyl |
| 139. | 2-pyrimidyl | 2-((cyclobutyl)$_2$NCH$_2$)phenyl |
| 140. | 2-pyrimidyl | 2-((cyclopentyl)NHCH$_2$)phenyl |
| 141. | 2-pyrimidyl | 2-((cyclopentyl)$_2$NCH$_2$)phenyl |
| 142. | 2-pyrimidyl | 2-((cyclohexyl)NHCH$_2$)phenyl |
| 143. | 2-pyrimidyl | 2-((cyclohexyl)$_2$NCH$_2$)phenyl |
| 144. | 2-pyrimidyl | 1-CH$_3$-2-imidazolyl |
| 145. | 2-pyrimidyl | 2-CH$_3$-1-imidazolyl |
| 146. | 2-pyrimidyl | 2-((CH$_3$)$_2$NCH$_2$)-1-imidazoiyl |
| 147. | 2-pyrimidyl | 2-((CH$_3$)NHCH$_2$)-1-imidazolyl |
| 148. | 2-pyrimidyl | 2-((CH$_3$CH$_2$)NHCH$_2$)-1-imidazolyl |
| 149. | 2-pyrimidyl | 2-((CH$_3$CH$_2$)$_2$NCH$_2$)-1-imidazolyl |
| 150. | 2-pyrimidyl | 2-((CH$_3$CH$_2$)N(CH$_3$)CH$_2$)-1-imidazolyl |
| 151. | 2-pyrimidyl | 2-(((CH$_3$)$_2$CH)NHCH$_2$)-1-imidazolyl |
| 152. | 2-pyrimidyl | 2-(((CH$_3$)$_2$CH)$_2$NCH$_2$)-1-imidazolyl |
| 153. | 2-pyrimidyl | 2-((cyclopropyl)NHCH$_2$)-1-imidazolyl |
| 154. | 2-pyrimidyl | 2-((cyclopropyl)$_2$NCH$_2$)-1-imidazolyl |
| 155. | 2-pyrimidyl | 2-((cyclobutyl)NHCH$_2$)-1-imidazolyl |
| 156. | 2-pyrimidyl | 2-((cyclobutyl)$_2$NCH$_2$)-1-imidazolyl |
| 157. | 2-pyrimidyl | 2-((cyclopentyl)NHCH$_2$)-1-imidazolyl |
| 158. | 2-pyrimidyl | 2-((cyclopentyl)$_2$NCH$_2$)-1-imidazolyl |
| 159. | 2-pyrimidyl | 2-((cyclohexyl)NHCH$_2$)-1-imidazolyl |
| 160. | 2-pyrimidyl | 2-((cyclohexyl)$_2$NCH$_2$)-1-imidazolyl |
| 161. | 5-pyrimidyl | 2-(NH$_2$SO$_2$)phenyl |
| 162. | 5-pyrimidyl | 2-(CH$_3$SO$_2$)phenyl |
| 163. | 5-pyrimidyl | 3-NH$_2$SO$_2$-4-pyridyl |
| 164. | 5-pyrimidyl | 3-CH$_3$SO$_2$-4-pyridyl |
| 165. | 5-pyrimidyl | 2-(CH$_3$NH)phenyl |
| 166. | 5-pyrimidyl | 3-((CH$_3$)$_2$NCH$_2$)-4-pyridyl |
| 167. | 5-pyrimidyl | 2-(N-(3-R-HO-pyrrolidinyl)CH$_2$)phenyl |
| 168. | 5-pyrimidyl | 2-(N-(4-HO-piperidinyl)CH$_2$)phenyl |
| 169. | 5-pyrimidyl | 2-((CH$_3$)$_2$NCH$_2$)phenyl |
| 170. | 5-pyrimidyl | 2-((CH$_3$)NHCH$_2$)phenyl |
| 171. | 5-pyrimidyl | 2-((CH$_3$CH$_2$)NHCH$_2$)phenyl |
| 172. | 5-pyrimidyl | 2-((CH$_3$CH$_2$)$_2$NCH$_2$)phenyl |
| 173. | 5-pyrimidyl | 2-((CH$_3$CH$_2$)N(CH$_3$)CH$_2$)phenyl |
| 174. | 5-pyrimidyl | 2-(((CH$_3$)$_2$CH)NHCH$_2$)phenyl |
| 175. | 5-pyrimidyl | 2-(((CH$_3$)$_2$CH)$_2$NCH$_2$)phenyl |
| 176. | 5-pyrimidyl | 2-((cyclopropyl)NHCH$_2$)phenyl |
| 177. | 5-pyrimidyl | 2-((cyclopropyl)$_2$NCH$_2$)phenyl |
| 178. | 5-pyrimidyl | 2-((cyclobutyl)NHCH$_2$)phenyl |
| 179. | 5-pyrimidyl | 2-((cyclobutyl)$_2$NCH$_2$)phenyl |
| 180. | 5-pyrimidyl | 2-((cyclopentyl)NHCH$_2$)phenyl |
| 181. | 5-pyrimidyl | 2-((cyclopentyl)$_2$NCH$_2$)phenyl |
| 182. | 5-pyrimidyl | 2-((cyclohexyl)NHCH$_2$)phenyl |
| 183. | 5-pyrimidyl | 2-((cyclohexyl)$_2$NCH$_2$)phenyl |
| 184. | 5-pyrimidyl | 1-CH$_3$-2-imidazolyl |
| 185. | 5-pyrimidyl | 2-CH$_3$-1-imidazdlyl |
| 186. | 5-pyrimidyl | 2-((CH$_3$)$_2$NCH$_2$)-1-imidazolyl |
| 187. | 5-pyrimidyl | 2-((CH$_3$)NHCH$_2$)-1-imidazolyl |
| 188. | 5-pyrimidyl | 2-((CH$_3$CH$_2$)NHCH$_2$)-1-imidazolyl |
| 189. | 5-pyrimidyl | 2-((CH$_3$CH$_2$)$_2$NCH$_2$)-1-imidazolyl |
| 190. | 5-pyrimidyl | 2-((CH$_3$CH$_2$)N(CH$_3$)CH$_2$)-1-imidazolyl |
| 191. | 5-pyrimidyl | 2-(((CH$_3$)$_2$CH)NHCH$_2$)-1-imidazolyl |
| 192. | 5-pyrimidyl | 2-(((CH$_3$)$_2$CH)$_2$NCH$_2$)-1-imidazolyl |
| 193. | 5-pyrimidyl | 2-((cyclopropyl)NHCH$_2$)-1-imidazolyl |
| 194. | 5-pyrimidyl | 2-((cyclopropyl)$_2$NCH$_2$)-1-imidazolyl |
| 195. | 5-pyrimidyl | 2-((cyclobutyl)NHCH$_2$)-1-imidazolyl |
| 196. | 5-pyrimidyl | 2-((cyclobutyl)$_2$NCH$_2$)-1-imidazolyl |
| 197. | 5-pyrimidyl | 2-((cyclopentyl)NHCH$_2$)-1-imidazolyl |
| 198. | 5-pyrimidyl | 2-((cyclopentyl)$_2$NCH$_2$)-1-imidazolyl |
| 199. | 5-pyrimidyl | 2-((cyclohexyl)NHCH$_2$)-1-imidazolyl |
| 200. | 5-pyrimidyl | 2-((cyclohexyl)$_2$NCH$_2$)-1-imidazolyl |
| 201. | 2-Cl-phenyl | 2-(NH$_2$SO$_2$)phenyl |
| 202. | 2-Cl-phenyl | 2-(CH$_3$SO$_2$)phenyl |
| 203. | 2-Cl-phenyl | 3-NH$_2$SO$_2$-4-pyridyl |
| 204. | 2-Cl-phenyl | 3-CH$_3$SO$_2$-4-pyridyl |
| 205. | 2-Cl-phenyl | 2-(CH$_3$NH)phenyl |
| 206. | 2-Cl-phenyl | 3-((CH$_3$)$_2$NCH$_2$)-4-pyridyl |
| 207. | 2-Cl-phenyl | 2-(N-(3-R-HO-pyrrolidinyl)CH$_2$)phenyl |
| 208. | 2-Cl-phenyl | 2-(N-(4-HO-piperidinyl)CH$_2$)phenyl |
| 209. | 2-Cl-phenyl | 2-((CH$_3$)$_2$NCH$_2$)phenyl |
| 210. | 2-Cl-phenyl | 2-((CH$_3$)NHCH$_2$)phenyl |
| 211. | 2-Cl-phenyl | 2-((CH$_3$CH$_2$)NHCH$_2$)phenyl |
| 212. | 2-Cl-phenyl | 2-((CH$_3$CH$_2$)$_2$NCH$_2$)phenyl |
| 213. | 2-Cl-phenyl | 2-((CH$_3$CH$_2$)N(CH$_3$)CH$_2$)phenyl |
| 214. | 2-Cl-phenyl | 2-(((CH$_3$)$_2$CH)NHCH$_2$)phenyl |
| 215. | 2-Cl-phenyl | 2-(((CH$_3$)$_2$CH)$_2$NCH$_2$)phenyl |
| 216. | 2-Cl-phenyl | 2-((cyclopropyl)NHCH$_2$)phenyl |
| 217. | 2-Cl-phenyl | 2-((cyclopropyl)$_2$NCH$_2$)phenyl |
| 218. | 2-Cl-phenyl | 2-((cyclobutyl)NHCH$_2$)phenyl |
| 219. | 2-Cl-phenyl | 2-((cyclobutyl)$_2$NCH$_2$)phenyl |
| 220. | 2-Cl-phenyl | 2-((cyclopentyl)NHCH$_2$)phenyl |
| 221. | 2-Cl-phenyl | 2-((cyclopentyl)$_2$NCH$_2$)phenyl |
| 222. | 2-Cl-phenyl | 2-((cyclohexyl)NHCH$_2$)phenyl |
| 223. | 2-Cl-phenyl | 2-((cyclohexyl)$_2$NCH$_2$)phenyl |
| 224. | 2-Cl-phenyl | 1-CH$_3$-2-imidazolyl |
| 225. | 2-Cl-phenyl | 2-CH$_3$-1-imidazolyl |
| 226. | 2-Cl-phenyl | 2-((CH$_3$)$_2$NCH$_2$)-1-imidazolyl |

-continued

| EX# | A | B |
|---|---|---|
| 227. | 2-Cl-phenyl | 2-(($CH_3$)NH$CH_2$)-1-imidazolyl |
| 228. | 2-Cl-phenyl | 2-(($CH_3CH_2$)NH$CH_2$)-1-imidazolyl |
| 229. | 2-Cl-phenyl | 2-(($CH_3CH_2$)$_2$N$CH_2$)-1-imidazolyl |
| 230. | 2-Cl-phenyl | 2-(($CH_3CH_2$)N($CH_3$)$CH_2$)-1-imidazolyl |
| 231. | 2-Cl-phenyl | 2-((($CH_3$)$_2$CH)NH$CH_2$)-1-imidazolyl |
| 232. | 2-Cl-phenyl | 2-((($CH_3$)$_2$CH)$_2$N$CH_2$)-1-imidazolyl |
| 233. | 2-Cl-phenyl | 2-((cyclopropyl)NH$CH_2$)-1-imidazolyl |
| 234. | 2-Cl-phenyl | 2-((cyclopropyl)$_2$N$CH_2$)-1-imidazolyl |
| 235. | 2-Cl-phenyl | 2-((cyclobutyl)NH$CH_2$)-1-imidazolyl |
| 236. | 2-Cl-phenyl | 2-((cyclobutyl)$_2$N$CH_2$)-1-imidazolyl |
| 237. | 2-Cl-phenyl | 2-((cyclopentyl)NH$CH_2$)-1-imidazolyl |
| 238. | 2-Cl-phenyl | 2-((cyclopentyl)$_2$N$CH_2$)-1-imidazolyl |
| 239. | 2-Cl-phenyl | 2-((cyclohexyl)NH$CH_2$)-1-imidazolyl |
| 240. | 2-Cl-phenyl | 2-((cyclohexyl)$_2$N$CH_2$)-1-imidazolyl |
| 241. | 2-F-phenyl | 2-($NH_2SO_2$)phenyl |
| 242. | 2-F-phenyl | 2-($CH_3SO_2$)phenyl |
| 243. | 2-F-phenyl | 3-$NH_2SO_2$-4-pyridyl |
| 244. | 2-F-phenyl | 3-$CH_3SO_2$-4-pyridyl |
| 245. | 2-F-phenyl | 2-($CH_3$NH)phenyl |
| 246. | 2-F-phenyl | 3-(($CH_3$)$_2$N$CH_2$)-4-pyridyl |
| 247. | 2-F-phenyl | 2-(N-(3-R-HO-pyrrolidinyl)$CH_2$)phenyl |
| 248. | 2-F-phenyl | 2-(N-(4-HO-piperidinyl)$CH_2$)phenyl |
| 249. | 2-F-phenyl | 2-(($CH_3$)$_2$N$CH_2$)phenyl |
| 250. | 2-F-phenyl | 2-(($CH_3$)NH$CH_2$)phenyl |
| 251. | 2-F-phenyl | 2-(($CH_3CH_2$)NH$CH_2$)phenyl |
| 252. | 2-F-phenyl | 2-(($CH_3CH_2$)$_2$N$CH_2$)phenyl |
| 253. | 2-F-phenyl | 2-(($CH_3CH_2$)N($CH_3$)$CH_2$)phenyl |
| 254. | 2-F-phenyl | 2-((($CH_3$)$_2$CH)NH$CH_2$)phenyl |
| 255. | 2-F-phenyl | 2-((($CH_3$)$_2$CH)$_2$N$CH_2$)phenyl |
| 256. | 2-F-phenyl | 2-((cyclopropyl)NH$CH_2$)phenyl |
| 257. | 2-F-phenyl | 2-((cyclopropyl)$_2$N$CH_2$)phenyl |
| 258. | 2-F-phenyl | 2-((cyclobutyl)NH$CH_2$)phenyl |
| 259. | 2-F-phenyl | 2-((cyclobutyl)$_2$N$CH_2$)phenyl |
| 260. | 2-F-phenyl | 2-((cyclopentyl)NH$CH_2$)phenyl |
| 261. | 2-F-phenyl | 2-((cyclopentyl)$_2$N$CH_2$)phenyl |
| 262. | 2-F-phenyl | 2-((cyclohexyl)NH$CH_2$)phenyl |
| 263. | 2-F-phenyl | 2-((cyclohexyl)$_2$N$CH_2$)phenyl |
| 264. | 2-F-phenyl | 1-$CH_3$-2-imidazolyl |
| 265. | 2-F-phenyl | 2-$CH_3$-1-imidazolyl |
| 266. | 2-F-phenyl | 2-(($CH_3$)$_2$N$CH_2$)-1-imidazolyl |
| 267. | 2-F-phenyl | 2-(($CH_3$)NH$CH_2$)-1-imidazolyl |
| 268. | 2-F-phenyl | 2-(($CH_3CH_2$)NH$CH_2$)-1-imidazolyl |
| 269. | 2-F-phenyl | 2-(($CH_3CH_2$)$_2$N$CH_2$)-1-imidazolyl |
| 270. | 2-F-phenyl | 2-(($CH_3CH_2$)N($CH_3$)$CH_2$)-1-imidazolyl |
| 271. | 2-F-phenyl | 2-((($CH_3$)$_2$CH)NH$CH_2$)-1-imidazolyl |
| 272. | 2-F-phenyl | 2-((($CH_3$)$_2$CH)$_2$N$CH_2$)-1-imidazolyl |
| 273. | 2-F-phenyl | 2-((cyclopropyl)NH$CH_2$)-1-imidazolyl |
| 274. | 2-F-phenyl | 2-((cyclopropyl)$_2$N$CH_2$)-1-imidazolyl |
| 275. | 2-F-phenyl | 2-((cyclobutyl)NH$CH_2$)-1-imidazolyl |
| 276. | 2-F-phenyl | 2-((cyclobutyl)$_2$N$CH_2$)-1-imidazolyl |
| 277. | 2-F-phenyl | 2-((cyclopentyl)NH$CH_2$)-1-imidazolyl |
| 278. | 2-F-phenyl | 2-((cyclopentyl)$_2$N$CH_2$)-1-imidazolyl |
| 279. | 2-F-phenyl | 2-((cyclohexyl)NH$CH_2$)-1-imidazolyl |
| 280. | 2-F-phenyl | 2-((cyclohexyl)$_2$N$CH_2$)-1-imidazolyl |
| 281. | 2,6-diF-phenyl | 2-($NH_2SO_2$)phenyl |
| 282. | 2,6-diF-phenyl | 2-($CH_3SO_2$)phenyl |
| 283. | 2,6-diF-phenyl | 3-$NH_2SO_2$-4-pyridyl |
| 284. | 2,6-diF-phenyl | 3-$CH_3SO_2$-4-pyridyl |
| 285. | 2,6-diF-phenyl | 2-($CH_3$NH)phenyl |
| 286. | 2,6-diF-phenyl | 3-(($CH_3$)$_2$N$CH_2$)-4-pyridyl |
| 287. | 2,6-diF-phenyl | 2-(N-(3-R-HO-pyrrolidinyl)$CH_2$)phenyl |
| 288. | 2,6-diF-phenyl | 2-(N-(4-HO-piperidinyl)$CH_2$)phenyl |
| 289. | 2,6-diF-phenyl | 2-(($CH_3$)$_2$N$CH_2$)phenyl |
| 290. | 2,6-diF-phenyl | 2-(($CH_3$)NH$CH_2$)phenyl |
| 291. | 2,6-diF-phenyl | 2-(($CH_3CH_2$)NH$CH_2$)phenyl |
| 292. | 2,6-diF-phenyl | 2-(($CH_3CH_2$)$_2$N$CH_2$)phenyl |
| 293. | 2,6-diF-phenyl | 2-(($CH_3CH_2$)N($CH_3$)$CH_2$)phenyl |
| 294. | 2,6-diF-phenyl | 2-((($CH_3$)$_2$CH)NH$CH_2$)phenyl |
| 295. | 2,6-diF-phenyl | 2-((($CH_3$)$_2$CH)$_2$N$CH_2$)phenyl |
| 296. | 2,6-diF-phenyl | 2-((cyclopropyl)NH$CH_2$)phenyl |
| 297. | 2,6-diF-phenyl | 2-((cyclopropyl)$_2$N$CH_2$)phenyl |
| 298. | 2,6-diF-phenyl | 2-((cyclobutyl)NH$CH_2$)phenyl |
| 299. | 2,6-diF-phenyl | 2-((cyclobutyl)$_2$N$CH_2$)phenyl |
| 300. | 2,6-diF-phenyl | 2-((cyclopentyl)NH$CH_2$)phenyl |
| 301. | 2,6-diF-phenyl | 2-((cyclopentyl)$_2$N$CH_2$)phenyl |
| 302. | 2,6-diF-phenyl | 2-((cyclohexyl)NH$CH_2$)phenyl |
| 303. | 2,6-diF-phenyl | 2-((cyclohexyl)$_2$N$CH_2$)phenyl |

-continued

| EX# | A | B |
|---|---|---|
| 304. | 2,6-diF-phenyl | 1-$CH_3$-2-imidazolyl |
| 305. | 2,6-diF-phenyl | 2-$CH_3$-1-imidazolyl |
| 306. | 2,6-diF-phenyl | 2-(($CH_3$)$_2$N$CH_2$)-1-imidazolyl |
| 307. | 2,6-diF-phenyl | 2-(($CH_3$)NH$CH_2$)-1-imidazolyl |
| 308. | 2,6-diF-phenyl | 2-(($CH_3CH_2$)NH$CH_2$)-1-imidazolyl |
| 309. | 2,6-diF-phenyl | 2-(($CH_3CH_2$)$_2$N$CH_2$)-1-imidazolyl |
| 310. | 2,6-diF-phenyl | 2-(($CH_3CH_2$)N($CH_3$)$CH_2$)-1-imidazolyl |
| 311. | 2,6-diF-phenyl | 2-((($CH_3$)$_2$CH)NH$CH_2$)-1-imidazolyl |
| 312. | 2,6-diF-phenyl | 2-((($CH_3$)$_2$CH)$_2$N$CH_2$)-1-imidazolyl |
| 313. | 2,6-diF-phenyl | 2-((cyclopropyl)NH$CH_2$)-1-imidazolyl |
| 314. | 2,6-diF-phenyl | 2-((cyclopropyl)$_2$N$CH_2$)-1-imidazolyl |
| 315. | 2,6-diF-phenyl | 2-((cyclobutyl)NH$CH_2$)-1-imidazolyl |
| 316. | 2,6-diF-phenyl | 2-((cyclobutyl)$_2$N$CH_2$)-1-imidazolyl |
| 317. | 2,6-diF-phenyl | 2-((cyclopentyl)NH$CH_2$)-1-imidazolyl |
| 318. | 2,6-diF-phenyl | 2-((cyclopentyl)$_2$N$CH_2$)-1-imidazolyl |
| 319. | 2,6-diF-phenyl | 2-((cyclohexyl)NH$CH_2$)-1-imidazolyl |
| 320. | 2,6-diF-phenyl | 2-((cyclohexyl)$_2$N$CH_2$)-1-imidazolyl |
| 321. | piperidinyl | 2-($NH_2SO_2$)phenyl |
| 322. | piperidinyl | 2-($CH_3SO_2$)phenyl |
| 323. | piperidinyl | 3-$NH_2SO_2$-4-pyridyl |
| 324. | piperidinyl | 3-$CH_3SO_2$-4-pyridyl |
| 325. | piperidinyl | 2-($CH_3$NH)phenyl |
| 326. | piperidinyl | 3-(($CH_3$)$_2$N$CH_2$)-4-pyridyl |
| 327. | piperidinyl | 2-(N-(3-R-HO-pyrrolidinyl)$CH_2$)phenyl |
| 328. | piperidinyl | 2-(N-(4-HO-piperidinyl)$CH_2$)phenyl |
| 329. | piperidinyl | 2-(($CH_3$)$_2$N$CH_2$)phenyl |
| 330. | piperidinyl | 2-(($CH_3$)NH$CH_2$)phenyl |
| 331. | piperidinyl | 2-(($CH_3CH_2$)NH$CH_2$)phenyl |
| 332. | piperidinyl | 2-(($CH_3CH_2$)$_2$N$CH_2$)phenyl |
| 333. | piperidinyl | 2-(($CH_3CH_2$)N($CH_3$)$CH_2$)phenyl |
| 334. | piperidinyl | 2-((($CH_3$)$_2$CH)NH$CH_2$)phenyl |
| 335. | piperidinyl | 2-((($CH_3$)$_2$CH)$_2$N$CH_2$)phenyl |
| 336. | piperidinyl | 2-((cyclopropyl)NH$CH_2$)phenyl |
| 337. | piperidinyl | 2-((cyclopropyl)$_2$N$CH_2$)phenyl |
| 338. | piperidinyl | 2-((cyclobutyl)NH$CH_2$)phenyl |
| 339. | piperidinyl | 2-((cyclobutyl)$_2$N$CH_2$)phenyl |
| 340. | piperidinyl | 2-((cyclopentyl)NH$CH_2$)phenyl |
| 341. | piperidinyl | 2-((cyclopentyl)$_2$N$CH_2$)phenyl |
| 342. | piperidinyl | 2-((cyclohexyl)NH$CH_2$)phenyl |
| 343. | piperidinyl | 2-((cyclohexyl)$_2$N$CH_2$)phenyl |
| 344. | piperidinyl | 1-$CH_3$-2-imidazolyl |
| 345. | piperidinyl | 2-$CH_3$-1-imidazolyl |
| 346. | piperidinyl | 2-(($CH_3$)$_2$N$CH_2$)-1-imidazolyl |
| 347. | piperidinyl | 2-(($CH_3$)NH$CH_2$)-1-imidazolyl |
| 348. | piperidinyl | 2-(($CH_3CH_2$)NH$CH_2$)-1-imidazolyl |
| 349. | piperidinyl | 2-(($CH_3CH_2$)$_2$N$CH_2$)-1-imidazolyl |
| 350. | piperidinyl | 2-(($CH_3CH_2$)N($CH_3$)$CH_2$)-1-imidazolyl |
| 351. | piperidinyl | 2-((($CH_3$)$_2$CH)NH$CH_2$)-1-imidazolyl |
| 352. | piperidinyl | 2-((($CH_3$)$_2$CH)$_2$N$CH_2$)-1-imidazolyl |
| 353. | piperidinyl | 2-((cyclopropyl)NH$CH_2$)-1-imidazolyl |
| 354. | piperidinyl | 2-((cyclopropyl)$_2$N$CH_2$)-1-imidazolyl |
| 355. | piperidinyl | 2-((cyclobutyl)NH$CH_2$)-1-imidazolyl |
| 356. | piperidinyl | 2-((cyclobutyl)$_2$N$CH_2$)-1-imidazolyl |
| 357. | piperidinyl | 2-((cyclopentyl)NH$CH_2$)-1-imidazolyl |
| 358. | piperidinyl | 2-((cyclopentyl)$_2$N$CH_2$)-1-imidazolyl |
| 359. | piperidinyl | 2-((cyclohexyl)NH$CH_2$)-1-imidazolyl |
| 360. | piperidinyl | 2-((cyclohexyl)$_2$N$CH_2$)-1-imidazolyl |

Numerous modifications and variations of the present invention are possible in light of the above teachings. It is therefore to be understood that within the scope of the appended claims, the invention may be practiced otherwise that as specifically described herein.

What is claimed is:

1. A compound of formula Ia, Ib, or Ic:

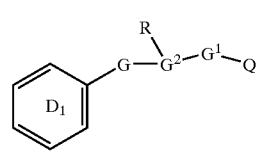

Ia

-continued

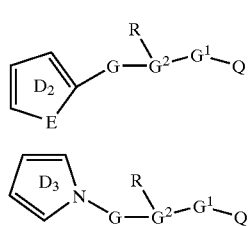

or a stereoisomer or pharmaceutically acceptable salt thereof, wherein;

ring $D_1$ is selected from pyridine, pyrazine, pyridazine, and pyrimidine and is substituted with 1 $R^a$ and 0–1 $R^b$;

ring $D_2$ is a 5-membered heteroaromatic ring system comprising E, carbon atoms, and 0–3 N atoms, wherein E is selected from O, S, and N—$R^c$ and ring $D_2$ is substituted with 1 $R^a$ and 0–1 $R^b$;

ring $D_3$ is a 5-membered heteroaromatic ring system comprising carbon atoms and from 0–3 additional N atoms and ring $D_3$ is substituted with 1 $R^a$ and 0–1 $R^b$;

R is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $NR^8CH(=NR^7)$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_tNR^7R^8$, $(CR^8R^9)_tC(O)NR^7R^8$, and $OCF_3$;

$R^a$ is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $NR^8CH(=NR^7)$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_tNR^7R^8$, $(CR^8R^9)_tC(O)NR^7R^8$, and $OCF_3$;

$R^b$ is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $NR^8CH(=NR^7)$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_tNR^7R^8$, $(CR^8R^9)_tC(O)NR^7R^8$, and $OCF_3$;

$R^c$ is selected from H, $C_{1-4}$ alkyl, $OCH_3$, $OCH_2CH_3$, $OCH(CH_3)_2$, $OCH_2CH_2CH_3$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_tNR^7R^8$, $(CR^8R^9)_tC(O)NR^7R^8$, and $OCF_3$;

G is absent or is selected from $CH_2$, C(O), O, $NR^3$, $S(O)_p$, $CH_2CH_2$, $C(O)CH_2$, $CH_2C(O)$, $OCH_2$, $CH_2O$, $NR^3CH_2$, $CH_2NR^3$, $S(O)_pCH_2$, $CH_2S(O)_p$, $CH_2CH_2CH_2$, $C(O)CH_2CH_2$, $CH_2C(O)CH_2$, $CH_2CH_2C(O)$, $OCH_2CH_2$, $CH_2OCH_2$, $CH_2CH_2O$, $NR^3CH_2CH_2$, $CH_2NR^3CH_2$, $CH_2CH_2NR^3$, $S(O)_pCH_2CH_2$, $CH_2S(O)_pCH_2$, and $CH_2CH_2S(O)_p$;

$G_1$ is absent or is selected from $(CR^3R^{3a})_{1-5}$, $(CR^3R^{3a})_{0-2}CR^3=CR^3(CR^3R^{3a})_{0-2}$, $(CR^3R^{3a})_{0-2}C\equiv C(CR^3R^{3a})_{0-2}$, $(CR^3R^{3a})_uC(O)(CR^3R^{3a})_w$, $(CR^3R^{3a})_uC(O)O(CR^3R^{3a})_w$, $(CR^3R^{3a})_uOC(O)(CR^3R^{3a})_w$, $(CR^3R^{3a})_uO(CR^3R^{3a})_w$, $(CR^3R^{3a})_uNR^3(CR^3R^{3a})_w$, $(CR^3R^{3a})_uC(O)NR^3(CR^3R^{3a})_w$, $(CR^3R^{3a})_uNR^3C(O)(CR^3R^{3a})_w$, $(CR^3R^{3a})_uOC(O)NR^3(CR^3R^{3a})_w$, $(CR^3R^{3a})_uNR^3C(O)O(CR^3R^{3a})_w$, $(CR^3R^{3a})_uNR^3C(O)NR^3(CR^3R^{3a})_w$, $(CR^3R^{3a})_uNR^3C(S)NR^3(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^3(CR^3R^{3a})_w$, $(CR^3R^{3a})_uNR^3S(O)_2(CR^3R^{3a})_w$, $(CR^3R^{3a})_uS(O)_2NR^3(CR^3R^{3a})_w$, and $(CR^3R^{3a})_uNR^3S(O)_2NR^3(CR^3R^{3a})_w$, wherein u+w total 0, 1, 2, 3, or 4, provided that $G_1$ does not form a N—N, N—O, N—S, $NCH_2N$, $NCH_2O$, or $NCH_2S$ bond with either group to which it is attached;

$G^2$ is phenyl, naphthyl, or a 5–10 membered heteroaryl consisting of carbon atoms and from 1–3 heteroatoms selected from N, O, and S;

Q is a group of formula II:

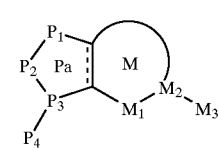

II one of $P_4$ and $M_3$ is —Z—A—B and the other is attached to $G_1$;

ring M, including $M_1$ and $M_2$, is dihydropyridinone wherein $M_2$ is N and $M_1$ is carbonyl;

ring M is substituted with 0–2 $R^{1a}$, ring P, including $P_1$, $P_2$, $P_3$, and $P_4$ is:

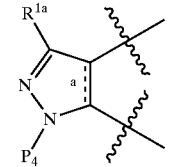

"a" is a bond;

Z is selected from a bond, $-(CR^2R^2a)_{1-4}-$, $(CR^2R^2a)_qO(CR^2R^{2a})_{q^1}$, $(CR^2R^2a)_qNR^3(CR^2R^{2a})_{q^1}$, $(CR^2R^2a)_qC(O)(CR^2R^2a)_{q^1}$, $(CR^2R^2a)_qC(O)O(CR^2R^{2a})_{q^1}$, $(CR^2R^{2a})_qOC(O)(CR^2R^{2a})_{q^1}$, $(CR^2R^{2a})_qC(O)NR^3(CR^2R^{2a})_{q^1}$, $(CR^2R^{2a})_qNR^3C(O)(CR^2R^{2a})_{q^1}$, $(CR^2R^{2a})_qOC(O)O(CR^2R^{2a})_{q^1}$, $(CR^2R^{2a})_qOC(O)NR^3(CR^2R^{2a})_{q^1}$, $(CR^2R^{2a})_qNR^3C(O)O(CR^2R^{2a})_{q^1}$, $(CR^2R^{2a})_qNR^3C(O)NR^3(CR^2R^{2a})_{q^1}$, $(CR^2R^{2a})_qS(CR^2R^{2a})_{q^1}$, $(CR^2R^{2a})_qS(O)(CR^2R^{2a})_{q^1}$, $(CR^2R^{2a})_qS(O)_2(CR^2R^{2a})_{q^1}$, $(CR^2R^{2a})_qSO_2NR^3(CR^2R^{2a})_{q^1}$, $(CR^2R^{2a})_qNR^3SO_2(CR^2R^{2a})_{q^1}$, and $(CR^2R^{2a})_qNR^3SO_2NR^3(CR^2R^{2a})_{q^1}$, wherein q+q$^1$ total 0, 1, or 2, provided that Z does not form a N—N, N—O, N—S, $NCH_2N$, $NCH_2O$, or $NCH_2S$ bond with either group to which it is attached;

$Z^2$ is selected from H, $C_{1-4}$ alkyl, phenyl, benzyl, $C(O)R^3$, and $S(O)_pR^{3c}$;

$R^{1a}$ is selected from H, $-(CH_2)_r-R^{1b}$, $-CH=CH-R^{1b}$, $NHCH_2R^{1c}$, $OCH_2R^{1c}$, $SCH_2R^{1c}$, $NH(CH_2)_2(CH_2)_rR^{1b}$, $O(CH_2)_2(CH_2)_rR^{1b}$, $S(CH_2)_2(CH_2)_rR^{1b}$, $S(O)_p(CH_2)_rR^{1d}$, $O(CH_2)_rR^{1d}$, $NR^3(CH_2)_rR^{1d}$, $OC(O)NR^3(CH_2)_rR^{1d}$, $NR^3C(O)NR^3(CH_2)_rR^{1d}$, $NR^3C(O)O(CH_2)_rR^{1d}$, and $NR^3C(O)(CH_2)_rR^{1d}$, provided that $R^{1a}$ forms other than an N-halo, N—N, N—S, N—O, or N—CN bond;

alternatively, when two $R^{1a}$'s are attached to adjacent atoms, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and comprising: 0–3 double bonds;

$R^{1b}$ is selected from H, $C_{1-3}$ alkyl, F, Cl, Br, I, —CN, —CHO, $(CF_2)_rCF_3$, $(CH_2)_rOR^2$, $NR^2R^{2a}$, $C(O)R^{2c}$, $OC(O)R^2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NHR^{2b}$, $NR^2C(O)_2R^{2a}$, $OC(O)NR^{2a}R^{2b}$, $C(O)NR^2R^{2a}$, $C(O)NR^2(CH_2)_rOR^2$, $SO_2NR^2R^{2a}$, $NR^2SO_2R^{2b}$, $C_{3-6}$ carbocycle substituted with 0–2 $R^{4a}$, and 5–10 membered heterocycle consisting of carbon atoms and from 1–4 heteroatoms selected from the group consisting of N, O, and $S(O)_p$ substituted with 0–2 $R^{4a}$, provided that $R^{1b}$ forms other than an N-halo, N—N, N—S, N—O, or N—CN bond;

$R^{1c}$ is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;

$R^{1d}$ is selected from $C_{3-13}$ carbocycle substituted with 0–2 $R^{4a}$, and 5–13 membered heterocycle consisting of carbon atoms and from 1–4 heteroatoms selected from the group consisting of N, O, and $S(O)_p$ substituted with 0–2 $R^{4a}$, provided that $R^{1d}$ forms other than an N—N, N—S, or N—O bond;

$R^2$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system comprising carbon atoms and from 1–4 heteroatoms selected from the group consisting of N, O, and S substituted with 0–2 $R^{4b}$;

$R^{2a}$, at each occurrence, is selected from H, $CF_3$, $C_{1-6}$ alkyl, benzyl, phenethyl, $C_{3-6}$ carbocyclic residue substituted with 0–2 $R^{4b}$, and 5–6 membered heterocyclic system comprising carbon atoms and from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{3-6}$ carbocyclic residue substituted with 0–2 $R^{4b}$, and 5–6 membered heterocyclic system comprising carbon atoms and from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic residue substituted with 0–2 $R^{4b}$, and 5–6 membered heterocyclic system comprising carbon atoms and from 1–4 heteroatoms selected from the group consisting of N, O, and S substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and comprising carbon atoms and from 0–1 additional heteroatoms selected from the group consisting of N, O, and S;

$R^3$, at each occurrence, is selected from H, $C_{1-4}$ alkyl, and phenyl;

$R^{3a}$, at each occurrence, is selected from H, $C_{1-4}$ alkyl, and phenyl;

$R^{3b}$, at each occurrence, is selected from H, $C_{1-4}$ alkyl, and phenyl;

$R^{3c}$, at each occurrence, is selected from $C_{1-4}$ alkyl, and phenyl;

$R^{3d}$, at each occurrence, is selected from H, $C_{1-4}$ alkyl, $C_{1-4}$ alkyl-phenyl, and $C(=O)R^{3c}$;

A is selected from: $C_{3-10}$ carbocyclic residue substituted with 0–2 $R^4$, and 5–12 membered heterocyclic system comprising carbon atoms and from 1–4 heteroatoms selected from the group consisting of N, O, and S substituted with 0–2 $R^4$;

B is selected from: H, Y, and X—Y, provided that Z and B are attached to different atoms on A;

X is selected from —$(CR^2R^{2a})_{1-4}$—, —$CR^2(CR^2R^{2b})(CH_2)_r$—, —C(O)—, —C(=NR^{1c})—, —$CR^2(NR^{1c}R^2)$—, —$CR^2(OR^2)$—, —$CR^2(SR^2)$—, —$C(O)CR^2R^{2a}$—, —$CR^2R^{2a}C(O)$, —S—, —S(O)—, —$S(O)_2$—, —$SCR^2R^{2a}$—, —$S(O)CR^2R^{2a}$—, —$S(O)_2CR^2R^{2a}$—, —$CR^2R^{2a}S$—, —$CR^2R^{2a}S(O)$—, —$CR^2R^{2a}S(O)_2$—, —$S(O)_2NR^2$—, —$NR^2S(O)_2$—, —$NR^2S(O)_2CR^2R^{2a}$—, —$CR^2R^{2a}S(O)_2NR^2$—, —$NR^2S(O)_2NR^2$—, —$C(O)NR^2$—, —$NR^2C(O)$—, —$C(O)NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)O$—, —$OC(O)NR^2$—, —$NR^2C(O)NR^2$—, —$NR^2$—, —$NR^2CR^2R^{2a}$—, $CR^2R^{2a}NR^2$—, O, —$CR^2R^{2a}O$—, and —$OCR^2R^{2a}$—;

Y is selected from:
$C_{3-10}$ carbocyclic residue substituted with 0–2 $R^{4a}$, and 5–12 membered heterocyclic system comprising carbon atoms and from 1–4 heteroatoms selected from the group consisting of N, O, and S substituted with 0–2 $R^{4a}$;

$R^4$, at each occurrence, is selected from H, =O, $(CH_2)_rOR^2$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^2R^{2a}$, $(CH_2)_rN(\rightarrow O)R^2R^{2a}$, $(CH_2)_rC(O)R^{2c}$, $(CH_2)_rNR^2C(O)R^{2b}$, $(CH_2)_rC(O)NR^2R^{2a}$, $(CH_2)_rNR^2C(O)NR^2R^{2a}$, $(CH_2)_rC(=NR^2)NR^2R^{2a}$, $(CH_2)_rC(=NS(O)_2R^5)NR^2R^{2a}$, $(CH_2)_rNHC(=NR^2)NR^2R^{2a}$, $(CH_2)_rC(O)NHC(=NR^2)NR^2R^{2a}$, $(CH_2)_rSO_2NR^2R^{2a}$, $(CH_2)_rNR^2SO_2NR^2R^{2a}$, $(CH_2)_rNR^2SO_2$—$C_{1-4}$ alkyl, $(CH_2)_rNR^2SO_2R^5$, $(CH_2)_r$—$NR^2SO_2R^{5a}$, $(CH_2)_rS(O)_pR^5$, $(CH_2)_r$—$S(O)_pR^{5a}$, $(CF_2)_rCF_3$, $(CH_2)_r$—$CF_3$, $(CR^{4c}R^{4d})(CR^{3e}R^{3e})_r$—$NR^{4e}R^{4f}$, $(CR^{4c}R^{4d})(CR^{3e}R^{3e})_r$—$OR^{4e}$, $(CR^{4c}R^{4d})(CR^{3e}R^{3e})_r$—$SR^{4e}$, $(CR^{4c}R^{4d})(CR^{3e}R^{3e})_r$—$N(\rightarrow O)R^{4e}R^{4f}$, $(CH_2)_rNHCH_2R^{1c}$, $(CH_2)_rOCH_2R^{1c}$, $(CH_2)_rSCH_2R^{1c}$, $(CH_2)_rNH(CH_2)_2(CH_2)_rR^{1b}$, $(CH_2)_rO(CH_2)_2(CH_2)_rR^{1b}$, $(CH_2)_rS(CH_2)_2(CH_2)_rR^{1b}$, $(CH_2)_r$,5–6 membered carbocycle substituted with 0–1 $R^5$, and $(CH_2)_r$,5–6 membered heterocycle consisting of: carbon atoms and 1–4 heteroatoms selected from the group consisting of N, O, and $S(O)_p$ substituted with 0–1 $R^5$;

$R^4$, at each occurrence, is selected from H, =O, $(CH_2)_rOR^2$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^2R^{2a}$, $C(O)R^{2c}$, $NR^2C(O)R^{2b}$, $C(O)NR^2R^{2a}$, $NR^2C(O)NR^2R^{2a}$, $C(=NR^2)NR^2R^{2a}$, $C(=NS(O)_2R^5)NR^2R^{2a}$, $NHC(=NR^2)NR^2R^{2a}$, $C(O)NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, $(CF_2)_rCF_3$, $(CH_2)_r$—$CF_3$, $NHCH_2R^{1c}$, $OCH_2R^{1c}$, $SCH_2R^{1c}$, $NH(CH_2)_2(CH_2)_rR^{1b}$, $O(CH_2)_2(CH_2)_rR^{1b}$, $S(CH_2)_2(CH_2)_rR^{1b}$, 5–6 membered carbocycle substituted with 0–1 $R^5$, and 5–6 membered heterocycle consisting of: carbon atoms and 1–4 heteroatoms selected from the group consisting of N, O, and $S(O)_p$ substituted with 0–1 $R^5$;

$R^{4a}$, at each occurrence, is selected from H, =O, $(CH_2)_rOR^2$, $(CF_2)_rCF_3$, $(CH_2)_r$—$CF_3$, $(CH_2)_r$—$F_3$, $(CH_2)_r$—Br, $(CH_2)_r$—Cl, $C_{1-4}$ alkyl, $(CH_2)_rCN$, $(CH_2)_rNO_2$, $(CH_2)_rNR^2R^{2a}$, $(CH_2)_rC(O)R^{2c}$, $NR^2C(O)R^{2b}$, $C(O)$ $NR^2R^{2a}$, $(CH_2)_rN=CHOR^3$, $C(O)NH(CH_2)_2NR^2R^{2a}$, $NR^2C(O)NR^2R^{2a}$, $C(=NR^2)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $C(O)NHSO_2$—$C_{1-4}$ alkyl, $S(O)_pR^5$, 5–6 membered carbocycle substituted with 0–1 $R^5$, and 5–6 membered heterocycle consisting of: carbon atoms and 1–4 heteroatoms selected from the group consisting of N, O, and $S(O)_p$ substituted with 0–1 $R^5$;

$R^{4b}$, at each occurrence, is selected from H, =O, $(CH_2)_rOR^3$, $(CH_2)_r$—F, $(CH_2)_r$—Cl, $(CH_2)_r$—Br, $(CH_2)_r$—I, $C_{1-4}$ alkyl, $(CH_2)_r$—CN, $(CH_2)_r$—$NO_2$, $(CH_2)_rNR^3R^{3a}$, $(CH_2)_rC(O)R^3$, $(CH_2)_rC(O)OR^{3c}$, $NR^3C(O)R^{3a}$, $C(O)NR^3R^{3a}$, $NR^3C(O)NR^3R^{3a}$, $C(=NR^3)NR^3R^{3a}$, $NR^3C(=NR^3)NR^3R^{3a}$, $SO_2NR^3R^{3a}$, $NR^3SO_2NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $(CH_2)_rCF_3$, and $(CF_2)_rCF_3$;

$R^5$, at each occurrence, is selected from H, $C_{1-6}$ alkyl, =O, $(CH_2)_rOR^3$, F, Cl, Br, I, —CN, $NO_2$, $(CH_2)_rNR^3R^{3a}$, $(CH_2)_rC(O)R^3$, $(CH_2)_rC(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, S(O)p-phenyl, $(CF_2)_rCF_3$, phenyl substituted with 0–2 $R^6$, naphthyl substituted with 0–2 $R^6$, and benzyl substituted with 0–2 $R^6$;

$R^6$, at each occurrence, is selected from H, OH, $(CH_2)_rOR^2$, halo, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-4}$ alkoxycarbonyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl, and $(CH_2)_n$-phenyl;

alternatively, $R^7$ and $R^8$, when attached to the same nitrogen, combine to form a 5–6 membered heterocyclic ring consisting of carbon atoms and 0–2 additional heteroatoms selected from the group consisting of N, O, and $S(O)_p$;

$R^9$, at each occurrence, is selected from H, $C_{1-6}$ alkyl, and $(CH_2)_n$-phenyl;

n, at each occurrence, is selected from 0, 1, 2, and 3;

m, at each occurrence, is selected from 0, 1, and 2;

p, at each occurrence, is selected from 0, 1, and 2;

r, at each occurrence, is selected from 0, 1, 2, and 3;

s, at each occurrence, is selected from 0, 1, and 2; and, t, at each occurrence, is selected from 0, 1, 2, and 3.

2. A compound according to claim 1, wherein the compound is of formula $Ia_1$–$Ic_1$, wherein:

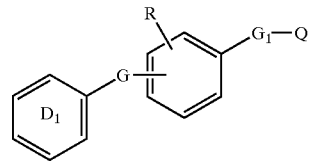

$Ia_1$

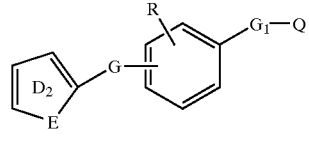

$Ib_1$

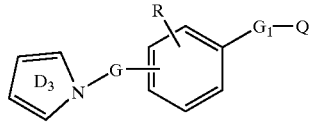

$Ic_1$ ring $D_2$ is a 5-membered heteroaromatic ring system comprising E, carbon atoms, and 0–2 N atoms, wherein E is selected from O, S, and N—$R^c$ and ring $D_2$ is substituted with 1 $R^a$ and 0–1 $R^b$;

ring $D_3$ is a 5-membered heteroaromatic ring system comprising carbon atoms and from 0–3 additional N atoms and ring $D_3$ is substituted with 1 $R^a$ and 0–1 $R^b$;

R is selected from H, Cl, F, Br, I, OH, $C_{1-3}$ alkoxy, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $CH_2CH_2NH_2$, $CH_2CH_2NH$ $(C_{1-3}$ alkyl), and $CH_2CH_2N(C_{1-3}$ alkyl$)_2$;

$R^a$ is selected from H, OH, SH, $C_{1-3}$ alkoxy, $C_{1-3}$ thioalkoxy, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), and $CH_2CH_2N$ $(C_{1-3}$ alkyl$)_2$;

$R^b$ is selected from H, $C_{1-4}$ alkyl, Cl, F, Br, I, OH, $C_{1-3}$ alkoxy, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), and $CH_2CH_2N(C_{1-3}$ alkyl$)_2$;

$R^c$ is selected from H, $C_{1-4}$ alkyl, $C_{1-3}$ alkoxy, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $CH_2CH_2NH_2$, $CH_2CH_2NH$ $(C_{1-3}$ alkyl), and $CH_2CH_2N$ $(C_{1-3}$ alkyl$)_2$;

$G_1$ is absent or is selected from $CH_2$, C(O), O, $NR^3$, $S(O)_p$, $CH_2CH_2$, $C(O)CH_2$, $CH_2C(O)$, $OCH_2$, $CH_2O$, $NR^3CH_2$, $CH_2NR^3$, $S(O)_pCH_2$, $CH_2S(O)_p$, $CH_2CH_2CH_2$, $C(O)CH_2CH_2$, $CH_2C(O)CH_2$, $CH_2CH_2C(O)$, $OCH_2CH_2$, $CH_2OCH_2$, $CH_2CH_2O$, $NR^3CH_2CH_2$, $CH_2NR^3CH_2$, $CH_2CH_2NR^3$, $S(O)_pCH_2CH_2$, $CH_2S(O)_pCH_2$, and $CH_2CH_2S(O)_p$, and provided that $G_1$-Q form other than a N—N, O—N, or S—N bond;

ring M is substituted with 0–2 $R^{1a}$ and is:

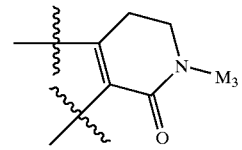

$Z^2$ is selected from H, $C_{1-4}$ alkyl, phenyl, benzyl, $C(O)R^3$, and $S(O)_pR^{3c}$;

ring P, including P₁, P₂, P₃, and P₄ is:

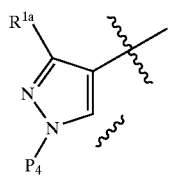

G₁ is absent or is selected from (CR³R³ᵃ)₁₋₃, (CR³R³ᵃ)ᵤC(O)(CR³R³ᵃ)ᵥᵥ, (CR³R³ᵃ)ᵤO(CR³R³ᵃ)ᵥᵥ, (CR³R³ᵃ)ᵤNR³(CR³R³ᵃ)ᵥᵥ, (CR³R³ᵃ)ᵤC(O)NR³ (CR³R³ᵃ)ᵥᵥ, (CR³R³ᵃ)ᵤNR³C(O)(CR³R³ᵃ)ᵥᵥ, (CR³R³ᵃ)ᵤS(CR³R³ᵃ)ᵥᵥ, (CR³R³ᵃ)ᵤS(O)(CR³R³ᵃ)ᵥᵥ, CR³R³ᵃ)ᵤS(O))₂(CR³R³ᵃ)ᵥᵥ, (CR³R³ᵃ)ᵤS(O)NR³ (CR³R³ᵃ)ᵥᵥ, and (CR³R³ᵃ)ᵤS(O)₂NR³(CR³R³ᵃ)ᵥᵥ, wherein u+w total 0, 1, or 2, provided that G₁ does not form a N—N, N—O, N—S, NCH₂N, NCH₂O, or NCH₂S bond with either group to which it is attached;

A is selected from one of the following carbocyclic and heterocyclic systems which are substituted with 0–2 R⁴; phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

X is selected from —(CR²R²ᵃ)₁₋₄—, —C(O)—, —C(=NR¹ᶜ)—, —CR²(NR¹ᶜR²)—, —C(O)CR²R²ᵃ—, —CR²R²ᵃC(O), —C(O)NR²—, —NR²C(O)—, —C(O)NR²CR²R²ᵃ—, —NR²C(O)CR²R²ᵃ—, —CR²R²ᵃC(O)NR²—, —CR²R²ᵃNR²C(O)—, —NR²C(O)NR²—, —NR²—, —NR²CR²R²ᵃ—, —CR²R²ᵃNR²—, O, —CR²R²ᵃO—, and —OCR²R²ᵃ—;

Y is selected from one of the following carbocyclic and heterocyclic systems that are substituted with 0–2 R⁴ᵃ; cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

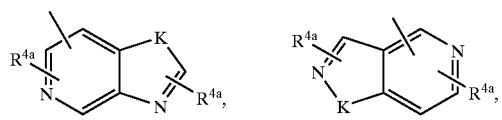

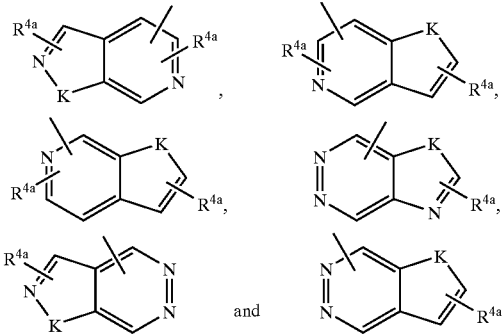

K is selected from O, S, NH, and N;

Z is selected from a bond, CH₂O, OCH₂, NH, CH₂NH, NHCH₂, CH₂C(O), C(O)CH₂, C(O)NH, NHC(O), CH₂S(O)₂, S(O)₂(CH₂), SO₂NH, and NHSO₂, provided that Z does not form a N—N, N—O, N—S, NCH₂N, NCH₂O, or NCH₂S bond with either group to which it is attached;

R⁴, at each occurrence, is selected from H, =O, (CH₂)ᵣOR², F, Cl, Br, I, C₁₋₄ alkyl, CN, NO₂, (CH₂)ᵣNR²R²ᵃ, C(O)R²ᶜ, NR²C(O)R²ᵇ, C(O)NR²R²ᵃ, NR²C(O)NR²R²ᵃ, C(=NR²)NR²R²ᵃ, SO₂NR²R²ᵃ, NR²SO₂NR²R²ᵃ, NR²SO₂—C₁₋₄ alkyl, NR²SO₂R⁵, S(O)ₚR⁵, CF₃, NHCH₂R¹ᶜ, OCH₂R¹ᶜ, SCH₂R¹ᶜ, NH(CH₂)₂(CH₂)ᵣR¹ᵇ, O(CH₂)₂(CH₂)ᵣR¹ᵇ, S(CH₂)₂ (CH₂)ᵣR¹ᵇ, 5–6 membered carbocycle substituted with 0–1 R⁵, and 5–6 membered heterocycle consisting of: carbon atoms and 1–4 heteroatoms selected from the group consisting of N, O, and S(O)ₚ substituted with 0–1 R⁵; and, R⁴ᵃ, at each occurrence, is selected from H, =O, (CH₂)ᵣOR², CF₃, F, Br, Cl, C₁₋₄ alkyl, CN, NO₂, (CH₂)ᵣNR²R²ᵃ, (CH₂)ᵣC(O)R²ᶜ, NR²C(O)R²ᵇ, C(O) NR²R²ᵃ, NR²C(O)NR²R²ᵃ, C(=NR²)NR²R²ᵃ, NHC(=NR²)NR²R²ᵃ, SO₂NR²R²ᵃ, NR²SO₂NR²R²ᵃ, NR²SO₂—C₁₋₄ alkyl, NR²SO₂R⁵, C(O)NHSO₂—C₁₋₄ alkyl, S(O)ₚR⁵, 5–6 membered carbocycle substituted with 0–1 R⁵, and 5–6 membered heterocycle consisting of: carbon atoms and 1–4 heteroatoms selected from the group consisting of N, O, and S(O)ₚ substituted with 0–1 R⁵.

3. A compound according to claim 2, wherein the compound is of formula Ib₁ or Ic₁, wherein:

ring D₂ is a 5-membered heteroaromatic ring system comprising E, carbon atoms, and 0–2 N atoms, wherein E is selected from O, S, and N—Rᶜ and ring D₂ is substituted with 1 Rᵃ and 0–1 Rᵇ;

R is selected from H, Cl, F, Br, I, OH, C₁₋₃ alkoxy, NH₂, NH(C₁₋₃ alkyl), N(C₁₋₃ alkyl)₂, CH₂NH₂, CH₂NH(C₁₋₃ alkyl), and CH₂N(C₁₋₃ alkyl)₂;

Rᵃ is selected from H, OH, SH, NH₂, NH(C₁₋₃ alkyl), N(C₁₋₃ alkyl)₂, CH₂NH₂, CH₂NH(C₁₋₃ alkyl), and CH₂N(C₁₋₃ alkyl)₂;

R is selected from H, C₁₋₄ alkyl, Cl, F, Br, I, OH, C₁₋₃ alkoxy, NH₂, NH(C₁₋₃ alkyl), N(C₁₋₃ alkyl)₂, CH₂NH₂, CH₂NH(C₁₋₃ alkyl), and CH₂N(C₁₋₃ alkyl)₂;

Rᶜ is selected from H, C₁₋₄ alkyl, C₁₋₃ alkoxy, NH₂, NH(C₁₋₃ alkyl), N(C₁₋₃ alkyl)₂, CH₂NH₂, CH₂NH(C₁₋₃ alkyl), and CH₂N (C₁₋₃ alkyl)₂;

Y is selected from one of the following carbocyclic and heterocyclic systems which are substituted with 0–2

R⁴ᵃ; phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzimidazolone, benzoxazole, benzthiazole, indazole, benzisoxazole, benzisothiazole, and isoindazole;

Z is selected from a bond, CH₂O, OCH₂, NH, CH₂NH, NHCH₂, CH₂C(O), C(O)CH₂, C(O)NH, NHC(O), CH₂S(O)₂, S(O)₂ (CH₂), SO₂NH, and NHSO₂, provided that Z does not form a N—N, N—O, N—S, NCH₂N, NCH₂O, or NCH₂S bond with either group to which it is attached;

R⁴, at each occurrence, is selected from H, =O, (CH₂)ᵣOR², F, Cl, Br, I, C₁₋₄ alkyl, CN, NO₂, (CH₂)ᵣNR²R²ᵃ, C(O)R²ᶜ, NR²C(O)R²ᵇ, C(O)NR²R²ᵃ, NR²C(O)NR²R²ᵃ, C(=NR²)NR²R²ᵃ, SO₂NR²R²ᵃ, NR²SO₂NR²R²ᵃ, NR²SO₂—C₁₋₄ alkyl, NR²SO₂R⁵, S(O)ₚR⁵, CF₃, 5–6 membered carbocycle substituted with 0–1 R⁵, and 5–6 membered heterocycle consisting of: carbon atoms and 1–4 heteroatoms selected from the group consisting of N, O, and S(O)ₚ substituted with 0–1 R⁵; and, R⁴ᵃ, at each occurrence, is selected from H, =O, (CH₂)ᵣOR², CF₃, F, Br, Cl, C₁₋₄ alkyl, CN, NO₂, (CH₂)ᵣNR²R²ᵃ, (CH₂)ᵣC(O)R²ᶜ, NR²C(O)R²ᵇ, C(O)NR²R²ᵃ, NR²C(O)NR²R²ᵃ, C(=NR²)NR²R²ᵃ, SO₂NR²R²ᵃ, C(O)NHSO₂—C₁₋₄ alkyl, S(O)ₚR⁵, 5–6 membered carbocycle substituted with 0–1 R⁵, and 5–6 membered heterocycle consisting of: carbon atoms and 1–4 heteroatoms selected from the group consisting of N, O, and S(O)ₚ substituted with 0–1 R⁵.

4. A compound according to claim 3, wherein the compound is of wherein the compound is of formula Ib₂:

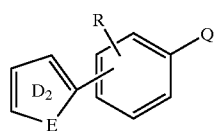

Ib₂ or a stereoisomer or pharmaceutically acceptable salt thereof, wherein;

ring D₂ is a 5-membered heteroaromatic ring system comprising E, carbon atoms, and 0–2 N atoms, wherein E is selected from O, S, and N—Rᶜ and ring D₂ is substituted with 1 Rᵃ and 0–1 Rᵇ;

R is selected from H, Cl, F, Br, I, OH, C₁₋₃ alkoxy, NH₂, NH(C₁₋₃ alkyl), N(C₁₋₃ alkyl)₂, CH₂NH₂, CH₂NH(C₁₋₃ alkyl), and CH₂N(C₁₋₃ alkyl)₂;

Rᵃ is selected from H, OH, SH, NH₂, NH(C₁₋₃ alkyl), and N(C₁₋₃ alkyl)₂;

Rᵇ is selected from H, C₁₋₄ alkyl, Cl, F, Br, I, OH, C₁₋₃ alkoxy, NH₂, NH(C₁₋₃ alkyl), N(C₁₋₃ alkyl)₂, CH₂NH₂, CH₂NH(C₁₋₃ alkyl), and CH₂N(C₁₋₃ alkyl)₂;

G₁ is absent or is selected from CH₂, CH₂CH₂, CH₂O, OCH₂, NH, CH₂NH, NHCH₂, CH₂C(O), C(O)CH₂, C(O)NH, NHC(O), CH₂S(O)₂, S(O)₂(CH₂), SO₂NH, and NHSO₂, provided that G₁ does not form a N—N, N—O, N—S, NCH₂N, NCH₂O, or NCH₂S bond with either group to which it is attached.

5. A compound according to claim 4, wherein the compound is selected from one of the formulas:

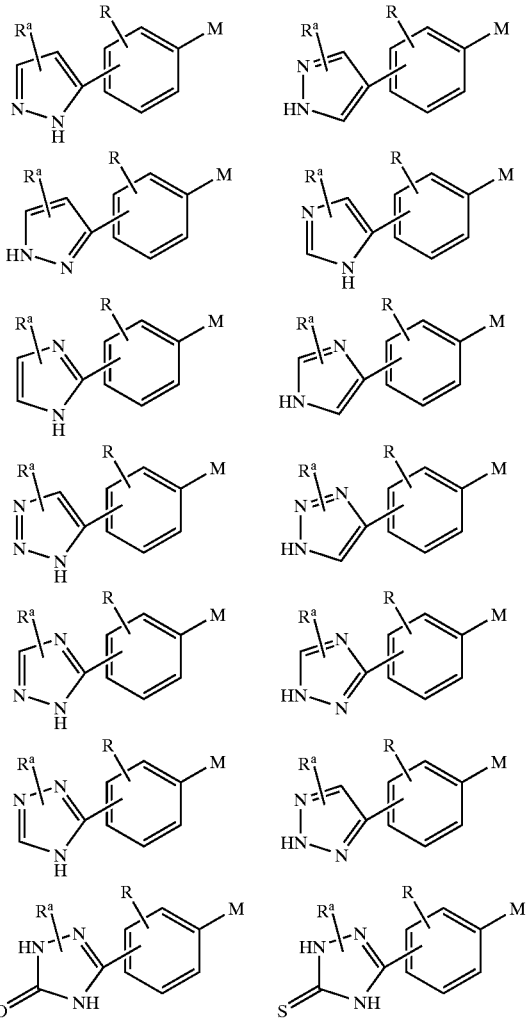

or a stereoisomer or pharmaceutically acceptable salt thereof, wherein;

G₁ is absent;

A is selected from phenyl, piperidinyl, pyridyl, and pyrimidyl, and is substituted with 0–2 R⁴; and, B is selected from phenyl, pyrrolidino, N-pyrrolidino-carbonyl, morpholino, N-morpholino-carbonyl, 1,2,3-triazolyl, imidazolyl, and benzimidazolyl, and is substituted with 0–1 R⁴ᵃ;

R², at each occurrence, is selected from H, CH₃, CH₂CH₃, cyclopropylmethyl, cyclobutyl, and cyclopentyl;

R²ᵃ, at each occurrence, is selected from H, CH₃, and CH₂CH₃;

alternatively, R² and R²ᵃ, together with the atom to which they are attached, combine to form pyrrolidine substituted with 0–2 R⁴ᵇ or piperidine substituted with 0–2 R⁴ᵇ;

R⁴, at each occurrence, is selected from OH, OR², (CH₂)OR², (CH₂)₂OR², F, Br, Cl, I, C₁₋₄ alkyl, NR²R²ᵃ, (CH₂)NR²R²ᵃ, (CH₂)₂NR²R²ᵃ, CF₃, and (CF₂)CF₃;

R⁴ᵃ is selected from C₁₋₄ alkyl, CF₃, OR², (CH₂)OR², (CH₂)₂OR², NR²R²ᵃ, (CH₂)NR²R²ᵃ, (CH₂)₂NR²R²ᵃ, SR⁵, S(O)R⁵, S(O)₂R⁵, SO₂NR²R²ᵃ, and 1-CF₃-tetrazol-2-yl;

$R^{4b}$, at each occurrence, is selected from H, $CH_3$, and OH;

$R^5$, at each occurrence, is selected from $CF_3$, $C_{1-6}$ alkyl, phenyl, and benzyl; and, r, at each occurrence, is selected from 0, 1, and 2.

6. A compound according to claim 5, wherein:

A is selected from the group: phenyl, piperidinyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N-methylaminomethyl)phenyl, 2-(N-ethyl-N-methylaminomethyl)phenyl, 2-(N-pyrrolidinylmethyl) phenyl, 1-methyl-2-imidazolyl, 2-methyl-1-imidazolyl, 2-(dimethylaminomethyl)-1-imidazolyl, 2-(methylaminomethyl)-1-imidazolyl, 2-(N-(cyclopropylmethyl)aminomethyl)phenyl, 2-(N-(cyclobutyl)aminomethyl)phenyl, 2-(N-(cyclopentyl) aminomethyl)phenyl, 2-(N-(4-hydroxypiperidinyl) methyl)phenyl, and 2-(N-(3-hydroxypyrrolidinyl) methyl)phenyl.

7. A compound according to claim 1, wherein the compound is selected from the group:

1-[3-(2'-Amino-3',4'-thiadiazol-5'-yl)phenyl]-3-methyl-6-[2'-aminosulfonyl-[1,1']-biphen-4-yl]-1,4,5,6-tetrahydropyrazolo-[3,4-c]-pyridin-7-one trifluoroacetic acid salt;

or a pharmaceutically acceptable salt thereof.

8. A compound according to claim 1, wherein the compound is selected from the group:

1-[3-(1',3',4'-Triazol-2'-on-5'-yl)phenyl]-3-cyano-6-[(2'-N,N-dimethylaminomethyl-[1,1']-biphen-4-yl) aminocarbonyl]-1,4,5,6-tetrahydropyrazolo-[3,4-c]-pyridin-7-one;

1-[3-(1',3',4'-Triazol-2'-on-5'-yl)phenyl]-3-trifluoromethyl-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-(ethoxycarbonyl)-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-methyl-6-[(2'-N,N-dimethylaminomethyl-[1,1']-biphen-4-yl) aminocarbonyl]-1,4,5,6-tetrahydropyrazolo-[3,4-c]-pyridin-7-one;

1-[3-(2'-Amino-3',4'-oxadiazol-5'-yl)phenyl]-3-cyano-6-[(2'-N,N-dimethylaminomethyl-[1,1']-biphen-4-yl) aminocarbonyl]-1,4,5,6-tetrahydropyrazolo-[3,4-c]-pyridin-7-one;

1-[3-(2'-Amino-3',4'-oxadiazol-5'-yl)phenyl]-3-trifluoromethyl-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-(ethoxycarbonyl)-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-methyl-6-[(2'-N,N-dimethylaminomethyl-[1,1']-biphen-4-yl) aminocarbonyl]-1,4,5,6-tetrahydropyrazolo-[3,4-c]-pyridin-7-one;

1-[3-(2'-Amino-1',3',4'-triazol-5'-yl)phenyl]-3-cyano-6-[(2'-N,N-dimethylaminomethyl-[1,1']-biphen-4-yl) aminocarbonyl]-1,4,5,6-tetrahydropyrazolo-[3,4-c]-pyridin-7-one;

1-[3-(2'-Amino-1',3',4'-triazol-5'-yl)phenyl]-3-trifluoromethyl-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-(ethoxycarbonyl)-6-[(2'-N,N-dimethylaminomethyl-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-methyl-6-[(2'-N,N-dimethylaminomethyl-[1,1']-biphen-4-yl) aminocarbonyl]-1,4,5,6-tetrahydropyrazolo-[3,4-c]-pyridin-7-one;

1-[3-(Pyrid-3'-yl)phenyl]-3-cyano-6-[(2'-N,N-dimethylaminomethyl-[1,1']-biphen-4-yl) aminocarbonyl]-1,4,5,6-tetrahydropyrazolo-[3,4-c]-pyridin-7-one;

1-[3-(Pyrid-3'-yl)phenyl]-3-trifluoromethyl-6-[(2'-N,N-dimethylaminomethyl-[1,1']-biphen-4-yl) aminocarbonyl]-1,4,5,6-tetrahydropyrazolo-[3,4-c]-pyridin-7-one;

1-[3-(Pyrid-3'-yl)phenyl]-3-(ethoxycarbonyl)-6-[(2'-N,N-dimethylaminomethyl-[1,1']-biphen-4-yl) aminocarbonyl]-1,4,5,6-tetrahydropyrazolo-[3,4-c]-pyridin-7-one;

1-[3-(Pyrid-3'-yl)phenyl]-3-methyl-6-[(2'-N,N-dimethylaminomethyl-[1,1']-biphen-4-yl) aminocarbonyl]-1,4,5,6-tetrahydropyrazolo-[3,4-c]-pyridin-7-one;

1-[3-(Pyrid-4'-yl)phenyl]-3-cyano-6-[(2'-N,N-dimethylaminomethyl-[1,1']-biphen-4-yl) aminocarbonyl]-1,4,5,6-tetrahydropyrazolo-[3,4-c]-pyridin-7-one;

1-[3-(Pyrid-4'-yl)phenyl]-3-trifluoromethyl-6-[(2'-N,N-dimethylaminomethyl-[1,1']-biphen-4-yl) aminocarbonyl]-1,4,5,6-tetrahydropyrazolo-[3,4-c]-pyridin-7-one;

1-[3-(Pyrid-4'-yl)phenyl]-3-(ethoxycarbonyl)-6-[(2'-N,N-dimethylaminomethyl-[1,1']-biphen-4-yl) aminocarbonyl]-1,4,5,6-tetrahydropyrazolo-[3,4-c]-pyridin-7-one;

1-[3-(Pyrid-4'-yl)phenyl]-3-methyl-6-[(2'-N,N-dimethylaminomethyl-[1,1']-biphen-4-yl) aminocarbonyl]-1,4,5,6-tetrahydropyrazolo-[3,4-c]-pyridin-7-one;

1-[3-(1',3',4'-Triazol-2'-on-5'-yl)phenyl]-3-cyano-6-[(2'-N-pyrrolidinylmethyl-[1,1]-biphen-4-yl) aminocarbonyl]-1,4,5,6-tetrahydropyrazolo-[3,4-c]-pyridin-7-one;

1-[3-(1',3',4'-Triazol-2'-on-5'-yl)phenyl]-3-trifluoromethyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-(ethoxycarbonyl)-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-methyl-6-[(2'-N-pyrrolidinylmethyl-[1,1']-biphen-4-yl) aminocarbonyl]-1,4,5,6-tetrahydropyrazolo-[3,4-c]-pyridin-7-one;

1-[3-(2'-Amino-3',4'-oxadiazol-5'-yl)phenyl]-3-cyano-6-[(2'-N-pyrrolidinylmethyl-[1,1']-biphen-4-yl)

aminocarbonyl]-1,4,5,6-tetrahydropyrazolo-[3,4-c]-pyridin-7-one;

1-[3-(2'-Amino-3',4'-oxadiazol-5'-yl)phenyl]-3-trifluoromethyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-(ethoxycarbonyl)-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-methyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-cyano-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-trifluoromethyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-(ethoxycarbonyl)-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-methyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-cyano-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-trifluoromethyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-(ethoxycarbonyl)-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-methyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-cyano-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-trifluoromethyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-(ethoxycarbonyl)-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-methyl-6-[(2'-N-pyrrolidinylmethyl-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-cyano-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-trifluoromethyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-(ethoxycarbonyl)-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-methyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-cyano-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-trifluoromethyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-(ethoxycarbonyl)-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(2'-Amino-3',4'-oxadiazol-5'-yl)phenyl]-3-methyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-cyano-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-trifluoromethyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-(ethoxycarbonyl)-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(2'-Amino-1',3',4'-triazol-5'-yl)phenyl]-3-methyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-cyano-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-trifluoromethyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-(ethoxycarbonyl)-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(Pyrid-3'-yl)phenyl]-3-methyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-cyano-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-trifluoromethyl-6-[(2'-(3"-hydroxy-N-pyrrolidinylmethyl)-[1,1']-biphen-4-yl)

aminocarbonyl]-1,4,5,6-tetrahydropyrazolo-[3,4-c]-pyridin-7-one;

1-[3-(Pyrid-4'-yl)phenyl]-3-(ethoxycarbonyl)-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(Pyrid-4'-yl)phenyl]-3-methyl-6-[(2'-(3"-hydroxy-N-pyrrolidinylmethyl)-[1,1']-biphen-4-yl)aminocarbonyl]-1,4,5,6-tetrahydropyrazolo-[3,4-c]-pyridin-7-one;

1-[3-(1',3',4'-Triazol-2'-on-5'-yl)phenyl]-3-cyano-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(1',3',4'-Triazol-2'-on-5'-yl)phenyl]-3-trifluoromethyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(1',3',4'-Triazol-2'-on-5'-yl)phenyl]-3-(ethoxycarbonyl)-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(1',3',4, -Triazol-2'-on-5'-yl)phenyl]-3-methyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(2'-Amino-3',4'-oxadiazol-5'-yl)phenyl]-3-cyano-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(2'-Amino-3',4'-oxadiazol-5'-yl)phenyl]-3-trifluoromethyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(2'-Amino-3',4'-oxadiazol-5'-yl)phenyl]-3-(ethoxycarbonyl)-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(2'-Amino-3',4'-oxadiazol-5'-yl)phenyl]-3-methyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(2'-Amino-1',3',4'-triazol-5'-yl)phenyl]-3-cyano-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(2'-Amino-1',3',4'-triazol-5'-yl)phenyl]-3-trifluoromethyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(2'-Amino-1',3',4'-triazol-5'-yl)phenyl]-3-(ethoxycarbonyl)-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(2'-Amino-1',3',4'-triazol-5'-yl)phenyl]-3-methyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(Pyrid-3'-yl)phenyl]-3-cyano-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(Pyrid-3'-yl)phenyl]-3-trifluoromethyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(Pyrid-3'-yl)phenyl]-3-(ethoxycarbonyl)-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(Pyrid-3'-yl)phenyl]-3-methyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(Pyrid-4'-yl)phenyl]-3-cyano-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(Pyrid-4'-yl)phenyl]-3-trifluoromethyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(Pyrid-4'-yl)phenyl]-3-(ethoxycarbonyl)-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(Pyrid-4'-yl)phenyl]-3-methyl-6-[4-(2'-(N,N-dimethylamino)methylimidazol-1'-yl)-2-fluorophenyl)aminocarbonyl]-1,4,5,6-tetrahydropyrazolo-[3,4-c]-pyridin-7-one;

1-[3-(1',3',4'-Triazol-2'-on-5'-yl)phenyl]-3-cyano-6-[4-(2'-methylimidazol-1'-yl)-2-fluorophenyl)aminocarbonyl]-1,4,5,6-tetrahydropyrazolo-[3,4-c]-pyridin-7-one;

1-[3-(1',3',4'-Triazol-2'-on-5'-yl)phenyl]-3-trifluoromethyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(1',3',4'-Triazol-2'-on-5'-yl)phenyl]-3-(ethoxycarbonyl)-6-[4-(2'-methylimidazol-1'-yl)-2-fluorophenyl)aminocarbonyl]-1,4,5,6-tetrahydropyrazolo-[3,4-c]-pyridin-7-one;

1-[3-(1',3',4'-Triazol-2'-on-5'-yl)phenyl]-3-methyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(2'-Amino-3',4'-oxadiazol-5'-yl)phenyl]-3-cyano-6-[4-(2'-methylimidazol-1'-yl)-2-fluorophenyl)aminocarbonyl]-1,4,5,6-tetrahydropyrazolo-[3,4-c]-pyridin-7-one;

1-[3-(2'-Amino-3',4'-oxadiazol-5'-yl)phenyl]-3-trifluoromethyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(2-Amino-3',4'-oxadiazol-5'-yl)phenyl]-3-(ethoxycarbonyl)-6-[4-(2'-methylimidazol-1'-yl)-2-fluorophenyl)aminocarbonyl]-1,4,5,6-tetrahydropyrazolo-[3,4-c]-pyridin-7-one;

1-[3-(2'-Amino-3',4'-oxadiazol-5'-yl)phenyl]-3-methyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(2'-Amino-1',3',4'-triazol-5'-yl)phenyl]-3-cyano-6-[4-(2'-methylimidazol-1'-yl)-2-fluorophenyl)

aminocarbonyl]-1,4,5,6-tetrahydropyrazolo-[3,4-c]-pyridin-7-one;

1-[3-(2'-Amino-1',3',4'-triazol-5'-yl)phenyl]-3-trifluoromethyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(2'-Amino-1',3',4'-triazol-5'-yl)phenyl]-3-(ethoxycarbonyl)-6-[4-(2'-methylimidazol-1'-yl)-2-fluorophenyl)aminocarbonyl]-1,4,5,6-tetrahydropyrazolo-[3,4-c]-pyridin-7-one;

1-[3-(2'-Amino-1',3',4'-triazol-5'-yl)phenyl]-3-methyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(Pyrid-3'-yl)phenyl]-3-cyano-6-[4-(2'-methylimidazol-1'-yl)-2-fluorophenyl)aminocarbonyl]-1,4,5,6-tetrahydropyrazolo-[3,4-c]-pyridin-7-one;

1-[3-(Pyrid-3'-yl)phenyl]-3-trifluoromethyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(Pyrid-3'-yl)phenyl]-3-(ethoxycarbonyl)-6-[4-(2'-methylimidazol-1'-yl)-2-fluorophenyl)aminocarbonyl]-1,4,5,6-tetrahydropyrazolo-[3,4-c]-pyridin-7-one;

1-[3-(Pyrid-3'-yl)phenyl]-3-methyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(Pyrid-4'-yl)phenyl]-3-cyano-6-[4-(2'-methylimidazol-1'-yl)-2-fluorophenyl)aminocarbonyl]-1,4,5,6-tetrahydropyrazolo-[3,4-c]-pyridin-7-one;

1-[3-(Pyrid-4'-yl)phenyl]-3-trifluoromethyl-6-[4-(2'-methylimidazol-1'-yl)-2-fluorophenyl)aminocarbonyl]-1,4,5,6-tetrahydropyrazolo-[3,4-c]-pyridin-7-one;

1-[3-(Pyrid-4'-yl)phenyl]-3-(ethoxycarbonyl)-6-[4-(2'-methylimidazol-1'-yl)-2-fluorophenyl)aminocarbonyl]-1,4,5,6-tetrahydropyrazolo-[3,4-c]-pyridin-7-one; and, 1-[3-(Pyrid-4'-yl)phenyl]-3-methyl-6-[4-(2'-methylimidazol-1'-yl)-2-fluorophenyl)aminocarbonyl]-1,4,5,6-tetrahydropyrazolo-[3,4-c]-pyridin-7-one;

or a pharmaceutically acceptable salt thereof.

9. A compound according to claim 1, wherein the compound is selected from the group:

1-[3-(5-oxo-4,5-Dihydro-1H-1,2,4-triazol-3-yl)phenyl]-6-[2'-(1-pyrrolidinylmethyl)-1,1-biphenyl-4-yl]-3-(trifluoromethyl)-1,4,5,6-tetrahydro-7H-pyrazolo[3,4-c]pyridin-7-one;

6-(2'-{[(3S)-3-Hydroxy-1-pyrrolidinyl]methyl}-1,1'-biphenyl-4-yl)-1-[3-(5-oxo-4,5-dihydro-1H-1,2,4-triazol-3-yl)phenyl]-3-(trifluoromethyl)-1,4,5,6-tetrahydro-7H-pyrazolo[3,4-c]pyridin-7-one;

6-{2'-[(Dimethylamino)methyl]-1,1'-biphenyl-4-yl}-1-[3-(5-oxo-4,5-dihydro-1H-1,2,4-triazol-3-yl)phenyl]-3-(trifluoromethyl)-1,4,5,6-tetrahydro-7H-pyrazolo[3,4-c]pyridin-7-one;

6-[2'-(Methylsulfonyl)-1,1'-biphenyl-4-yl]-1-[3-(5-oxo-4,5-dihydro-1H-1,2,4-triazol-3-yl)phenyl]-3-(trifluoromethyl)-1,4,5,6-tetrahydro-7H-pyrazolo[3,4-c]pyridin-7-one;

1-[3-(5-Amino-1,3,4-oxadiazol-2-yl)phenyl]-6-{2'-[(dimethylamino)methyl]-1,1'-biphenyl-4-yl}-3-(trifluoromethyl)-1,4,5,6-tetrahydro-7H-pyrazolo[3,4-c]pyridin-7-one;

1-[3-(5-Amino-1,3,4-thiadiazol-2-yl)phenyl]-6-{2'-[(dimethylamino)methyl]-1,1'-biphenyl-4-yl}-3-(trifluoromethyl)-1,4,5,6-tetrahydro-7H-pyrazolo[3,4-c]pyridin-7-one;

1-[3-(5-Amino-1,3,4-thiadiazol-2-yl)phenyl]-6-[2'-(1-pyrrolidinylmethyl)-1,1'-biphenyl-4-yl]-3-(trifluoromethyl)-1,4,5,6-tetrahydro-7H-pyrazolo[3,4-c]pyridin-7-one;

1-[3-(5-Amino-1,3,4-thiadiazol-2-yl)phenyl]-6-(4-{2-[(dimethylamino)methyl]-1H-imidazol-1-yl}phenyl)-3-(trifluoromethyl)-1,4,5,6-tetrahydro-7H-pyrazolo[3,4-c]pyridin-7-one;

1-[3-(5-Amino-1,3,4-thiadiazol-2-yl)phenyl]-6-{4-[2-(1-pyrrolidinylmethyl)-1H-imidazol-1-yl]phenyl}-3-(trifluoromethyl)-1,4,5,6-tetrahydro-7H-pyrazolo[3,4-c]pyridin-7-one;

6-(4-{2-[(Dimethylamino)methyl]-1H-imidazol-1-yl}phenyl)-1-[3-(5-oxo-4,5-dihydro-1H-1,2,4-triazol-3-yl)phenyl]-3-(trifluoromethyl)-1,4,5,6-tetrahydro-7H-pyrazolo[3,4-c]pyridin-7-one;

3-Methyl-1-[3-(5-oxo-4,5-dihydro-1H-1,2,4-triazol-3-yl)phenyl]-6-{4-[2-(1-pyrrolidinylmethyl)-1H-imidazol-1-yl]phenyl}-1,4,5,6-tetrahydro-7H-pyrazolo[3,4-c]pyridin-7-one;

7-Oxo-1-[3-(5-oxo-4,5-dihydro-1H-1,2,4-triazol-3-yl)phenyl]-6-[2'-(1-pyrrolidinylmethyl)-1,1'-biphenyl-4-yl]-4,5,6,7-tetrahydro-1H-pyrazolo[3,4-c]pyridine-3-carboxamide; and, 1-[2-(5-Oxo-4,5-dihydro-1H-1,2,4-triazol-3-yl)phenyl]-6-[2'-(1-pyrrolidinylmethyl)-1,1'-biphenyl-4-yl]-3-(trifluoromethyl)-1,4,5,6-tetrahydro-7H-pyrazolo[3,4-c]pyridin-7-one;

or a pharmaceutically acceptable salt thereof.

10. A pharmaceutical composition, comprising: a pharmaceutically acceptable carrier and a therapeutically effective amount of a compound according to claim 1 or a pharmaceutically acceptable salt form thereof.

11. A pharmaceutical composition, comprising: a pharmaceutically acceptable carrier and a therapeutically effective amount of a compound according to claim 2 or a pharmaceutically acceptable salt form thereof.

12. A pharmaceutical composition, comprising: a pharmaceutically acceptable carrier and a therapeutically effective amount of a compound according to claim 3 or a pharmaceutically acceptable salt form thereof.

13. A pharmaceutical composition, comprising: a pharmaceutically acceptable carrier and a therapeutically effective amount of a compound according to claim 4 or a pharmaceutically acceptable salt form thereof.

14. A pharmaceutical composition, comprising: a pharmaceutically acceptable carrier and a therapeutically effective amount of a compound according to claim 5 or a pharmaceutically acceptable salt form thereof.

15. A pharmaceutical composition, comprising: a pharmaceutically acceptable carrier and a therapeutically effective amount of a compound according to claim 6 or a pharmaceutically acceptable salt form thereof.

16. A pharmaceutical composition, comprising: a pharmaceutically acceptable carrier and a therapeutically effective amount of a compound according to claim 7 or a pharmaceutically acceptable salt form thereof.

17. A pharmaceutical composition, comprising: a pharmaceutically acceptable carrier and a therapeutically effective amount of a compound according to claim 8 or a pharmaceutically acceptable salt form thereof.

18. A pharmaceutical composition, comprising: a pharmaceutically acceptable carrier and a therapeutically effective amount of a compound according to claim 9 or a pharmaceutically acceptable salt form thereof.

19. A method for treating a thromboembolic disorder, comprising: administering, to a patient in need thereof, a therapeutically effective amount of a compound according to claim 1 or a pharmaceutically acceptable salt form thereof.

20. A method according to claim 19, wherein the thromboembolic disorder is selected from: an arterial cardiovascular thromboembolic disorder, an arterial cerebrovascular thromboembolic disorder, a venous cardiovascular thromboembolic disorder, a venous cerebrovascular thromboembolic disorder, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

21. A method for treating a thromboembolic disorder, comprising: administering, to a patient in need thereof, a therapeutically effective amount of a compound according to claim 2 or a pharmaceutically acceptable salt form thereof.

22. A method according to claim 21, wherein the thromboembolic disorder is selected from: an arterial cardiovascular thromboembolic disorder, an arterial cerebrovascular thromboembolic disorder, a venous cardiovascular thromboembolic disorder, a venous cerebrovascular thromboembolic disorder, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

23. A method for treating a thromboembolic disorder, comprising: administering, to a patient in need thereof, a therapeutically effective amount of a compound according to claim 3 or a pharmaceutically acceptable salt form thereof.

24. A method according to claim 23, wherein the thromboembolic disorder is selected from: an arterial cardiovascular thromboembolic disorder, an arterial cerebrovascular thromboembolic disorder, a venous cardiovascular thromboembolic disorder, a venous cerebrovascular thromboembolic disorder, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

25. A method for treating a thromboembolic disorder, comprising: administering, to a patient in need thereof, a therapeutically effective amount of a compound according to claim 4 or a pharmaceutically acceptable salt form thereof.

26. A method according to claim 25, wherein the thromboembolic disorder is selected from: an arterial cardiovascular thromboembolic disorder, an arterial cerebrovascular thromboembolic disorder, a venous cardiovascular thromboembolic disorder, a venous cerebrovascular thromboembolic disorder, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

27. A method for treating a thromboembolic disorder, comprising: administering, to a patient in need thereof, a therapeutically effective amount of a compound according to claim 5 or a pharmaceutically acceptable salt form thereof.

28. A method according to claim 27, wherein the thromboembolic disorder is selected from: an arterial cardiovascular thromboembolic disorder, an arterial cerebrovascular thromboembolic disorder, a venous cardiovascular thromboembolic disorder, a venous cerebrovascular thromboembolic disorder, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

29. A method for treating a thromboembolic disorder, comprising: administering, to a patient in need thereof, a therapeutically effective amount of a compound according to claim 6 or a pharmaceutically acceptable salt form thereof.

30. A method according to claim 29, wherein the thromboembolic disorder is selected from: an arterial cardiovascular thromboembolic disorder, an arterial cerebrovascular thromboembolic disorder, a venous cardiovascular thromboembolic disorder, a venous cerebrovascular thromboembolic disorder, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

31. A method for treating a thromboembolic disorder, comprising: administering, to a patient in need thereof, a therapeutically effective amount of a compound according to claim 7 or a pharmaceutically acceptable salt form thereof.

32. A method according to claim 31, wherein the thromboembolic disorder is selected from: an arterial cardiovascular thromboembolic disorder, an arterial cerebrovascular thromboembolic disorder, a venous cardiovascular thromboembolic disorder, a venous cerebrovascular thromboembolic disorder, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

33. A method for treating a thromboembolic disorder, comprising: administering, to a patient in need thereof, a therapeutically effective amount of a compound according to claim 8 or a pharmaceutically acceptable salt form thereof.

34. A method according to claim 33, wherein the thromboembolic disorder is selected from: an arterial cardiovascular thromboembolic disorder, an arterial cerebrovascular thromboembolic disorder, a venous cardiovascular thromboembolic disorder, a venous cerebrovascular thromboembolic disorder, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

35. A method for treating a thromboembolic disorder, comprising: administering, to a patient in need thereof, a therapeutically effective amount of a compound according to claim 9 or a pharmaceutically acceptable salt form thereof.

36. A method according to claim 35, wherein the thromboembolic disorder is selected from: an arterial cardiovascular thromboembolic disorder, an arterial cerebrovascular thromboembolic disorder, a venous cardiovascular thromboembolic disorder, a venous cerebrovascular thromboembolic disorder, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

\* \* \* \* \*